(12) United States Patent
Sutherland et al.

(10) Patent No.: US 10,870,875 B2
(45) Date of Patent: Dec. 22, 2020

(54) METALLOPROTEIN COMPOSITIONS

(71) Applicant: Commonwealth Scientific and Industrial Research Organisation, Acton (AU)

(72) Inventors: Tara Sutherland, Watson (AU); Trevor Rapson, Palmerston (AU)

(73) Assignee: Commonwealth Scientific and Industrial Research Organisation, Campbell (AU)

(*) Notice: Subject to any disclaimer, the term of this patent is extended or adjusted under 35 U.S.C. 154(b) by 281 days.

(21) Appl. No.: 15/527,266

(22) PCT Filed: Nov. 16, 2015

(86) PCT No.: PCT/AU2015/050717
§ 371 (c)(1),
(2) Date: May 16, 2017

(87) PCT Pub. No.: WO2016/077877
PCT Pub. Date: May 26, 2016

(65) Prior Publication Data
US 2018/0119194 A1 May 3, 2018

(30) Foreign Application Priority Data
Nov. 17, 2014 (AU) .................................. 2014904612

(51) Int. Cl.
| | | |
|---|---|---|
| C07K 14/435 | (2006.01) | |
| C07K 14/795 | (2006.01) | |
| D01F 4/02 | (2006.01) | |
| G01N 21/76 | (2006.01) | |
| G01N 21/77 | (2006.01) | |
| G01N 21/78 | (2006.01) | |
| G01N 31/22 | (2006.01) | |
| C12Q 1/00 | (2006.01) | |
| C12Q 1/28 | (2006.01) | |
| C12Q 1/26 | (2006.01) | |
| D01F 6/68 | (2006.01) | |

(52) U.S. Cl.
CPC ........ *C12Q 1/001* (2013.01); *C07K 14/43572* (2013.01); *C07K 14/795* (2013.01); *C12Q 1/005* (2013.01); *C12Q 1/26* (2013.01); *C12Q 1/28* (2013.01); *C12Y 111/01* (2013.01); *G01N 21/76* (2013.01); *G01N 21/766* (2013.01); *G01N 21/78* (2013.01); *G01N 21/783* (2013.01); *G01N 31/223* (2013.01); *G01N 31/224* (2013.01); *G01N 31/225* (2013.01); *D01F 4/02* (2013.01); *D01F 6/68* (2013.01)

(58) Field of Classification Search
CPC ............ C07K 14/795; C07K 14/43563; C07K 14/43572; C07K 14/43586; D01F 4/02; G01N 21/76; G01N 21/766; G01N 21/7756; G01N 21/7763; G01N 21/7769; G01N 21/7786; G01N 21/78; G01N 21/783; G01N 31/22; G01N 31/223; G01N 31/224; G01N 31/225
See application file for complete search history.

(56) References Cited

U.S. PATENT DOCUMENTS

| | | | |
|---|---|---|---|
| 5,603,820 A * | 2/1997 | Malinski | B01J 31/1658 204/282 |
| 8,481,681 B2 * | 7/2013 | Sutherland | C07K 14/43563 530/350 |
| 2015/0056256 A1 * | 2/2015 | Essaidi | D06B 1/00 424/402 |
| 2016/0281266 A1 * | 9/2016 | Omenetto | A61L 27/56 |

FOREIGN PATENT DOCUMENTS

| | | |
|---|---|---|
| WO | WO2004050693 | 6/2004 |
| WO | WO2008127402 | 10/2008 |

OTHER PUBLICATIONS

Hepburn, et al. (Physical properties of honeybee silk: a review, Apidologie 2013) (Year: 2013).*
Rapson, et al. (Micromolar biosensing of nitric oxide using myoglobin immobilized in a synthetic silk film, Biosensors and Bioelectronics 2014, 62: 214-220, of record Nov. 7, 2017 IDS, NPL line 8) (Year: 2014).*
Peacock (Incorporating metals into de novo proteins, Current Opinion in Chemical Biology 2013, 17:934-939) (Year: 2013).*
Sutherland (Conservation of Essential Design Features in Coiled Coil Silks, Mol. Biol. Evol. 2007, 24:2424-2432) (Year: 2007).*
Lu (Water-Insoluble Silk Films with Silk I Structure, Acta Biomater. Apr. 2010 ; 6(4): 1380-1387) (Year: 2010).*
Dublin, et al. (2008) "Design of a Selective Metal Ion Switch for Self-Assembly of Peptide-Based Fibrils", American Chemical Society, 130, 49-51.
European Search Report for PCT/AU2015050717, dated Mar. 14, 2018, 9 pages.
Peacock, et al., (2013) "Incoirporating metals into de novo proteins", Chemical Biology, 17; 934-939.
Rapson, et al. (2014) "Micromolarbiosensingofnitricoxideusingmy oglobinimmobilized in asyntheticsilk film", Biosensors and Bioelectronics, 62; 214-220.
Taggart, et al. (2014) "Testing the Role of Charge and Structure on the Stability of PeptidePorphyrin Complexes", Bio Mac, 15; 4544-4550.
Yu, et al. (2014) "Protein Design: Toward Functional Metalloenzymes", Bioinorganic Enzymology, 114; 3495-3578.
Zaytsev, et al. (2010) "Nanometer to Millimeter Scale Peptide-Porphyrin Materials", Bio Mac, 11; 2602-2609.

(Continued)

*Primary Examiner* — Jeffrey E. Russel
(74) *Attorney, Agent, or Firm* — Carol L. Francis; Bozicevic, Field & Francis LLP

(57) ABSTRACT

The present invention relates to compositions comprising: a polypeptide, wherein at least a portion of the polypeptide has a coiled coil structure; and a chelate comprising a chelating agent and a metal ion; and wherein the chelate is bound to at least one amino acid of the polypeptide. In a preferred embodiment the polypeptide is a silk fibroin, wherein at least a portion of the silk fibroin has a coiled coil structure.

23 Claims, 13 Drawing Sheets

Specification includes a Sequence Listing.

(56) References Cited

OTHER PUBLICATIONS

Glykos. et al., 'Loopless Rop: structure and dynamics of an engineered homotetrameric variant of the repressor of primer protein', Biochemistry, 2006, vol. 45, pp. 10905-10919.—Paid.

Huson, et al., 'Controlling the molecular structure and physical properties of artificial honeybee silk by heating or by immersion in solvents', PLoS One, 2012, vol. 7.

Krishna, et al., 'Protein- and peptide-modified synthetic polymeric biomaterials', Biopolymers, 2010, vol. 94, pp. 32-48.—Paid.

McAllister, et al., 'Using alpha-helical coiled-coils to design nanostructured metalloporphyrin arrays', Journal of the American Chemical Society, 2008, vol. 130, pp. 11921-11927.

Mutter, et al., 'Rational design of a zinc phthalocyanine binding protein', Journal of Structural Biology, Feb. 2014, vol. 185, pp. 178-185.

Pazos, et al., 'Sensing coiled-coil proteins through conformational modulation of energy transfer processes—selective detection of the oncogenic transcription factor c-Jun', Chemical Science, 2011, vol. 2, pp. 1984-1987 (downloaded Sep. 21, 2017, pp. S1-S18).

Rapson, et al., 'De novo engineering of solid-state metalloproteins using recombinant coiled-coil silk', ACS Biomaterials Science & Engineering, 2015, vol. 1, pp. 1114-1120.

Rapson, et al., 'Micromolar biosensing of nitric oxide using myoglobin immobilized in a synthetic silk film', Biosensors and Bioelectronics, 2014, vol. 62, pp. 214-220.

Sutherland, et al., 'Single honeybee silk protein mimics properties of multi-protein silk', PLoS One, 2011, vol. 6, e16489.

Wang, et al., 'Hybrid hydrogels assembled from synthetic polymers and coiled-coil protein domains', Nature, 1999, vol. 397, pp. 417-420.—Paid.

Yin, et al., 'Amperometric biosensor based on tyrosinase immobilized onto multiwalled carbon nanotubes-cobalt phthalocyanine-silk fibroin film and its application to determine bisphenol A', Analytica Chimica Acta, 2010, vol. 659, pp. 144-150.—Paid.

International Search Report for PCT application serial No. PCT/AU2015/050717, dated Feb. 18, 2016, 9 pages.

NCBI Ref Sequence Accession NP_001129680, silk fibroin 3 precursor, Aug. 19, 2013, 1 page.

Cohen-Ofri, Ilit, et al., (2011) "Zinc-Bacteriochlorophyllide Dimers in de Novo Designed Four-Helix Bundle Proteins. A Model System for Natural Light Energy Harvesting and Dissipation", J. Am. Chem. Soc., 133:9526-9535.

Kameda, Tsunenori, et al., (2014) "Evolution and Application of Coiled Coil Silks from Insects", Biotechnology of Silk, 87-106.

Mason, Jody M. and Arndt, Katja M., (2004) "Coiled Coil Domains: Stability, Specificity, and Biological Implications", ChemBioChem, 5:170-176.

Thomas, Jens M.H., et al., (2015) "Routine phasing of coiled-coil protein crystal structures with AMPLE", IUCrJ, 2:198-206.

Kaneko et. al., (1991) "Luminescence from excited tris(2,2'-bipyridine)-ruthenium(II) incorporated into a silk fibroin membrane.", J. Photochem. Photobiol. A: Chem., 61:373-380.

Yashimizu et. al., (1991) "Luminescent characteristics of tris(2,2'-bipyridine)-ruthenium(II) adsorbed in a silk fibroin membrane.", Makromol. Chem., 192:1649-1654.

* cited by examiner

A

B

A

B

A

B

A

B

A

B

METALLOPROTEIN COMPOSITIONS

CROSS-REFERENCE TO RELATED APPLICATIONS

The present application claims priority benefit under 35 U.S.C. § 371 to International Application No. PCT/AU2015/050717, filed Nov. 16, 2015, which application claims priority from AU 2014904612, filed Nov. 17, 2014, the entire contents of which are incorporated herein by reference.

TECHNICAL FIELD

The present invention relates to compositions comprising a polypeptide and a chelate comprising a chelating agent and a metal ion, and uses thereof.

BACKGROUND OF INVENTION

Detecting the presence of, and levels of, molecules in mixtures of interest is of great commercial importance.

As a consequence, there have been efforts to develop methods for detecting and monitoring levels of molecules of interest using molecules able to interact with the molecules of interest. Some of the most promising of these methods involve the use of a biosensor. Biosensors are devices capable of providing specific quantitative or semi-quantitative analytical information using a biological recognition element. The biological recognition element of a biosensor determines the selectivity, so that the molecule which has to be measured generates a signal. The selection may be based on biochemical recognition of the molecule where the chemical structure of the molecule is unchanged, or biocatalysis in which the element catalyzes a biochemical reaction of the molecule. A transducer translates the recognition of the biological recognition element into a semi-quantitative or quantitative signal. Possible transducer technologies are optical, electrochemical, acoustical/mechanical or colorimetrical. The optical properties that have been exploited include absorbance, fluorescence/phosphorescence, bio/chemiluminescence, reflectance, light scattering and refractive index. Conventional reporter groups such as fluorescent compounds may be used, or alternatively, there is the opportunity for direct optical detection, without the need for a label.

Because the biological recognition element of a biosensor determines the specificity, proteins are of great interest for use in biosensors, since there are a wide variety of protein domains known to bind molecules of interest with high specificity and sensitivity, for example monoclonal antibodies and derivative single-chain variable fragments (scFvs), enzymes, viral proteins, protein aptamers etc.

However, the characteristics of many proteins make them less amenable to use in biosensors. For example, many proteins become unstable after purification, undergoing irreversible conformational changes, denaturing, and loss of biochemical activity.

The immobilisation of proteins within or onto materials also presents problems. For example, proteins are frequently immobilised onto surfaces by non-specific covalent bonding and therefore can exist in a large number of possible orientations, for example, with some proteins oriented such that their binding or active sites are exposed whereas others may be oriented such that there active sites are not exposed, and thus not able to undergo selective binding reactions with the molecule of interest. In addition to orientation, protein density may also be poorly controlled. Proteins are also subject to time-dependent denaturing, denaturing during immobilization, and leaching of the entrapped protein subsequent to immobilization. Furthermore, immobilisation may limit contact between the protein and the diagnostic molecule of interest.

Therefore, there is a need in the art for stable protein biosensors that can be formed into materials, or incorporated into or onto materials.

SUMMARY OF INVENTION

The present inventors have surprisingly found that polypeptides comprising a portion with a coiled coil structure, such as coiled coil silk polypeptides, a chelating agent, such as a macrocycle, and metal ion can be used to provide compositions and materials having desired characteristics, for example for use as biosensors and the like.

Thus, in one aspect, the present invention provides a composition comprising; a polypeptide wherein at least a portion of the polypeptide has a coiled coil structure; and a chelate comprising a chelating agent and a metal ion; and wherein the chelate is bound to at least one amino acid of the polypeptide. In some embodiments, the chelating agent is bound to at least one amino acid of the polypeptide. In some embodiments, the at least one amino acid residue bound to the chelating agent is a charged amino acid residue. In some embodiments, the metal ion is bonded to at least one amino acid of the polypeptide by a co-ordinate bond. In some embodiments, the at least one amino acid bound to the metal ion by a co-ordinate bond is a Tyr, Cys, His, Met, Lys, Glu or a non-natural amino acid.

In some embodiments, the portion of the polypeptide that has a coiled coil structure comprises at least 35 amino acids, or at least 63 amino acids.

In some embodiments, at least 20% of the amino acids in the coiled coil structure are alanine residues.

In some embodiments, the chelating agent comprises a ring of atoms. In some embodiments, the chelating agent is selected from the group consisting of porphryins, corrins, chlorins, corphins, porphines and phthalocyanines.

In some embodiments, the metal ion is an ion of a transition metal, alkali earth metal or p-block metal. For example, the metal ion may be selected from the group consisting of an ion of Fe, Sn, Cd, Cr, Mn, Co, Cu, Ru, Zn, Mg, Sc, Ru, Rh, Os, Ag, Pd, Zn, Re, Pt, Ti, V, Ni, Mo, Tc, W and Ir. In an embodiment, the alkali earth metal is Mg.

In some embodiments, the composition of the present invention is capable of binding a target compound. In some embodiments, the composition of the present invention comprises a binding site for a target compound. The target compound may be selected from the group consisting of oxygen, carbon monoxide, carbon dioxide, hydrogen peroxide, compounds having an atom of P, S, or N, and mixtures thereof. In some embodiments, the target compound is NO.

In some embodiments, the composition comprises more than one polypeptide.

In another aspect, the present invention provides a material comprising a composition of the present invention, wherein the polypeptides are crosslinked by ionic bonds, Hydrogen-bonds, covalent bonds or a combination thereof and the material is insoluble in water. The material may be in the form of a silk fibre, film, powder or sponge.

In yet another aspect, the present invention provides a copolymer comprising a composition of the present invention and a further polypeptide, wherein at least a portion of the further polypeptide has a coiled coil structure. In some embodiments, at least some of the polypeptides are cross-linked. In some embodiments, at least some of the residues of the polypeptides are covalently crosslinked.

In yet another aspect, the present invention provides a sensor for detecting a target compound comprising a composition, material or copolymer of the present invention. In some embodiments, the composition, material or copolymer comprises a binding site for the target compound, and wherein binding of the target compound results in a detectable change. The detectable change may be a change in colour, spectrophotometric, fluorescent or electrochemical change. In some embodiments, the spectrophotometric change is a change in the Soret peak. In other embodiments, the spectrophotometric change is a change in at least one spectrophotometric peak with a wavelength between 500 and 600 nm.

In yet another aspect, the present invention provides a method of binding a target compound, said method comprising the steps of (a) providing a composition, material or copolymer of the present invention and (b) contacting said composition, material or copolymer with a target compound under conditions for binding said compound to said composition. In some embodiments, the method further comprises detecting binding of the target compound by detecting a change in the composition and/or target compound upon binding.

In yet another aspect, the present invention also provides a method for producing a biosensor, said method comprising providing a polypeptide wherein at least a portion of the polypeptide has a coiled coil structure; and contacting the polypeptide to a chelate comprising a chelating agent and a metal ion under conditions for binding said chelate to at least one amino acid of said polypeptide. In some embodiments, the chelating agent is bound to at least one amino acid of the polypeptide. In some embodiments, the at least one amino acid residue bound to the chelating agent is a charged amino acid residue. In some embodiments, the metal ion is bonded to at least one amino acid of the polypeptide by a co-ordinate bond. In some embodiments, the at least one amino acid bound to the metal ion by a co-ordinate bond is a Tyr, Cys, His, Met, Lys, Glu or a non-natural amino acid.

In a further aspect, the present invention provides a method of detecting nitric oxide, the method comprising (a) contacting a sample with a composition or material of the invention, (b) determining if step (a) results in a detectable change in the composition or material, wherein a detectable change indicates that nitric oxide is in the sample. In an embodiment, the chelate is haem b.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

As used herein, the term about, unless stated to the contrary, refers to +/−10%, more preferably +/−5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF DRAWINGS

(FIG. 20, Panel A) No change in both the shape and the position of the Soret peak was noted for Y76H A97H indicating that an extra heme binding site had been introduced and the modified AmelF3 was now able to bind two heme cofactors. (FIG. 20, Panel B)

KEY TO THE SEQUENCE LISTING

Figure 1:
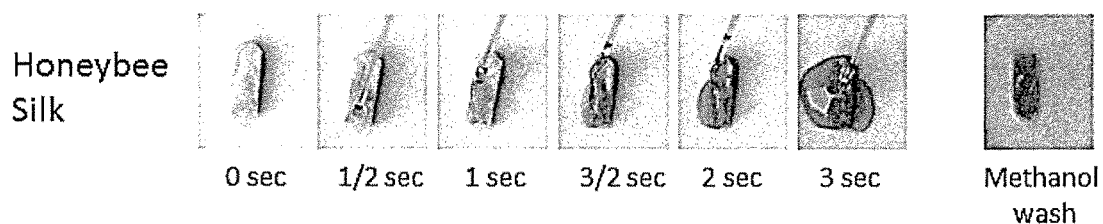
FIG. 1 shows evidence for the binding and coordination of haem b within honeybee silk sponges. A solution of haem is added drop-wise onto a honeybee silk sponge (A; top panel) or silkworm silk sponge (B; bottom panel). The honeybee silk sponge changes to a red colouration, while no colour change occurs in the silkworm silk sponge. The haem-induced colouration of the honeybee sponge remains after washing with 70% methanol, whereas the green haem b colour is washed out of the silkworm silk sponge. This figure demonstrates binding and coordination of a chelate to a polypeptide of the present invention.
Figure 1:
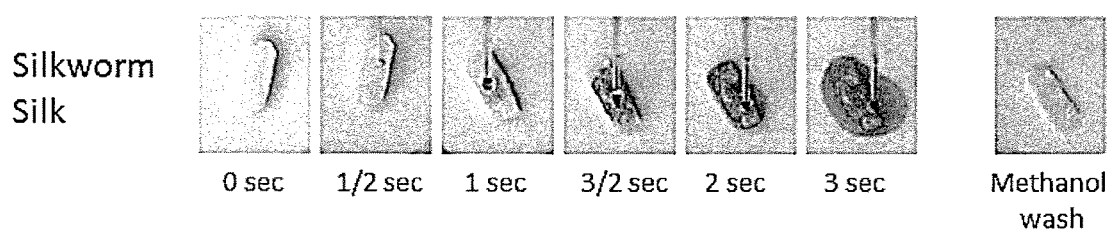

SEQ ID NO: 1—amino acid sequence of *Apis mellifera* (honey bee) silk fibroin 1 (also termed AmelF1 or Xenospira1) with signal sequence SEQ ID NO: 2—amino acid sequence of *Apis mellifera* silk fibroin 2 (also termed AmelF2 or Xenospira2) with signal sequence SEQ ID NO: 3—amino acid sequence of *Apis mellifera* silk fibroin 3 (also termed AmelF3 or Xenospira3) with signal sequence SEQ ID NO: 4—amino acid sequence of *Apis mellifera* silk fibroin 4 (also termed AmelF4 or Xenospira4) with signal sequence SEQ ID NO: 5—nucleotide sequence of *Apis mellifera* silk fibroin 1 (also termed AmelF1 or Xenospira1)

SEQ ID NO: 6—nucleotide sequence of *Apis mellifera* silk fibroin 2 (also termed AmelF2 or Xenospira2)

SEQ ID NO: 7—nucleotide sequence of *Apis mellifera* silk fibroin 3 (also termed AmelF3 or Xenospira3)

SEQ ID NO: 8—nucleotide sequence of *Apis mellifera* silk fibroin 4 (also termed AmelF4 or Xenospira4)

SEQ ID NO: 9—amino acid sequence of *Oecophylla smaragdina* (weaver ant) silk fibroin 1 (also termed F1 or GAF1) with signal sequence SEQ ID NO: 10—amino acid sequence of *Oecophylla smaragdina* silk fibroin 2 (also termed F2 or GAF2) with signal sequence SEQ ID NO: 11—amino acid sequence of *Oecophylla smaragdina* silk fibroin 3 (also termed F3 or GAF3) with signal sequence SEQ ID NO: 12—amino acid sequence of *Oecophylla smaragdina* silk fibroin 4 (also termed F4 or GAF4) with signal sequence SEQ ID NO: 13—nucleotide sequence of *Oecophylla smaragdina* silk fibroin 1 (also termed F1 or GAF1)

SEQ ID NO: 14—nucleotide sequence of *Oecophylla smaragdina* silk fibroin 2 (also termed F2 or GAF2)

SEQ ID NO: 15—nucleotide sequence of *Oecophylla smaragdina* silk fibroin 3 (also termed F3 or GAF3)

SEQ ID NO: 16—nucleotide sequence of *Oecophylla smaragdina* silk fibroin 4 (also termed F4 or GAF4)

SEQ ID NO: 17—amino acid sequence of *Apis cerana* (Asiatic honey bee) silk fibroin 1

SEQ ID NO: 18—amino acid sequence of *Apis cerana* silk fibroin 2

SEQ ID NO: 19—amino acid sequence of *Apis cerana* silk fibroin 3

SEQ ID NO: 20—amino acid sequence of *Apis cerana* silk fibroin 4

SEQ ID NO: 21—amino acid sequence of *Oecophylla smaragdina* silk fibroin 1

SEQ ID NO: 22—amino acid sequence of *Oecophylla smaragdina* silk fibroin 2

SEQ ID NO: 23—amino acid sequence of *Oecophylla smaragdina* silk fibroin 3

SEQ ID NO: 24—amino acid sequence of *Oecophylla smaragdina* silk fibroin 4

SEQ ID NO: 25—amino acid sequence of *Polistes dominula* (European paper wasp) silk fibroin 1

SEQ ID NO: 26—amino acid sequence of *Polistes dominula* silk fibroin 2

SEQ ID NO: 27—amino acid sequence of *Polistes dominula* silk fibroin 3

SEQ ID NO: 28—amino acid sequence of *Polistes dominula* silk fibroin 4

SEQ ID NO: 29—amino acid sequence of *Apis dorsata* (Giant honeybee) silk fibroin 1

SEQ ID NO: 30—amino acid sequence of *Apis dorsata* silk fibroin 2

SEQ ID NO: 31—amino acid sequence of *Apis dorsata* silk fibroin 3

SEQ ID NO: 32—amino acid sequence of *Apis dorsata* silk fibroin 4

SEQ ID NO: 33—amino acid sequence of *Apis florea* (Dwarf honeybee) silk fibroin 1

SEQ ID NO: 34—amino acid sequence of *Apis florea* silk fibroin 2

SEQ ID NO: 35—amino acid sequence of *Apis florea* silk fibroin 3

SEQ ID NO: 36—amino acid sequence of *Apis florea* silk fibroin 4

SEQ ID NO: 37—amino acid sequence of *Apis mellifera* silk fibroin 1

SEQ ID NO: 38—amino acid sequence of *Apis mellifera* silk fibroin 2

SEQ ID NO: 39—amino acid sequence of *Apis mellifera* silk fibroin 3

SEQ ID NO: 40—amino acid sequence of *Apis mellifera* silk fibroin 4

SEQ ID NO: 41—amino acid sequence of *Bombus impatiens* (common eastern bumblebee) silk fibroin 2

SEQ ID NO: 42—amino acid sequence of *Bombus terrestris* (buff tailed bumblebee) silk fibroin 1

SEQ ID NO: 43—amino acid sequence of *Bombus terrestris* silk fibroin 2

SEQ ID NO: 44—amino acid sequence of *Bombus terrestris* silk fibroin 3

SEQ ID NO: 45—amino acid sequence of *Bombus terrestris* silk fibroin 4

SEQ ID NO: 46—amino acid sequence of *Camponotus floridanus* (florida carpenter ant) silk fibroin 2

SEQ ID NO: 47—amino acid sequence of *Camponotus floridanus* silk fibroin 3

SEQ ID NO: 48—amino acid sequence of *Camponotus floridanus* silk fibroin 4

SEQ ID NO: 49—amino acid sequence of *Harpegnathos saltator* (indian jumping and or Jerdon's jumping ant) silk fibroin 1

SEQ ID NO: 50—amino acid sequence of *Harpegnathos saltator* silk fibroin 2

SEQ ID NO: 51—amino acid sequence of *Harpegnathos saltator* silk fibroin 3

SEQ ID NO: 52—amino acid sequence of *Harpegnathos saltator* silk fibroin 4

SEQ ID NO: 53—amino acid sequence of *Myrmecia forficate* (bulldog ant) silk fibroin 1

SEQ ID NO: 54—amino acid sequence of *Myrmecia forficate* silk fibroin 2

SEQ ID NO: 55—amino acid sequence of *Myrmecia forficate* silk fibroin 3

SEQ ID NO: 56—amino acid sequence of *Myrmecia forficate* silk fibroin 4

SEQ ID NO: 57—amino acid sequence of *Megachile rotundata* (alfalfa leafcutter bee) silk fibroin 2

SEQ ID NO: 58—amino acid sequence of *Megachile rotundata* silk fibroin

SEQ ID NO: 59—amino acid sequence of *Megachile rotundata* silk fibroin

SEQ ID NO: 60—amino acid sequence of *Osmia cornuta* (builder bee) silk fibroin 2

SEQ ID NO: 61—amino acid sequence of *Osmia cornuta* silk fibroin 4

SEQ ID NO: 62—amino acid sequence of *Vespa simillima xanthoptera* (Japanese yellow hornet) silk fibroin 1

SEQ ID NO: 63—amino acid sequence of *Vespa simillima xanthoptera* silk fibroin 2

SEQ ID NO: 64—amino acid sequence of *Vespa simillima xanthoptera* silk fibroin 3

SEQ ID NO: 65—amino acid sequence of *Vespa simillima xanthoptera* silk fibroin 4

SEQ ID NO: 66—amino acid sequence of *Vespa analis* (yellow-vented hornet) silk fibroin 1

SEQ ID NO: 67—amino acid sequence of *Vespa analis* silk fibroin 2

SEQ ID NO: 68—amino acid sequence of *Vespa analis* silk fibroin 3

SEQ ID NO: 69—amino acid sequence of *Vespa analis* silk fibroin 4

SEQ ID NO: 70—amino acid sequence of *Vespa mandarinia* (Asian giant hornet) silk fibroin 1

SEQ ID NO: 71—amino acid sequence of *Vespa mandarinia* silk fibroin 2

SEQ ID NO: 72—amino acid sequence of *Vespa mandarinia* silk fibroin 3

SEQ ID NO: 73—amino acid sequence of *Vespa mandarinia* silk fibroin 4

SEQ ID NO: 74—amino acid sequence of *Tenodera australasiae* protein Mantis Fibroin 1

SEQ ID NO: 75—amino acid sequence of *Tenodera australasiae* protein Mantis Fibroin 2

SEQ ID NO: 76—amino acid sequence of *Archimantis monstrosa* silk fibroin 1

SEQ ID NO: 77—amino acid sequence of *Archimantis monstrosa* silk fibroin 2

SEQ ID NO: 78—amino acid sequence of *Pseudomantis albofimbriata* silk fibroin 1

SEQ ID NO: 79—amino acid sequence of *Pseudomantis albofimbriata* silk fibroin 2

SEQ ID NO's: 80 to 82—Oligonucleotide primers.

DETAILED DESCRIPTION

The present invention is based in part on the characterisation that polypeptides having a coiled coil structure are able to bind a chelate comprising a chelating agent and a metal ion. For example, the present inventors have demonstrated a silk polypeptide having a coiled coil structure is able to bind a chelate and co-ordinate the metal ion of the chelate. Furthermore, the present inventors have demonstrated that the co-ordination of the metal ion of the chelate can causes a shift in the location of a peak in the UV-visible spectrum (e.g. the Soret peak). The present inventors have also shown that the binding of a molecule able to bind the chelate bound to the polypeptide causes a detectable change, and this can be used as the basis of a sensor, for example a biosensor, that may be used for detecting a molecule of interest.

Accordingly, in a first aspect, the present invention provides a composition comprising: a polypeptide wherein at least a portion of the polypeptide has a coiled coil structure; and a chelate comprising a chelating agent and a metal ion; and wherein the chelate is bound to at least one amino acid of the polypeptide. In some embodiments, the chelating agent is bound to at least one amino acid of the polypeptide. In some embodiments, the metal ion is bonded to at least one amino acid of the polypeptide by a co-ordinate bond. In some embodiments, the metal ion is bonded to at least one amino acid of the polypeptide by a co-ordinate bond and the chelating agent is bound to at least one amino acid of the polypeptide.

Advantageously, the compositions of the present invention may be processed to form a material, preferably a water insoluble material, and are highly stable at room temperature for extended periods of time. In some embodiments, the compositions of the present invention and materials formed from the compositions of the present invention are able to reversibly bind a molecule of interest. Importantly, the compositions of the present invention, and materials formed from the compositions retain the ability to bind and/or detect the molecule of interest over extended periods.

Polypeptides

The term "polypeptide", as used herein, includes amino acid polymers of any length. The protein may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labelling component. Also included are, for example, proteins containing one or more analogs of an amino acid (including, for example, unnatural or non-natural amino acids, etc.), as well as other modifications known in the art. Proteins can occur as single chains or associated chains. Associated chains may be joined by non-covalent or covalent interactions. In an embodiment, the polypeptide is a chain of naturally occurring amino acids.

Polypeptides useful for the invention can be prepared by various means (e.g. isolation and purification from source, recombinant expression, purification from cell culture, chemical synthesis, etc.) and in various forms (e.g. native, fusions, non-glycosylated, lipidated, etc.). They are preferably prepared in substantially pure form (i.e. substantially free from host cell proteins). Typically, the polypeptide is substantially pure when it is at least 60%, by weight, of total protein present. For example, the preparation is at least 75%, at least about 80%, at least about 85%, at least about 90%, at least about 91%, at least about 92%, at least about 93%, at least about 94%, at least about 95%, at least about 96%, at least about 97%, at least about 98%, at least about 99%, more preferably at least 90%, by weight, of total protein present. In an embodiment, the polypeptide is produced by recombinant means, such as expression in a suitable host cell such as a yeast cell or bacterial cell.

As used herein, "portion" is understood to refer to a portion of a polypeptide which maintains a defined characteristic or activity of the full-length polypeptide. For example, having the ability to form a coiled coil structure and/or having the ability to reproduce any one or more characteristics of a silk protein.

As disclosed herein, at least a portion of the polypeptide may form a coiled coil structure. A coiled coil structure comprises at least two alpha helices that coil together like the strands of a rope. A coiled coil structure may comprise between two and seven alpha helices, such as two, three, four, five, six or seven alpha helices. In some embodiments, the coiled coil structure comprises three, four or five alpha helices. Coiled coil structures may form from intra-chain or inter-chain interactions.

In some embodiments, the portion of the polypeptide that has a coiled coil structure comprises at least 35 amino acids, at least 42 amino acids, at least 49 amino acids, at least 56 amino acids, at least 63 amino acids, at least 70 amino acids, at least 77 amino acids, at least 84 amino acids, at least 91 amino acids, at least 98 amino acids, at least 105 amino acids, at least 112 amino acids, at least 119 amino acids, at least 126 amino acids, at least 133 amino acids, at least 140 amino acids, at least 147 amino acids, at least 154 amino acids, at least 161 amino acids, at least 168 amino acids, at least 175 amino acids, at least 182 amino acids, at least 189 amino acids, at least 196 amino acids, at least 203 amino acids, at least 210 amino acids or at least 217 amino acids. In an embodiment, the portion of the polypeptide that has a coiled coil structure comprises about 35 to about 500 amino acids.

In some embodiments, at least 16% of the amino acids in the coiled coil structure are alanine residues. For example, at least 18%, at least 20%, at least 22%, at least 24%, at least 26%, at least 28% or at least 30% of the amino acids in the coiled coil structure are alanine residues.

Typically, alpha-helices contain about 3.6 amino acid residues per helical turn. In the case of alpha-helices capable of forming a coiled coil structure, hydrophobic and hydrophilic amino acid residues are spaced along the linear sequence of the peptide such that when the polypeptide or portion of a polypeptide assumes an alpha-helical conformation, the hydrophobic and hydrophilic amino acid residues are respectively segregated to separate faces of the helix, forming an amphipathic structure. The segregation of hydrophobic and hydrophilic amino acid residues in an alpha-helix can be visualized in a helical wheel. Certain hydrophobic and hydrophilic amino acid residues are preferred in constructing alpha-helical peptides capable of forming a coiled coil structure. Naturally occurring hydrophobic amino acid residues are Leu, Ala, Ile, Val and Phe. Preferred naturally occurring hydrophilic amino acid residues are Ser, Glu, Lys, Gln and Asp. As will be understood by a person skilled in the art the polypeptide sequence capable of forming a coiled structure can vary. A large number of combinations and permutations of different amino acids in the polypeptide sequence can achieve the effect of producing an amphipathic alpha helix, which allows the formation of a coiled coil in association with another polypeptide. For example, in some embodiments serine is common in the core of coiled coils formed by the polypeptides of the present invention but not in other coiled coils.

Polypeptides capable of forming a coiled coil structure usually comprise repeats of the heptad sequence abcdefg. In one embodiment the polypeptide comprises a portion comprising at least 5 copies of the heptad sequence abcdefg. Polypeptides useful for the invention may comprise any number of heptad repeats greater than 4. For example, the polypeptides may comprise a portion having a coiled coil structure comprising at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39 at least 40, at least 41, at least 42, at least 43, at least 44, at least 45, at least 46, at least 47, at least 48, at least 49, at least 50, or more copies of the heptad sequence abcdefg. In one particular example, the polypeptides comprise a portion having a coiled coil structure comprising at least 19, or at least 23 copies of the heptad sequence abcdefg.

In one embodiment, the polypeptides useful for the invention comprise about 9 to about 30, such as about 15 to about 25, or about 19 to about 23 heptad repeats, or about 19 to about 23 repeats. In some embodiments, the polypeptides comprise a portion having a coiled coil structure comprising between 22 and 28 repeats.

The heptad repeats may be contiguous in the polypeptide sequence or may not be contiguous in the polypeptide sequence. Thus, the polypeptide may comprise any number of contiguous heptad sequences, provided that the total number of heptad sequences in the polypeptide is at least 5. Preferably, the polypeptide comprises at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25 or more contiguous heptad sequences. In one example, the polypeptide comprises at least 19, such as at least 20, at least 21, at least 22, or at least 23 contiguous heptad sequences. In another example, the polypeptide comprises about 10 to about 30, such as about 15 to about 25, or about 19 to about 23 contiguous heptad repeats. Preferably, the polypeptides comprise about 19 or about 23 contiguous heptad repeats.

The heptad repeats may comprise any portion of the polypeptide useful for the invention. For example, the heptad repeats may comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, of the length of the polypeptide, or the entire polypeptide.

In another example, the heptad repeats may comprise about 60% to about 90%, such as about 70% to about 80% of the polypeptide. Thus, about 60% to about 90%, such as about 70% to about 80% of the polypeptide may comprise a coiled coil structure.

In the classic coiled coil, the amino acids at the a and d position are hydrophobic residues, such as but not limited to alanine, isoleucine, leucine or valine. These amino acids tend to be more hydrophobic on average than amino acids at other positions in the heptad sequence. This is thought to stabilise the formation of the coiled coil via hydrophobic and van der Waals interactions. Hydrophobicity of an amino acid residue can be determined by any method known in the art. For example, hydrophobicity can be predicted based on the physiochemical properties of the amino acid side chains, or may be determined by partitioning of an amino acid between two immiscible liquid phases. The use of these methods to determine the relative hydrophobicity of each of the naturally occurring amino acids has resulted in the production of several known hydrophobicity scales (see, by way of example only, Kallol et al., 2003; Kyte and Doolittle, 1982; Eisenberg, 1984; Rose and Wolfenden, 1993). Any of these, or other known hydrophobicity scales, can be used to determine the hydrophobicity (and hence, the average hydrophobicity) of the amino acids present at each position in the heptad sequence abcdefg. In one example, amino acid hydrophobicity is determined according to the Eisenberg scale. In a particular example, the average hydrophobicity of amino acids at positions a and/or d in the heptad sequence is positive according to the Eisenberg scale, and the average hydrophobicity of amino acids at each of the remaining positions in the heptad sequence is negative according to the Eisenberg scale. Generally, the following amino acids are considered to be more hydrophobic than others: cysteine, glycine, isoleucine, leucine, methionine and valine. Aromatic amino acids are also generally considered to be more hydrophobic than non-aromatic amino acids.

The amino acids at the e and g positions may be charged, for example but not limited to glutamate or lysine. This is thought to facilitate the formation of interhelical electrostatic interactions that stabilise the coiled coil structure. Amino acids at the b, c and f positions tend to be hydrophilic as these amino acids are often exposed to solvent. However, the above is only a guide and the person skilled in the art would be aware that variations may occur at any of the a, b, c, d, e, f and g positions to facilitate specificity, novel functions, oligomerisation and the like.

In one embodiment of the present invention, the amino acids at positions a and/or d in the heptad sequence are selected from alanine, serine, isoleucine, leucine or valine, preferably serine or alanine.

In an embodiment, at least 15% of the amino acids at position a in the heptad repeats in the polypeptides useful for the invention are alanine residues. For example, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more of the amino acids at position a may be alanine residues. Preferably at least 45% of the amino acids at position a in the heptad repeats in the polypeptides useful for the invention are alanine residues.

In another example, from about 30% to about 70%, such as from about 40% to about 60%, or from about 45% to about 55% of the amino acids at position a in the heptad repeats in the polypeptides useful for the invention are alanine residues. In one example, about 50% of the amino acids at position a in the heptad repeats in the polypeptides useful for the invention are alanine residues.

The relative proportions of alanine at position a and d in the heptad repeats can vary, provided that at least 15% of the amino acids at position a and d are alanine residues Thus, the polypeptides useful for the invention can comprise heptad repeats wherein at least 25% of the amino acids at position a are alanine residues.

The composition of amino acids making up each heptad repeat may be the same or may differ from one heptad sequence to another. As will be understood by a person skilled in the art, a large number of combinations and permutations of different amino acids in the heptad sequence abcdefg can achieve the same effect of producing a coiled coil structure, which allows the formation of a coiled coil in association with another polypeptide. Guidance regarding amino acid substitutions which can be made to the polypeptides disclosed herein is provided, by way of example only, in Table 1. Where a predicted useful amino acid substitution based on the experimental data provided herein is in any way in conflict with the exemplary substitutions provided in Table 1 it is preferred that a substitution based on the experimental data is used.

In addition, the polypeptides may comprise certain disruptions within and/or between each heptad repeat which nevertheless allow the formation of a coiled coil structure. For example, a heptad sequence may be truncated by one or more amino acids or extended by one or more amino acids, whilst still forming a coiled coil structure. Thus, as stated above, two copies of the heptad sequence abcdefg may be separated by one or more amino acids, which nevertheless still allows the formation of an coiled coil structure.

Any portion of the polypeptide may comprise a coiled coil structure. For example, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or the entire polypeptide may comprise a coiled coil structure. In one example, at least 70% of the polypeptide comprises a coiled coil structure.

The remainder of the polypeptide that does not form a coiled coil structure can form any secondary protein structure or may not be structured. For example, the remainder of the polypeptide may form random coils, alpha helices, beta strands, and/or beta-sheets and the like.

In some embodiments, at least a portion of the polypeptide may form or be capable of forming a beta sheet. A beta sheet comprises beta strands connected by backbone hydrogen bonds. A beta sheet may comprise at least two beta strands. For example, in a material described herein, at least a portion of the polypeptide may form a beta sheet. Beta sheets may form from intra-chain or inter-chain interactions between beta strands.

The present inventors have demonstrated that silk polypeptides can bind to a chelate comprising a chelating agent and a metal ion. Accordingly, in one aspect the polypeptide is a silk polypeptide. In some embodiments, the polypeptides are silk proteins (including recombinant silk proteins) from, or are a mutant thereof, aculeate Hymenoptera. Examples of Hymenopterans include, but are not limited to, any species of the Suborder Apocrita (bees, ants and wasps), which include the following Families of insects; Chrysididae (cuckoo wasps), Formicidae (ants), Mutillidae (velvet ants), Pompilidae (spider wasps), Scoliidae, Vespidae (paper wasps, potter wasps, hornets), Agaonidae (fig wasps), Chalcididae (chalcidids), Eucharitidae (eucharitids), Eupelmidae (eupelmids), Pteromalidae (pteromalids), Evaniidae (ensign wasps), Braconidae, Ichneumonidae (ichneumons), Megachilidae, Apidae, Colletidae, Halictidae, and Melittidae (oil collecting bees). For example, the Hymenoptera may be, but not limited to, *Apis mellifera* (common names include honeybee), *Apis dorsata, Apis florea, Oecophylla smaragdina* (common names include weaver ant and green ant), *Polistes dominula, Megachile rotundata, Myrmecia foricata, Camponotus floridanus, Harpegnathos saltator, Osmia cornuta, Vespa simillima xanthoptera, Vespa analis, Vespa mandarins, Bombus impatiens* or *Bombus terrestris*. In some embodiments, the polypeptides are silk proteins (including recombinant silk proteins) from, or are a mutant thereof, Dictyoptera. For example, the Dictyoptera may be, but not limited to, *Pseudomantis albofimbriata, Tenodera australasiae* or *Archimantis monstrosa*. In some embodiments, the polypeptides are silk proteins (including recombinant silk proteins) from, or are a mutant thereof, Neuroptera. Examples of Neuropterans include species from the following insect Families: Mantispidae (see Walker et al., 2012), Chrysopidae (lacewings), Myrmeleontidae (antlions), and Ascalaphidae (owlflies). For example, the Neuroptera may be, but not limited to, *Mallada signata*. Examples of such proteins are described in WO 2007/038837 and WO 2013/

142901. These silk polypeptides have the advantage that they can be readily expressed in high levels using fermentation (at least 1 g/litre).

In a preferred embodiment, a polypeptide useful for the invention can be purified from, or is a mutant of a polypeptide purified from, a species of Hymenoptera or Neuroptera. Preferably, the species of Hymenoptera is *Apis mellifera*.

In some embodiments, a polypeptide useful for the invention can be purified from, or is a mutant of a polypeptide purified from, a species of *Oecophylla*. Preferably, the species of *Oecophylla* is *Oecophylla smaragdina*.

The polypeptides useful for the invention are exemplified by a number of particular proteins whose sequences are provided in the following SEQ ID NOs. For example, the polypeptides useful for the invention include, but are not limited to, *Apis mellifera* (honey bee) silk fibroin 1 (also termed AmelF1 or Xenospira1) (SEQ ID NO:1), *A. mellifera* silk fibroin 2 (also termed AmelF2 or Xenospira2) (SEQ ID NO:2), *A. mellifera* silk fibroin 3 (also termed AmelF3 or Xenospira3) (SEQ ID NO:3), *A. mellifera* silk fibroin 4 (also termed AmelF4 or Xenospira4) (SEQ ID NO:4), *Oecophylla smaragdina* (weaver ant) silk fibroin 1 (also termed F1, GA1 or GAF1) (SEQ ID NO:9), *O. smaragdina* silk fibroin 2 (also termed F2, GA2 or GAF2) (SEQ ID NO:10), *O. smaragdina* silk fibroin 3 (also termed F3, GA3 or GAF3) (SEQ ID NO:11) and *O. smaragdina* silk fibroin 4 (also termed F4, GA4 or GAF4) (SEQ ID NO:12), as well as those described in WO2013142901 A.

In a preferred embodiment, the polypeptide is AmelF3.

In another embodiment, the polypeptide is GA1 or GA3.

As used herein, the terms "silk protein" and "silk polypeptide" are used interchangeably and refer to a fibrous protein/polypeptide that can be used to produce materials such as silk fibre, silk film, silk sponges, silk particles and/or a fibrous protein complex. Typically, the silk proteins will be produced by recombinant expression. However, the silk proteins can be purified from a natural source or produced artificially such as, for example, by solid phase peptide synthesis or the like. Silk proteins may have a sequence corresponding to a naturally occurring silk protein or be a man-made variant thereof. Such variants not only include small substitutions, deletions and additions, but also encompass significant rearrangement of the native sequences where, for example, heptads are reordered so they bear no resemblance to the primary amino acid sequence of the native protein but because of the heptad structure are still functional silk proteins.

As discussed above, the present inventors have demonstrated at least one amino acid of a polypeptide as described herein is able to bind to a chelate. In some embodiments, a polypeptide as described herein is able to bind to at least one chelate as described herein. In other embodiments, a polypeptide described herein is able to bind to two or more chelates described herein.

Accordingly, a polypeptide as described herein comprises at least one chelate binding site. For example, when the chelate is haem, the chelator binding site is a haem binding site. In some embodiments, a polypeptide as described herein comprises two or more chelate binding sites.

In some embodiments, a polypeptide as described herein is able to bind to at least one chelating agent as described herein. In other embodiments, a polypeptide described herein is able to bind to two or more chelating agents described herein. In some embodiments, the polypeptide useful for the invention comprises at least one charged residue which can bind to the chelating agent. Charged residues comprise but are not limited to arginine, lysine, glutamate and aspartate. In some embodiments, the at least one amino acid residue bound to the chelating agent is a positively charged amino acid such as arginine or lysine. In some embodiments, the at least one amino acid residue bound to the chelating agent is arginine. In some embodiments, the at least one amino acid residue bound to the chelating agent is a charged residue located up to 12 Å from the at least one amino acid residue bound to the metal ion by a co-ordinate bond.

Furthermore, the present inventors have demonstrated that in some embodiments the metal ion is bound to at least one amino acid of the polypeptide by a co-ordinate bond. As used herein the term "coordinate bond" refers to a kind of 2-center, 2-electron covalent bond in which the two electrons derive from the same atom. A coordinate bond can also be referred to as a dipolar bond or a dative covalent bond.

In an embodiment, the core of the coiled coil portion comprises at least one, or two, or three, or four or more, coordinating amino acid residues at amino acid position a and/or d of the heptads in the core. The "core" of coiled coil proteins is well known in the art (Lupas and Gruber, 2005). Coiled coil regions form alpha helixes, and two or more such helixes coil around each other with the hydrophobic residues inside and forming a long thin hydrophobic core. Thus, the coiled coil core is more hydrophobic than the outside of the core.

In one embodiment, the polypeptide includes a single coordinating amino acid residue. In one embodiment, the polypeptide includes two coordinating amino acid residues. In one embodiment, the polypeptide includes three coordinating amino acid residues. In one embodiment, the polypeptide includes four coordinating amino acid residues. In some embodiments, the coordinating amino acid is selected from the group consisting of histidine, cysteine, methionine, tyrosine, lysine or tryptophan.

An amino acid residue that is present in a polypeptide and which residue provides a coordinating contact with a metal ion-chelator complex is referred to herein as a coordinating amino acid or coordinating residue. Amino acids suitable for use as a coordinating amino acid in a polypeptide include naturally-occurring amino acids known in the art to provide a ligand for metal cations in metalloproteins, and include His, Cys, Met, Lys, Trp, Glu and Tyr. Amino acids suitable for use as a coordinating amino acid residue in a polypeptide also include non-naturally-occurring amino acids known in the art to provide a ligand for metal cations. Such non-naturally occurring amino acids may include, but are not limited to, (2,2-bipyridin-5-yl)alanine (Bpy-Ala), (8-hydroxyquinolin-3-yl)alanine, 2-amino-3-[4-hydroxy-3-(1H-pyrazol-1-yl)phenyl] propanoic acid (pyTyr) and 2-amino-3-(8-hydroxyquinolin-5-yl)propanoic acid (HqAla).

For example, the present inventors demonstrate that when a solution of haem b (which is found in haemoglobin and cytochromes P450) in aqueous methanol was added to a honeybee silk sponge, the greyish green haem b solution was immediately absorbed into the sponge and within seconds the colour of the sponge changed to red. This red colouration in honeybee silk remained after exhaustive washing of the silk-haem material. The colour change observed with honeybee silk indicates a change in the coordination of the iron metal centre within the haem group, producing a material with a similar coordination to red haemoglobin. Furthermore, the haem group remained bound within the silk protein matrix and could not be washed out, indicating that the haem group was held within the protein matrix. Somewhat unexpectedly, without any modification, naturally honeybee silk was able to bind and coordinate haem cofactors in a manner resembling naturally occurring haem proteins.

To test the coordination of the iron centre, transparent honeybee silk films were prepared to monitor the spectral properties of the material using UV/Vis spectroscopy. Haem b was introduced either through co-drying a solution of silk protein and haem b, or by "leaching" haem b into a pre-formed film by soaking the film in solutions of haem b overnight. Haem proteins have a characteristic Soret peak in their UV/Vis spectrum at ~400 nm which is extremely sensitive to changes in the coordination of the iron haem atom. In the case of iron porphyrins such as haem b, broad Soret peaks below 400 nm indicate a 4 coordinate iron centre with the iron only coordinated to the porphyrin ring. When the haem group is coordinated to an amino acid (5 coordinate iron centre), the Soret band red shifts to above 400 nm and sharpens. The ultraviolet-visible spectrum from honeybee silk-haem b films show a sharp Soret peak at 410 nm confirming that that iron haem centre is coordinated to the honeybee silk protein.

Accordingly, the present invention also provides a composition comprising: a polypeptide wherein at least a portion of the polypeptide has a coiled coil structure; and a chelate comprising a chelating agent and a metal ion; and wherein the chelate is bonded to at least one amino acid of the polypeptide, and wherein the metal ion is bonded to the at least one amino acid of the polypeptide by a co-ordinate bond.

The coordination of haem b to unmodified honeybee silk protein was unexpected, given that the silk protein does not contain any of the typical coordinating residues such as histidine, cysteine of methionine. To determine the nature of the coordinating amino residue the present inventors investigated the stoichiometry of haem binding through varying the amount of haem b added to the silk protein and using Raman spectroscopy. At low haem loadings (haem:protein molar ratios of 1:1 and 1:2), a sharp Soret peak at 410 nm was observed, indicative of all the haem being coordinated. As the concentration of haem b relative to the protein was increased, the Soret peak broadened and shifted to lower wavelengths indicating an increase in the amount of uncoordinated haem. The finding that all haem was coordinated at 1:1 haem:silk ratio suggested that a single amino acid within each silk monomer was responsible for coordination.

The identity of the coordinating amino acid of the polypeptide was investigated using Raman spectroscopy. Raman spectroscopy measures stretching frequencies between the iron centre and the coordinating ligand, these stretching frequencies are indicative of the nature of ligand. The Raman spectrum of the silk-haem film excited at 785 nm excitation showed a broad peak centred at 594 $cm^{-1}$, which was specific to the silk-haem film. Haem proteins which have a tyrosine coordinating ligand show similar Fe-Tyr stretches. Mature recombinant honeybee silk protein 3 (SEQ ID NO:39) contains a single tyrosine residue (Tyr76) located in the core of the predicted coiled coil. The Raman spectrum indicated that Tyr76 was the most likely candidate coordinating to the haem centre.

To test whether Tyr76 was indeed the coordinating ligand, Tyr76 was replaced with an alanine using site directed mutagenesis of the silk gene. The UV/Vis spectrum of the Tyr76Ala substituted protein had a broad Soret peak at 395 nm indicating that the coordination noted in unmodified honeybee silk had been reversed through this single amino acid substitution. When haem b was added to sponges prepared using Tyr76Ala silk protein, no pronounced colour change was observed, however the green haem b colour does not wash out with aqueous methanol indicating that the haem b cofactor is bound to the silk protein through hydrogen bonding, but not coordinated to the silk. Accordingly, bonding of a metal ion to at least one amino acid of the polypeptide is a preferred feature of the present invention.

When the at least one polypeptide comprises an AmelF3 polypeptide, the present inventors have demonstrated that, the tyrosine at position 76 of AmelF3 (SEQ ID NO: 39) forms a co-ordinate bond with the metal ion of the chelate.

Amino acids surrounding the coordinating amino acid in space may play a role in coordinating with the metal ion of the chelate. In some embodiments, a neighboring polar or charged residue may play a role in polarizing and/or activating the coordinating residue so that it may coordinate the metal ion. For example, the inventors have demonstrated that mutating Ser80 of AmelF3 to an alanine does not impact binding of the polypeptide to the chelating agent but prevents coordination of the metal ion. As another example, the inventors have demonstrated that Ser80 of AmelF3 plays a role in the coordination of the metal ion. Without wishing to be bound by theory it is thought that the serine polarises the coordinating residue allowing coordinate binding to the metal ion.

In some embodiments, the coordinating amino acid residue is located 20 Å or less, 18 Å or less, 16 Å or less 14 Å or less, 12 Å or less, 10 Å or less or 8 Å or less from at least one charged residue, for example, Asp, Glu, Lys or Arg. In some embodiments, the coordinating amino acid residue is located 20 Å or less, 18 Å or less, 16 Å or less 14 Å or less, 12 Å or less, 10 Å or less or 8 Å or less from at least one polar residue, for example, Ser, Thr, Gln, Asn, His, Tyr, Cys, Met or Trp.

In one embodiment a metal ion binding site and/or chelating agent binding site is engineered into a polypeptide. For example, random mutagenesis or site directed mutagenesis is performed to engineer the protein such that it contains the necessary residues to enable chelate binding to the protein and/or coordination of a metal ion. Therefore the DNA sequence which encodes the polypeptide of this invention, either isolated or incorporated into a vector can be used to produce a polypeptide useful for the invention. This sequence is then expressed in, and the polypeptide purified from, a cell. (Alternatively it is possible that the polypeptide can be produced using a solid phase peptide synthesis). The resulting polypeptide, which is capable of binding a chelate, is then incubated with an excess of that chelate to ensure binding to the polypeptide.

In one example, the Ala residue at position 97 of mature AmelF3 (SEQ ID NO: 39) is mutated to a coordinating amino acid residue such as His, Cys, Met, Lys, Trp, Glu or Tyr. In one particular example, the Ala residue at position 97 of AmelF3 is mutated to His.

In another example, the Tyr residue at position 76 of the mature form of AmelF3 (SEQ ID NO: 39) is mutated to His.

Metal ions are found in one-third of all proteins and play important structural and functional roles. Significant effort has been directed towards understanding the role of the polypeptide in tuning the metal ion properties. A goal of de novo synthesis is to utilise design principles so as to generate functional artificial metalloproteins. Much research has focussed on the mutagenesis studies of native protein scaffolds, or re-engineering of metal ion sites into other protein scaffolds, however this work has been hampered by the complexity of natural scaffolds. Accordingly, in another embodiment, forming a composition of the present invention involves the de novo (from scratch) design of a polypeptide able to bind a chelator and/or bond to a metal ion.

In one embodiment, the polypeptides useful for the invention may have a size ranging from between about 29 kDa to about 45 kDa. For example, the polypeptides may have a size of about 33 kDa.

In one embodiment, the polypeptide of the present invention is a derived from a native polypeptide. For example, a native polypeptide may be modified by incorporating natural or non-natural amino acids (herein, the terms unnatural and non-natural amino acids are used interchangeably) to enhance or modify binding of a chelator and/or a bonding to a metal ion.

As will be appreciated from the present disclosure, the exact amino acid sequence of the polypeptides (and hence, the exact nucleic acid sequence of the polynucleotides) can vary whilst still providing a polypeptide having a structure that is capable of forming a coiled coil in association with itself or another polypeptide. The exemplified sequences should therefore be considered as examples only, and it will be appreciated that significant variation from these particular sequences may be tolerable.

In a particular example, the polypeptide comprises an amino acid sequence selected from:
i) an amino acid sequence as provided in any one of SEQ ID NO:1 to SEQ ID NO:4 or SEQ ID NO:9 to SEQ ID NO:12; and
ii) an amino acid sequence which is at least 25% identical to any one or more of SEQ ID NO:1 to SEQ ID NO:4 or SEQ ID NO:9 to SEQ ID NO:12; and
iii) a biologically active fragment of i) or ii).

In another particular example, the polypeptide comprises an amino acid sequence selected from:
i) an amino acid sequence as provided in any one of SEQ ID NO:1 to SEQ ID NO:4 or SEQ ID NO:9 to SEQ ID NO:12 or SEQ ID NO:17 to SEQ ID NO:79; and
ii) an amino acid sequence which is at least 25% identical to any one or more of SEQ ID NO:1 to SEQ ID NO:4 or SEQ ID NO:9 to SEQ ID NO:12 or SEQ ID NO:17 to SEQ ID NO:79; and
iii) a biologically active fragment of i) or ii).

In another particular example, the polypeptide comprises an amino acid sequence selected from:
i) an amino acid sequence as provided in any one of SEQ ID NO:17 to SEQ ID NO:79; and
ii) an amino acid sequence which is at least 25% identical to any one or more of SEQ ID NO:17 to SEQ ID NO:79; and
iii) a biologically active fragment of i) or ii).

The % identity of a polypeptide is determined by GAP (Needleman and Wunsch, 1970) analysis (GCG program) with a gap creation penalty=5, and a gap extension penalty=0.3. The query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

With regard to a polypeptide, it will be appreciated that % identity figures higher than those provided herein will encompass preferred embodiments. Thus, where applicable, in light of the minimum % identity figures, it is preferred that the polypeptide or polynucleotide comprises an amino acid sequence which is at least 25%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides useful for the invention can be prepared by introducing appropriate nucleotide changes into a nucleic acid, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics.

Mutant (altered) polypeptides can be prepared using any technique known in the art. For example, a polynucleotide disclosed herein can be subjected to in vitro mutagenesis. Such in vitro mutagenesis techniques include sub-cloning the polynucleotide into a suitable vector, transforming the vector into a "mutator" strain such as the E. coli XL-1 red (Stratagene) and propagating the transformed bacteria for a suitable number of generations. In another example, the polynucleotides are subjected to DNA shuffling techniques as broadly described by Harayama (1998). These DNA shuffling techniques may include genes encoding polypeptides described herein and possibly also genes related to those described herein. Products derived from mutated/altered DNA can readily be screened using techniques described herein to determine if they can be used as silk proteins.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions may be any length but generally range from about 1 to 15 residues, preferably about 1 to 10 residues or about 1 to 7 residues and typically about 1 to 7 contiguous residues.

Substitution mutants have at least one amino acid residue in the polypeptide molecule removed and a different residue inserted in its place. The sites of greatest interest for substitutional mutagenesis include sites identified as important for function. Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

TABLE 1

Exemplary substitutions

| Original Residue | Exemplary Substitutions |
|---|---|
| Ala (A) | val; leu; ile; gly; cys; ser; thr |
| Arg (R) | lys |
| Asn (N) | gln; his |
| Asp (D) | glu |
| Cys (C) | ser; thr; ala; gly; val |
| Gln (Q) | asn; his |
| Glu (E) | asp |
| Gly (G) | pro; ala; ser; val; thr |
| His (H) | asn; gln |
| Ile (I) | leu; val; ala; met |
| Leu (L) | ile; val; met; ala; phe |
| Lys (K) | arg |
| Met (M) | leu; phe; ile |
| Phe (F) | leu; val; ala |
| Pro (P) | gly |
| Ser (S) | thr; ala; gly; val; gln; cys |
| Thr (T) | ser; gln; ala; cys |
| Trp (W) | tyr |
| Tyr (Y) | trp; phe |
| Val (V) | ile; leu; met; phe; ala; ser; thr; cys |
| A non-cordinating residue (for example Ala) | A cordinating residue (his, cys, met, tyr, lys, glu or trp) |
| A cordinating residue | A different cordinating residue (selected from his, cys, met, tyr, lys, glu or trp where relevant) |

As used herein, a "biologically active fragment" of a polypeptide may be capable of forming or may form a semi-crystalline material (that is, a material with regions of ordered molecular structure (crystallites) within an amorphous matrix). Alternatively or in addition, the biologically active fragment may be capable of forming or may form filamentous molecules. Thus, the biologically active fragment may be capable of being used to produce a silk fibre, silk film, silk powder, silk sponge, silk mat and the like. Biologically active fragments can be any size as long as they maintain the defined activity.

Furthermore, if desired, non-natural amino acids, unnatural amino acids or chemical amino acid analogues can be introduced as a substitution or addition into the polypeptides useful for the invention. Such amino acids include, but are not limited to, the D-isomers of the common amino acids, 2,4-diaminobutyric acid, a-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogues in general.

The polypeptides useful for the invention can also be differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide.

The polypeptides useful for the invention may or may not comprise a signal peptide. Thus, the polynucleotides encoding these polypeptides may or may not encode a signal peptide. Examples of polypeptides useful for the invention without signal sequences are provided as SEQ ID NO's 17 to 79. Many examples of particular signal peptides which direct the polypeptides to particular cellular locations during expression in a host cell (for example, which facilitate translocation of the polypeptides across a host cell membrane) are known in the art. Particular examples of signal peptides are provided in the specific sequences disclosed herein. The SignalP 4.1 Server (available at http://www.cbs.dtu.dk/services/SignalP/) (Petersen et al., 2011) may be used to predict the presence and location of signal peptide cleavage sites in a polypeptide. The polynucleotides and polypeptides may include these specific signal peptides or may not include these specific signal peptides. Thus, the polypeptides may comprise a sequence comprising any one or more of: SEQ ID NO:1 to SEQ ID NO:4 or SEQ ID NO:9 to SEQ ID NO:12; a polypeptide comprising a sequence which is at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 99.9% identical to any one of SEQ ID NO:1 to SEQ ID NO:4 or SEQ ID NO:9 to SEQ ID NO:12, and a polypeptide comprising a biologically active fragment thereof.

In one example, the polypeptides may comprise alternative signal peptides in place of the endogenous signal peptides.

The polypeptides useful for the invention can be produced in a variety of ways, including production and recovery of natural polypeptides, production and recovery of recombinant polypeptides, and chemical synthesis of the polypeptides. In one embodiment, an isolated polypeptide is produced by culturing a cell capable of expressing the polypeptide under conditions effective to produce the polypeptide, and recovering the polypeptide. A preferred cell to culture is a recombinant cell as disclosed herein. Effective culture conditions include, but are not limited to, effective media, bioreactor, temperature, pH and oxygen conditions that permit polypeptide production. An effective medium refers to any medium in which a cell is cultured to produce a polypeptide. Such medium typically comprises an aqueous medium having assimilable carbon, nitrogen and phosphate sources, and appropriate salts, minerals, metals and other nutrients, such as vitamins. Cells can be cultured in conventional fermentation bioreactors, shake flasks, test tubes, microliter dishes, and petri plates. Culturing can be carried out at a temperature, pH and oxygen content appropriate for a recombinant cell. Such culturing conditions are within the expertise of one of ordinary skill in the art.

The polypeptides of the present invention may be extracted and purified from recombinant cells, such as plant, bacteria or yeast cells, producing said polypeptide by methods known to the person skilled in the art. In one embodiment, the method involves removal of native cell proteins from homogenized cells/tissues/plants etc. by lowering pH and heating, followed by ammonium sulfate fractionation. Briefly, total soluble proteins are extracted by homogenizing cells/tissues/plants. Native proteins are removed by precipitation at pH 4.7 and then at 60° C. The resulting supernatant is then fractionated with ammonium sulfate at 40% saturation. The resulting protein will be of the order of, at least 50%, or at least 75%, or at least 90%, or at least 95%, pure. Additional purification may be achieved with conventional gel or affinity chromatography.

In another example, cell lysates are treated with high concentrations of acid e.g. HCl or propionic acid to reduce pH to ~1-2 for 1 hour or more which will solubilise the silk proteins but precipitate other proteins.

By nature of the inherent coiled coil super secondary or tertiary structure, the polypeptide will spontaneously form the coiled coil secondary structure upon dehydration. As described below, the strength of the coiled coil can be enhanced through enzymatic or chemical cross-linking of lysine residues in close proximity. For example, cross-linking may be promoted according to the method of disclosed in WO2013/120143.

Recombinant Vectors

A recombinant vector comprising a polynucleotide/nucleic acid encoding a polypeptide defined herein can be used in the production of, for example, a composition of the invention. The polynucleotide/nucleic acid can be inserted into any vector capable of delivering the polynucleotide molecule into a host cell. Such a vector contains heterologous polynucleotide sequences, that is polynucleotide sequences that are not naturally found adjacent to polynucleotide molecules of the present invention and that preferably are derived from a species other than the species from which the polynucleotide molecule(s) are derived. The vector can be either RNA or DNA, either prokaryotic or eukaryotic, and typically is a transposon (such as described in U.S. Pat. No. 5,792,294), a virus or a plasmid.

One type of recombinant vector comprises the polynucleotide molecule being operatively linked to an expression vector. The phrase operatively linked refers to insertion of a polynucleotide molecule into an expression vector in a manner such that the molecule is able to be expressed when transformed into a host cell. As used herein, an expression vector is a DNA or RNA vector that is capable of transforming a host cell and of effecting expression of a specified polynucleotide molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, animal, and plant cells. Particularly preferred expression vectors of the present invention can direct gene expression in bacterial or yeast cells. Vectors can also be used to produce the polypeptide in a cell-free expression system; such systems are well known in the art.

In particular, expression vectors of the present invention contain regulatory sequences such as transcription control sequences, translation control sequences, origins of replication, and other regulatory sequences that are compatible with the recombinant cell and that control the expression of the polynucleotide. In particular, recombinant molecules include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one recombinant cell such as a recombinant bacterial cell. A variety of such transcription control sequences are known to those skilled in the art. Preferred transcription control sequences include those which function in bacterial, yeast, arthropod, plant or mammalian cells, such as, but not limited to, tac, lac, trp, trc, oxy-pro, omp/lpp, rrnB, bacteriophage lambda, bacteriophage T7, T7l ac, bacteriophage T3, bacteriophage SP6, bacteriophage SPOT, metallothionein, alpha-mating factor, Pichia alcohol oxidase, alphavirus subgenomic promoters (such as Sindbis virus subgenomic promoters), antibiotic resistance gene, baculovirus, Heliothis zea insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells.

Recombinant molecules of the present invention may also (a) contain secretory signals (i.e., signal segment nucleic acid sequences) to enable an expressed polypeptide of the present invention to be secreted from the cell that produces the polypeptide and/or (b) contain fusion sequences which lead to the expression of nucleic acid molecules of the present invention as fusion proteins. Examples of suitable signal segments include any signal segment capable of directing the secretion of a polypeptide of the present invention. Preferred signal segments include, but are not limited to, tissue plasminogen activator (t-PA), interferon, interleukin, growth hormone, viral envelope glycoprotein signal segments, *Nicotiana* nectarin signal peptide (U.S. Pat. No. 5,939,288), tobacco extensin signal, the soy oleosin oil body binding protein signal, *Arabidopsis thaliana* vacuolar basic chitinase signal peptide, as well as native signal sequences of a polypeptide useful for the invention. In addition, the nucleic acid molecule can be joined to a fusion segment that directs the encoded polypeptide to the proteosome, such as an ubiquitin fusion segment. Recombinant molecules may also include intervening and/or untranslated sequences surrounding and/or within the nucleic acid sequences.

Host Cells

Another embodiment of the present invention includes the use of a recombinant cell comprising a host cell transformed with one or more recombinant molecules, or progeny cells thereof. Transformation of a polynucleotide molecule into a cell can be accomplished by any method by which a polynucleotide molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed polynucleotide molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide useful for the invention. Host cells useful for the invention either can be endogenously (i.e., naturally) capable of producing polypeptides defined herein or can be capable of producing such polypeptides after being transformed with at least one polynucleotide molecule encoding the polypeptide. Host cells can be any cell capable of producing at least one protein as defined herein, and include bacterial, fungal (including yeast), parasite, arthropod, animal and plant cells. Examples of host cells include *Salmonella, Escherichia, Bacillus, Listeria, Saccharomyces, Spodoptera, Mycobacteria, Trichoplusia,* BHK (baby hamster kidney) cells, MDCK cells, CRPK cells, CV-I cells, COS (e.g., COS-7) cells, and Vero cells. Further examples of host cells are *E. coli*, including *E. coli* K-12 derivatives; *Salmonella typhi; Salmonella typhimurium*, including attenuated strains; *Spodoptera frugiperda; Trichoplusia ni* and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK cells and/or HeLa cells. Other host cells are plant cells such as those available from Deutsche Sammlung von Mikroorganismen and Zellkulturen GmbH (German Collection of Microorganisms and Cell Cultures).

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules of the present invention include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules of the present invention to correspond to the codon usage of the host cell, and the deletion of sequences that destabilize transcripts.

The host cell may be present in a transgenic animal or transgenic plant as described in, for example, WO 2007/038837 and WO 2013/142901.

Chelates

In one aspect, the polypeptide useful for the invention forms a complex with a chelate comprising a chelating agent and a metal ion.

As used herein to refer to the association between the chelate and the polypeptide, the term "bound" indicates that the chelating agent forms covalent and/or non-covalent bonds with residues of the polypeptide, forming a complex. As used herein, "bound", "bind" and the like is understood to encompass covalent and/or noncovalent interactions. For example, the chelating agent may be bound to at least one amino acid of the polypeptide either covalently or non-covalently. The interactions should be specific, that is the polypeptide should bind the chelate through specific means.

In an embodiment, the chelating agent is not a polypeptide. In a preferred embodiment, the polypeptide and the chelating agent do not form a single polypeptide chain, such as expressed from a single open reading frame.

The complex may be more or less labile, depending on the specific nature of the chelating agent and the polypeptide in use. In one embodiment, the complex between the chelating agent and the polypeptide is stable enough for the complex to be useful within the needs of the invention.

As used herein, the term "coordinates" indicates that the metal ion forms a coordinate bond with one or more residues of the polypeptide.

The term "chelation" refers to the formation of two or more separate coordinate bonds between a polydentate (multiple bonded) ligand and a single central atom, typically a metal ion. The ligands are typically organic compounds, often in anionic form, and can be referred to as chelants, chelators chelating agents, or sequestering agents. Accordingly, the term "chelating agent" as used herein refers to a compound that can form a complex with a metal ion. As used herein, a ligand forming a chelate complex is also referred to as a chelator.

While chelate complexes typically form from polydentate ligands, as used herein the term chelate also refers to coordination complexes formed from monodentate ligands and a central atom.

As used herein, the term "chelate" includes a complex of a chelating agent with a mono-, di-, tri-, tetra-, penta-, or hexa-valent cation. The cation may be a metal, for example, but not limited to, a lanthanide or transition metal cation, alkali earth metal or p-block metal. The chelate may be a simple complex with the cation, involving only non-ionic-bond, non-covalent attractions, or it may be a complex involving ionic bonds and/or other non-covalent attractions. In the latter case, the chelating agent may become ionized by reaction with the cation and/or with a solvent, e.g., water. For example, an oxo-acid-type group of the (neutral) chelating agent, e.g., a phosphonate group or phosphonate ester group, may lose a hydrogen from a hydroxyl thereof, and the resulting oxide moiety might then participate in ionic bonding with the metal ion.

Many different metal ions are suitable for use as a metal ion in this invention. Preferably, the metal ion is polyvalent and has between 2 to 8 coordination sites, for example, 2, 3, 4, 5, 6, 7 or 8 coordination sites.

Importantly, the metal ion is selected to allow the compositions described herein to bind a desired target molecule. For example, the metal ion can be any ion that is capable of chelating with heteroatoms such as C, P, N, S, O and the like.

In some embodiments, the chelated metal ion is an ion of a transition metal.

In some embodiments, the chelated metal ion is an ion of a p-block metal.

In some embodiments, the chelated metal ion is selected from the group consisting of an ion of Fe, Sn, Cd, Cr, Mn, Co, Cu, Ru, Zn, Mg, Sc, Rh, Os, Ag, Pd, Zn, Re, Pt, Ti, V, Ni, Mo, Tc, W, and Ir.

In some embodiments, the metal ion is an alkali earth metal ion. In some embodiments, the alkali earth metal ion is selected from the group consisting of Mg, Be, Ca, Sr, Ba and Ra.

Exemplary metal ions that can be used in the present invention include zinc (Zn), cadmium (Cd), copper (Cu), nickel (Ni), ruthenium (Ru), platinum (Pt), palladium (Pd), cobalt (Co), magnesium (Mg), barium (Ba), strontium (Sr), iron (Fe), vanadium (V), chromium (Cr), manganese (Mn), rhodium (Rh), silver (Ag), mercury (Hg), molybdenum (Mo) tungsten (W), calcium (Ca), lead (Pb), cerium (Ce), aluminum (Al) and thorium (Th), Tin (Sn), Ruthenium (Ru), Scandium (Sc), Rhodium (Rh), Osmium (Os), Zinc (Zn), Rhenium (Re), Thallum (Ti), Vanadium (V), Technetium (Tc), and Iridium (Ir).

The ionic state of the polyvalent metal ions can vary, as is well known. A preferred oxidation or ionic state of a polyvalent metal ion is preferably Zn(II), Cd(II), Cu(I), Cu(II), Ni(II), Ru(II), Ru(III), Pt(II), Pd(II), Co(II), Co(III), Mg(II), Ba(II), Sr(II), Fe(II), Fe(III), Fe(IV), V(III), Cr(II), Cr(III), Mn(II), Rh(III), Ag(I), Hg(II), (Mo(III), Mo(IV), Mo(V), Mo(VI), W(III), W(IV), W(V), W(VI), Ca(II), Pb(II), Ce(III), Al(III), or Th(IV), where the oxidation state is indicated in parenthesis.

As described above, a chelating agent is a ligand which is capable of forming two or more separate coordinate bonds with a single central atom. The chelating agent is selected to allow the compositions described herein to bind a desired target molecule. For example, the chelating agent may be any chelating agent that is capable of chelating with the desired metal ion and is capable of binding the polypeptide.

Importantly, the chelating agent is selected to bind a desired metal ion to allow the compositions described herein to bind a desired target molecule.

In one embodiment the chelating agent comprises a ring of atoms. Preferably, the chelating agent is a macrocycle. The phrases "macrocycles," "macrocyclic compounds," and "cyclic compounds" are used interchangeably herein to refer to both single cyclic and multi-cyclic compounds having one or more ring structures. The total number of atoms on each of such ring structures may be widely varied, e.g., in a range of from 3 to about 100 or more. Such single cyclic or multi-cyclic compound may further contain one or more linear functional groups, branched functional groups, and/or arched functional groups that bridge across a plane defined by a ring structure. In the case of multi-cyclic compounds having two or more ring structures, any pair of such ring structures may be separated from each another by a non-cyclic spacing structure, or the rings can be in side-by-side relationship to each another, sharing one chemical bond or one atom, or alternatively, the rings may partially overlap with each other, or one ring structure can be enclosed by or intertwined with the other ring. The three-dimensional structures of such compounds can be characterized by any geometric shape, either regular or irregular, including, but not limited to, planar, cylindrical, semispherical, spherical, ovoidal, helical, pyrimidyl, etc.

In some embodiments, the chelating agent comprises a negatively charged group. In some embodiments, the chelating agent comprises at least one carboxylate group. Without wishing to be bound by theory, it is thought that the carboxylate groups assist binding of the chelating agent to the polypeptide through the formation of non-covalent interactions, for example via electrostatic interactions.

In some embodiments, the macrocycle comprises at least one pendant group. In some embodiments, the at least one pendant group has a negative charge. In some embodiments, the macrocycle comprises at least one pendant group which is a carboxylate group. Without wishing to be bound by theory, it is thought that the negatively charged pendant group binds to positively charged groups in the polypeptide to assist binding of the chelate (and chelating agent) to the polypeptide.

Such macrocyclic compounds may include naturally occurring macrocycles and artificial macrocycles. Naturally occurring macrocycles include, but are not limited to, porphryins, including protoporphyrins (e.g. haem b), phytoporphryins (e.g. chlorophyll c) and porphyrinogens (e.g. uroporphryinogen, a biosynthetic precursor), corrins, chlorins, and corphins. Artificial macrocycles include but are not limited to, porphine and phthalocyanines.

Porphyrins are a group of compounds found in all living matter and contain a tetrapyrrolic macrocycle capable of binding to metals. Haem, chlorophyll and corrins are examples of this class of compounds containing iron, magnesium and cobalt, respectively.

Suitable metalloporphyrins for use in the present invention that are commercially available through Frontier Scientific, Inc.

The macrocycles of the present invention include, but are not limited to, porphyrinogens, porphyrins, saphyrins, texaphyrins, bacteriochlorins, chlorins, coproporphyrin I, corrins, corroles, cytoporphyrins, deuteroporphyrins, etioporphyrin I, etioporphyrin III, hematoporphyrins, pheophorbide a, pheophorbide b, phorbines, phthalocyanines, phyllochlorins, phylloporphyrins, phytochlorins, phytoporphyrins, protoporphyrins, pyrrochlorins, pyrroporphyrins, rhodochlorins, rhodoporphyrins, uroporphyrin I, calix[n]pyrroles, calix[n]erines, cycloalkanes, cycloalkenes, cycloalkynes, piperidines, morpholines, pyrrolidines, aziridines, anilines, thiophenes, quinolines, isoquinolines, naphthalenes, pyrimidines, purines, benzofurans, oxiranes, pyrroles, thiazides, ozazoles, imidazoles, indoles, furans, benzothiophenes, polyazamacrocycles, carbohydrates, acetals, crown ethers, cyclic anhydrides, lactams, lactones, cyclic peptides, phenylthiohydantoins, thiazolinones, succinimides, coronenes, macrolides, carbocyclics, cyclodextrins, squalene oxides, ionophore antibiotics, cyclic bis-N,O-acetals, cyclic disulfides, terpenoids, spirocycles, resorcinarene macrocycles, cyclic oligo(siloxane)s, stannylated cyclic oligo(ethyleneoxide)s, cyclic poly(dibutyltindicarboxylate)s, cyclic poly(pyrrole), cyclic poly(thiophene)s, cyclic poly(amide)s, cyclic poly(ether)s, cyclic poly(carbonate)s, cyclic poly(ethersulfone)s, cyclic poly(etherketone)s, cyclic poly(urethane)s, cyclic poly(imide)s, cyclic poly(decamethylene fumarate)s, cyclic poly(decamethylethylene maleate)s, etc.

In one embodiment, the chelating agent is selected from the group consisting of porphryins, corrins, chlorins, corphins, porphines and phthalocyanines. In another embodiment the chelating agent is a porphyrin selected from the group consisting of protoporphyrins, phytoporphryins, and porphyrinogens. In another embodiment, the chelating agent is a porphyrin selected from the group consisting of haem b, chlorophyll c or uroporphryinogen. In another embodiment the chelating agent is corrin, Chlorophyll a, or cofactor F430.

In one embodiment, the chelating agent is haem. As used herein, the term "haem" refers to a chelate or prosthetic group formed of an iron atom contained in the center of a large heterocyclic organic ring called a porphyrin. Not all porphyrins contain iron, but a substantial fraction of porphyrin-containing metalloproteins have haem as their prosthetic subunit; these are known as hemoproteins or haem proteins. Non-limiting examples of haems are haem A, haem B, haem C, haem O, mesohaems, deuterohaems, synthetic dicyano porphyrins and symmetrical porphyrins (such as, but not limited to, protoporphyrin III).

Haem proteins are ubiquitous in biological systems carrying out a range of functions such as electron transfer, small molecule transport, catalysis and sensing. Included within the haem protein family are the versatile cytochromes P450, of interest to the pharmaceutical and agrochemical industry and the nitric oxide sensor protein, soluble guanylate cyclase, which selectively binds nitric oxide over other gases such as oxygen and has been investigated for use in nitric oxide biosensors.

Haem proteins contain a haem cofactor consisting of a porphyrin ring with an iron coordinated to four nitrogen atoms. The haem cofactor is highly reactive to a wide range of diatomic gases, anions and bases. In biological systems, this reactivity is controlled by the protein environment surrounding the haem cofactor. In most haem proteins, the haem group is held within the protein matrix through hydrogen bonding between the porphyrin ring and amino acid residues such as arginine, tyrosine and serine. In addition, amino acid residues coordinate (forms a chemical bond) with the iron centre. Varying the coordinating ligand is one of the principle ways in which haem proteins regulate the function of the haem cofactor. For example, oxygen transport proteins such as haemoglobin coordinate their metal cofactor using a conserved histidine, the catalytic cytochromes P450 use a conserved cysteine, while electron transport proteins such as cytochrome c typically have a bis coordinated iron centre with a histidine and methionine residue.

Generally, the identification of a preferred chelating agent for linking to a metal ion can be made by either first determining the desired chelator to be bonded to the polypeptide backbone, then identifying metal ions that link strongly to that chelator, or the desired metal ion can be first identified with preferred chelator identified subsequently. Thus, preferred chelator are identified and then metal ion candidates are screened for their effectiveness in linking to that chelator. Alternatively, chelators can be screened following identification of a preferred metal ion. Such methods of screening are well known to those skilled in the art.

In yet a further aspect, the present invention provides a method of producing a composition of the invention, the method comprising (a) combining a candidate polypeptide wherein at least a portion of the polypeptide has a coiled coil structure; a candidate chelating agent and a candidate metal ion (b) determining if the polypeptide, chelating agent and metal ion associate and the chelate is bound to at least one amino acid of the polypeptide. In an embodiment, the method comprises modifying a candidate to polypeptide, such as a silk polypeptide, to introduce at least one, possibly additional, coordinating amino acid. In an embodiment, the method further comprises testing the ability of the composition to bind and/or modify a target compound.

The cation, e.g. metal or radionuclide, chosen will depend upon the most appropriate cation, metal ion or isotope for sensing, therapeutic or diagnostic purposes. For example, the introduction of metallo-porphyrins into a polypeptide as described herein. Haem-proteins are capable of performing a large range of functions including oxygen transport, electron transfer/transport and catalysis. Accordingly, metalloporphyrins can be used for this large range of functions as part of a biosensor according to the present invention. For example, polypeptides comprising iron-porphyrins can be used to bind dioxygen. In one embodiment the metal ion and/or chelator are chosen for their capability of binding a target compound.

Compositions

In one aspect, the compositions of the present invention comprise a polypeptide wherein at least a portion of the polypeptide has a coiled coil structure; and a chelate comprising a chelating agent and a metal ion; and wherein the chelate is bound to at least one amino acid of the polypeptide.

In one embodiment, a composition described herein includes more than one polypeptide as described herein. For example, a composition can include two different polypeptides as described herein. In other embodiments, a composition can include a polypeptide as described herein, and a further polypeptide that functions to increase the stability and/or bioactivity of the composition.

Compositions of the present invention may include an "acceptable carrier".

Examples of such acceptable carriers include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used.

The compositions of the present invention may be formed in solution (for instance AmelF3 with a His substitution) or in material form. In an embodiment, the composition is formed in material form.

As described herein, the silk polypeptides can be fabricated into a range of extremely stable, load bearing materials such as fibres, sponges or films. Accordingly, in some embodiment the polypeptides described herein are provided in a solid material form, and the compositions of the present invention are provided in a solid material form.

In one embodiment, the polypeptide is formed into a material described herein, and a composition of the invention formed by contacting the material with a chelate. For example, after a polypeptide of the present invention is formed into a material such as a fibre, film, powder, sponge and the like, the material is contacted with a solution containing a chelate under conditions and for a time period sufficient for the chelate to bind to the polypeptide such that the material comprises the composition of the present invention.

In one embodiment, the polypeptide is formed into a material described herein, and the material is contacted with a chelating agent in the absence of a metal ion under conditions and for a time period sufficient for the chelating agent to bind to the polypeptide and thus form a material comprising a polypeptide-chelating agent complex. The composition of the invention may then be formed by contacting the material comprising polypeptide-chelating agent complex with a metal ion.

In one embodiment, a composition as described herein is formed into a material such as those described herein. In another embodiment, the composition of the present invention formed by contacting the polypeptide with a chelate under conditions which promote binding of the chelate to the polypeptide. For example, the polypeptide of the present invention is contacted with a solution containing a chelate as disclosed above. The solution contains the chelate at concentrations that favor complex formation, and the polypeptide and chelate are contacted under conditions for a time period sufficient for the chelate to bind to the polypeptide and form a composition of the present invention.

In another embodiment, the composition of the present invention is formed by contacting the polypeptide with a chelating agent under conditions which promote binding of the chelating agent to the polypeptide such that a polypeptide-chelating agent complex forms. The chelating agent is at concentrations that favor complex formation, and the polypeptide and chelating agent are contacted under conditions and for a time period sufficient for the chelating agent to bind to the polypeptide and form a polypeptide-chelating agent complex. The composition of the invention may then be formed by contacting the polypeptide-chelating agent complex with a metal ion. The metal ion is at concentrations that favor formation of the composition of the present invention, and the polypeptide-chelating agent complex and metal ion are contacted under conditions and for a time period sufficient to form the composition of the present invention. Optionally, the composition of the present invention may be formed into a material described herein.

For example, as illustrated in Example 3, a composition of the present invention was formed by combining AmelF3 silk protein and haem b in hexafluoroisopranol. The composition was then air dried at room temperature to form a film. The dried film was soaked overnight in 70% methanol for a period sufficient to render the material water insoluble. Without wishing to be bound by theory it is thought that soaking in 70% methanol induces formation of β-sheet structure and helps make the film insoluble in water. Other organic solvents such as ethanol, ethyl acetate and the like can be used to introduce the chelate.

In some embodiments, the material and/or polypeptide of the present invention is contacted with a solution comprising chelate and a solvent. The amount of chelate can be in excess compared to the amount of polypeptide. In some embodiments, the concentration of the chelate is between about 0.001 to 50 mg/mL. In some embodiments, the concentration of the chelate is between about 0.01 to 10 mg/mL. In some embodiments, the concentration of the chelate is between about 0.1 mg/ml to 5 mg/ml, for example 0.1 mg/ml, 0.2 mg/mi, 0.3 mg/ml, 0.4 mg/ml. 0.5 mg/ml, 0.6 mg/ml, 0.7 mg/ml, 0.8 mg/ml, 0.9 mg/ml, 1.0 mg/ml, 1.5 mg/ml, 2.0 mg/ml, 2.5 mg/ml, 3.0 mg/ml, 3.5 mg/ml, 4.0 mg/ml, 4.5 mg/ml or 5.0 mg/ml.

In some embodiments, the material and/or polypeptide of the present invention is contacted with a solution comprising chelating agent and a solvent. The amount of chelating agent can be in excess compared to the amount of polypeptide. In some embodiments, the concentration of the chelating agent is between about 0.001 to 50 mg/mL. In some embodiments, the concentration of the chelating agent is between about 0.01 to 10 mg/mL. In some embodiments, the concentration of the chelating agent is between about 0.1 mg/ml to 5 mg/ml, for example 0.1 mg/ml, 0.2 mg/ml, 0.3 mg/ml, 0.4 mg/ml. 0.5 mg/ml, 0.6 mg/ml, 0.7 mg/ml, 0.8 mg/ml, 0.9 mg/ml, 1.0 mg/ml, 1.5 mg/ml, 2.0 mg/ml, 2.5 mg/ml, 3.0 mg/ml, 3.5 mg/ml, 4.0 mg/ml, 4.5 mg/ml or 5.0 mg/ml.

The solvent is one in which the chelate and/or chelating agent is soluble at the desired concentration and which does not adversely affect the material and/or polypeptide. In some embodiments, the solvent may be a polar or non-polar solvent. For example, the solvent may selected from the group consisting of water, alcohol, halogenated alcohols, hydrocarbon, halogenated hydrocarbon, sulfoxide, nitrile, ether, ester, carboxylic acid, ketone and aldehyde. In some embodiments, the solvent is selected from the group consisting of water, pentane, cyclopentane, hexane, cyclohexane, benzene, toluene, diethyl ether, dichloromethane, tetrahydrofuran, ethyl acetate, acetone, dimethylformamide, acetonitrile, dimethylsulfoxide, propylene carbonate, formic acid, n-butanol, isopropanol, n-propanol, ethanol, methanol, acetic acid, chloroform, 2-butanone, hexafluoroisopropanol and mixtures thereof. In some preferred embodiments, the solvent is selected from the group consisting of water, methanol, chloroform, 2-butanone, hexafluoroisopropanol and mixtures thereof. In some [more preferred] embodiments, the solvent is selected from the group consisting of water, methanol, hexafluoroisopropanol and mixtures thereof. For example, the solvent may comprise between 10-100% (v/v) methanol in water, such as 10%, 15%, 20%, 25%, 30%, 35%, 40%, 45%, 50%, 55%, 60%, 65%, 70%, 75%, 80%, 85%, 90%, 95% or 100% (v/v). Preferably, the solvent comprises greater than 50% and less than 100% methanol in water (v/v).

As described above, the polypeptide and chelate are contacted under conditions for a time period sufficient for the chelate to bind to the polypeptide and form a composition of the present invention. The person skilled in the art would understand that the conditions and the time period will vary depending on the concentration of the chelate, the solvent, the desired effect and the like. In some embodiments, the chelate and the polypeptide are contacted for a period of time varying between about 1 second and 7 days. In some embodiments, the chelate and the polypeptide are contacted for a period of time of least 3 seconds, such as but not limited to, 3, 6, 9, 12, 18, 24, 30, 36, 42, 28, 54, 60, 66, or 72 seconds. In some embodiments, the chelate and the polypeptide are contacted for a period of time of least 3 minutes, such as but not limited to, 3, 6, 9, 12, 18, 24, 30, 36, 42, 28, 54, 60, 66, or 72 minutes. In some embodiments, the chelate and the polypeptide are contacted for a period of time of least 3 hours, such as but not limited to, 3, 6, 9, 12, 18, 24, 30, 36, 42, 28, 54, 60, 66, or 72 hours. In some embodiments, the polypeptide and chelate are contacted at a temperature between about 10° C. and 30° C. or between about 18° C. and 24° C.

As described above, the polypeptide and chelating agent are contacted under conditions for a time period sufficient for the chelating agent to bind to the polypeptide and form a polypeptide-chelating agent complex. The person skilled in the art would understand that the conditions and the time period will vary depending on the concentration of the chelating agent, the solvent used, the desired effect and the like. In some embodiments, the chelating agent and the polypeptide are contacted for a period of time of least 3 seconds, such as but not limited to, 3, 6, 9, 12, 18, 24, 30, 36, 42, 28, 54, 60, 66, or 72 seconds. In some embodiments, the chelating agent and the polypeptide are contacted for a period of time of least 3 minutes, such as but not limited to, 3, 6, 9, 12, 18, 24, 30, 36, 42, 28, 54, 60, 66, or 72 minutes. In some embodiments, the chelating agent and the polypeptide are contacted for a period of time of least 3 hours, such as but not limited to, 3, 6, 9, 12, 18, 24, 30, 36, 42, 28, 54, 60, 66, or 72 hours. In some embodiments, the polypeptide and chelating agent are contacted at a temperature between about 10° C. and 30° C. or between about 18° C. and 24° C.

In some embodiments, the composition of the invention may be formed by contacting a polypeptide-chelating agent complex or a material comprising a polypeptide-chelating agent complex with a solution comprising a metal ion and a solvent. In some embodiments, the concentration of the metal ion is between about 0.001 to 50 mg/mL. In some embodiments, the concentration of the metal ion is between about 0.01 to 10 mg/mL. In some embodiments, the concentration of the metal ion is between about 0.1 mg/ml to 5 mg/ml, for example 0.1 mg/ml, 0.2 mg/ml, 0.3 mg/ml, 0.4 mg/ml. 0.5 mg/ml, 0.6 mg/ml, 0.7 mg/ml, 0.8 mg/ml, 0.9 mg/ml, 1.0 mg/ml, 1.5 mg/ml, 2.0 mg/ml, 2.5 mg/ml, 3.0 mg/ml, 3.5 mg/ml, 4.0 mg/ml, 4.5 mg/ml or 5.0 mg/ml. The solvent is one in which the metal ion is soluble at the desired concentration and which does not adversely affect the material and/or polypeptide. For example, the solvent may be a polar solvent or a mixture of polar solvents such as water, alcohols, ammonia and the like.

As described above, the polypeptide-chelating agent complex and metal ion or a material comprising a polypeptide-chelating agent complex and metal ion are contacted under conditions for a time period sufficient for a composition of the present invention or a material comprising the composition of the present invention to form. The person skilled in the art would understand that the conditions and the time period will vary depending on the surface to volume ratio of the material, the concentration of the metal ion, the solvent used, the desired effect and the like. In some embodiments, the time period varies between about 2 seconds and 7 days. In some embodiments, the time period is at least 1 minute, such as but not limited to, 1, 2, 4, 6, 12, 18, 24, 30, 36, 42, 28, 54, 60, 66, or 72 minutes. In some embodiments, the time period is at least 1 hour, such as but not limited to, 1, 2, 4, 6, 12, 18, 24, 30, 36, 42, 28, 54, 60, 66, or 72 hours. In some embodiments, the temperature is between about 10° C. and 30° C. or between about 18° C. and 24° C.

In one embodiment, composition comprises haem b and AmelF3 (SEQ ID NO: 3) without the signal sequence (SEQ ID NO:39). In this embodiment, the chelate is haem b, the chelating agent is protoporphyrin IX, the metal ion is iron, and the at least one polypeptide is an AmelF3. The present inventors have demonstrated that when chelator is haem b, the metal ion is iron and the at least one polypeptide is an AmelF3, the tyrosine at position 76 of AmelF3 (SEQ ID NO:

39) forms a co-ordinate bond with iron and haem b is bound to at least one positively charged residue of the polypeptide.

In one embodiment, the composition comprises GA1 and haem b. In one embodiment, the composition comprises GA3 and haem b.

In other embodiments, the composition comprises a metal protoporphyrin IX, wherein the metal ion is selected from Fe, Co and Cu, and AmelF3.

In one embodiment, the composition comprises phthalocyanine tetrasulfonic acid, and AmelF3.

In other embodiments, the composition comprises a chelate selected from dicyanocobyrinic acid heptamethyl ester or dicyanocobyrinic acid heptamethyl ester, and AmelF3.

Compositions of the present invention such as those using iron-porphyrin bound to a polypeptide can be used for example, for detecting a target compound, quantifying a target compound, catalysis, electron transfer applications and as antimicrobials.

The metal or cation and chelator may be combined under any conditions which allow the two to form a complex.

Materials

In contrast to much work on de novo synthesis, the present invention provides protein scaffolds with high stability and which can be easily formed into materials such as fibres, gels, sheets, films, mats, sponges and the like. The present inventors have demonstrated a polypeptide wherein at least a portion of the polypeptide forms a coiled coil structure; and a chelate comprising a chelating agent and a metal ion; and wherein the chelate is bonded to at least one amino acid of the polypeptide is highly stable and able to be formed into materials. Accordingly, the present invention relates to materials comprising compositions of the present invention and methods of producing the materials. Alternatively, the composition of the present invention may be in the form of a material.

As used herein, the term "stable" refers to the ability of the composition and/or material of the present invention to retain its functional characteristics over time or in different conditions. For example, to retain the ability to bind a detectable compound over a period of time, for example 10 months, 11 months or more.

As described herein, the compositions of the present invention can be formed as materials that are stable in water. In a preferred embodiment, the materials retain the ability to bind a molecule of interest after a period of time, for example, a week, a month, a year or more. Materials include, but are not limited to, fibres, gels, sheets, films, mats, sponges, powders and the like.

As used herein, the term "solvent stability" refers the ability of the material to stay insoluble in solvents such as water, SDS (for example 2% SDS), guanadium (for example 8M guanadium) or urea (for example 8M urea). As used herein, "stay insoluble in solvent" means that the material losses than less than 10% of its protein mass after 24 hours at room temperature in the solvent.

As mentioned herein, in some embodiments of the present invention the polypeptide may be a silk polypeptide. Silk polypeptides are particularly useful for the creation of new materials because of their toughness and strength.

When the polypeptide is a silk polypeptide, the silk material may be formed from a silk dope. As used herein, the term "silk dope" refers to an aqueous solution comprising silk proteins. Preferably, the silk dope comprises at least 0.05% w/v, more preferably at least 0.1% w/v, and even more preferably at least 0.5% w/v of a silk protein as defined herein. In an embodiment, silk dope is produced by a method which comprises about 0.5% to about 15% (wt %) silk protein. However, if the further step of increasing the concentration of silk proteins in the silk dope is not performed the more typical yield is about 0.5% to about 4% (wt %) silk protein. Silk dope is amenable to extrusion for the formation of a fibre and/or film casting.

Methods of making silk dope and materials drawn or extruded from silk dope etc. are disclosed in WO 2011/022771 and WO 2013/120143.

For example, in one embodiment, the silk dope is produced by a method comprising: i) lysing cells producing one or more silk proteins, ii) solubilising the silk proteins by contacting them with a surfactant or an ionic liquid, and iii) concentrating the silk proteins to produce silk dope, wherein the one or more silk proteins are capable of forming a tertiary structure which comprises a coiled-coil structure. In an embodiment, the surfactant is SDS.

In one embodiment, a silk dope is provided from which silk materials such as silk fibres, nanofibres, gels, sheets, films, mats, sponges and the like may be produced.

As used herein, a "silk fibre" refers to filaments comprising silk proteins which can be woven into various items such as textiles. Silk fibres may be formed by techniques known to the person skilled in the art. Silk fibres useful for the invention have a low processing requirement. The silk proteins useful for the invention require minimal processing e.g. spinning to form a strong fibre as they spontaneously form strong coiled coils which can be reinforced with crosslinks such as lysine crosslinks.

In some embodiments, silk fibers may spun from solution. Fibrillar aggregates will form from solutions by spontaneous self-assembly of silk proteins useful for the invention when the protein concentration exceeds a critical value. The aggregates may be gathered and mechanically spun into macroscopic fibers according to the method of O'Brien et al. ("Design, Synthesis and Fabrication of Novel Self-Assembling Fibrillar Proteins", in Silk Polymers: Materials Science and Biotechnology, pp. 104-117, Kaplan, Adams, Farmer and Viney, eds., c. 1994 by American Chemical Society, Washington, D.C.).

In some embodiments, fibers may be spun from solutions having properties characteristic of a liquid crystal phase. The fiber concentration at which phase transition can occur is dependent on the composition of a protein or combination of proteins present in the solution. Phase transition, however, can be detected by monitoring the clarity and birefringence of the solution. Onset of a liquid crystal phase can be detected when the solution acquires a translucent appearance and registers birefringence when viewed through crossed polarizing filters.

In one fiber-forming technique, fibers can first be extruded from the protein solution through an orifice into methanol, until a length sufficient to be picked up by a mechanical means is produced. Then a fiber can be pulled by such mechanical means through a methanol solution, collected, and dried. Methods for drawing fibers are considered well-known in the art.

Further examples of methods which may be used for producing silk fibres and/or copolymers are described in US 2004/0170827 and US 2005/0054830.

Silk fibres may be used in the manufacture of medical devices such as sutures, skin grafts, cellular growth matrices, replacement ligaments, and surgical mesh, and in a wide range of industrial and commercial products, such as, for example, cable, rope, netting, fishing line, clothing fabric, bullet-proof vest lining, container fabric, backpacks, knapsacks, bag or purse straps, adhesive binding material, non-adhesive binding material, strapping material, tent fabric, tarpaulins, pool covers, vehicle covers, fencing material, sealant, construction material, weatherproofing material, flexible partition material, sports equipment, and, in fact, in nearly any use of fibre or fabric for which high tensile strength and elasticity are desired characteristics.

As used herein, a "nanofibre" refers to a fibre with a diameter of less than 1000 nm. Nanofibres may be manufactured by techniques known to the person skilled in the art, for example electrospinning (for example, see Wittmer et. al., 2011). In some embodiments, nanofibres cannot be woven into items. Nanofibres may be used in the manufacture of biomaterials that may be used for wound dressings, cell culture and the like.

As used herein, a "silk film" refers to a film comprising silk proteins. Silk film may be formed by techniques known to the person skilled in the art.

Silk films may be used in the manufacture of medical devices such as wound dressings, films for biosensor applications such as nitric oxide sensors and in fact, in nearly any use of film for which stability is a desired characteristic.

As used herein, a "silk sponge" refers to a sponge comprising silk proteins. Silk sponges may be formed by techniques known to the person skilled in the art. Silk sponges may be used for a variety of uses, such as tissue/cell culture scaffolds; catalysis; wound dressings; sensor applications and in fact, in nearly any use of sponge for which stability is a desired characteristic.

As used herein, a "silk mat" refers to a mat comprising silk proteins. Silk mats may be formed by techniques known to the person skilled in the art. The mat may be an electrospun mat. Silk sponges may be used in a variety of uses, such as tissue/cell culture scaffolds; wound dressings; sensor applications and in fact, in nearly any use of mat for which stability is a desired characteristic.

In one embodiment, the composition is in the form of a powder.

In some embodiments, the polypeptide is a recombinant silk protein from aculeate Hymenoptera. Preferably, the recombinant silk protein from aculeate Hymenoptera is a recombinant honeybee silk such as, but not limited to AmelF3. Recombinant honeybee silk can be manufactured into multiple material forms including fibres and films (Weisman et al., 2010; Sutherland et al., 2011), electrospun mats (Wittmer et al., 2011) and sponges (WO 2011/022771 and WO 2013/120143).

Preferably, the materials are subject to post-manufacture treatment of some description to render them water insensitive. Examples of post-manufacture treatment include but are not limited to cross-linking, heat treatment or chemical treatment.

As used herein, a "copolymer" is composition comprising two or more different polypeptides useful for the invention. For example, two or more different silk polypeptides useful for the invention, or two or more silk polypeptides described in WO 2007/038837. As an example, the copolymer (and hence composition) of the invention may comprise AmelF3 and AmelF1, or AmelF3, AmelF1 and AmelF2, or AmelF2, AmelF1 and AmelF4, or GAF3 and AmelF3 etc. Accordingly, the present invention provides a composition comprising a copolymer comprising at least two polypeptides useful for the invention.

As used herein, "cross-link" is used to refer to both covalent and non-covalent bonds bridging one polymer (such as a polypeptide) chain to another. The person skilled in the art will appreciate that a polymer may fold back on itself and therefore cross-link to itself. Non-covalent cross-links may include ionic bonds and hydrogen bonds. In polypeptides, cross-links may form between backbone atoms, side chain atoms or both.

As used herein, "cross-linking" is used to refer to the process of joining one polymer to another or one part of a polymer to another by cross-links.

In some embodiments, polypeptides, silk fibres, silk films, silk powder, silk sponges and/or copolymers etc of the invention are crosslinked. In one embodiment, the polypeptides, silk fibres, silk films, silk powder, silk sponges and/or copolymers etc are crosslinked to a surface/article/product etc of interest using techniques known in the art. In another embodiment (or in combination with the previous embodiment), at least some silk proteins in the silk fibres, silk films, silk powder, silk sponges and/or copolymers etc are cross-linked to each other. In some embodiments, the silk proteins are crosslinked via lysine residues in the proteins. Such crosslinking can be performed using chemical and/or enzymatic techniques known in the art. For example, enzymatic cross links can be catalysed by lysyl oxidase, whereas nonenzymatic cross links can be generated from glycated lysine residues (Reiser et al., 1992). In some embodiments, the silk proteins comprise a beta sheet structure in which beta stands are cross-linked to other beta strands in the same or different polypeptide. In these embodiments, the cross-links are non-covalent bonds, preferably hydrogen bonds.

In some embodiments, the materials are subject to heat-treatment. Heat treatment may comprise heating the material to temperatures that induce formation of lysinoalanine and/or methyllysinoalanine, isopeptide and/or ester cross-links through lysine, serine, threonine asparagine, aspartic acid and/or glutamic acid, residues. Treatment may include heating to around or above 180° C., or heating to lower temperatures (i.e. 120° C.) in the presence of a vacuum.

In one embodiment, the present invention comprises a material formed by a process for heat-treatment of a material comprising the composition of the present invention, the process comprising i) obtaining the material in a solid state, and ii) dry heating the material to a temperature for a sufficient time for the cross-links to form. Preferably, the temperature is at least about 120° C., at least about 120° C. or at least about 180° C. In another embodiment, the present invention comprises a material formed by a process for heat-treatment of a material comprising the polypeptide of the present invention, the process comprising i) obtaining the material in a solid state, ii) dry heating the material to a temperature for a sufficient time for the cross-links to form, and iii) contacting the dry heated material with a solution containing a chelate under conditions and for a time period sufficient for the chelate to bind to the polypeptide such that the material comprises the composition of the present invention. Preferably, the temperature is at least about 120° C., at least about 120° C. or at least about 180° C. The solution contains the chelate at concentrations that favor complex formation.

Dry heat treatment of amorphous or helical regenerated silkworm silk materials to above their $T_g$ drives formation of thermally induced β-sheet crystals (Magoshi et al., 1977). Similarly, in regenerated tussah silk heated to 230° C. the random coil structure changes to β-sheet, although a-helix content remains fairly constant (Kweon et al., 2001). Regenerated collagen sponges and fibres are commonly stabilized by a form of heat curing involving heating the material under vacuum to temperatures of 100-120° C. for several days (Yannas and Tobolsky, 1967). Heat curing of collagen causes degradation of the collagen, with protein fragmentation increasing with increased temperatures (Gorham et al., 1992). β-sheet structure in coiled coil silk materials has been induced by dry heating to 215° C. which is well above the protein's glass transition temperature (Sutherland et al., 2011), however, increased mechanical strength was not observed through lack of cross-links which in hindsight was due to material not having been heated for a sufficient length of time. In contrast, the present inventors have found that exposing material comprising honeybee silk proteins, and/or related coiled coil silk proteins, to high levels of dry heat for a sufficient time promotes the formation of cross-links which confers increased the toughness and/or solvent stability to the heated material. As the skilled person would appreciate, "dry heating" does not necessarily mean that no moisture be present. For instance, dry heating is often performed under normal room humidity conditions such as about 20% to about 80% humidity, or about 30% to about 50% humidity. The processes can rely on heat treatment, the moisture content of the material before heating, and whether the heating step is performed under drying conditions (and the nature of the drying conditions). In light of the teachings herein, a suitable combination of these parameters can readily be determined using standard procedures. If there is any doubt, the benefits can readily be achieved by numerous means such as freeze-drying the material and heating to about 180° C. for about 30 minutes, or by heating the material to about 120° C. under a vacuum (such as that generated by standard laboratory equipment) for about 48 hours.

The material which is heated is in a solid state that has too much water will have the effect of boiling the silk proteins. As used herein, "solid state" does not mean that there is absolutely no water in the material at, for example, room temperature or when frozen. In an embodiment, the starting material has a $H_2O$ content of about 1% to about 10%. In an embodiment, the starting material has a $H_2O$ content of less than about 5% or less than about 1%.

Performing the method under conditions which promote drying counters the above-mentioned boiling effect. Thus, when performed under conditions which promote drying the moisture content of the heated (for example heated to about 100° C. to about 120° C.) material can be higher than material with a low water content which is heated above 180° C. For example, the closer the vacuum (when used as a drying condition) is to a perfect vacuum the higher the $H_2O$ content can be.

In one embodiment, the heating is performed in the presence of a vacuum. Broadly, a vacuum is a region with a gaseous pressure much less than atmospheric pressure. The quality of a partial vacuum refers to how closely it approaches a perfect vacuum. Ultra-high vacuum chambers, common in chemistry, physics, and engineering, operate below one trillionth (10) of atmospheric pressure (100 nPa), and can reach around 100 particles/cm.

In an embodiment, the material is heated in a vacuum to about 100° C. Such a vacuum will probably not be a perfect vacuum. If the vacuum is not particularly strong, and/or a desiccant is not present, it may be necessary to increase the heat, for example to about 120° C. to about 150° C. A specific combination of degree of vacuum (pressure) and temperature can readily be determined by the skilled person in view of the present teachings.

In another embodiment, the heating is performed in the presence of a desiccant (possibly also in the presence of a vacuum). Desiccants are well known to the skilled artisan and are commercially available and include, but are not limited to, silica gel, calcium sulfate, and calcium chloride. If the moisture content of the material which has been obtained is too high (for example the silk proteins are in solution), this can be reduced by drying the material using techniques such as, but not limited to, freeze-drying or precipitation (also known as coagulation).

Freeze-drying is also referred to in the art as, for example, lyophilization or cryodesiccation. Freeze-drying is achieved by freezing the material and then reducing the surrounding pressure to allow the frozen water in the material to sublimate directly from the solid phase to the gas phase. Examples of equipment that can be used to freeze-dry the material include a manifold freeze-dryer, a rotary freeze-dryer and a tray style freeze-dryer. This equipment typically comprises a vacuum pump to reduce the ambient gas pressure in a vessel containing the material and a condenser to remove the moisture by condensation on a surface cooled.

In an embodiment, the material or solution is frozen at about −20° C., about −30° C., about −40° C., about −50° C. or about −60° C. or less. In an embodiment, the frozen material or solution is freeze-dried for about 12 to about 48 hours. In a further embodiment, the frozen material or solution is freeze-dried for about 24 hours.

With regard to precipitation (coagulation), this term refers to converting the starting material (composition comprising silk proteins) from a fluid to a solid state. The material can be precipitated by a variety of techniques such as, but not limited to, the addition of an alcohol or a salt (salting out using, for example, using fluoride, sulfate, hydrogen phosphate, acetate, chloride, nitrate, bromide, chlorate, perchlorate, thiocyanate, ammonium, potassium, sodium, lithium, magnesium, calcium or guanidinium) to a solution comprising the silk proteins, or by reducing the pH of the solution to at least about 5.5, preferably at least about 4.5, or a combination of two or more thereof. In one embodiment, the silk proteins are precipitated in a solution comprising alcohol, the precipitate collected, air dried and used in step ii). Any suitable alcohol can be used, with preferred examples including methanol and ethanol.

The material can be dry heated using any suitable means known in the art. Examples include, but are not limited to, using an oven, a heat lamp or heat block. As the skilled person would appreciate, dry heat excludes processes which occur in high humidity such as autoclaving.

Dry heating results in a substantial degree of cross-linking between individual protein, such as silk protein, chains. For silk proteins, the cross-linking appears to be a result of the presence of large number of amino acids in the protein with the potential to form cross-links and the presence of these residues on the surface of the proteins, hence available to form cross-links, when in a coiled coil form. In some embodiments, the cross links are amide cross-links between one or more of glutamine, glutamic acid and aspartic acid residues, and/or ester cross-links between threonine and/or serine with glutamic acid and/or aspartic acid. In an embodiment, there are about two Lys-Glu isopeptide links on average between individual protein molecules.

The process for heat treatment results in improved properties of the material, for example heat treatment increased toughness and/or solvent stability. The extent of improvement depends on the nature of the material before heating. For example, when compared to an "untreated" sponge the process essentially confers stability when immersed in water. Whilst there is little improvement in water solubility when compared to material previously treated with methanol, heat treatment as described herein essentially confers stability in a solution comprising SDS (for example 2% SDS), urea (for example 8 M urea) or guanadinium (for example 6 M guanadinium), whereas methanol (for example 60% methanol) treated material is soluble in SDS, urea and guanadinium. In yet a further embodiment, heat treatment as described herein increases toughness by at least about 20%, at least about 30%, at least about 40%, at least about 50% when compared to methanol (for example 60% methanol) treated material. In an embodiment, improved toughness and/or solvent stability is assessed when compared to untreated material where the silk proteins have been allowed to associate without additional treatments such as methanol treatment, water annealing or autoclaving.

As used herein, the term "toughness" refers to the energy required to break the material. Toughness can be measured using any suitable technique known in the art. In one instance, toughness is measured by determining the area under a standard stress-strain curve. In one embodiment, material produced using the method of the invention requires energy to break of at least about 120 MJ/m$^3$, or least about 130 MJ/m$^3$, or least about 140 MJ/m$^3$, or least about 150 MJ/m$^3$, or least about 160 MJ/m$^3$. In a further embodiment, the method results in at least about a 1.5 fold increase, or at least about a 1.75 fold increase, or at least about a 2 fold increase, in toughness (energy to break) when compared to methanol (for example 60% methanol) treated material.

In some embodiments, the materials are subject to chemical treatment. In some embodiments, the materials are subject to chemical-treatment with aqueous $C_1$-$C_4$ alkanol, for example methanol or ethanol in water. Preferably, the $C_1$-$C_4$ alkanol is methanol.

In one embodiment, the present invention comprises a material formed by a process for chemical-treatment of a material comprising the composition of the present invention, the process comprising i) obtaining the material in a solid state, and ii) contacting the material with aqueous $C_1$-$C_4$ alkanol, such as methanol or ethanol in water, for a sufficient time to render the treated material insoluble. In another embodiment, the present invention comprises a material formed by a process for chemical-treatment of a material comprising the polypeptide as defined herein, the process comprising i) obtaining the material in a solid state, ii) contacting the material with a solution containing a chelate and aqueous $C_1$-$C_4$ alkanol under conditions and for a time period sufficient for the chelate to bind to the polypeptide such that the material comprises the composition of the present invention.

The aqueous $C_1$-$C_4$ alkanol contains the chelate at concentrations that favor complex formation, for example where the amount of chelate is in excess. In some embodiments, the aqueous $C_1$-$C_4$ alkanol comprises the chelate at a concentration between about 0.001 to 50 mg/mL. In some embodiments, the concentration of the chelate is between about 0.01 to 10 mg/mL. In some embodiments, the concentration of the chelate is between about 0.1 mg/ml to 5 mg/ml, for example 0.1 mg/ml, 0.2 mg/ml, 0.3 mg/ml, 0.4 mg/ml. 0.5 mg/ml, 0.6 mg/ml, 0.7 mg/ml, 0.8 mg/ml, 0.9 mg/ml, 1.0 mg/ml, 1.5 mg/ml, 2.0 mg/ml, 2.5 mg/ml, 3.0 mg/ml, 3.5 mg/ml, 4.0 mg/ml, 4.5 mg/ml or 5.0 mg/ml.

In some embodiments, the aqueous methanol comprises an amount of $C_1$-$C_4$ alkanol which is sufficient to render the treated material less soluble compared to untreated material. In an embodiment, the aqueous $C_1$-$C_4$ alkanol comprises at least about 50% methanol, at least about 60% $C_1$-$C_4$ alkanol, at least about 70% $C_1$-$C_4$ alkanol, at least about 80% $C_1$-$C_4$ alkanol or less than about 90% $C_1$-$C_4$ alkanol. In an embodiment, the aqueous $C_1$-$C_4$ alkanol comprises greater the 50% but less than 100% $C_1$-$C_4$ alkanol by volume.

Without wishing to be bound by theory, it is thought that treating the material and/or composition with aqueous $C_1$-$C_4$ alkanol (preferably methanol) generates beta sheet cross-links between the coiled coil polypeptides. It is thought that the formation of the beta-sheet cross-links helps stabilize the material in aqueous solutions. It is thought methanol induces formation of beta-sheets by increasing the hydrophobicity of the solvent and therefore weakening internal protein-protein hydrophobic interactions. At the same time it though to decrease the availability of water for hydrogen bonding thereby driving protein-protein hydrogen bonding.

In a preferred embodiment, the aqueous $C_1$-$C_4$ alkanol comprises between 50% and 90% methanol in water by volume. It is thought that water acts as a plasticizer, lowering the glass transition temperature of the protein and thus increasing the mobility of the protein and allowing structural rearrangement to occur more readily. Since water is also a solvent for the protein, stabilization of the material requires a compromise to be reached; too much water and the dissolution process dominates, too little or no water and the rate of structural rearrangement becomes unacceptably slow. The present inventors found that materials treated in 50-90% methanol were in an environment with sufficient water to allow protein structural rearrangement but also sufficient methanol to keep the protein precipitated and in the solid form.

Solubility can be measured using any suitable technique known in the art. In one instance, solubility is measured by assessing the performance of the material in water. Soluble material swells and eventually dissolves after complete immersion in water within 24 hrs.

As described above, the material was contacted with aqueous $C_1$-$C_4$ alkanol for a sufficient time to render the treated material insoluble compared to untreated material. The time depends on the concentration of the $C_1$-$C_4$ alkanol in the aqueous solution. In some embodiments, the material is contacted with aqueous $C_1$-$C_4$ alkanol for at least about 1 hour, at least about 6 hours, at least about 12 hours, at least about 18 hours, at least about 24 hours, at least about 30 hours, at least about 36 hours, at least about 42 hours, at least about 48 hours, at least about 54 hours or at least about 60 hours. Optionally, the material is dried before use. In an embodiment, the material is dried before use.

The process for chemical treatment as described herein results in improved properties of the material, at least an increased toughness and/or solvent stability. The extent of improvement depends on the nature of the material before heating. For example, when compared to an "untreated" sponge the process essentially confers stability when immersed in water. While "untreated" sponges swelled and rapidly dissolved in water, sponges treated with aqueous methanol showed lower levels of swelling and/or dissolution in water.

Surprisingly, the compositions and/or materials described herein show remarkable stability when stored dry at room temperature. For example, a composition and/or material of the present invention has been demonstrated to be stable when stored dry at room temperature with no deterioration of spectral signal observed over twelve months.

A solid material form may be used in a number of applications such as a recoverable biocatalytic sponge, a reusable sensing film, or antimicrobial wound dressing and the like.

Binding Target Compounds

The present inventors have demonstrated that the compositions, materials and/or copolymers of the present invention are capable of binding target compounds.

Accordingly, the present invention provides a composition as described herein wherein the composition is capable of binding a target compound. The present invention also provides a composition comprising a binding site for a target compound. The target compound may be in the gas phase or dissolved in a liquid phase.

The term "target compound" is defined broadly and includes, but is not limited to, small molecules such as oxygen, carbon monoxide, carbon dioxide, nitric oxide and hydrogen cyanide and the like and ions or functional groups such as isocyanide and cyanide hydroxide and the like. For example, target compounds which can be bound by the compositions of the present invention include those selected from the group consisting of oxygen, carbon monoxide, carbon dioxide, compounds having an atom of P, S, or N, and mixtures thereof.

The present invention is particularly useful for reversibly binding NO and oxygen. The present inventors have demonstrated that the binding of NO with a composition of the present invention results in a detectable change in the composition, and therefore the compositions are suitable for use in biosensor technology.

In some embodiments, the compositions and/or materials of the present invention are selective for a particular target compound. Selectivity may be altered by altering the chelating agent and/or metal ion present in the composition and/or material and/or the transduction method used (for example, electrochemical versus optical). Selectivity may also be affected by substituting one or more amino acids in the polypeptide sequence.

The compositions of the present invention can be designed to bind a target compound of interest under the particular conditions of use contemplated. More particularly, the composition will include a chelate which includes a metal ion and a chelating agent, wherein the composition is capable of binding target compound in a target compound-containing environment.

The term "target compound-containing environment" refers to a medium which includes one or more target compounds, as defined above.

As discussed above, the chelates may be coordination complexes of any of a variety of transition metals or p-block metals including iron, titanium, tin, manganese, chromium, cobalt, nickel, copper, ruthenium, rhodium, palladium, osmium, iridium, vanadium, zinc, and platinum of a metal ion referred to above. In one embodiment, the metal ion forms complexes and has a first valence state in which the chelate binds a desired target compound. In one embodiment, the metal ion will also have a second valence state in which the chelate is substantially inert to binding the target compound.

The metal ion and/or the chelating agent in the composition can be varied to perform functions (e.g. target compound binding) not naturally occurring. For example, there are a wide range of artificial porphyrins such as those described herein which are either commercially available or can be readily prepared which can be used to introduce an alternative function. For example cobalt porphyrins are known to have superior nitric oxide affinity while a lower affinity for oxygen, while ruthenium porphyrins can be used as fluorescent oxygen sensors and MRI contrast agents.

Sensors

The present inventors have demonstrated that the binding of a polypeptide as defined herein to a chelate introduces new properties such as gas binding ability. Accordingly, the compositions of the present invention can be used as biosensors.

The term "biosensor" when used in the specification is to be understood to mean a system, substrate or device that detects a chemical or biological species with selectivity on the basis of molecular recognition. A biosensor uses a biological recognition element. A chemical or biological species is referred to herein as a target compound. A biosensor uses a composition described herein, as a sensor. A biosensor may use a detectable change in the composition upon binging of a target compound. A biosensor may use specific biochemical reactions to detect molecules by electrical, thermal, optical signals and the like.

A biosensor typically comprises a biological element of recognition (for example an element capable of binding a target compound). The biosensor may also comprise a signal transducer which measures binding of the target compound to the element of recognition. In some embodiments, the compositions and/or materials of the present invention may be used as an element of recognition in a biosensor.

For example, haem protein function requires the ability to reversibly reduce and re-oxidise the haem cofactor. Reduction and oxidation can be monitored spectroscopically, since reduction causes a shift in the Soret peak from ~400 nm to higher wavelengths (~420-430 nm). When honeybee silk-haem films are exposed to reducing agents, the Soret peak shifts to 421 nm and there is pronounced splitting in the alpha beta peaks at 527 nm and 558 nm, indicating that $Fe^{3+}$ has been reduced to $Fe^{2+}$. Similar shifts are observed in the spectrum of haem proteins such as haemoglobin or myoglobin. Reduction is reversed upon the addition of oxidising agents, as demonstrated herein.

Accordingly, a composition described herein could be used as a nitric oxide biosensor suitable for many applications ranging from monitoring industrial pollutants to biomedical areas (e.g. NO is both a vasodilatory messenger and an endothelial-derived relaxing factor and plays a key role in cellular communication. NO is also produced by inflamed tissue and can be used as a diagnostic tool e.g. NO in breath to diagnose lung inflammation).

The present inventors investigated the nitric oxide binding of haem b-silk material. NO exposure caused a shift in the Soret peak position from 421 nm to 395 nm with increasing NO concentration. The pronounced concentration effect observed demonstrated that a material formed from a composition described herein could be used at a nitric oxide sensor. The films showed remarkable stability, when stored dry at room temperature, no deterioration of spectral signal was observed over at least twelve months.

The ability to detect a detectable change in the composition allows complicated detection systems (e.g. such as those using marked analytes) or complicated intermediate manipulations to be avoided. The recognition of the target compound by composition may be directly detected by a detectable change. For example, a cascading of events in the transduction of the signal may not be required to detect the detectable change.

As used herein "detectable change" may be any change in a physical or chemical properties of the composition that serves to indicate to a user the bound or associated state of the target compound and composition, such as, for example, colour, fluorescence, bioluminescence, protein activity, electrochemical (such as conductance or a flow of current) and the like. The indication may, for example, be visually detectable and/or detectable using instrumentation such as a spectrophotometer, for example an absorbance spectrophotometer or fluorescence spectrometer, or a luminometer or a potentiostat for electrochemical measurements. In an embodiment, the detectable change can be detected by electrochemical measurements.

For example, in some embodiments, the property may be is selected from the group consisting of redox state, electrical conductivity/resistivity, electrochemical, current, potential, capacity, light absorbance, light transmittance, impedance, reflectivity, refractive index, fluorescence, phosphorescence, luminescence, mass as determined by gravimetry or mass-sensitive resonance techniques, heat as determined by calorimetry, conformation and physiological activity of said composition.

In some embodiments said physical property is light absorbance, light transmittance, reflectivity, refractive index, fluorescence, phosphorescence, or luminescence, and a transducer converts said change in light absorbance, light transmittance, reflectivity, refractive index, fluorescence, phosphorescence, or luminescence into an electrical signal, for example a photometer or spectrophotometer or other device to measure light intensity or any of the aforementioned optical properties.

In embodiments, wherein said physical property is light absorbance or any of the afore-mentioned other optical properties, the composition may be immobilized on a transparent or reflective electrode, or may be immobilized on an electrically non-conducting transparent or reflective substrate, such as glass.

In embodiments where the detectable change is electrochemical, the detectable change may be measured using electrochemical methods, such as potentiometric or voltammetric methods.

In some embodiments, the chelate in the composition or material of the present invention can be a metal-containing group (e.g., a transition metal-containing group, an alkali earth metal or a p-block metal containing group) that is capable of reversibly or semi-reversibly transferring one or more electrons. A number of possible transition metal-containing chelates, an alkali earth metal or p-block metal containing groups can be used.

The chelate can be capable of undergoing an amperometric or potentiometric change in response to target compound binding.

In some embodiments, the composition of the present invention may be used as an electron carrier either on its own or in a series of electron carriers. A series of electron carriers may be an electron transport chain, or it may include an electrode. An electron transfer chain transports electrons from a higher to a lower energy level along a series of electron carrier molecules. An electron carrier molecule is a molecule that transfers an electron from a donor molecule to an acceptor molecule. An electron acceptor is a molecule that takes up electrons easily, thereby gaining an electron and becoming reduced, whereas an electron donor is a molecule that easily gives up an electron, becoming oxidised in the process. Therefore a composition of this invention can be used in a method which involves passing electrons along a sequence of electron carriers, in which each electron carrier is reduced and then oxidised (or vice versa) by electron movement and the sequence of electron carriers includes the protein of this invention. The electron transport chain may comprise natural or synthetic electron carriers. The compositions of this invention can be used in a method involving passing electrons along a sequence of electron carriers, in which each electron carrier is reduced and then oxidised or vice versa by electron movement and the protein of this invention forms part of the sequence of electron carriers. In such a method electrons are generally moved along a gradient of electron carriers with successively lower or higher redox potential.

An alternative use of the compositions of this invention is as part of an apparatus comprising the composition associated with an electrode in a manner that electrons may be passed from one to the next. The composition may be bound or adsorbed onto the electrode. This includes use of the compositions of this invention in cyclic voltammetry, which is used to provide information about the complex's midpoint potential (redox potential).

Uses

The present inventors have demonstrated that the compositions of the present invention can bind photosensitising agents such as Zn phthalocyanine tetrasulfonic acid. Accordingly, the compositions and/or materials of the present invention may be used in photodynamic therapy.

Photodynamic therapy (PDT) is the treatment of malignant tumors with photosensitizers, such as porphyrins and phthalocyanines. Briefly, certain photosensitizers, including porphyrins, metalloporphyrins, and phthalocyanines, localize preferentially in tumor cells. Irradiation of the tissue results in selective cell death of the cells carrying the photosensitizer. Red light in the therapeutically useful range of 600-1200 nm is used. Light in this region of the spectrum has increased transmittance in biological tissue. Both porphyrins and the structurally similar phthalocyanines absorb red light. While porphyrins have been studied more extensively, phthalocyanines have improved absorbance properties and higher extinction coefficients in this region of the spectrum. The photochemistry and photophysics of porphyrins, metalloporphyrins, and phthalocyanines have been studied in detail. Processes observed include radiationless decay to ground, loss of an axial ligand, energy transfer, electron transfer, formation of singlet oxygen, phosphorescence and fluorescence. The photoprocesses observed in each system depend greatly on the central ligand, normally a metal (2H for porphyrin), the oxidation state of the metal and the axial ligand bound to the metal. A dependence of the photophysical properties on the nature of the macrocycle is also observed. Upon exposure to light the photosensitizing compound may become toxic or may release toxic substances such as singlet oxygen or other oxidizing radicals that are damaging to cellular material or biomolecules, including the membranes of cells and cell structures, and such cellular or membrane damage can eventually kill the cells.

PDT may also be used to treat or prevent microbial infections. As described above, PDT is based on the use of a photosensitizing molecule that, once activated by light, generates reactive oxygen species ("ROS"). These ROS are toxic to a large variety of prokaryotic and eukaryotic cells (such as the tumour cells described above), including bacteria, mycoplasma, and yeasts. PDT may also comprise the use of trinuclear species [Ru(pc)(pz)2{Ru(bpy)2(NO)}2](PF6)6 (pc=phthalocyanine; pz=pyrazine; bpy=bipyridine) to produce NO and a singlet oxygen as a cancer treatment.

Accordingly, the invention further comprises methods of killing microbes including Gram-positive and/or Gram-negative bacteria utilizing a composition as describe herein.

The term microbe is used herein to include microorganisms such as bacteria, fungi, algae, and viruses. An embodiment of this method comprises the steps of providing a composition as describe herein, exposing Gram-positive and/or Gram-negative bacteria to said composition and irradiating the composition for a period of time.

In one aspect the present invention provides a method of treating a tumour in a subject, said method comprising administering a composition described herein.

Subjects can be treated by administering to the patient a pharmaceutically effective amount of a composition described herein in the presence of a pharmaceutically acceptable carrier or diluent to produce an effective concentration.

The compositions according to the present invention are included in the pharmaceutically acceptable carrier or diluent in an amount sufficient to exert a therapeutically useful effect in vivo without exhibiting adverse toxic effects on the patient treated.

There may also be included as part of the composition pharmaceutically compatible binding agents, and/or adjuvant materials. The active materials can also be mixed with other active materials including antibiotics, antifungals, other antivirals and immunostimulants which do not impair the desired action and/or supplement the desired action. The active materials according to the present invention can be administered by any route, for example, orally, parenterally, intravenously, intradermally, subcutaneously, or topically, in liquid or solid form.

A preferred mode of administration of the compounds of this invention is oral. Oral compositions will generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colourings and flavours. Materials used in preparing these various compositions should be pharmaceutically pure and non-toxic in the amounts used.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methylparabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

The concentration of active ingredient in the composition itself will depend on bioavailability of the drug and other factors known to those of skill in the art.

It is to be noted that dosage values will also vary with the specific severity of the disease condition to be alleviated, and that, for any particular subject, specific dosage regimens should be adjusted to the individual need and the professional judgment of the person administering or supervising the administration of the aforesaid compositions. The active ingredient may be administered at once, or may be divided into a number of smaller doses to be administered at varying intervals of time.

The compositions of the present invention are prepared as formulations with pharmaceutically acceptable carriers. Preferred are those carriers that will protect the active compound against rapid elimination from the body, such as a controlled release formulation, including implants and microencapsulated delivery systems. Biodegradable, biocompatible polymers can be used, such as polyanhydrides, polyglycolic acid, collagen, and polylactic acid. Methods for preparation of such formulations will be apparent to those skilled in the art.

According to one particular embodiment, the compositions of the present invention can be used to decrease an anti-inflammatory response. More specifically, such anti-inflammatory response may be accompanied by a decrease or reduction in the amount or expression of pro-inflammatory cytokines such as IL-2, IL-17, IL-23, IFN-gamma, IL-6. Such decrease or reduction according to the invention may be a reduction of about 5% to 99%, specifically, a reduction of about 5%, 10%, 15%, 20%, 25%, 30%, 35%, 40%, 45%, 50%, 55%, 60%, 65%, 70%, 75%, 80%, 85%, 90%, 95% or 99% as compared to untreated control. In yet another specific embodiment, the composition of the invention may elevate and increase the amount or expression of anti-inflammatory cytokines such as TGF-beta, IL-10, IL-4, IL-5, IL-9 and IL-13. More specifically, the increase, induction or elevation of the anti-inflammatory cytokines may be an increase of about 5%, 10%, 15%, 20%, 25%, 30%, 35%, 40%, 45%, 50%, 55%, 60%, 65%, 70%, 75%, 80%, 85%, 90%, 95% or 99% as compared to untreated control.

The compositions of the present invention are useful in a variety of applications including use as a magnetic resonance imaging agent, as a radiation sensitizer, for RNA hydrolysis, and for DNA photocleavage.

The present inventors have also demonstrated that the compositions of the present invention can function to catalyse the oxidation of substrates. In particular, the present inventors have demonstrated that a composition of the present invention can function as a peroxidase.

Many enzymes that use an iron (IV) oxoporphyrin radical cation intermediate to catalyze the oxidation of various substrates are known.

The chelates, in particular the metal ion and/or chelating agent, can be chosen to function as catalysts, for example as peroxidases. For example, the peroxidase activity of a haem b coiled coil silk protein composition of the invention can be used for the bioremediation of phenolic waste.

In some embodiments, the compositions of the present invention can be used for processes, such as catalytic processes, where cycling of oxidation states is required. For example, the present inventors have demonstrated that the metal ion in a film comprising haem b and AmelF3 can be reversibly oxidised from $Fe^{2+}$ to $Fe^{3+}$ The chelates, in particular the metal ion and/or chelating agent, can be chosen based on the redox potential of the metal ion.

EXAMPLES

The invention is now described with reference to the following examples. These examples are provided for the purpose of illustration only, and the invention is not limited to these examples, but rather encompasses all variations that are evident as a result of the teachings provided herein.

Materials & Methods

All standard chemicals used were purchased from Sigma Aldrich. Haem b was purchased from Frontier Scientific. UV/Vis absorption measurements were carried out on a SpectraMax M2 plate reader.

Polypeptide Synthesis

Full length, recombinant honeybee silk proteins (AmelF3) without affinity purification tags, were produced by fermentation in *Escherichia coli* as described in Weisman et al. (2010). Full length, recombinant Weaver Ant/Green Ant (*Oecophylla smaragdina*) silk proteins (GA1, GA2, GA3, GA4) without affinity purification tags, were produced by fermentation in *Escherichia coli* following the same procedures as outlined in Weisman et al. (2010).

Site directed mutagenesis of honeybee silk proteins was carried using methods known to the person skilled in the art. For example, to generate AmelF3 Tyr76Ala, the forward primer 5'-CTCTTGCAGAGGCCGCGTTGCGAGCGTCCG-3' (SEQ ID NO: 80) with the corresponding reverse primer was employed and site directed mutagenesis was carried out using Pfx 50 DNA polymerase from Invitrogen following the Pfx50 manufactures instructions. All AmelF3 mutants were expressed and purified using a similar procedure as the unmodified AmelF3 silk protein. To generate AmelF3 Tyr76His, the forward primer 5'-CTCTTGCAGAGGCC-CATTTGCGAGCGTCCG-3' (SEQ ID NO: 81) with the corresponding reverse primer was employed. To generate AmelF3 Ala97His, the forward primer 5'-CCTGAAAAAT-CATCAACAAGCGCAATTAAACGCCCAG-GAAAAGTC-3' (SEQ ID NO: 82) was used.

Example 1: Preparation of Recombinant Silk-Based Materials

Recombinant silk proteins were fabricated into sponges or films using methods described previously (Weisman et al., 2010; Huson et al., 2012; Rapson et al., 2014). Materials manufactured from silk polypeptides, such as sponges or films, were stored at room temperature until required.

Example 2: Polypeptides Having a Coiled Coil Region Bind Strongly to a Chelate Comprising a Chelating Agent and a Metal Ion AmelF3 sponges were prepared as described in example 1. When a solution of haem b (0.5 mg/mL) in 70% methanol haem b is added to honeybee silk sponge (haem b in excess), the greyish green haem b solution is immediately absorbed into the sponge and within seconds the colour of the sponge changes to red indicating that the haem has become bound to the silk protein (FIG. 1A). The colour change observed with honeybee silk indicates a change in the coordination of the iron metal centre within the haem group, producing a material with a similar coordination to red haemoglobin. The colour was not removed by extensive washing with 70% methanol, 0.1M HCl or 0.1M NaCl. The retention of the red colour indicates that the haem is strongly bound in the bee silk sponge.

FIG. 1 demonstrates strong binding of a chelate to a polypeptide of the present invention.

Example 3: Polypeptides Comprising a Coiled Coil Region Form a Coordinate Bond with the Metal Ion Transparent silk films were prepared as described in example 1 from AmelF3 to monitor the spectral properties of the material using UV/Vis spectroscopy.

An embodiment of the composition of the present invention was formed by co-drying a solution of AmelF3 and haem b. Briefly, 2 mg haem b and 20 mg AmelF3 silk sponge was dissolved in 1 mL of HFIP overnight at room temperature. The solution was aliquoted into either a cuvette or 24-well plate and dried at room temperature. The dried film was soaked overnight in 70% methanol to make the film insoluble in water.

Alternatively, haem b was 'leached' into a pre-formed film. The AmelF3 material was formed as described in example 1. The silk material was soaked in a solution of haem b (0.5 mg/mL; haem b in excess) in 70% methanol solution for between 1 and 48 hours followed by washing with 70% methanol to remove any unbound haem b and dried at room temperature.

Haem proteins have a characteristic Soret peak in their UV/Vis spectrum at ~400 nm which is extremely sensitive to changes in the coordination of the iron haem atom. In the case of iron porphyrins such as haem b, broad Soret peaks below 400 nm indicate a 4 coordinate iron centre with the iron only coordinated to the porphyrin ring. When the haem group is coordinated to an amino acid (5 coordinate iron centre), the Soret band red shifts to above 400 nm and sharpens.

Figure 2:
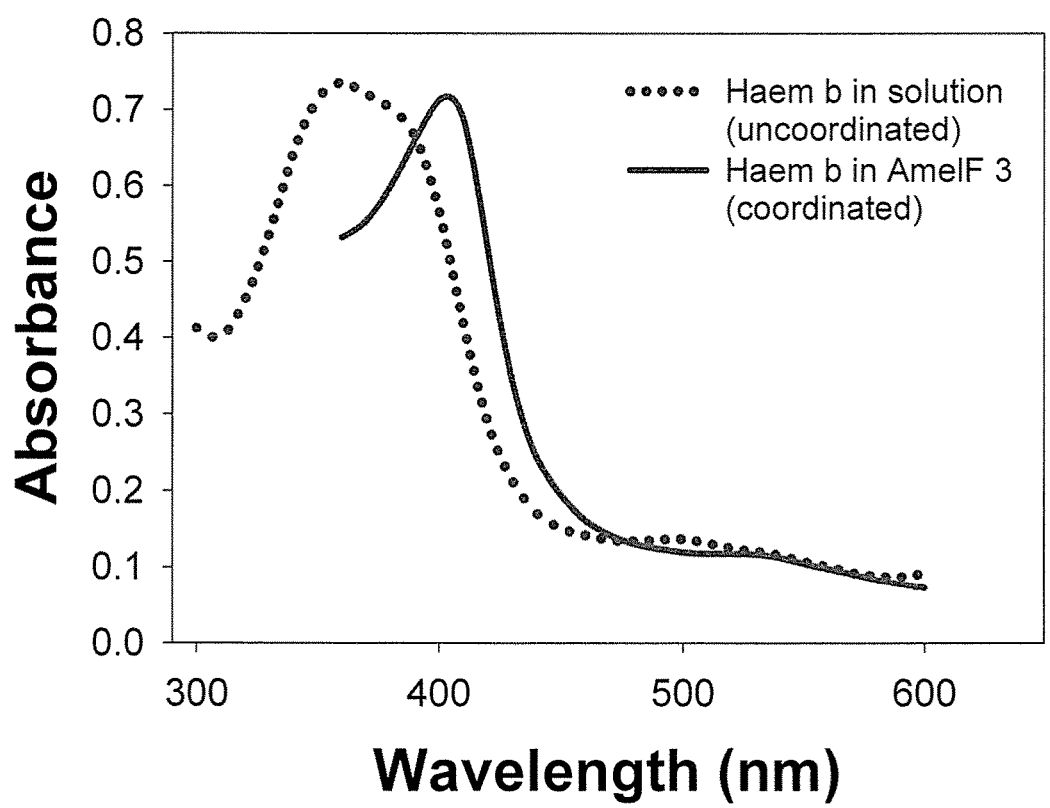
FIG. 2 shows evidence for the binding and coordination of haem b within honeybee silk films. UV/Vis spectra obtained from an AmelF3-haem b composite film generated from honeybee silk protein AmelF3 show a sharp Soret peak at 410 nm (solid line). In contrast the spectrum from uncoordinated haem b in aqueous solution shows a broad Soret peak below 400 nm (dotted line). The shift in the Soret peak indicates that the haem centre is coordinated to a residue in an AmelF3 polypeptide of the silk protein film. This figure demonstrates binding and coordination of a chelate to a polypeptide of the present invention.

UV/Vis absorption measurements were collected between 300 to 600 nm. FIG. 2 shows UV/Vis absorption spectra for a solution of haem b (0.05 mg/mL) in water and silk film generated from recombinant honeybee silk protein AmelF3 containing haem b. The UV/Vis spectrum for the film shows a sharp Soret peak at between 400 nm and 410 nm. This is characteristic of Fe coordination to one or two amino acids of the silk polypeptide. In contrast, solutions of haem b show a broad peak below 400 nm. This peak is characteristic of uncoordinated Fe in haem b.

In the case of honeybee silk, the fact that the Fe in the haem b coordinates to unmodified silk protein was unexpected and surprising, given that the silk protein does not contain any of the typical coordinating residues such as histidine, cysteine of methionine.

To determine the nature of the coordinating amino residue the inventors investigated the stoichiometry of haem b binding through varying the amount of haem b added to the silk protein and using Raman spectroscopy.

Figure 3:
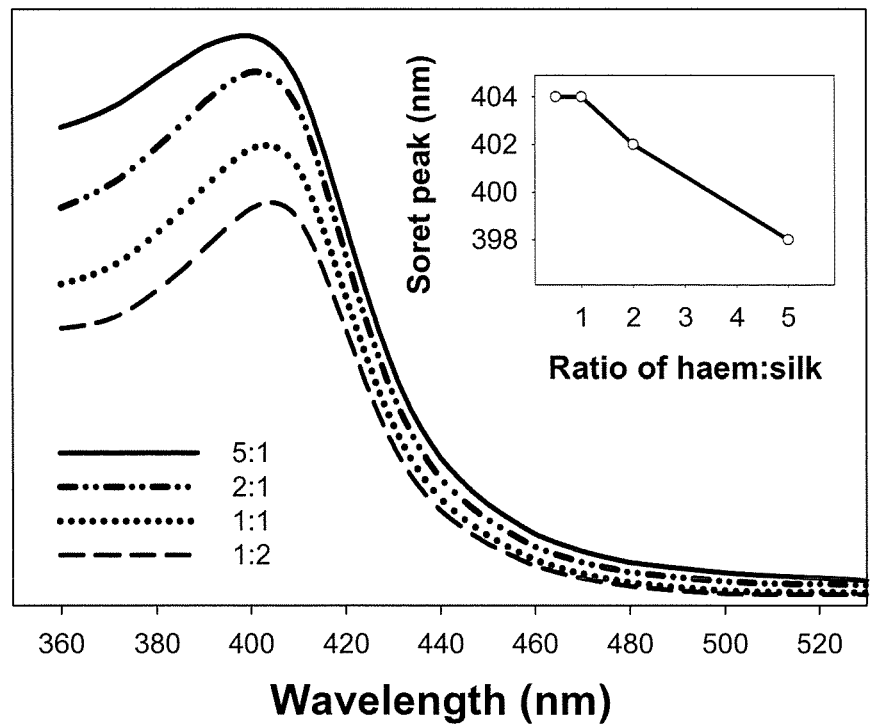
FIG. 3 shows a comparison between the UV/Vis spectra obtained when the molar ratio of haem b to AmelF3 was varied. As the concentration of haem b relative to the protein was increased, the Soret peak broadened and shifted to lower wavelengths indicating an increase in the amount of uncoordinated haem. At ratios of 1:1 haem:AmelF3 or lower, the Soret peak at 404 nm indicates that all the haem is coordinated. As haem:AmelF3 ratios increase, the Soret peak widens and shifts to 398 (insert), indicating an increase in the amount of uncoordinated haem. The stoichiometry demonstrated in this figure indicates specific saturable binding of a chelate to a polypeptide of the present invention.

AmelF3 films with different ratios of haem b to AmelF3 were prepared by co-drying haem and AmelF3 HFIP solutions. At low haem loadings (haem:protein molar ratios of 1:1 and 1:2), a sharp Soret peak at 404 nm was observed, indicative of all the haem being coordinated (FIG. 3). As the concentration of haem b relative to the protein was increased, the Soret peak broadened and shifted to lower wavelengths indicating an increase in the amount of uncoordinated haem (FIG. 3). The finding that all haem was coordinated at 1:1 haem:silk ratio suggested that a single amino acid within each silk monomer was responsible for coordination.

The identity of the coordinating amino acid was investigated using Raman spectroscopy. Raman spectroscopy measures stretching frequencies between the iron centre and the coordinating ligand, these stretching frequencies are indicative of the nature of ligand. Raman spectra were obtained using an inVia confocal microscope system (Renishaw, Gloucestershire, UK) with 754 nm excitation from a Modu-Laser (USA) Stellar-Pro ML/150 Ar ion laser through a ×50 (0.75 na) objective. Incident laser power, as measured using an Ophir (Israel) Nova power meter fitted with a PD300-3W head, was 0.59 mW for the silk films and 0.32 mW for the myoglobin powder. Films were held on a mirrored backing while the powder was compressed into a 2 mm cavity cell. A coaxial backscatter geometry was employed. Spectra were collected over the range of 100 to 3200 cm-1 and averaged over at least 20 scans, each with an accumulation time of 20 seconds. The Raman shifts were calibrated using the 520 cm-1 line of a silicon wafer. The spectral resolution was ~1 cm-1. All data manipulation was carried out using Grams Al software V 9.1 (Thermo Scientific, USA).

Figure 4:
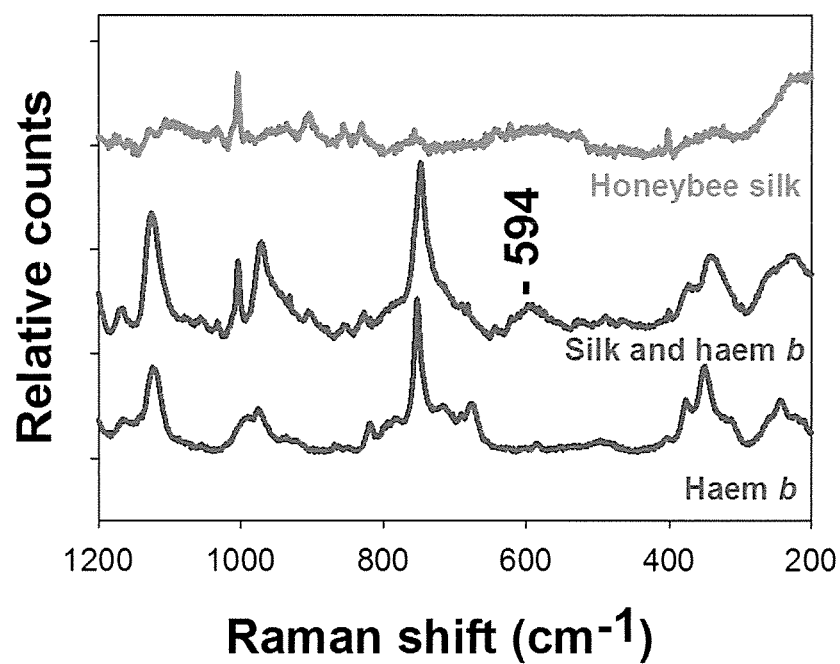
FIG. 4 shows that polypeptides of the present invention coordinate the metal ion of the chelate through a tyrosine residue. Raman spectra of AmelF3-haem b (middle trace) shows a broad feature centred at 594 $cm^{-1}$. Raman spectra of AmelF3 (top trace) and haem b trace (middle trace) do not display a broad feature centred at 594 $cm^{-1}$. These spectra are consistent with a tyrosine residue coordinating to the haem centre.

The Raman spectrum of the silk-haem film excited at 785 nm excitation showed a broad peak centred at 594 cm$^{-1}$ (FIG. 4), which was specific to the silk-haem film. Haem proteins which have a tyrosine coordinating ligand show similar Fe-Tyr stretches (Nagai et al., 1983 and 1989). Mature recombinant honeybee silk protein 3 contains a single tyrosine residue (Tyr76) located in the core of the predicted coiled coil (SEQ ID NO:39). The Raman spectrum indicated that Tyr76 of AmelF3 was the most likely candidate coordinating to the haem centre.

Figure 5:
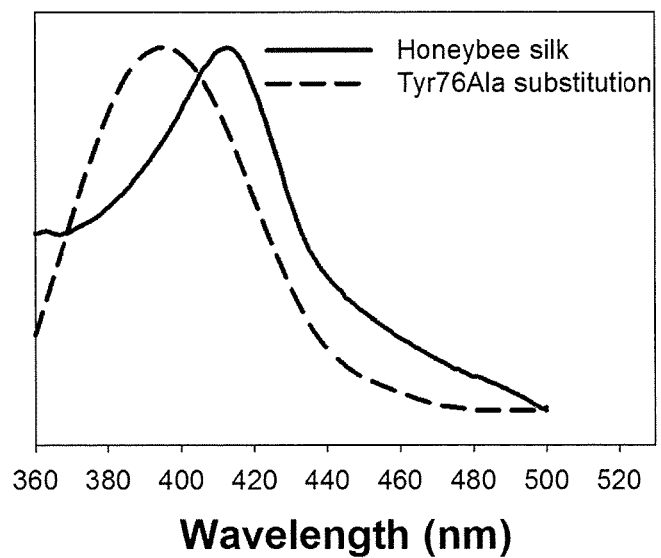
FIG. 5 shows binding and coordination of a chelate to a polypeptide of the present invention both in solution and in a material. The figure also shows that Tyr76 of AmelF3 is important for co-ordinating haem b. A. Comparison between the UV/Vis spectra obtained when haem b was added to silk protein films generated from recombinant honeybee silk protein AmelF3 and AmelF3 with a mutation of tyrosine 76 to alanine (AmelF3.Tyr76Ala). The broad Soret peak at 395 nm indicates that the modified honeybee silk does not coordinate to haem b. B. Aqueous solutions of AmelF3 with a mutation of tyrosine 76 to histidine (AmelF3.Tyr76His) and haem b in a 1:1 ratio. The sharp peak at around 400 nm, known as the Soret peak, is indicative of the coordination of an amino acid residue to the iron haem centre. The data show that the metal ion is coordinated in solution and in film.
Figure 5:
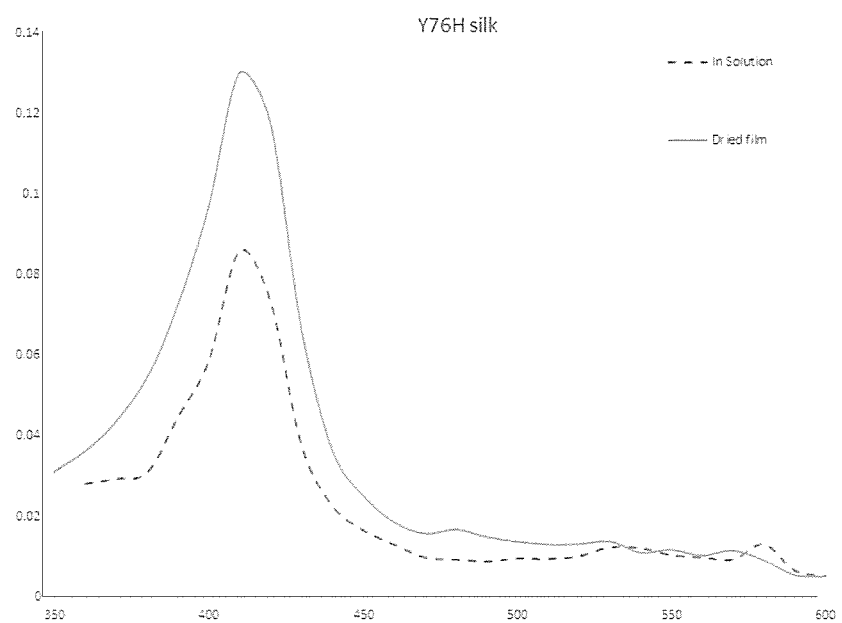

To test whether Tyr76 was indeed the coordinating ligand, the present inventors replaced Tyr76 with an alanine using site directed mutagenesis of the AmelF3 silk gene. The UV/Vis spectrum of the Tyr76Ala substituted protein (AmelF3 Tyr76Ala) had a broad Soret peak at 395 nm indicating that the coordination noted in unmodified honeybee silk had been reversed through this single amino acid substitution (FIG. 5A). When haem b was added to sponges prepared using Tyr76Ala silk protein, no pronounced colour change was observed and the green haem b colour did not wash out with aqueous methanol indicating that while the haem b cofactor bound to the silk protein, the metal ion was not coordinated to the polypeptide.

This data indicates that recombinant honeybee silk can be used as a stable protein scaffold for haem protein engineering. A tyrosine residue in the core of the coiled-coil was determined to be coordinating to the iron haem centre. Site directed mutagenesis has demonstrated that it is possible to control the coordination of the haem centre.

Example 4: The Polypeptide can be Modified Using Site-Directed Mutagenesis to Control Co-Ordination of the Metal Ion The present inventors also mutated Tyr76 to a histidine and investigated the effect the single amino acid substitution had on binding to haem b. As indicated by the UV/Vis spectrum AmelF3, Tyr76His bound haem b via a co-ordinate bond (FIG. 5B) in solution and when formed into a film. The sharp peak observed at around 400 nm is indicative of the coordination of an amino acid residue to the iron haem centre. This data indicates that polypeptides having a coiled coil region can be used as a stable protein scaffold for binding to a chelating agent. Site directed mutagenesis has demonstrated that it is possible to alter binding to the chelating agent.

Figure 6:
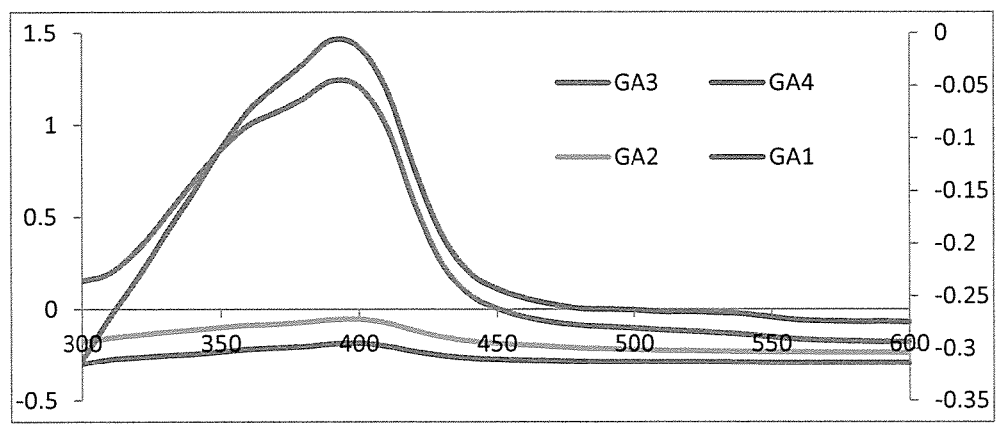
FIG. 6 shows UV/Vis spectra of silk films generated from recombinant green ant silk proteins (GA1-4) after haem b was leached in. This data shows that for GA1 and GA3, a strong signal was observed at around 400 nm demonstrating that these proteins strongly bound haem. This data shows that other polypeptides, besides honey bee silk polypeptides, having a coiled coil structure are capable of binding a chelate comprising a chelating agent and a metal ion.

Example 5: Binding of a Chelate Comprising a Chelating Agent and a Metal Ion to a Polypeptide Having a Coiled Coil Region is not Unique to Beesilk Polypeptide Transparent films from the Green Ant (*Oecophylla smaragdina*) (GA1-4) silk proteins were prepared as described above. Haem b in 70% methanol was leached into the preformed Green Ant silk film as described at Example 3. UV/Vis spectra were collected for Green Ant silk film after haem b had been leached. For GA1 and GA3, a strong signal was observed at around 400 nm demonstrating that these proteins strongly bound haem (FIG. 6). This data show that other polypeptides having a coiled coil structure are capable of binding a chelate comprising a chelating agent and a metal ion.

Figure 7:
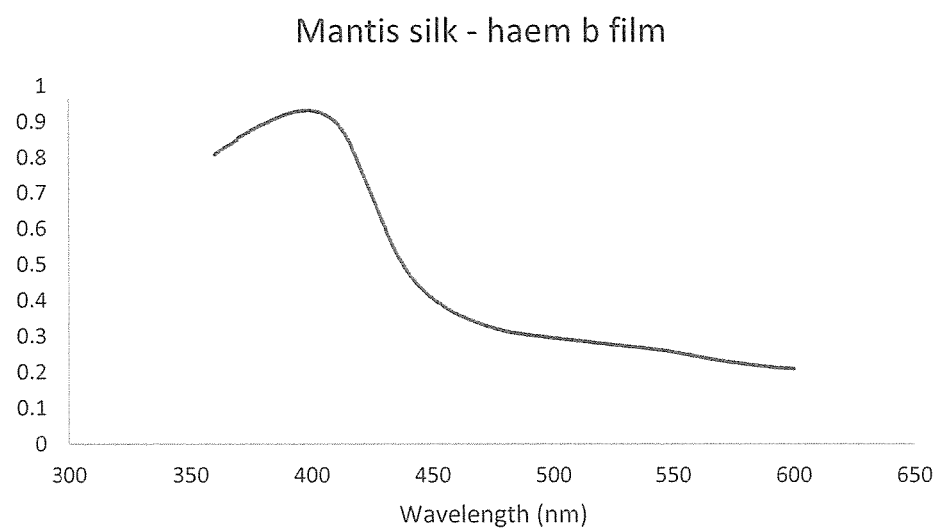
FIG. 7 shows UV/Vis spectra of silk films generated from recombinant praying mantis silk proteins after haem b was leached in. A strong signal was observed at ~400 nm demonstrating that these proteins strongly bound haem. This data show that other polypeptides having a coiled coil structure are capable of binding a chelate comprising a chelating agent and a metal ion.

Transparent film from praying mantis silk were prepared as described above. Haem b was leached into the preformed films as described in Example 3. UV/Vis spectra were collected. A strong signal was observed at ~400 nm demonstrating that these proteins strongly bound haem (FIG. 7). This data show that other polypeptides having a coiled coil structure are capable of binding a chelate comprising a chelating agent and a metal ion.

Example 6: Coiled Coil Silk Polypeptides Bind Other Macrocycles in Addition to Haem b The ability of sponges generated from recombinant AmelF3 to bind a range of macrocyles was tested by adding a solution of the macrocmacrocycle containing an excess of the macrocycle to be tested to the AmelF3 sponge and observing the colour of the sponge and whether the sponge retained colour after washing. The strength of macrocycle binding was assessed qualitatively by assessing the intensity of the colour retained by the sponge after washing. Strong binding to the sponge refers to the finding that the macrocycle cannot be washed out with aqueous methanol, organic solvents, 0.1 M HCl or 0.1 M NaOH. Some of the macrocycles were noted to weakly bind the macrocycle—in this case a faint colouration of the sponge was observed and UV-Vis spectra showed weak absorption peaks.

The sponges were able to bind a number of porphyrins and phthalocyanines as summarised in Table 2 below.

TABLE 2
Binding properties of different macrocycles to materials generated from recombinant honeybee silk proteins.
| Macrocycle | Binding properties |
|---|---|
| Porphyrins | |
| Protoporphyrin IX (PPIX) | Strongly binds to silk |
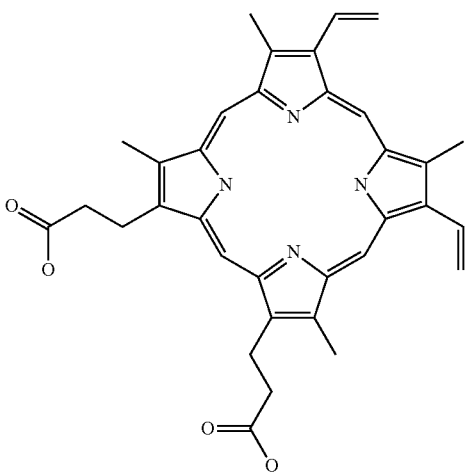
Etioporphyrin I      Does not bind
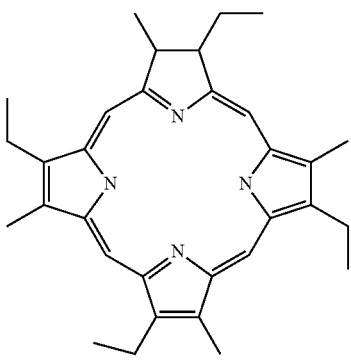
Protoporphyrin IX dimethyl ester      Does not bind
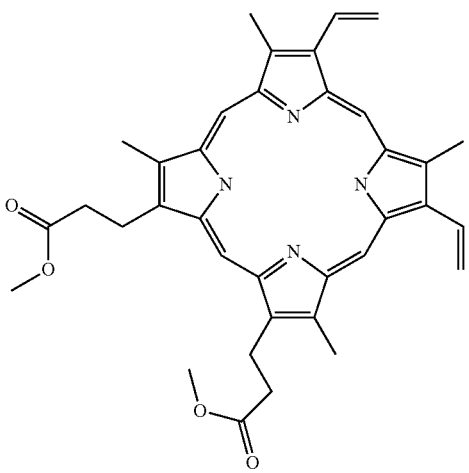

TABLE 2-continued
Binding properties of different macrocycles to materials generated from recombinant honeybee silk proteins.
| Macrocycle | Binding properties |
| --- | --- |
| Deuteroporphyrin IX 2,4-disulfonic acid dimethyl ester | Weak binding |
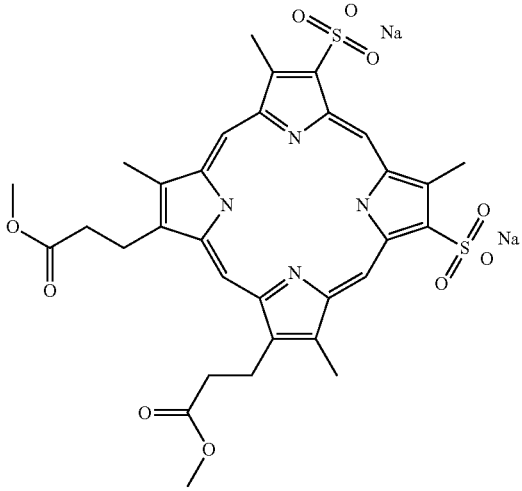
| Metal protoporphyrin IX contaning either Fe, Co and Cu | Strongly binds |
| --- | --- |
Phthalocyanines
| Phthalocyanine | Does not bind |
| --- | --- |
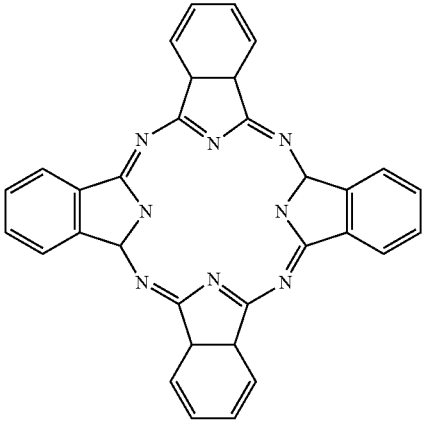

TABLE 2-continued

Binding properties of different macrocycles to materials generated from recombinant honeybee silk proteins.

| Macrocycle | Binding properties |
|---|---|
| Phthalocyanine tetrasulfonic acid | Strongly binds |

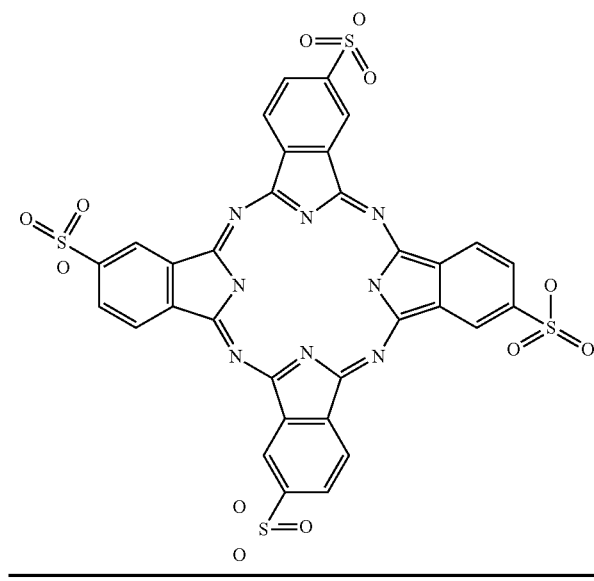

These results indicate that, in the absence of a metal within the macrocycle, a charge in the macrocycle (such as a carboxyl group e.g. PPIX or sulfonate group e.g. phthalocyanine) is preferred to allow the macrocycle to bind to a residues of the opposite charge in the silk protein. If no charge is present e.g. Phthalocyanine or etioporphryin I, no binding is obtained.

This data also shows that the metal ion is not required for strong binding between the polypeptide and the chelate. Therefore, interactions between the polypeptide and the chelating agent are sufficient for strong binding.

These results suggest that an appropriately located negative charged residue in the silk will bind a macrocycle with a positive charge, and that an appropriately located positive charged residue in the silk will bind a macrocycle with a negative charge.

Figure 8:
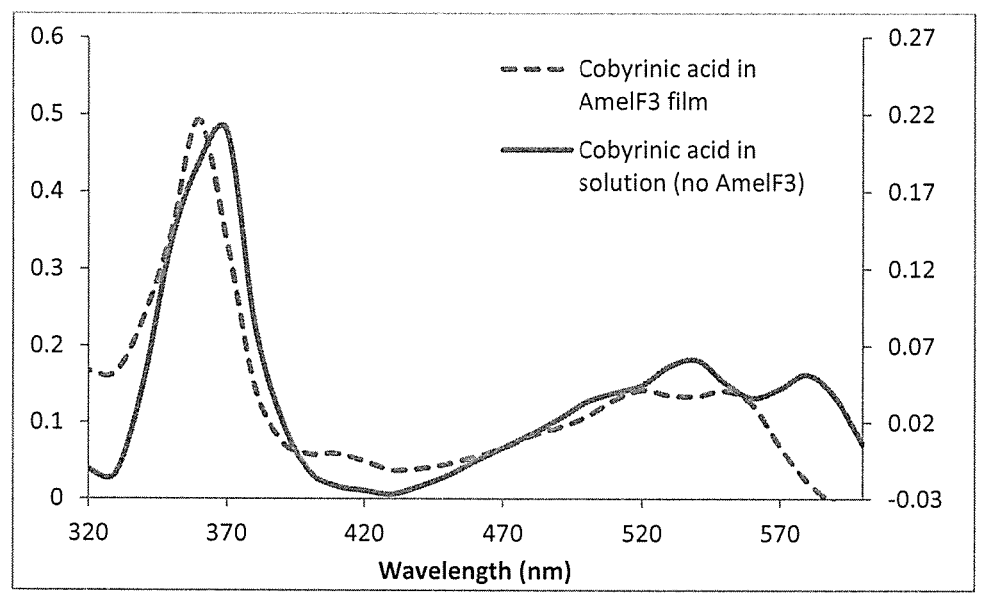
FIG. 8 shows the chelator of the chelate may be varied. The non-porphyrin chelator cobyrnic acid (dicyanocobyrinic acid heptamethyl ester) was added to silk protein films generated from recombinant honeybee silk protein AmelF3. The shift in the maximum absorbance of the sharp peak from 370 nm to 360 nm, upon addition of the chelator to the silk film, is indicative of the coordination of an amino acid residue to the cobalt centre when dicyanocobyrinc acid heptamethyl ester is leached into the AmelF3 film.

Example 7: Coordination of a Metal Ion Contained within a Chelating Agent with at Least One Amino Acid of the Polypeptide is Sufficient for Binding Films generated from recombinant honeybee silk protein AmelF3 containing dicyanocobyrinic acid heptamethyl ester were prepared as described in example 3. UV/Vis spectrum were recorded for a film generated from recombinant AmelF3 containing dicyanocobyrinic acid heptamethyl ester and a solution of dicyanocobyrinic acid heptamethyl ester without AmelF3 (FIG. 8).

Dicyanocobyrinic acid heptamethyl ester was found to strongly blind to AmelF3 in film. The shift in the position of the peaks from 370-360 and changes in the 500-600 nm when dicyanocobyrinic acid heptmethyl ester is bound to the silk protein suggests that the Tyrosine residue is coordinating to the cobalt centre. When a solution of dicyanocobrynic acid heptmethyl ester was added to sponges prepared from AmelF3 Try76Ala and washed extensively with 70% methanol the pink colour washed out of the sponge indicating that AmelF3 Try76Ala did not bind to dicyanocobyrinic acid heptamethyl ester.

This indicates that binding of dicyanocobyrinic acid heptamethyl ester takes place through coordination of the tyrosine residue to the cobalt metal centre alone. There is unlikely to be binding between the chelating agent and the polypeptide. Therefore, a coordinate bond between the polypeptide and the metal ion is sufficient for binding. Dicyanocobyrinic acid heptmethyl ester has been introduced to both preformed films and also sponges (data not shown).

Example 8: A Composition According to the Invention can be Reversibly Reduced and Oxidised Haem protein function such as gas binding requires reduction of the haem group from $Fe^{3+}$ to $Fe^{2+}$, while catalysis requires cycles of reduction and re-oxidisation. Reduction and oxidation of Fe can be monitored spectroscopically, since reduction causes a shift in the Soret peak from ~400 nm to higher wavelengths (~420-430 nm, depending on the coordination system).

Freshly prepared sodium dithionite (100 mM) in 50 mM phosphate buffer (pH 7) was used as the reducing agent. 10-100 µL was added to a 50 mM phosphate buffer (pH 7) covering the porphyrin-AmelF3 film. Sodium persulfate was used at the oxidising agent in a similar manner to sodium dithionite.

Figure 9:
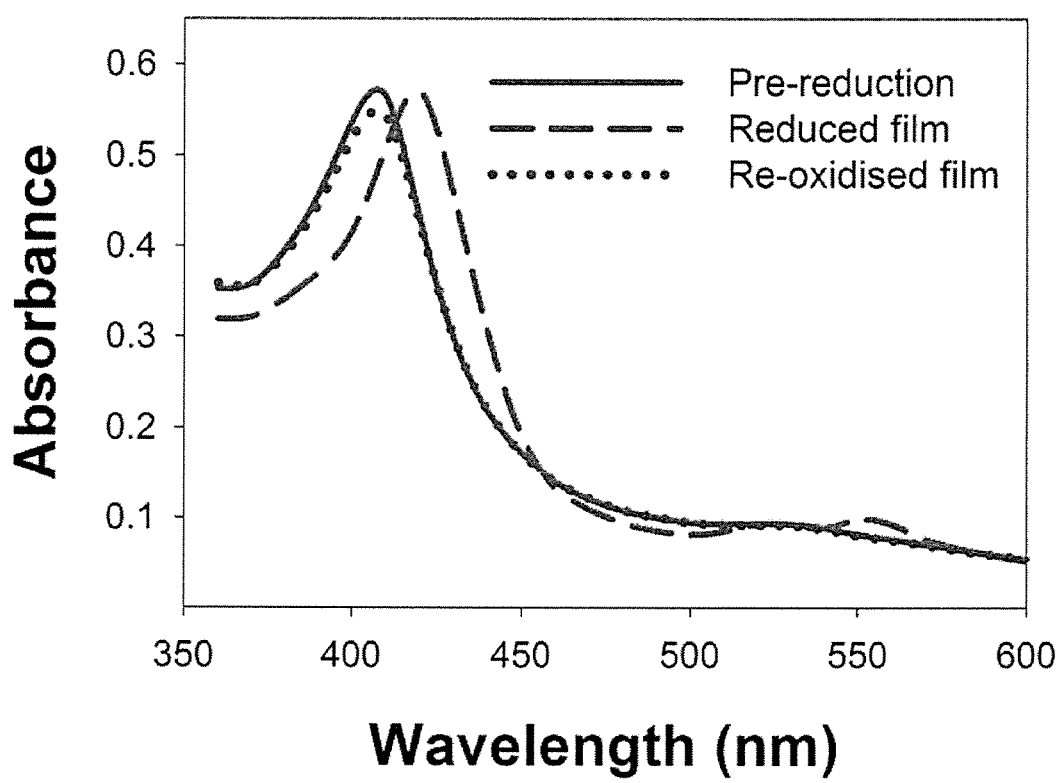
FIG. 9 shows UV/Vis spectra obtained when silk protein films generated from recombinant honeybee silk protein AmelF3 were reduced and then re-oxidised, showing that the reaction can be reversed. The oxidation state of the haem centre is determined from the UV/Vis spectral shifts. With reduction the Soret peak shifts from 410 nm to 420 nm and an increase in peak at 550 nm observed. This data shows compositions of the present invention are capable of being reversibly reduced.

When the AmelF3-haem films were exposed to reducing agents, the Soret peak shifted to 421 nm indicating that $Fe^{3+}$ has been reduced to $Fe^{2+}$ (FIG. 9). Reduction was reversed upon the addition of an oxidising agent (FIG. 9). This data demonstrates that haem-silk materials can be used for catalytic processes, for example catalytic processes where cycling of oxidation states is required.

Example 9: A Composition According to the Invention can Bind Nitric Oxide

Artificial haem materials hold potential for sensing a range of gases and volatile organic compounds. For example, artificial haem proteins are excellent candidates for sensing nitric oxide (NO), for which there is a need in many fields, ranging from monitoring industrial pollutants to clinical diagnosis and biomedical research. The inventors therefore investigated the nitric oxide (NO) binding ability of the silk-haem b material.

Figure 10:
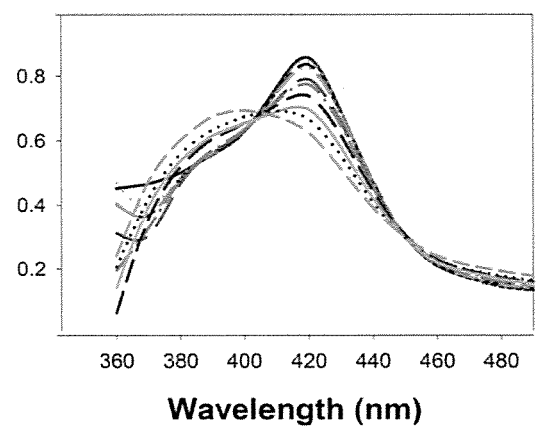
FIG. 10 shows binding of a target compound and a detectable change in the target compound on binding. A. UV/Vis spectra obtained when silk protein films generated from recombinant honeybee silk protein AmelF3 were bound to increasing NO concentrations. B. Ratio change of absorbance change at 420 nm as NO concentrations are increased. Either the decrease in absorbance at 420 nm or increase in absorbance at 390 nm can be used. The decrease in absorbance at 420 nm can be converted into the fraction of nitric oxide binding site occupied by NO and plotted against NO concentration, and fitted to a sigmoidal curve modified from the Hill equation with a dissociation constant of 6.7 µM and a limit of detection of ~1 µM. This data shows compositions of the present invention are capable of binding a target molecule (b), and that target molecule binding results in a detectable change in the composition.
Figure 10:
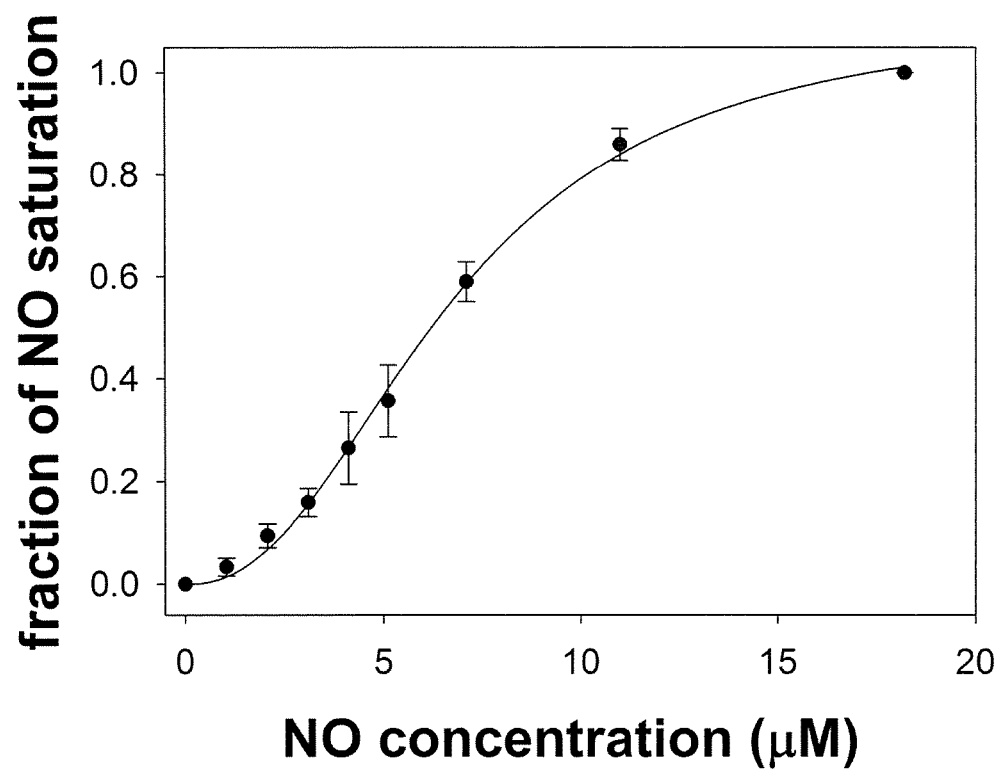

AmelF3-haem b film was used as the porphyrin-silk film. Freshly prepared sodium dithionite (100 mM) in 50 mM phosphate buffer (pH 7) were used as the reducing agent. 10-100 µL was added to a 50 mM phosphate buffer (pH 7) covering the porphyrin-silk film. Sodium persulfate was used at the oxidising agent a similar manner to sodium dithionite. Diethylamine 2-nitrosohydrazine sodium hydrate (NONOate) was dissolved in 50 mM phosphate (pH 7) to generate 1.5 mol equivalent of dissolved NO. Aliquots of the diethylamine NONOate solution was added to a dithionite reduced film. Changes in the UV/Vis spectrum were monitored to determine redox states and measure NO binding (FIGS. 10A and 10B). NO exposure caused a shift in the Soret peak position from 421 nm to 395 nm with increasing NO concentration.

Exposure to increasing NO concentration caused the Soret peak to shift from 421 nm to 395 nm. From 0-7 µM, there was a linear relationship between the decrease in absorbance at 421 nm and the concentration of NO, with a limit of detection for NO of 1 µM. NO binding was found to be reversible and the silk-haem b films.

This data shows compositions of the present invention are capable of binding a target molecule (e.g. NO), and that target molecule binding results in a detectable change in the composition.

Figure 11:
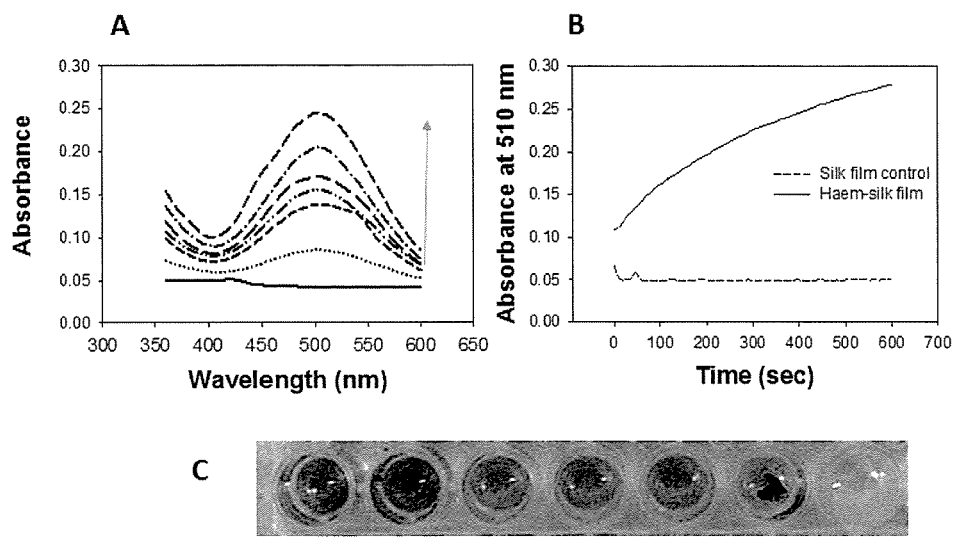
FIG. 11 shows peroxidase activity of haem-silk materials. A. Shows the spectral changes over time when a haem b-AmelF3 sponge (lmg) was added to a solution of $H_2O_2$, aminoantipyrine and phenol. The increase in absorbance at 510 nm is due to the formation of an oxidation product between aminoantipyrine and phenol. The oxidation product is in the red wavelength. B. Peroxidase assay monitoring the change in absorbance at 510 nm with time. As can be seen in the silk film control (without haem; dashed line), peroxidase activity is due to the addition of haem to the film. C. Demonstration that haem b-AmelF3 sponges can be used as recoverable and reusable catalysts. The picture shows a series of wells with 4-aminoantipyrine, phenol and $H_2O_2$. When a haem-silk sponge is added, the colour changes to the red wavelength. The sponge was taken out of each well and placed into the well next to it (left to right). The final well is a colourless solution to which the sponge has not yet been added, the second well to the right still has the haem b-AmelF3 sponge.

Example 10: A Composition According to the Invention can be Used as a Catalyst The present inventors investigated whether haem silk materials generated from recombinant honeybee silk containing bound haem b can act as peroxidases. This activity was demonstrated using a modification of the Worthington assay (www.worthington-biochem.com/hpo/assay.html). The assay uses 4-aminoantipyrine as hydrogen donor. The reaction rate is determined by measuring an increase in absorbance at 510 nm resulting from the oxidative coupling of aminoantipyrine with phenol with decomposition of hydrogen peroxide (FIG. 11).

Example 11: A Composition According to the Invention can be Used to Bind ZnPc which has Antimicrobial Activity Photodynamic therapy uses nontoxic, light-sensitive compounds that, when exposed to selective wavelengths of light become toxic to microbes (bacteria, fungi and viruses), targeted malignant cells or other diseased cells. Photodynamic therapy requires a photosensitizer, light source and tissue oxygen. The light excites the photosensitizer which leads to the production of toxic reactive oxygen species.

Figure 12:
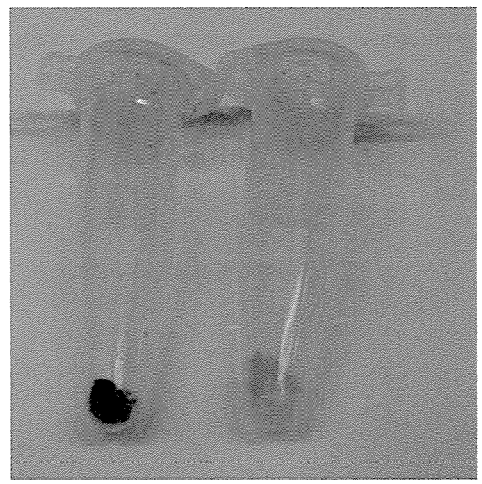
FIG. 12 shows that a composition of the present invention can be used to bind ZnPc which has antimicrobial activity. Left; recombinant honeybee silk protein material after leaching in of the photosensitizer zinc phthalocyanine tetrasulfonic acid and extensive washing, will show a strong blue colour characteristic of bound zinc phthalocyanine. Right; recombinant silk film without bound zinc phthalocyanine, washed with 70% MeOH.

Macrocycles that can act as photosensitizer can be bound within protein films generated from recombinant honeybee silk (FIG. 12). It can be expected that these materials ideally suited for photodynamic therapy.

Figure 13:
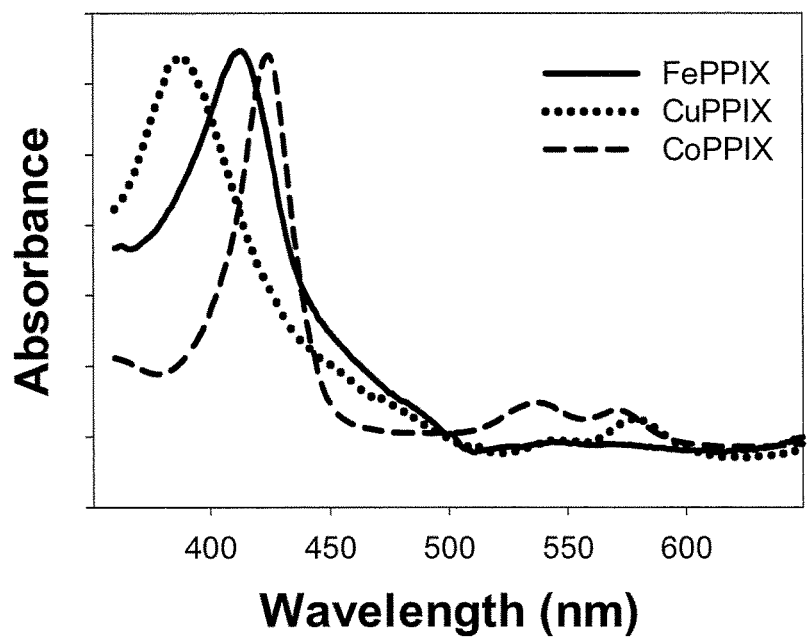
FIG. 13 shows the identity of the metal chelate may be varied, whilst maintaining the features of the invention. Different artificial porphyrins were introduced into honeybee silk films. UV/Vis spectra of honeybee silk films containing artificial porphyrin (copper protoporphyrin IX—CuPPIX), cobalt protoporphyrin IX (CoPPIX) and haem b (FePPIX). The ability to vary the metal ion can be used to alter the function of the composition. For example, CoPPIX could be used as nitric oxide sensor with improved sensitivity for nitric oxide and decreased affinity for molecular oxygen.

Example 12: The Composition of the Present Invention May Comprise Different Metal Ions FIG. 13 shows the metal ion of the chelate may be varied. Chelates including copper (CuPPIX), cobalt (CoPPIX) and haem b (FePPIX) were introduced into Amelf3 silk films. The ability to vary the metal ion can be used to alter the function of the composition, for example, different target compound binding.

Figure 14:
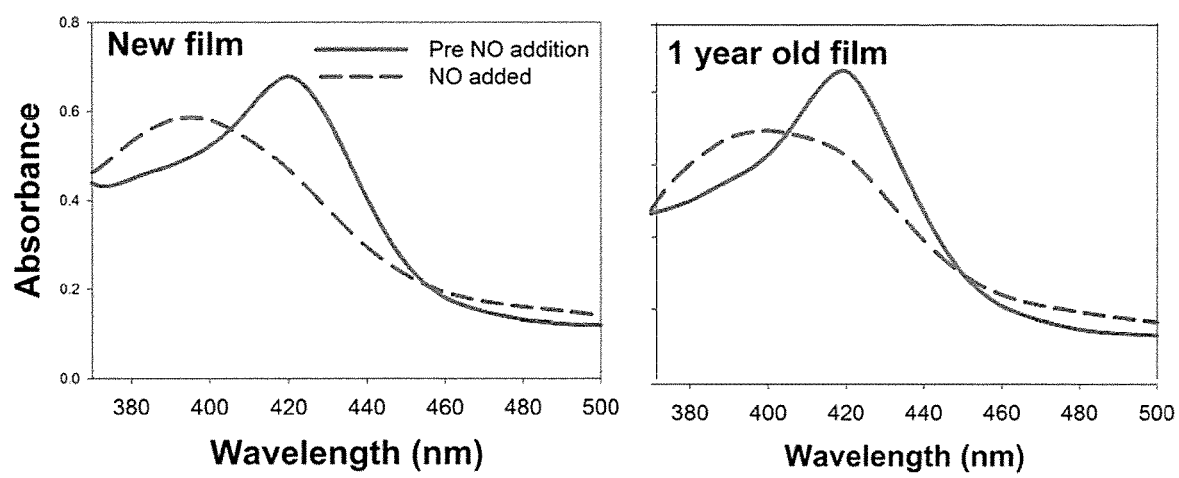
FIG. 14 shows an example of the stability of the compositions of the present invention. UV/Vis spectra were measured with freshly prepared (new film) and one year old (1 year old film) composite films comprising recombinant honeybee silk protein AmelF3 and bound haem b, showing that neither the position nor the intensity of the peak has changed, with prolonged storage at ambient room temperatures. Both the new film and one year old film were able to bind NO (dashed line).

Example 13: A Composition According to the Invention is Stable for at Least a Year AmelF3-haem b films showed remarkable stability; they could be stored dry at room temperature for at least one year, with no deterioration in NO binding ability (FIG. 14). This data also demonstrates the materials showed no deterioration of spectral signal over ten months.

Figure 15:
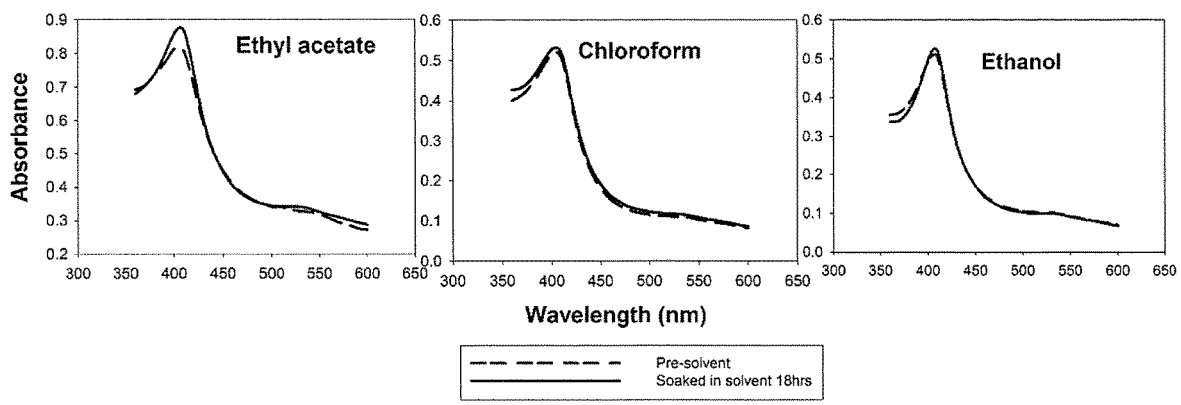
FIG. 15 shows that composite materials of the present invention are unchanged after exposure to a variety of different solvents. A. UV/Vis spectra (untreated: dashed line; treated: solid line) obtained from silk protein films generated from recombinant honeybee silk protein AmelF3 containing bound haem b after treatment with various solvents (left: ethyl acetate; middle: chloroform; right: ethanol) showing that the treatment did not significantly affect the position or intensity of the Soret peak. B. Sponges are unchanged after exposure to solvents for 24 hrs (no chelate was added to either the silk sponge or the solvent).

Example 14: A Composition According to the Invention is Stable in Organic Solvents The present inventors have demonstrated that the silk films and sponges are stable in a variety of different organic solvents. UV/Vis spectra of AmelF3 silk film in different solvents were recorded. FIG. 15 shows silk materials are stable in a variety of aqueous and non-aqueous solvents such as water, chloroform, ethyl acetate and ethanol. This data demonstrates compositions of the present invention can be used in catalytic applications where non-aqueous solvents are required.

Figure 16:
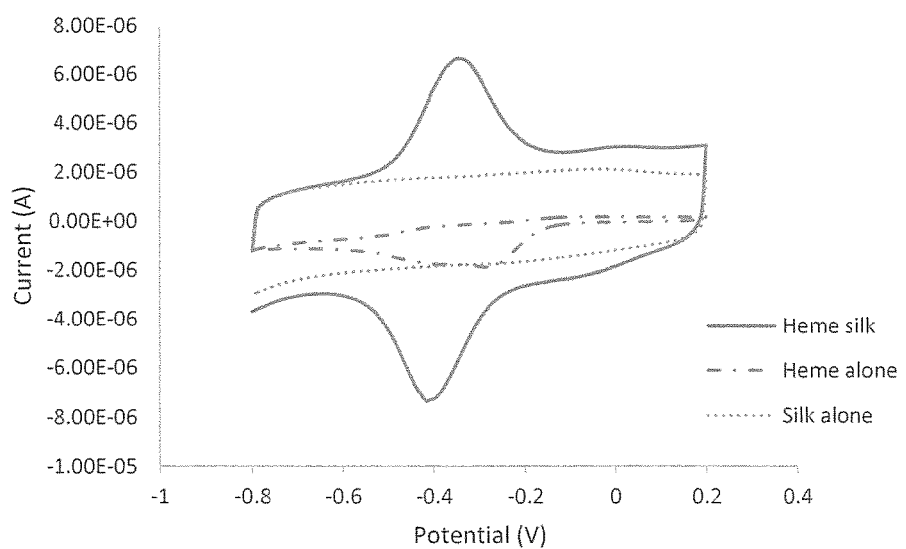
FIG. 16 shows an example of the use of haem-silk materials in electrochemical measurements. Haem b in AmelF3 films were cast onto glassy carbon electrode modified with carbon nanotubes. A clear reversible peak is seen which can be attributed to the $Fe^{3+}/Fe^{2+}$ redox couples. These redox peaks are not observed in the absence of heme (dotted line) or without AmelF3 silk (dashed-dotted line).

Example 15: A Composition of Haem-Silk Materials is Compatible with Electrochemical Signal Transduction A glassy carbon electrode was modified with carbon nanotubes by drying a dispersion of carbon nanotubes (single walled; 1-5 µm) in DMF. A film of AmelF3 was cast on top of the nanotube layer by drying a solution of AmelF3 in water (10 mg/ml). Haem b was leached into the AmelF3 as described previously from a 70% methanol solution. A reversible voltammetric response was noted for the haem b-AmelF3 samples which are not observed in the absence of heme (dotted line) or without AmelF3 silk (dashed-dotted line) and can be attributed to the Fe3+/Fe2+ redox couples. FIG. 16). This difference demonstrates that silk-haem materials are compatible with electrochemical signal transduction methods.

Figure 17:
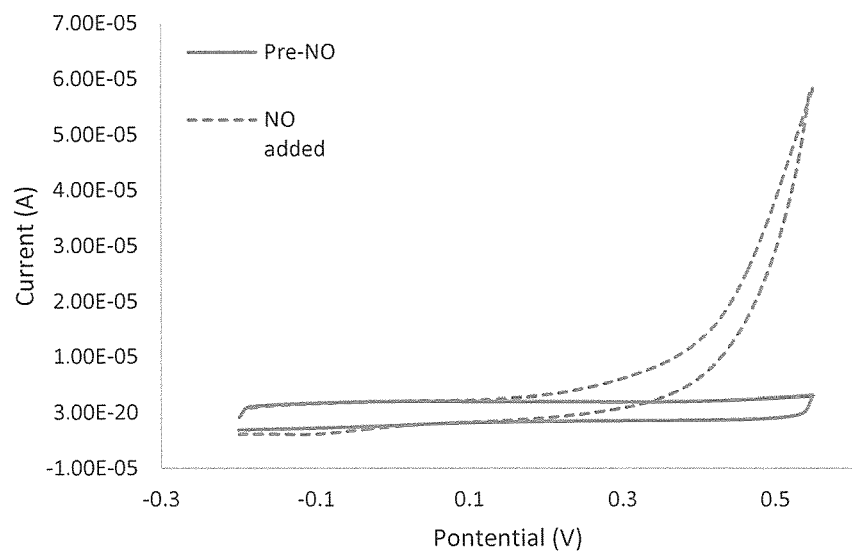
FIG. 17 shows the use of the haem-silk electrode prepared as described in Example 15 to detect nitric oxide. Upon the addition of nitric oxide a pronounced catalytic current is noted. This catalytic current is attributed to the oxidation of nitric oxide by haem-silk materials can be to determine the nitric oxide concentration in samples.

Example 16: A Composition of Haem-Silk Materials can be Used to Detect Nitric Oxide Using the electrode prepared as described in Example 15, upon the addition of nitric oxide a pronounced catalytic current is noted (FIG. 17). This catalytic current is attributed to the oxidation of nitric oxide by haem-silk materials can be used to determine the nitric oxide concentration in samples.

Figure 18:
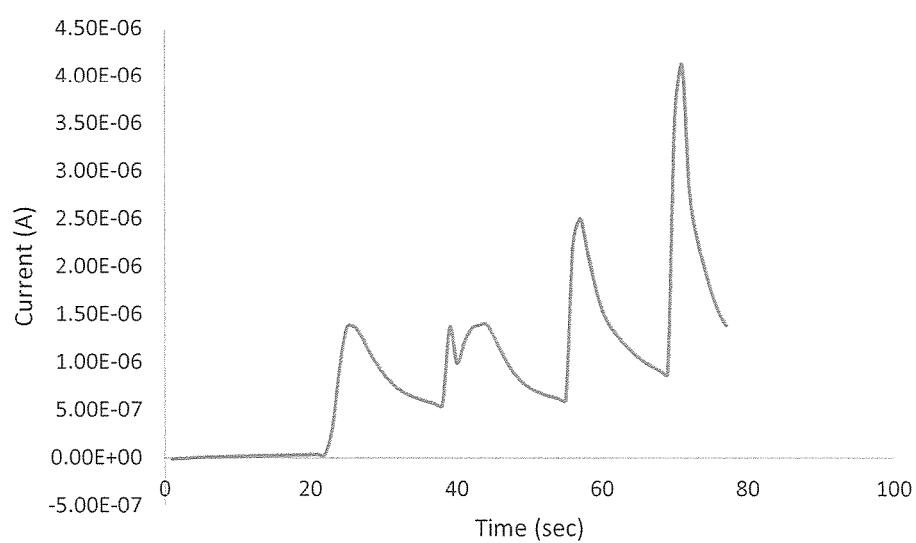
FIG. 18 shows the use of the haem-silk electrode prepared as described in Example 15 to detect oxygen. The electrode was held at a constant potential (−300 mV vs Ag/AgCl) under anaerobic conditions (through purging with argon gas). Aliquots of aerated buffer solution we added to introduce oxygen at varying concentrations. The sharp increase in catalytic current is due to the reduction of oxygen by haem-silk materials demonstrating that these materials can be used as an oxygen sensor.

Example 17: A Composition of Haem-Silk Materials can be Used to Detect Oxygen A haem-silk electrode was prepared as in Example 15. The electrode was held at a constant potential (−300 mV vs Ag/AgCl) under anaerobic conditions (through purging with argon gas). Aliquots of aerated buffer solution were added to introduce oxygen at varying concentrations. The sharp increase in catalytic current is due to the reduction of oxygen by haem-silk materials demonstrating that these materials can be used as an oxygen sensor (FIG. 18).

Example 18: An Additional Haem Binding Site can be Introduced into AmelF3

Figure 19:
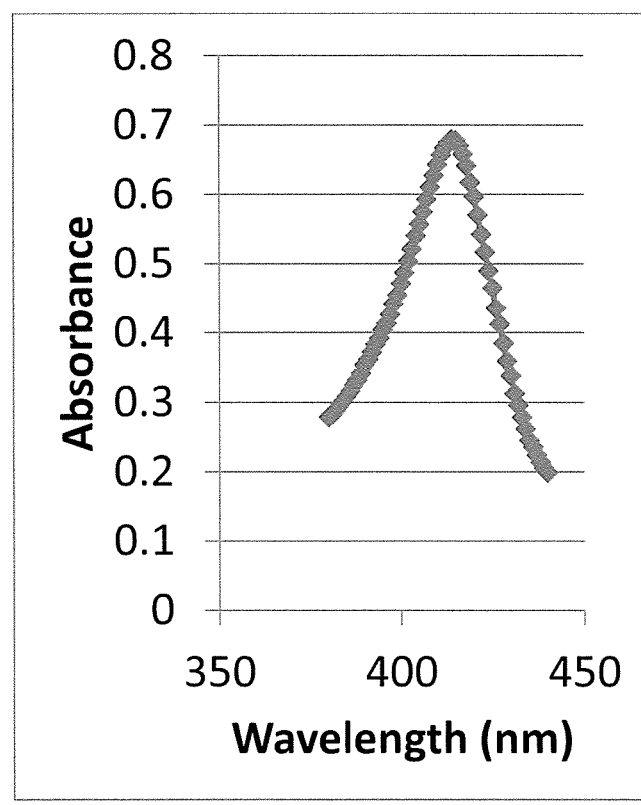
FIG. 19 shows that an additional haem binding site can be introduced into AmelF3. A coordinating His residue was introduced into AmelF3 with Y76A in the a-position of the coiled-coil. The resulting protein (Y76A A97H) showed a sharp Soret peak at 413 nm indicative of histidine coordination.

A coordinating His residue was introduced into AmelF3 with Y76A in the a-position of the coiled-coil. The resulting protein (Y76A A97H) showed a sharp Soret peak at 413 nm indicative of histidine coordination (FIG. 19). This demonstrates that additional binding sites can be introduced in coiled-coil polypeptides.

Example 19: Demonstration of Increased Heme Binding in AmelF3

Figure 20:
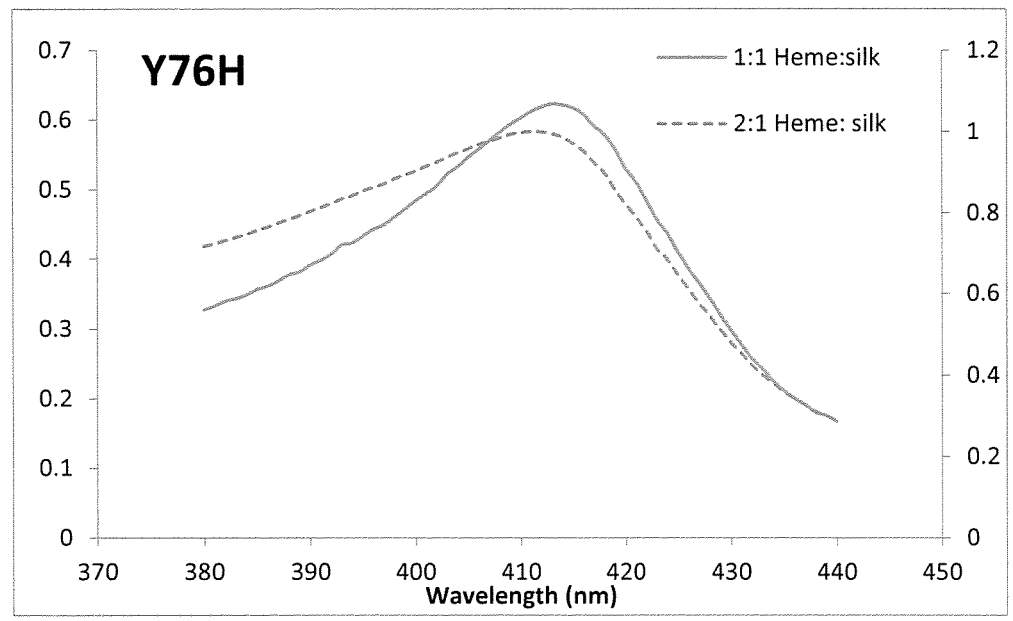
FIG. 20 demonstrates that heme binding in AmelF3 can be increased by addition of a further coordinating residue. A coordinating His residue (His97) was introduced into AmelF3 with Y76H substitution in the a-position of the coiled-coil. Y76H shows a distinct 1:1 ratio of heme binding to silk protein, indicated by the broadening of the Soret peaks a heme ratios above 1:1 and a shift in the position of the peak maxima.
Figure 20:
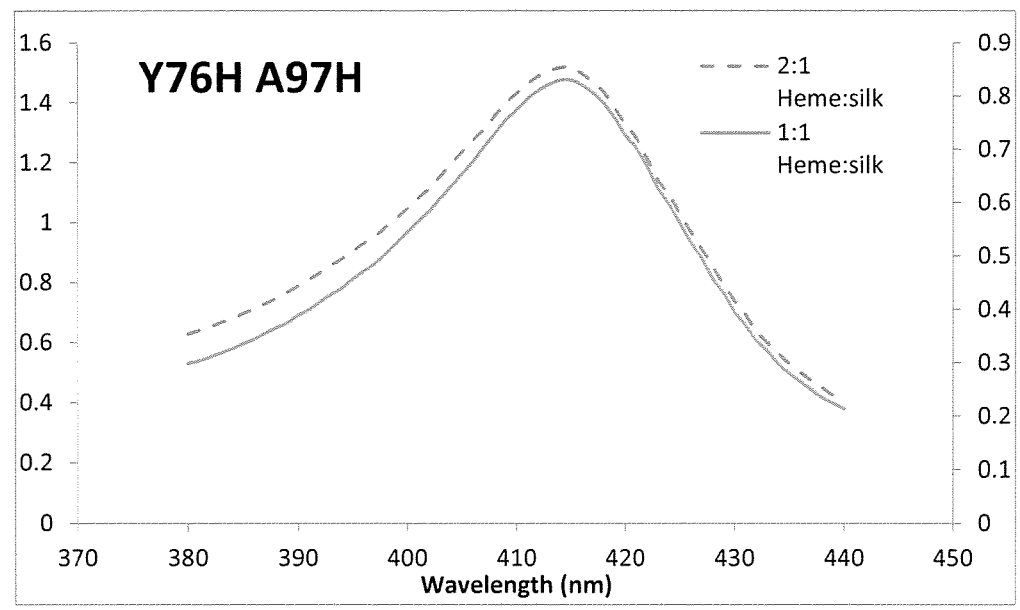

A coordinating His residue (His97) was introduced into AmelF3 with Y76H substitution in the a-position of the coiled-coil. Y76H shows a distinct 1:1 ratio of heme binding to silk protein, indicated by the broadening of the Soret peaks a heme ratios above 1:1 and a shift in the position of the peak maxima (FIG. 20). No change in both the shape and the position of the Soret peak was noted for Y76H A97H indicating that an extra heme binding site had been introduced and the modified AmelF3 was now able to bind two heme cofactors.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Eisenberg (1984) Annual Review of Biochemistry 53: 595-623.
Gorham et al (1992) Int. J. Biol. Macromol. 14: 129-136.
Harayama (1998) Trends in Biotechnology 16:76-82.
Huson et al. (2012) PLoS One 7, e52308.
Kallol et al. (2003) Journal of Chromatography 1000, 637-655.
Kweon et al. (2001) J. App. Polym. Sci. 81: 2271-2276.
Kyte and Doolittle (1982) Journal of Molecular Biology 157: 105-132.
Lupas and Gruber (2005) Ad. Protein Chem. 70:37-78.
Magoshi et al. (1977) J. Polym. Sci. 15: 1675-1683.
Nagai et al. (1983) Biochemistry 22: 1305-1311.
Nagai et al. (1989) Biochemistry 28, 2418-2422.
Needleman and Wunsch (1970) Journal of Molecular Biology 48:443-453.
Petersen et al. (2011) Nature Methods 8: 785-786.
Rapson et al. (2014) Biosens. Bioelectron, doi:10.1016/j.bios.2014.06.045.
Reiser et al. (1992) Nucleic Acids Research 32: W321-W326.
Rose and Wolfenden (1993) Annual Review of Biophysics and Biomolecular Structure 22: 381-415.
Sutherland et al. (2011) PLoS One 6: e16489.
Walker et al. (2012) Biomacromolecules 10: 4264-4272.
Weisman et al. (2010) Biomaterials 31: 2695-2700.
Wittmer et al. (2011) Acta Biomaterialia 7: 3789-3795.
Yannas and Tobolsky (1967) Nature 215: 509-510.

The invention claimed is:

1. A composition comprising:
   a silk polypeptide wherein at least a portion of the silk polypeptide has a coiled coil structure, wherein the silk polypeptide comprises at least 5 copies of the heptad sequence abcdefg, and wherein at least 15% of the amino acids at position a in the heptad repeats are alanine; and
   a chelate comprising a chelating agent and a metal ion; and
   wherein the chelate is bound to at least one amino acid of the silk polypeptide.

2. A composition of claim 1, wherein the chelating agent is bound to at least one amino acid of the silk polypeptide via electrostatic interactions.

3. A composition of claim 1, wherein the metal ion is bonded to at least one amino acid of the silk polypeptide by a co-ordinate bond.

4. A composition of claim 1 consisting of the silk polypeptide and the chelate.

5. A composition of claim 1, wherein the silk polypeptide comprises about 9 to about 30 heptad repeats.

6. A composition of claim 5, wherein the silk polypeptide comprises about 22 to about 28 heptad repeats.

7. A composition of claim 3, wherein the at least one amino acid bound to the metal ion by a co-ordinate bond is a Tyr, Cys, His, Met, Lys, Glu or a non-natural amino acid.

8. A composition of claim 1, wherein at least one amino acid residue bound to the chelating agent is a charged amino acid residue.

9. A composition of claim 1, wherein the chelating agent is selected from the group consisting of porphryins, corrins, chlorins, corphins, porphines and phthalocyanines.

10. A composition of claim 1, wherein the metal ion is an ion of a transition metal, alkali earth metal or p-block metal.

11. A composition of claim 1, wherein the composition is capable of binding a target compound.

12. A material comprising a composition of claim 1, wherein the composition comprises a plurality of the silk polypeptides which are crosslinked by ionic bonds, hydrogen bonds, covalent bonds or a combination thereof and the material is insoluble in water.

13. A sensor for detecting a target compound comprising a composition of claim 1.

14. A sensor of claim 13, wherein the target compound is selected from the group consisting of oxygen, carbon monoxide, carbon dioxide, compounds having an atom of P, S, or N, and mixtures thereof.

15. A sensor of claim 14, wherein the target compound is NO.

16. A sensor of claim 14, wherein the target compound is oxygen.

17. A sensor of claim 13, wherein binding of the target compound to the sensor results in a detectable change selected from colour, spectrophotometric, fluorescent or electrochemical change.

18. A sensor of claim 17, wherein the spectrophotometric change is a change in the Soret peak, or a change in at least one spectrophotometric peak with a wavelength between 500 and 600 nm.

19. A method of detecting a target compound, said method comprising the steps of
   (a) providing a sensor of claim 13, and
   (b) contacting the sensor with a target compound under conditions for binding said compound to said sensor.

20. The method of claim 19 which further comprises detecting binding of the target compound by detecting a change in the sensor upon binding to the target compound.

21. The composition of claim 1, wherein at least 25% of the amino acids at position a in the heptad repeats are alanine.

22. The composition of claim 1, wherein 30% to 70% of the amino acids at position a in the heptad repeats are alanine.

23. The composition of claim 1, wherein at least 25% of the amino acids at positions a and d are alanine residues.

* * * * *

SEQUENCE LISTING

```
<160> NUMBER OF SEQ ID NOS: 82

<210> SEQ ID NO 1
<211> LENGTH: 333
<212> TYPE: PRT
<213> ORGANISM: Apis mellifera

<400> SEQUENCE: 1

Met Lys Ile Pro Val Leu Leu Ala Thr Cys Leu Tyr Leu Cys Gly Phe
1               5                   10                  15

Ala Ser Ala Gly Leu Glu Gly Pro Gly Asn Ser Leu Pro Glu Leu Val
            20                  25                  30

Lys Gly Ser Ala Ser Ala Thr Ala Ser Thr Ala Val Thr Ala Arg Ser
        35                  40                  45

Gly Leu Arg Ala Gly Gln Val Ala Leu Ala Ser Gln Lys Asp Ala Val
    50                  55                  60

Leu Gln Ala Gln Ala Ala Ala Ser Ala Ala Ser Glu Ala Arg Ala Ala
65                  70                  75                  80

Ala Asp Leu Thr Ala Lys Leu Ser Gln Glu Ser Ala Ser Val Gln Ser
                85                  90                  95

Gln Ala Ala Ala Lys Gly Lys Glu Thr Glu Glu Ala Ala Val Gly Gln
            100                 105                 110

Ala Arg Ala Gly Leu Glu Ser Val Ser Met Ala Ala Ser Ala Thr Ser
```

-continued

```
                    115                 120                 125
Ala Ala Lys Glu Ala Ser Thr Ala Ala Lys Ala Ala Ser Ala Leu
            130                 135                 140

Ser Thr Ala Val Val Gln Ala Lys Ile Ala Glu Arg Ala Ala Lys Ala
145                 150                 155                 160

Glu Ala Val Ala Ser Asp Glu Ala Lys Lys Ala Ile Ala Ala Ala
                165                 170                 175

Asn Leu Ala Ala Glu Ala Ser Val Ala Ala Glu Ala Ala Leu Lys Ala
                    180                 185                 190

Glu Lys Val Ala Glu Glu Ala Ile Ala Arg Ala Ala Ser Ala Lys Ala
            195                 200                 205

Ala Ala Arg Ala Ala Ala Ala Ala Leu Ala Ser Ser Lys Glu Ala Ala
                210                 215                 220

Thr Ala Ser Ala Arg Asn Ala Ala Glu Ser Gly Ala Arg Asn Glu Val
225                 230                 235                 240

Ala Val Leu Ile Ala Glu Ile Asp Lys Lys Ser Arg Glu Ile Asp Ala
                    245                 250                 255

Ala Ser Ser Leu Asn Ala Arg Ala Ala Ala Lys Ala Ser Ser Arg Asn
                260                 265                 270

Val Glu Thr Ala Thr Ile Gly Ala Asn Ile Asn Ser Ser Lys Gln Val
                275                 280                 285

Val Ser Ile Pro Val Glu Ile Lys Lys Phe Ser Glu Pro Glu Val Ser
                290                 295                 300

Thr Ser Trp Arg Glu Asp Glu Glu Val Thr Lys Glu Lys Lys Glu His
305                 310                 315                 320

Ile Asn Leu Asn Asp Phe Asp Leu Lys Ser Asn Val Phe
                    325                 330

<210> SEQ ID NO 2
<211> LENGTH: 309
<212> TYPE: PRT
<213> ORGANISM: Apis mellifera

<400> SEQUENCE: 2

Met Lys Ile Pro Ala Ile Phe Val Thr Ser Leu Leu Val Trp Gly Leu
1               5                   10                  15

Ala Glu Gly Arg Val Ile Asn His Glu Ser Leu Lys Thr Ser Glu Asp
                20                  25                  30

Ile Gln Gly Gly Tyr Ser Ala Gly Ile Val Gly Asp Gly Ser Asp Ala
            35                  40                  45

Leu Gly Ser Ser Ile Glu Asn Ala Gln Lys Val Ala Arg Ala Ala Glu
        50                  55                  60

Asn Val Gly Leu Asn Leu Glu Leu Gly Ala Gly Ala Arg Ala Ala Ser
65                  70                  75                  80

Val Ala Ala Ala Ala Gln Ala Lys Asn Thr Glu Ala Ala Glu Ala Gly
                85                  90                  95

Ala Asn Ala Ala Leu Ala Ala Ala Ile Ala Lys Arg Glu Glu Ala Ile
                100                 105                 110

Lys Ala Ser Glu Ile Ala Asn Gln Leu Leu Thr Asn Ala Ala Lys Ala
            115                 120                 125

Ala Glu Ala Thr Val Ser Ala Thr Lys Arg Ala Ala Gln Leu Thr Ala
        130                 135                 140

Ala Ala Lys Glu Ala Thr Arg Ala Ser Ala Ala Ala Glu Ala Ala
145                 150                 155                 160
```

```
Thr Glu Ala Gln Val Lys Ala Asn Ala Asp Ser Ile Ile Thr Lys Arg
                165                 170                 175
Ala Ala Ile Ala Glu Ala Gln Ala Ala Glu Ala Gln Val Lys Ala
        180                 185                 190
Ala Ile Ala Arg Lys Ser Ala Ala Asn Phe Leu Ala Lys Ala Gln Ile
        195                 200                 205
Ala Ala Ala Ala Glu Ser Glu Ala Thr Lys Leu Ala Ala Glu Ala Val
        210                 215                 220
Val Ala Leu Thr Asn Ala Glu Val Ala Val Asn Gln Ala Arg Asn Ala
225                 230                 235                 240
Gln Ala Asn Ala Ser Thr Gln Ala Ser Met Ala Val Arg Val Asp Ser
            245                 250                 255
Gln Ala Ala Asn Ala Glu Ala Ala Val Ala Gln Ala Glu Thr Leu
            260                 265                 270
Leu Val Thr Ala Glu Ala Val Ala Ala Glu Ala Glu Val Ala Asn
    275                 280                 285
Lys Ala Ala Thr Phe Ala Lys Gln Ile Val Asn Glu Lys Lys Ile His
    290                 295                 300
Val Ala Lys Leu Glu
305

<210> SEQ ID NO 3
<211> LENGTH: 335
<212> TYPE: PRT
<213> ORGANISM: Apis mellifera

<400> SEQUENCE: 3

Met Gln Ile Pro Thr Phe Val Ala Ile Cys Leu Leu Thr Ser Gly Leu
1               5                   10                  15
Val His Ala Gly Val Glu Glu Phe Lys Ser Ser Ala Thr Glu Glu Val
            20                  25                  30
Ile Ser Lys Asn Leu Glu Val Asp Leu Leu Lys Asn Val Asp Thr Ser
        35                  40                  45
Ala Lys Arg Arg Glu Asn Gly Ala Pro Val Leu Gly Lys Asn Thr Leu
    50                  55                  60
Gln Ser Leu Glu Lys Ile Lys Thr Ser Ala Ser Val Asn Ala Lys Ala
65                  70                  75                  80
Ala Ala Val Val Lys Ala Ser Leu Ala Leu Ala Glu Ala Tyr Leu
            85                  90                  95
Arg Ala Ser Ala Leu Ser Ala Ala Ser Lys Ala Ala Ala
        100                 105                 110
Leu Lys Asn Ala Gln Gln Ala Gln Leu Asn Ala Gln Glu Lys Ser Leu
    115                 120                 125
Ala Ala Leu Lys Ala Gln Ser Glu Glu Ala Ala Ser Ala Arg Ala
        130                 135                 140
Asn Ala Ala Thr Ala Ala Thr Gln Ser Ala Leu Glu Arg Ala Gln Ala
145                 150                 155                 160
Ser Ser Arg Leu Ala Thr Val Ala Gln Asn Val Ala Ser Asp Leu Gln
            165                 170                 175
Lys Arg Thr Ser Thr Lys Ala Ala Ala Glu Ala Ala Thr Leu Arg
        180                 185                 190
Gln Leu Gln Asp Ala Glu Arg Thr Lys Trp Ser Ala Asn Ala Ala Leu
    195                 200                 205
Glu Val Ser Ala Ala Ala Ala Ala Glu Thr Lys Thr Thr Ala Ser
        210                 215                 220
```

```
Ser Glu Ala Ala Asn Ala Ala Lys Lys Ala Ala Ile Ala Ser
225                 230                 235                 240

Asp Ala Asp Gly Ala Glu Arg Ser Ala Ser Thr Glu Ala Gln Ser Ala
                245                 250                 255

Ala Lys Ile Glu Ser Val Ala Ala Glu Gly Ser Ala Asn Ser Ala
            260                 265                 270

Ser Glu Asp Ser Arg Ala Ala Gln Leu Glu Ala Ser Thr Ala Ala Arg
                275                 280                 285

Ala Asn Val Ala Ala Val Gly Asp Gly Ala Ile Ile Gly Leu Gly
            290                 295                 300

Glu Glu Ala Gly Ala Ala Ala Gln Leu Leu Ala Gln Ala Lys Ala Leu
305                 310                 315                 320

Ala Glu Val Ser Ser Lys Ser Glu Asn Ile Glu Asp Lys Lys Phe
            325                 330                 335

<210> SEQ ID NO 4
<211> LENGTH: 342
<212> TYPE: PRT
<213> ORGANISM: Apis mellifera

<400> SEQUENCE: 4

Met Lys Ile Pro Ser Ile Leu Ala Val Ser Leu Leu Ile Trp Gly Leu
1               5                   10                  15

Ala Ser Gly Ala Arg Glu Val Glu Thr Arg Asp Lys Thr Lys Thr
            20                  25                  30

Ser Thr Val Val Lys Ser Glu Lys Val Glu Val Val Ala Pro Ala Lys
                35                  40                  45

Asp Glu Leu Lys Leu Thr Ser Glu Pro Ile Phe Gly Arg Arg Val Gly
    50                  55                  60

Thr Gly Ala Ser Glu Val Ala Ser Ser Gly Glu Ala Ile Ala Ile
65              70                  75                  80

Ser Leu Gly Ala Gly Gln Ser Ala Ala Glu Ser Gln Ala Leu Ala Ala
                85                  90                  95

Ser Gln Ser Lys Thr Ala Ala Asn Ala Ala Ile Gly Ala Ser Glu Leu
            100                 105                 110

Thr Asn Lys Val Ala Ala Leu Val Ala Gly Ala Thr Gly Ala Gln Ala
            115                 120                 125

Arg Ala Thr Ala Ala Ser Ser Ser Leu Lys Ala Ser Leu Ala Thr
130                 135                 140

Glu Glu Ala Ala Glu Ala Glu Ala Val Ala Asp Ala Lys Ala
145                 150                 155                 160

Ala Ala Glu Lys Ala Glu Ser Leu Ala Lys Asn Leu Ala Ser Ala Ser
                165                 170                 175

Ala Arg Ala Ala Leu Ser Ser Glu Arg Ala Asn Glu Leu Ala Gln Ala
            180                 185                 190

Glu Ser Ala Ala Ala Glu Ala Gln Ala Lys Thr Ala Ala Ala Ala
    195                 200                 205

Lys Ala Ala Glu Ile Ala Leu Lys Val Ala Glu Ile Ala Val Lys Ala
210                 215                 220

Glu Ala Asp Ala Ala Ala Ala Val Ala Ala Lys Ala Arg Ala
225                 230                 235                 240

Val Ala Asp Ala Ala Ala Arg Ala Ala Val Asn Ala Ile Ala
            245                 250                 255

Lys Ala Glu Glu Glu Ala Ser Ala Gln Ala Glu Asn Ala Ala Gly Val
```

```
              260                 265                 270
Leu Gln Ala Ala Ser Ala Ala Glu Ser Arg Ala Ala Ala
        275                 280                 285
Ala Ala Ala Ala Thr Ser Glu Ala Ala Glu Ala Gly Pro Leu Ala
        290                 295                 300
Gly Glu Met Lys Pro Pro His Trp Lys Trp Glu Arg Ile Pro Val Lys
305                 310                 315                 320
Lys Glu Glu Trp Lys Thr Ser Thr Lys Glu Gly Trp Lys Thr Thr Asn
                325                 330                 335
Glu Glu Trp Glu Val Lys
            340

<210> SEQ ID NO 5
<211> LENGTH: 1002
<212> TYPE: DNA
<213> ORGANISM: Apis mellifera

<400> SEQUENCE: 5
atgaagattc cagtattgct tgcaacgtgc ctctaccttt gcggatttgc gtccgccggt     60 ttggagggc cgggcaactc gttgcccgag ctcgtgaaag gtagcgcatc ggccaccgcg    120
tcgaccgctg tgaccgctag atcaggactt agagccggac aagtagcttt agcttcgcag    180
aaggatgccg tactccaagc tcaagctgct gcatccgccg cgtcagaggc gcgcgctgct    240
gccgatctga cggctaaact tagccaagaa tcggcatcag tgcaatcgca ggctgccgcc    300
aaagggaagg aaacggagga ggcagctgtt ggtcaagcta gggctggcct cgagtcggtg    360
tccatggccg catcagccac atctgctgcc aagaagcat cgaccgccgc caaagccgca    420
gcatccgcac tatccacagc cgtggtgcaa gcgaaaatag ctgagagggc agccaaagct    480
gaagctgttg cctcggacga agccaaggcc aaggcgattg cagcagccaa cttggcggct    540
gaggccagtg tagccgcaga agcagctctc aaggccgaga agtggccga agaagccatc    600 gcaagagcgg cctctgcaaa ggctgccgca agagctgctg ctgccgctct agcctcctcg    660
aaggaagcag ccacggccag cgcaagaaac gccgcggaat ccgaggccag gaacgaagta    720
gctgtattga tcgccgagat tgataaaaag gtaggaaa tcgacgcagc cagttcgctt    780
aatgcgcgtg ccgctgccaa ggcaagctcc aggaacgtag aaacggcgac aatcggggcc    840
aacatcaact cttcgaaaca gtcgtgtca attccagtgg aaataaagaa attctcggag    900
ccggaagtgt caacatcatg gagagaagat gaagaggtta cgaaagagaa aaggagcac    960 ataaatctga cgacttcga cttgaagagc aacgtatttt ag                       1002

<210> SEQ ID NO 6
<211> LENGTH: 930
<212> TYPE: DNA
<213> ORGANISM: Apis mellifera

<400> SEQUENCE: 6
atgaagattc cagcaatatt cgtcacgtct ctgctggtct ggggattggc cgagggccgc     60
gtgattaatc acgagtccct gaagacgagc gaggatattc aaggaggata ttcagcagga    120
atagtcggtg atggatctga cgcgcttggc tcctccatag aaaacgccca aaaagtcgct    180
cgagcggctg aaaacgtggg cttgaatctg gaattgggcg caggcgcgcg tgctgccagt    240
gttgccgctg ctgcccaggc caaaaacaca gaggctgcgg aagcaggagc aaacgccgct    300
ctggccgccg ccattgccaa acgggaggaa gcgattaaag ccagcgagat agcaaaccaa    360
```

```
ttgttgacca atgcagcaaa agcggcagaa gcgactgtat cggcaacgaa gagggcagca      420
caattgacgg ctgcagcgaa agaagcaacc agagcttctg cagccgctgc tgaagctgct      480
acggaggccc aggtaaaggc taacgccgat tcaatcatca cgaagagggc tgcgattgcc      540
gaggctcaag ctgcggcgga agctcaagtt aaggcggcaa tcgccagaaa tcggcagcg       600 aatttttttgg ctaaggctca aatagcggct gccgcggaat ccgaggccac gaaactcgcg     660
gccgaagctg tagtggcact aacaaacgcc gaagtcgccg tgaaccaggc tagaaacgca      720
caggcaaacg cctcgactca agcttccatg gctgttaggg tagattctca agcagcgaac      780
gctgaagcag ccgctgtagc gcaagccgaa actctcttgg ttacggcaga gctgtcgca       840 gctgcggagg ctgaggttgc gaacaaagcc gccacatttg caaaacagat cgtcaacgag      900
aagaaaatac atgtagcaaa gttggaataa                                      930
```

<210> SEQ ID NO 7
<211> LENGTH: 1008
<212> TYPE: DNA
<213> ORGANISM: Apis mellifera

<400> SEQUENCE: 7

```
atgcagatcc caacgtttgt cgccatatgc ttgctcacat cgggcttggt gcacgcaggc       60
gtcgaggaat tcaagtcctc ggcaaccgag gaggtgatca gcaaaaactt agaagtcgac      120
ctgttgaaaa atgtggacac tagcgcgaaa cgaagagaga acggcgcccc ggtgctcggc      180
aagaacacac ttcaatccct ggagaagatc aagacgtcgg cgagcgtgaa tgccaaagca      240
gcagccgtgg tgaaagcgtc cgctctggct cttgcagagg cctatttgcg agcgtccgca      300
ttgtcagccg ccgcttcagc caaggcagcc gccgccctga aaaatgctca acaagcgcaa      360
ttaaacgccc aggaaaagtc tttggccgcg ttgaaagctc agtccgagga agaggcagct      420
tctgctcgtg caaacgcagc aaccgccgcg acacagtcgg cactggaacg cgctcaagcc      480
tcctccaggt tagcaacggt cgcccaaaac gtagccagcg acttgcagaa acggaccagc      540
accaaggccg cggctgaagc cgctgccacc ctcagacaat tacaggacgc ggaacgaacg      600
aaatggagtg ccaacgctgc cttagaagtc tccgccgctg cagctgccgc agaaaccaag      660
accactgcct cctcggaggc cgccaacgcc gccgccaaaa aggcggccgc gatagcttct      720
gacgcggacg cgcggaaag gtcggcatct accgaggcac aatcagctgc gaagatcgag      780
agtgtggcag ccgccgaggg atccgccaac tcggcctctg aggattcccg gccgctcaa      840 ttggaagcct ccaccgcggc gagagccaac gtggccgcag ctgtcgggga tggagcgatt      900
ataggacttg gagaggaagc gggtgccgcg gctcagttgc ttgcacaggc gaaggcattg      960
gccgaagtta gctcgaaatc cgaaaatatt gaggataaaa aattttga               1008
```

<210> SEQ ID NO 8
<211> LENGTH: 1029
<212> TYPE: DNA
<213> ORGANISM: Apis mellifera

<400> SEQUENCE: 8

```
atgaagatcc catccatact cgcggtttcc ctgctgatct ggggtttggc aagcggcgca       60
agggaagagg tggagacacg ggacaagacc aagacctcga cagtggtgaa aagcgagaaa      120
gtggaagtcg ttgctcccgc taaggatgaa cttaaattaa cgagcgagcc tatctttgga      180
agaagagtgg gaactggagc atccgaggtg gcatctagca gcggtgaagc catcgcgata      240
agtcttggag cagggcagtc agcggcagag tctcaggcct tggccgcctc gcaatccaaa      300
```

-continued

```
acggcagcga acgccgccat aggcgcgagc gagcttacca acaaagttgc tgctctagtt    360
gctggcgcga ctggtgcgca ggcgagagct acggccgcct cctcgagcgc gttgaaggcc    420
agcttggcga ccgaagaagc ggcggaagag gccgaggcgg ccgtggctga cgccaaggct    480
gccgcggaaa aggccgaatc cctggcgaaa aatctcgcgt cggcgagcgc tcgcgcggcc    540
ctctcctccg aaagggcgaa cgaattggct caagctgaga gcgctgcagc ggccgaggcg    600
caggccaaga cagcagccgc cgccaaagca gcggaaatcg cccttaaggt cgctgagata    660
gcggtgaagg cggaagcgga cgcagcagct gccgccgtgg cagctgcaaa ggcaagagcc    720
gtggcagacg cggccgctgc ccgtgccgca gccgtgaacg ccatcgccaa gcggaagag     780
gaggcctcgg cccaagcaga aacgccgcc ggtgttttgc aagcagccgc tccgccgcg     840
gcggaatcgc gagccgctgc agctgccgcc gctgctacct cggaggcagc ggctgaagct    900
ggcccgttgg caggtgagat gaaaccaccg cactggaaat gggaacggat tcctgtgaag    960
aaggaggagt ggaaaacgtc aacgaaggaa gaatggaaaa cgacgaatga agaatgggag   1020
gtgaagtaa                                                           1029

<210> SEQ ID NO 9
<211> LENGTH: 391
<212> TYPE: PRT
<213> ORGANISM: Oecophylla smaragdina

<400> SEQUENCE: 9

Met Lys Ile Pro Ala Ile Ile Ala Thr Thr Leu Leu Leu Trp Gly Phe
1               5                   10                  15

Ala Asp Ala Ser Lys Ser Tyr Leu Leu Gly Ser Ser Ala Ser Ala Ser
                20                  25                  30

Ala Ser Ala Ser Ala Ser Ala Ser Ala Gly Gly Ser Thr Gly Gly Val
            35                  40                  45

Gly Val Gly Ser Val Ile Ser Gly Gly Asn Asn Ile Ile Arg Gly Ala
        50                  55                  60

Ser Thr Thr Ser Val Thr Leu Ala Ala Ala Ala Glu Ala Lys Ala
65                  70                  75                  80

Ala Leu Asn Ala Gly Lys Ala Thr Val Glu Glu Gln Arg Glu Ala Leu
                85                  90                  95

Gln Leu Leu Thr Ala Ser Ala Glu Lys Asn Ala Glu Ala Arg Ser Leu
            100                 105                 110

Ala Asp Asp Ala Ala Val Leu Val Gln Gly Ala Ala Glu Ala Gln Ser
        115                 120                 125

Val Ala Ala Ala Lys Thr Val Ala Val Glu Gln Gly Ser Asn Ser Leu
    130                 135                 140

Asp Ala Ala Ala Ala Glu Ala Glu Ala Ala Ala Ala Ser Arg Val
145                 150                 155                 160

Ser Ala Gln Gln Ala Leu Gln Ala Ala Gln Thr Ser Ala Ala Ile
                165                 170                 175

Gln Thr Ala Ala Gly Ser Ala Leu Thr Ala Leu Lys Leu Ala Arg Lys
            180                 185                 190

Gln Glu Ala Glu Ser Asn Asn Ala Ala Glu Gln Ala Asn Lys Ala Leu
        195                 200                 205

Ala Leu Ser Arg Ala Ala Ser Ala Ala Thr Gln Arg Ala Val Ala Ala
    210                 215                 220

Gln Asn Ala Ala Ala Ser Ala Ala Ser Ala Gly Ala Ala Gln Ala
225                 230                 235                 240
```

Glu Ala Arg Asn Ala Tyr Ala Lys Ala Ala Ile Ala Ala Leu
            245                 250                 255

Thr Ala Ala Gln Arg Asn Tyr Ala Ala Lys Ala Ser Ala Ser Ala
            260                 265                 270

Gly Ser Val Val Ala Glu Gln Asp Ala Gln Ser Arg Ala Ala Asp Ala
            275                 280                 285

Glu Val Asn Ala Val Ala Gln Ala Ala Arg Ala Ser Val Arg Asn
            290                 295                 300

Gln Glu Ile Val Glu Ile Gly Ala Glu Phe Gly Asn Ala Ser Gly Gly
305                 310                 315                 320

Val Ile Ser Thr Gly Thr Arg Ser Ser Gly Lys Gly Val Ser Val
            325                 330                 335

Thr Ala Gly Ala Gln Ala Ser Ala Ser Ala Ser Ala Thr Ser Ser Ser
            340                 345                 350

Ser Ser Ser Ser Gly Ile Asn Lys Gly His Pro Arg Trp Gly His Asn
            355                 360                 365

Trp Gly Leu Gly Ser Ser Glu Ala Ser Ala Asn Ala Glu Ala Glu Ser
            370                 375                 380

Ser Ala Ser Ser Tyr Ser Ser
385                 390

<210> SEQ ID NO 10
<211> LENGTH: 400
<212> TYPE: PRT
<213> ORGANISM: Oecophylla smaragdina

<400> SEQUENCE: 10

Met Lys Ile Pro Ala Ile Phe Val Thr Ser Leu Leu Ala Trp Gly Leu
1               5                   10                  15

Ala Ser Gly Gly Val Ile Gly Pro Asp Thr Ser Ser Ser Ser Gln Ala
            20                  25                  30

Ser Ala Ser Ala Ser Ala Ser Ala Ser Ala Ser Ala Ser Ser Ser Ala
            35                  40                  45

Ser Ile Gly Tyr Asn Glu Leu His Lys Ser Ile Asn Ala Pro Ala Leu
        50                  55                  60

Ala Val Gly Val Lys Asn Gly Gly Val Asp Val Ala Lys Gly Ala Ala
65                  70                  75                  80

Val Val Glu Ser Ala Ile Ser Asp Val Ser Thr Leu Thr Asp Asp Arg
            85                  90                  95

Thr Leu Asn Gly Leu Ala Ile Ile Gly Asn Ser Ala Glu Ser Leu Ala
            100                 105                 110

Arg Ala Gln Ala Ser Ser Ala Ser Ala Gly Ala Lys Ala Asn Ala
            115                 120                 125

Leu Ile Lys Gln Ser Ile Ala Ala Ile Glu Ile Thr Glu Lys Ala Glu
130                 135                 140

Tyr Leu Ala Ser Ile Val Ala Thr Lys Ala Ala Lys Ala Ala Glu Ala
145                 150                 155                 160

Thr Ala Ala Ala Thr Ala Arg Ala Thr Ala Val Ala Glu Ala Ala Lys
            165                 170                 175

Val Ser Ser Glu Gln Phe Ala Ala Glu Ala Arg Ala Ala Asp Ala
            180                 185                 190

Glu Ala Lys Ala Asn Ala Ala Ser Ile Ile Ala Asn Lys Ala Asn Ala
            195                 200                 205

Val Leu Ala Glu Ala Ala Thr Gly Leu Ser Ala Ser Ala Gly Lys Ala

```
            210                 215                 220
Gln Gln Ser Ala Thr Arg Ala Leu Gln Ala Ala Arg Ala Ala Ala Lys
225                 230                 235                 240

Ala Gln Ala Glu Leu Thr Gln Lys Ala Ala Gln Ile Leu Val Leu Ile
                245                 250                 255

Ala Glu Ala Lys Ala Ala Val Ser Arg Ala Ser Ala Asp Gln Ser Val
            260                 265                 270

Cys Thr Ser Gln Ala Gln Ala Ala Ser Gln Ile Gln Ser Arg Ala Ser
        275                 280                 285

Ala Ala Glu Ser Ala Ala Ser Ala Gln Ser Glu Ala Asn Thr Ile Ala
    290                 295                 300

Ala Glu Ala Val Ala Arg Ala Asp Ala Glu Ala Ala Ser Gln Ala Gln
305                 310                 315                 320

Ala Trp Ala Glu Ser Phe Lys Arg Glu Leu Ser Ser Val Val Leu Glu
                325                 330                 335

Ala Glu Ala Asn Ala Ser Ala Ser Ala Ser Ala Gly Ala Leu Ala Ser
            340                 345                 350

Gly Ser Ser Ser Gly Ala Ser Ser Ala Asp Ala Ser Ala Gly
        355                 360                 365

Ala Ser Ser Tyr Gly Ser Leu Gly Gly Tyr Arg His Gly Gly Ser Phe
    370                 375                 380

Ser Glu Ala Ser Ala Ala Ala Ser Ala Ala Ser Arg Ala Glu Ala Ala
385                 390                 395                 400

<210> SEQ ID NO 11
<211> LENGTH: 395
<212> TYPE: PRT
<213> ORGANISM: Oecophylla smaragdina

<400> SEQUENCE: 11

Met Lys Ile Pro Ala Ile Leu Val Thr Ser Phe Leu Ala Trp Gly Leu
1               5                   10                  15

Ala Ser Gly Gly Val Pro Lys Glu Leu Gly Thr Ser Ile Ser Ser Ala
            20                  25                  30

Ser Ala Ser Ala Ser Ala Ser Ala Thr Ala Ser Ser Ser Ser
        35                  40                  45

Lys Asn Val His Leu Leu Pro Leu Lys Ser Glu His Gly Ile Val Ile
    50                  55                  60

Asp Lys Ser Lys Phe Asn Ile Arg Lys Val Val Leu Ser Ala Ile Asp
65                  70                  75                  80

Glu Ile Asn Gly Ala Pro Asn Ile Gly Leu Gly Lys Gln Val Ser
                85                  90                  95

Leu Ala Leu Ala Lys Ala Gln Ala Ser Ala Gln Ser Ser Ala Glu Ala
            100                 105                 110

Leu Ala Ile Ile Lys Lys Ile Val Ala Leu Leu Ile Ser Ala Tyr Val
        115                 120                 125

Arg Ala Ala Glu Ala Ala Ala Arg Ala Ser Ala Glu Ala Leu Ala Thr
    130                 135                 140

Val Arg Ala Ala Glu Gln Ala Gln Lys Ile Ala Glu Ala Lys Gly Arg
145                 150                 155                 160

Ala Ala Ala Glu Ala Leu Ser Glu Leu Val Glu Ala Ser Gln Lys Ala
                165                 170                 175

Asp Ala Ala Ala Gly Thr Thr Asp Ala Ile Glu Arg Thr Tyr Gln
            180                 185                 190
```

```
Asp Ala Arg Ala Ala Thr Ser Ala Gln Thr Lys Ala Ser Gly Glu Ala
            195                 200                 205

Glu Asn Ala Asn Arg Asn Ala Ala Thr Leu Ala Ala Val Leu Ser
210                 215                 220

Ile Ala Lys Ala Ala Ser Gly Gln Gly Gly Thr Arg Ala Ala Val Asp
225                 230                 235                 240

Ala Ala Ala Ala Ala Ala Ala Ala Leu His Ala Lys Ala Asn
            245                 250                 255

Ala Val Ser Gln Ala Thr Ser Lys Ala Ala Glu Ala Arg Val Ala
            260                 265                 270

Ala Glu Glu Ala Ala Ser Ala Gln Ala Ser Ala Ser Ala Gln
            275                 280                 285

Leu Thr Ala Gln Leu Glu Glu Lys Val Ser Ala Asp Gln Gln Ala Ala
290                 295                 300

Ser Ala Ser Thr Asp Thr Ser Ala Ala Ile Ala Glu Ala Glu Ala Ala
305                 310                 315                 320

Ala Leu Ala Ser Thr Val Asn Ala Ile Asn Asp Gly Val Val Ile Gly
                325                 330                 335

Leu Gly Asn Thr Ala Ser Ser Ala Gln Ala Ser Ala Gln Ala Ser
            340                 345                 350

Ala Leu Ala Arg Ala Lys Asn Ala Arg Pro Lys Ile Lys Gly Trp Tyr
            355                 360                 365

Lys Ile Gly Gly Ala Thr Ser Ala Ser Ala Ser Ala Ser Ala
370                 375                 380

Ser Ala Gln Ser Ser Gln Gly Leu Val Tyr
385                 390                 395

<210> SEQ ID NO 12
<211> LENGTH: 443
<212> TYPE: PRT
<213> ORGANISM: Oecophylla smaragdina

<400> SEQUENCE: 12

Met Lys Ile Pro Ala Ile Leu Ala Thr Ser Leu Phe Val Trp Gly Leu
1               5                   10                  15

Val Gly Ala Ser Glu Leu Val Gly Ser Asp Ala Ser Ala Thr Ala Ser
                20                  25                  30

Ala Glu Ala Ser Ala Ser Ser Ala Tyr Gly Ser Lys Tyr Gly Ile
            35                  40                  45

Gly Ser Gly Ala Val Ser Gly Ala Ser Ala Ser Ala Ser Ala
        50                  55                  60

Ser Ala Ser Ala Ser Ala Ser Ser Ala Pro Ala Ile Glu Gly Val Asn
65                  70                  75                  80

Val Gly Thr Gly Val Ser Asn Thr Ala Ser Ala Ser Ala Glu Ala Leu
                85                  90                  95

Ser Arg Gly Leu Gly Ile Gly Gln Ala Ala Ala Glu Ala Gln Ala Ala
            100                 105                 110

Ala Ala Gly Gln Ala Ala Ile Ala Ala Lys Ser Cys Ala Leu Ala Ala
        115                 120                 125

Lys Ser Thr Ala Gln Ala Val Ala Leu Val Glu Lys Val Ala Arg Ala
    130                 135                 140

Glu Val Asp Leu Ala Glu Ser Ala Arg Lys Ala Thr Arg Leu Ser Ala
145                 150                 155                 160

Glu Ala Ala Lys Ala Ala Ala Glu Val Glu Lys Asp Leu Val Gly Leu
                165                 170                 175
```

Arg Gly Ala Ala Gly Lys Leu Asn Leu Ala Ala Arg Ala Gly Ser Lys
                180                 185                 190

Ala Gln Glu Arg Ala Asn Glu Asp Ser Ile Glu Ala Asn Glu Leu Ala
            195                 200                 205

Gln Ala Thr Ala Ala Gly Ala Glu Ala Glu Ala Lys Ala Asn Ala
210                 215                 220

Ala Gln Glu Ala Gly Ala Ser Ala Leu Ala Ile Ala Gln Ala Ala Leu
225                 230                 235                 240

Asn Ile Glu Gln Glu Thr Val Lys Leu Thr Arg Gln Ala Gln Asn Thr
                245                 250                 255

Arg Leu Arg Ser Glu Asn Ile Leu Ala Ala Ala Ser Asn Ala Arg Ala
            260                 265                 270

Ile Ala Ser Ala Glu Ala Glu Ala Ser Ser Asp Leu Asn Asn Arg Ala
        275                 280                 285

Asn Ala Ala Arg Ser Asn Ala Arg Ala Ala Ala Glu Thr Arg Ala Val
    290                 295                 300

Ala Thr Glu Ala Ala Ser Thr Ala Glu Ile Ala Ala Tyr Ser Ser Ser
305                 310                 315                 320

Glu Lys Gly Glu Ile Thr Asn Pro Gly Pro Leu Pro Lys Ile Val Ser
                325                 330                 335

Val Thr Ala Gly Leu Thr Gln Asn Glu Ile Ala Gly Ser Gly Ala Ala
            340                 345                 350

Ala Ser Ala Ser Ala Ser Ala Leu Ala Ser Ser Ala Gly Ala Gly
        355                 360                 365

Ala Gly Ala Gly Ala Gly Ala Gly Ala Ser Ala Gly Ala Gly Ala Val
    370                 375                 380

Ala Gly Ala Gly Ala Gly Ala Gly Ala Gly Ala Ser Ala Gly Ala Ser
385                 390                 395                 400

Ala Gly Ala Asn Ala Gly Ala Gly Ala Ser Ser Leu Leu Pro Gln
                405                 410                 415

Ser Lys Leu His Pro Ile Ser Arg Ser Ser Ala Ser Ala Ser Ala Ser
            420                 425                 430

Ala Glu Ala Glu Ala Asn Ser Ser Ala Tyr Ala
        435                 440

<210> SEQ ID NO 13
<211> LENGTH: 1176
<212> TYPE: DNA
<213> ORGANISM: Oecophylla smaragdina

<400> SEQUENCE: 13
atgaagatcc cagcgataat cgcaacgacc ctccttctct ggggtttcgc cgacgccagc      60
aagtcgtacc tcttaggctc atccgcgtct gcttccgctt ccgcttccgc ctcggcatca     120 gcggaggaa gcaccggcgg cgtcggcgtc ggatctgtaa tatccggtgg caacaacatc     180
atcagaggag cttcgaccac atccgtgaca ttggcagccg ccgcagcgga ggccaaggca     240
gctctgaatg ctggaaaagc gactgtcgaa gagcaagggg aagcgttaca gttgctcacc     300
gcgtccgctg aaaaaaacgc cgaggcgcgt tccttggccg acgatgcggc cgttctagtt     360
cagggtgccg ctgaggcgca atcggtcgcc gccgcgaaga cggtcgcggt cgagcaagga     420
tccaactctc tggatgcagc tgcagccgaa gcggaagccg ccgccgccgc atccagggta     480
tcggcccagc aggcactcca ggccgcgcag acctccgccg ccgctattca aaccgctgcc     540
ggtagcgccc tgacggctct caaattggca cgcaaacagg aagcggaatc caataatgcc     600

```
gccgaacagg caaataaagc attggcctta agtcgcgcag ccagcgctgc cactcaacga      660
gccgtggcag ctcagaacgc ggctgccgca tcagcggctt cggctggagc cgcacaagct      720
gaggcaagga acgcctacgc caaagccaaa gcagcgatag ctgctcttac ggccgcccaa      780
agaaattacg ccgcggccaa ggctagcgca agcgcgggta cgtggtggc cgaacaagat       840 gctcaatcta gagcggccga tgccgaggtg aacgccgttg cccaagccgc tgcccgagcc      900
agcgttcgca atcaggagat cgttgaaatc ggcgcggaat cggcaacgc cagcggcgga      960 gtgatctcga ccggcacacg ttcttccgga ggcaagggtg tctccgttac cgctggagct      1020
caggctagcg cgtccgcttc cgcgacctcc tcctcctcct cctcctccgg catcaacaaa      1080
ggacatccca gatgggggca caattggggt ttaggttctt cggaagcgtc agcaaacgct      1140
gaagccgaaa gcagcgcttc ctcttattca tcttaa                                1176
```

<210> SEQ ID NO 14
<211> LENGTH: 1203
<212> TYPE: DNA
<213> ORGANISM: Oecophylla smaragdina

<400> SEQUENCE: 14

```
atgaagattc cagcgatatt cgtgacgtct ctgctcgcct ggggactcgc cagcggcgga      60
gtcataggtc ccgacacgtc ctcatcgtcc caggcatcgg catcggcatc ggcgtcagca      120
tcggcgtcgg catcatcgtc ggcatcgatc ggttacaacg aactccataa atcgatcaat      180
gcgcccgcct ggcggtcgg cgtcaagaac ggcggagtgg atgtcgccaa gggcgcggcc      240
gttgtcgaat cagcgatatc cgacgtatcg actctaaccg atgatcgtac gttgaacggt      300
ctcgctatca tcgggaatag cgccgagagt ctggcaagag cacaggcttc ctcgagcgcc      360
agcgccggcg caaaagccaa tgctctcatc aaacaatcga tagcggctat agagatcacc      420
gaaaaggcag agtaccttgc gtcgatcgtc gccaccaagg cagcgaaggc cgccgaggcc      480
acagcggccg cgaccgctcg cgccactgcc gtcgccgagg ctgccaaggt ttccagcgag      540
caattcgcgg ccgaggcacg cgcggccgcc gacgccgaag ccaaggccaa cgccgcttcc      600
atcatcgcca acaaagcgaa cgccgtcctc gcggaggcag ccaccggact tagcgccagc      660
gctggcaaag cccaacaatc ggcgaccagg gcgttgcaag ccgcacgagc tgccgctaag      720
gctcaagccg aacttaccca gaaagccgct caaatcttag tcctcattgc tgaagccaaa      780
gccgccgtga gccgagcaag cgccgatcaa tccgtctgta cgtcccaggc acaagccgcc      840
agtcagattc aatcgagagc ctccgcggcc gaatccgcgg catcggctca atcggaagcc      900
aacaccattg cggccgaggc ggtcgctaga gctgacgccg aggcggccag tcaagctcaa      960
gcgtgggccc aatccttcaa acgcgaactc tcgagtgtcc ttttggaggc cgaggccaat      1020
gcctcggcta gtgcctcggc tggtgccctg ccagtggta gcagcagctc gggcgcgagt      1080
tccagcgcgg atgccagcgc cggagcgagc agctatggat ccttgggcgg atatcgacac      1140
ggcggaagct tcagcgaggc atcggcagcc gcgtcagcgg ccagtcgcgc cgaggctgcg      1200
taa                                                                    1203
```

<210> SEQ ID NO 15
<211> LENGTH: 1188
<212> TYPE: DNA
<213> ORGANISM: Oecophylla smaragdina

<400> SEQUENCE: 15

| | |
|---|---|
| atgaagattc cagcgatact cgtgacgtcc ttcctcgcct ggggactggc cagcgggggt | 60 |
| gtccctaaag agttgggaac ttccatttct tccgcgtccg catccgcatc cgcatccgca | 120 |
| tccgcgaccg cgtcctccag tagcaagaat gttcacttat taccattgaa aagcgagcat | 180 |
| ggcatcgtaa ttgacaagtc aaaattcaac atcagaaagg tagtgttgag cgcaatcgat | 240 |
| gagatcaacg gcgcgcccaa catcggtctg ggattgaaac aggtcagttt ggcgctcgca | 300 |
| aaagcccagg ctagtgctca atcgagcgcc gaggcattgg caatcatcaa gaaaatcgtc | 360 |
| gcgctcctca tctcggccta cgtcagagca gccgaggccg cggctcgagc atccgccgaa | 420 |
| gctttagcta ccgttagggc tgcggaacaa gcgcaaaaaa ttgctgaagc gaagggtaga | 480 |
| gcggctgctg aggcgctctc cgagttagtc gaggcgtccc agaaggccga tgcggcggcc | 540 |
| gcgggaacga cggacgcgat cgaacgcacc taccaggatg ccagagcggc cacttccgca | 600 |
| cagaccaagg ccagcggcga agccgagaat gctaatcgca atgctgccgc caccctcgcg | 660 |
| gcggtcttga gcatcgctaa ggccgcctcc ggtcaaggag gcactcgagc cgctgtcgat | 720 |
| gcagctgctg ccgctgccgc cgcagccgct ctgcatgcta aagctaacgc ggtttcgcaa | 780 |
| gctaccagca aagcagccgc tgaagctaga gtcgcggctg aggaggcagc atccgcccag | 840 |
| gcatccgcct cagcaagcgc acagctgacc gcacaattag aggagaaagt cagcgccgat | 900 |
| caacaagcag cctccgccag tactgatacc tccgctgcta tagccgaggc tgaagctgcc | 960 |
| gcgttagcgt ccaccgtcaa cgcgatcaac gacgagtgg tcatcggatt aggaaatacc | 1020 |
| gccagttctt ctgcccaagc ttccgcacag gccagtgctc tcgctcgcgc aaaaaatgcg | 1080 |
| cgcccctaaaa taagggctg gtacaaaatc ggaggcgcga cttccgcttc tgcaagcgca | 1140 |
| tcggccagcg cttccgccca gtcatcctcg caaggactgg tatactag | 1188 |

<210> SEQ ID NO 16
<211> LENGTH: 1332
<212> TYPE: DNA
<213> ORGANISM: Oecophylla smaragdina

<400> SEQUENCE: 16

| | |
|---|---|
| atgaagattc cagcgatact tgcgacgtcc cttttcgtct ggggtcttgt cggcgccagc | 60 |
| gaactcgtcg gatcggacgc gagcgcgacg gcatctgctg aagcgtcagc atcgtcatcc | 120 |
| gcatacggta gcaagtatgg tattggtagt ggtgctgtct ccggtgcatc agccagcgcc | 180 |
| tctgccagcg cgtctgctag cgcatcagcc agcagtgctc ccgcgatcga aggagtaaac | 240 |
| gttggcaccg gagtcagtaa caccgcttcc gcgtccgcag aagctctctc ccgtggactc | 300 |
| ggcatcggac aagcggctgc cgaagcgcaa gccgctgccg ctggccaagc ggcgatcgct | 360 |
| gcgaaatcgt gcgcgctagc ggccaagagc accgctcaag cggttgccct ggttgagaaa | 420 |
| gtggcccgcg ccgaggtaga tctggccgaa agcgcgagaa aggctacaag attatcggca | 480 |
| gaagcagcca aggcagcggc ggaagtcgag aaggacctcg tcggtctgag aggggctgcc | 540 |
| ggtaaactga atctggctgc gagagccggt tctaaagccc aagaacgcgc caacgaagac | 600 |
| tctatagagg ctaacgaact tgcccaagca acggccgccg ccggtgccga ggctgaagcc | 660 |
| aaggcgaatg ccgcccagga ggcaggcgcc tccgctttgg ccatcgccca agccgccctt | 720 |
| aacatcgagc aagagactgt taaattgacc cgccaggccc agaatactcg tctcagatct | 780 |
| gaaaatattc tcgccgcggc cagcaatgcc cgcgccatcg cttccgctga ggccgaggcc | 840 |
| agtagtgatt tgaataatcg tgcgaatgca gcgcgttcca atgcccgagc tgctgccgag | 900 |
| accagagccg tagctaccga agccgcttct accgccgaga tcgcagctta tagttcatcc | 960 |

```
gagaaaggcg agatcaccaa tcccggtcct ctgcccaaga tcgtcagtgt accgcaggt    1020 ctgacccaga acgaaatagc gggatcagga gcggccgcta gtgctagtgc cagtgctctt    1080
gccagtgcca gtgccggtgc cggtgccggt gcaggtgcag agccggtgc aagtgcagga    1140 gccggtgcag ttgcaggtgc aggagccggt gcaggagccg tgctagtgc cggagcgagt    1200 gccggagcga atgccggtgc cggtgccagc agtttactct tgccgcagag taaactccat    1260
ccaatctcca ggtcttccgc ctctgcctcc gcttccgccg aggccgaagc taacagttcg    1320
gcgtatgcgt aa                                                       1332
```

<210> SEQ ID NO 17
<211> LENGTH: 314
<212> TYPE: PRT
<213> ORGANISM: Apis cerana

<400> SEQUENCE: 17

```
Gly Leu Glu Gly Ser Gly Asn Pro Leu Pro Glu Leu Val Lys Gly Ser
1               5                   10                  15

Ala Ser Ala Thr Ala Ser Thr Ala Val Thr Ala Arg Ser Gly Leu Arg
            20                  25                  30

Val Gly Gln Val Ala Leu Ala Ser Gln Lys Asp Ala Val Leu Gln Ala
        35                  40                  45

Glu Ala Ala Ser Ala Ala Ser Glu Ala Arg Ala Ala Ala Asp Leu
    50                  55                  60

Thr Ala Lys Leu Ser Gln Glu Ser Ala Ser Val Gln Ser Gln Ala Ala
65                  70                  75                  80

Ala Lys Gly Lys Glu Thr Glu Ala Ala Val Gly Gln Ala Arg Ala
                85                  90                  95

Gly Leu Glu Ser Val Ser Ile Ala Ala Ser Ala Thr Ser Ala Ala Lys
            100                 105                 110

Glu Ala Ser Thr Ala Ala Arg Ala Ala Ser Ala Leu Ser Thr Ala
        115                 120                 125

Thr Val Gln Ala Lys Ile Ala Glu Arg Ala Ala Lys Ala Glu Ala Val
    130                 135                 140

Ala Ser Glu Glu Ala Lys Ala Lys Ala Ile Ala Ala Asn Leu Ala
145                 150                 155                 160

Ala Ala Ala Ser Glu Ala Ala Glu Thr Ala Leu Lys Ala Glu Lys Val
                165                 170                 175

Ala Glu Glu Ala Ile Ala Arg Ala Ala Ser Ala Lys Ala Ala Ala Arg
            180                 185                 190

Ala Ala Ala Ala Leu Ala Ser Ser Lys Glu Ala Ala Thr Ala Ser
        195                 200                 205

Ala Arg Asn Ala Ala Glu Ser Glu Ala Arg Asn Glu Val Ala Val Leu
    210                 215                 220

Ile Ala Glu Ile Asp Lys Lys Ser Arg Glu Ile Asp Ala Ala Thr Ser
225                 230                 235                 240

Leu Asn Ala Arg Ala Ala Ala Lys Ala Ser Ser Arg Asn Val Glu Thr
                245                 250                 255

Ala Thr Ile Gly Ala Asn Ile Asp Ser Ser Lys Gln Val Ser Ile
            260                 265                 270

Pro Val Glu Ile Lys Lys Phe Pro Glu Pro Glu Leu Ser Thr Ser Trp
        275                 280                 285

Arg Glu Asp Glu Glu Val Thr Lys Gly Lys Lys Glu Asp Ile Asn Leu
    290                 295                 300
```

Asn Ser Phe Glu Leu Lys Ser Asn Val Phe
305             310

<210> SEQ ID NO 18
<211> LENGTH: 288
<212> TYPE: PRT
<213> ORGANISM: Apis cerana

<400> SEQUENCE: 18

Arg Val Ile Asn His Glu Ser Leu Lys Thr Asn Val Asp Ile Gln Val
1               5                   10                  15

Thr Pro Gly Gln Val Gly Asp Gly Ser Asp Ala Thr Ser Ser Ser Ile
            20                  25                  30

Glu Asn Ala Leu Lys Val Ala Arg Ala Ser Glu Asn Val Gly Leu Asn
        35                  40                  45

Leu Glu Leu Asn Ala Gly Ala His Ala Ala Ser Val Ala Ala Ala Ala
    50                  55                  60

Gln Ala Lys Asn Thr Glu Ala Ala Glu Val Gly Ala Asn Ala Ala Leu
65                  70                  75                  80

Ala Ala Ala Ile Ala Lys Arg Glu Gln Ala Ile Lys Ala Ser Glu Ile
                85                  90                  95

Ala Ser Gln Leu Leu Thr Asn Ala Ala Lys Ala Ala Glu Ala Thr Val
            100                 105                 110

Ser Ala Thr Lys Arg Ala Ala Gln Leu Thr Ala Ala Ala Lys Glu Ala
        115                 120                 125

Thr Arg Ala Ser Ala Ala Ala Glu Ala Ala Thr Glu Ala Gln Val
    130                 135                 140

Lys Ala Asn Ala Asp Ser Ile Ile Thr Lys Arg Thr Ala Ile Ala Glu
145                 150                 155                 160

Ala Gln Ala Ala Ala Glu Ala Gln Val Lys Ala Ala Ile Ala Arg Lys
                165                 170                 175

Ala Ala Ala Asn Phe Leu Ala Lys Ala Gln Ile Ala Ala Ala Ala Glu
            180                 185                 190

Ser Glu Ala Thr Lys Leu Ala Ala Glu Ala Thr Val Ala Leu Ser Asn
        195                 200                 205

Ala Glu Val Ala Val Asn Gln Ala Arg Asn Ala Gln Ala Thr Ala Ser
    210                 215                 220

Thr Gln Ala Ser Ala Ala Val Arg Val Asp Ser Gln Ala Ala Asn Ala
225                 230                 235                 240

Glu Ala Ala Ala Val Ala Gln Ala Glu Thr Leu Leu Val Thr Ala Glu
                245                 250                 255

Ala Ile Ala Ala Ala Glu Ala Glu Ala Ala Ser Lys Ala Ala Ser Phe
            260                 265                 270

Ala Lys Lys Ile Val Asp Glu Lys Lys Ile His Val Glu Lys Leu Glu
        275                 280                 285

<210> SEQ ID NO 19
<211> LENGTH: 316
<212> TYPE: PRT
<213> ORGANISM: Apis cerana

<400> SEQUENCE: 19

Gly Val Glu Glu Phe Lys Ser Ser Thr Thr Glu Glu Val Ile Gly Lys
1               5                   10                  15

Asn Leu Glu Val Asp Leu Leu Lys Asn Val Asp Thr Ser Ala Lys Arg
            20                  25                  30

Arg Glu Asn Gly Ala Pro Val Leu Gly Lys Asn Val Phe Lys Ser Leu
            35                  40                  45

Glu Asn Ile Lys Ala Ser Ala Gly Ala Asp Ala Lys Ala Ser Ala Val
 50                  55                  60

Val Lys Ala Ser Ala Leu Ala Leu Ala Glu Ala Tyr Leu Arg Ala Ser
 65                  70                  75                  80

Ala Leu Ser Ala Ala Ala Ser Ala Lys Ala Ala Ala Leu Lys Asn
                 85                  90                  95

Ala Gln Gln Ala Gln Leu Ile Ala Gln Glu Lys Ala Leu Ala Ala Leu
                100                 105                 110

Lys Ala Gln Ser Glu Glu Glu Ala Ala Ser Ala Arg Ala Asn Ala Ala
                115                 120                 125

Ala Ala Ala Thr Gln Ser Ala Val Glu Arg Ala Gln Ala Ser Ser Arg
        130                 135                 140

Thr Ala Thr Ala Ala Gln Asn Val Ala Ser Asn Leu Gln Lys Arg Thr
145                 150                 155                 160

Ser Thr Lys Ala Ala Ala Glu Ala Ala Ala Thr Leu Arg Gln Leu Gln
                165                 170                 175

Asp Ala Glu Gln Thr Lys Trp Ser Ala Asn Ala Ala Leu Glu Val Ser
                180                 185                 190

Ala Ala Ala Thr Ala Ala Glu Thr Lys Thr Thr Ala Ser Ser Glu Ala
                195                 200                 205

Ala Ser Ala Ala Ala Lys Lys Ala Ala Ile Ala Ser Asp Ala Asp
        210                 215                 220

Gly Ala Glu Lys Ser Ala Ser Thr Glu Ala Gln Ser Ala Ala Lys Ile
225                 230                 235                 240

Glu Ser Val Ala Ala Ala Glu Gly Ser Ala Asn Ser Ala Ser Glu Asp
                245                 250                 255

Ser Gln Ala Ala Gln Leu Glu Ala Ser Thr Ala Ala Arg Ala Asn Val
        260                 265                 270

Ala Thr Ala Ile Gly Asp Gly Ala Ile Leu Gly Leu Gly Gln Asp Val
        275                 280                 285

Gly Ala Ala Ala Gln Leu Leu Ala Gln Ala Lys Ala Leu Ala Glu Val
        290                 295                 300

Ser Ser Lys Ser Glu Asn Ile Glu Asp Lys Lys Phe
305                 310                 315

<210> SEQ ID NO 20
<211> LENGTH: 320
<212> TYPE: PRT
<213> ORGANISM: Apis cerana

<400> SEQUENCE: 20

Ala Ser Glu Glu Val Glu Thr Arg Gly Lys Thr Lys Thr Ser Thr Val
 1               5                  10                  15

Val Lys Ser Glu Lys Val Glu Val Pro Ala Lys Asp Glu Leu Lys
                 20                  25                  30

Leu Thr Ser Glu Pro Ile Leu Gly Arg Arg Val Gly Thr Gly Ala Ser
            35                  40                  45

Glu Val Ala Ser Ser Gly Glu Ile Ile Ala Ile Ser Leu Gly Thr
         50                  55                  60

Gly Gln Ala Ala Ala Glu Ser Gln Ala Val Ala Ser Gln Ser Lys
 65                  70                  75                  80

Ser Ala Ala Ser Ala Ala Ile Ser Ala Ser Glu Leu Ala Asn Lys Val

```
                85                  90                  95
Ala Ala Leu Val Val Gly Ala Thr Ala Ala Gln Ala Arg Ala Ala Ala
            100                 105                 110

Ala Ser Ser Gly Ala Leu Lys Ala Ser Leu Ala Thr Glu Glu Ser Ala
            115                 120                 125

Glu Glu Ala Glu Ala Ala Val Ala Val Ala Lys Ala Ala Ala Glu Lys
130                 135                 140

Ala Glu Ser Leu Ala Arg Asn Leu Ala Ser Ala Ser Ala Arg Ala Ala
145                 150                 155                 160

Ile Ser Ser Glu Ser Ala Asn Glu Leu Ala Gln Ala Glu Ser Ala Ala
                165                 170                 175

Ala Ala Glu Ala Gln Ala Lys Thr Ala Ala Ala Ala Lys Ala Ala Glu
            180                 185                 190

Ile Ala Leu Lys Val Ala Glu Ile Ala Val Lys Ala Glu Ala Asp Ala
            195                 200                 205

Ala Ala Ala Ala Val Ala Ala Ala Lys Ala Arg Ala Val Ala Asp Ala
            210                 215                 220

Ala Ala Ala Arg Ala Ala Ala Val Asn Ala Ile Ala Lys Ala Glu Glu
225                 230                 235                 240

Glu Ala Ser Ala Gln Ala Glu Asn Thr Ala Gly Val Ser Gln Ala Ala
                245                 250                 255

Ala Ser Ala Ala Glu Ser Arg Ala Ala Ala Ala Ala Ala Ala Ala Ala
            260                 265                 270

Thr Ser Glu Thr Ala Ala Glu Ala Gly Pro Leu Ala Gly Glu Leu Lys
            275                 280                 285

Pro Pro Gln Trp Lys Arg Ile Pro Val Lys Lys Glu Glu Trp Lys Thr
            290                 295                 300

Ser Thr Lys Glu Glu Trp Lys Thr Thr Asn Glu Glu Trp Glu Val Lys
305                 310                 315                 320

<210> SEQ ID NO 21
<211> LENGTH: 372
<212> TYPE: PRT
<213> ORGANISM: Oecophylla smaragdina

<400> SEQUENCE: 21

Ser Lys Ser Tyr Leu Leu Gly Ser Ser Ala Ser Ala Ser Ala Ser Ala
1               5                   10                  15

Ser Ala Ser Ala Ser Ala Gly Gly Ser Thr Gly Gly Val Gly Val Gly
            20                  25                  30

Ser Val Ile Ser Gly Gly Asn Asn Ile Ile Arg Gly Ala Ser Thr Thr
            35                  40                  45

Ser Val Thr Leu Ala Ala Ala Ala Glu Ala Lys Ala Ala Leu Asn
        50                  55                  60

Ala Gly Lys Ala Thr Val Glu Glu Gln Arg Glu Ala Leu Gln Leu Leu
65                  70                  75                  80

Thr Ala Ser Ala Glu Lys Asn Ala Glu Ala Arg Ser Leu Ala Asp Asp
                85                  90                  95

Ala Ala Val Leu Val Gln Gly Ala Ala Glu Ala Gln Ser Val Ala Ala
            100                 105                 110

Ala Lys Thr Val Ala Val Glu Gln Gly Ser Asn Ser Leu Asp Ala Ala
            115                 120                 125

Ala Ala Glu Ala Glu Ala Ala Ala Ala Ser Arg Val Ser Ala Gln
            130                 135                 140
```

Gln Ala Leu Gln Ala Ala Gln Thr Ser Ala Ala Ile Gln Thr Ala
145                 150                 155                 160

Ala Gly Ser Ala Leu Thr Ala Leu Lys Leu Ala Arg Lys Gln Glu Ala
            165                 170                 175

Glu Ser Asn Asn Ala Ala Glu Gln Ala Asn Lys Ala Leu Ala Leu Ser
            180                 185                 190

Arg Ala Ala Ser Ala Ala Thr Gln Arg Ala Val Ala Ala Gln Asn Ala
            195                 200                 205

Ala Ala Ala Ser Ala Ala Ser Ala Gly Ala Ala Gln Ala Glu Ala Arg
        210                 215                 220

Asn Ala Tyr Ala Lys Ala Lys Ala Ala Ile Ala Ala Leu Thr Ala Ala
225                 230                 235                 240

Gln Arg Asn Tyr Ala Ala Ala Lys Ala Ser Ala Ser Ala Gly Ser Val
            245                 250                 255

Val Ala Glu Gln Asp Ala Gln Ser Arg Ala Ala Asp Ala Glu Val Asn
            260                 265                 270

Ala Val Ala Gln Ala Ala Ala Arg Ala Ser Val Arg Asn Gln Glu Ile
        275                 280                 285

Val Glu Ile Gly Ala Glu Phe Gly Asn Ala Ser Gly Gly Val Ile Ser
290                 295                 300

Thr Gly Thr Arg Ser Ser Gly Gly Lys Gly Val Ser Val Thr Ala Gly
305                 310                 315                 320

Ala Gln Ala Ser Ala Ser Ala Ser Ala Thr Ser Ser Ser Ser Ser Ser
            325                 330                 335

Ser Gly Ile Asn Lys Gly His Pro Arg Trp Gly His Asn Trp Gly Leu
            340                 345                 350

Gly Ser Ser Glu Ala Ser Ala Asn Ala Glu Ala Glu Ser Ser Ala Ser
            355                 360                 365

Ser Tyr Ser Ser
        370

<210> SEQ ID NO 22
<211> LENGTH: 381
<212> TYPE: PRT
<213> ORGANISM: Oecophylla smaragdina

<400> SEQUENCE: 22

Gly Val Ile Gly Pro Asp Thr Ser Ser Ser Gln Ala Ser Ala Ser
1               5                   10                  15

Ala Ser Ala Ser Ala Ser Ala Ser Ala Ser Ser Ala Ser Ile Gly
            20                  25                  30

Tyr Asn Glu Leu His Lys Ser Ile Asn Ala Pro Ala Leu Ala Val Gly
            35                  40                  45

Val Lys Asn Gly Gly Val Asp Val Ala Lys Gly Ala Ala Val Val Glu
        50                  55                  60

Ser Ala Ile Ser Asp Val Ser Thr Leu Thr Asp Asp Arg Thr Leu Asn
65                  70                  75                  80

Gly Leu Ala Ile Ile Gly Asn Ser Ala Glu Ser Leu Ala Arg Ala Gln
                85                  90                  95

Ala Ser Ser Ser Ala Ser Ala Gly Ala Lys Ala Asn Ala Leu Ile Lys
            100                 105                 110

Gln Ser Ile Ala Ala Ile Glu Ile Thr Glu Lys Ala Glu Tyr Leu Ala
            115                 120                 125

Ser Ile Val Ala Thr Lys Ala Ala Lys Ala Ala Glu Ala Thr Ala Ala
        130                 135                 140

Ala Thr Ala Arg Ala Thr Ala Val Ala Glu Ala Ala Lys Val Ser Ser
145                 150                 155                 160

Glu Gln Phe Ala Ala Glu Ala Arg Ala Ala Asp Ala Glu Ala Lys
            165                 170                 175

Ala Asn Ala Ala Ser Ile Ile Ala Asn Lys Ala Asn Ala Val Leu Ala
        180                 185                 190

Glu Ala Ala Thr Gly Leu Ser Ala Ser Ala Gly Lys Ala Gln Gln Ser
            195                 200                 205

Ala Thr Arg Ala Leu Gln Ala Ala Arg Ala Ala Lys Ala Gln Ala
        210                 215                 220

Glu Leu Thr Gln Lys Ala Ala Gln Ile Leu Val Leu Ile Ala Glu Ala
225                 230                 235                 240

Lys Ala Ala Val Ser Arg Ala Ser Ala Asp Gln Ser Val Cys Thr Ser
            245                 250                 255

Gln Ala Gln Ala Ala Ser Gln Ile Gln Ser Arg Ala Ser Ala Ala Glu
        260                 265                 270

Ser Ala Ala Ser Ala Gln Ser Glu Ala Asn Thr Ile Ala Ala Glu Ala
        275                 280                 285

Val Ala Arg Ala Asp Ala Glu Ala Ala Ser Gln Ala Gln Ala Trp Ala
        290                 295                 300

Glu Ser Phe Lys Arg Glu Leu Ser Ser Val Val Leu Glu Ala Glu Ala
305                 310                 315                 320

Asn Ala Ser Ala Ser Ala Ser Ala Gly Ala Leu Ala Ser Gly Ser Ser
        325                 330                 335

Ser Ser Gly Ala Ser Ser Ala Asp Ala Ser Ala Gly Ala Ser Ser
        340                 345                 350

Tyr Gly Ser Leu Gly Gly Tyr Arg His Gly Gly Ser Phe Ser Glu Ala
        355                 360                 365

Ser Ala Ala Ala Ser Ala Ala Ser Arg Ala Glu Ala Ala
        370                 375                 380

<210> SEQ ID NO 23
<211> LENGTH: 376
<212> TYPE: PRT
<213> ORGANISM: Oecophylla smaragdina

<400> SEQUENCE: 23

Gly Val Pro Lys Glu Leu Gly Thr Ser Ile Ser Ser Ala Ser Ala Ser
1               5                   10                  15

Ala Ser Ala Ser Ala Ser Ala Thr Ala Ser Ser Ser Ser Lys Asn Val
            20                  25                  30

His Leu Leu Pro Leu Lys Ser Glu His Gly Ile Val Ile Asp Lys Ser
        35                  40                  45

Lys Phe Asn Ile Arg Lys Val Val Leu Ser Ala Ile Asp Glu Ile Asn
    50                  55                  60

Gly Ala Pro Asn Ile Gly Leu Gly Leu Lys Val Ser Leu Ala Leu
65                  70                  75                  80

Ala Lys Ala Gln Ala Ser Ala Gln Ser Ser Ala Glu Ala Leu Ala Ile
            85                  90                  95

Ile Lys Lys Ile Val Ala Leu Leu Ile Ser Ala Tyr Val Arg Ala Ala
            100                 105                 110

Glu Ala Ala Ala Arg Ala Ser Ala Glu Ala Leu Ala Thr Val Arg Ala
        115                 120                 125

Ala Glu Gln Ala Gln Lys Ile Ala Glu Ala Lys Gly Arg Ala Ala Ala

Glu Ala Leu Ser Glu Leu Val Glu Ala Ser Gln Lys Ala Asp Ala Ala
145                 150                 155                 160

Ala Ala Gly Thr Thr Asp Ala Ile Glu Arg Thr Tyr Gln Asp Ala Arg
            165                 170                 175

Ala Ala Thr Ser Ala Gln Thr Lys Ala Ser Gly Glu Ala Glu Asn Ala
            180                 185                 190

Asn Arg Asn Ala Ala Ala Thr Leu Ala Ala Val Leu Ser Ile Ala Lys
        195                 200                 205

Ala Ala Ser Gly Gln Gly Gly Thr Arg Ala Ala Val Asp Ala Ala Ala
        210                 215                 220

Ala Ala Ala Ala Ala Ala Leu His Ala Lys Ala Asn Ala Val Ser
225                 230                 235                 240

Gln Ala Thr Ser Lys Ala Ala Glu Ala Arg Val Ala Ala Glu Glu
            245                 250                 255

Ala Ala Ser Ala Gln Ala Ser Ala Ser Ala Gln Leu Thr Ala
            260                 265                 270

Gln Leu Glu Glu Lys Val Ser Ala Asp Gln Gln Ala Ala Ser Ala Ser
        275                 280                 285

Thr Asp Thr Ser Ala Ala Ile Ala Glu Ala Glu Ala Ala Ala Leu Ala
290                 295                 300

Ser Thr Val Asn Ala Ile Asn Asp Gly Val Val Ile Gly Leu Gly Asn
305                 310                 315                 320

Thr Ala Ser Ser Ser Ala Gln Ala Ser Ala Gln Ala Ser Ala Leu Ala
            325                 330                 335

Arg Ala Lys Asn Ala Arg Pro Lys Ile Lys Gly Trp Tyr Lys Ile Gly
        340                 345                 350

Gly Ala Thr Ser Ala Ser Ala Ser Ala Ser Ala Ser Ala Gln
            355                 360                 365

Ser Ser Ser Gln Gly Leu Val Tyr
        370                 375

<210> SEQ ID NO 24
<211> LENGTH: 424
<212> TYPE: PRT
<213> ORGANISM: Oecophylla smaragdina

<400> SEQUENCE: 24

Ser Glu Leu Val Gly Ser Asp Ala Ser Ala Thr Ala Ser Ala Glu Ala
1               5                   10                  15

Ser Ala Ser Ser Ser Ala Tyr Gly Ser Lys Tyr Gly Ile Gly Ser Gly
            20                  25                  30

Ala Val Ser Gly Ala Ser Ala Ser Ala Ser Ala Ser Ala Ser
            35                  40                  45

Ala Ser Ala Ser Ser Ala Pro Ala Ile Glu Gly Val Asn Val Gly Thr
50                  55                  60

Gly Val Ser Asn Thr Ala Ser Ala Ser Ala Glu Ala Leu Ser Arg Gly
65                  70                  75                  80

Leu Gly Ile Gly Gln Ala Ala Glu Ala Gln Ala Ala Ala Gly
        85                  90                  95

Gln Ala Ala Ile Ala Ala Lys Ser Cys Ala Leu Ala Ala Lys Ser Thr
            100                 105                 110

Ala Gln Ala Val Ala Leu Val Glu Lys Val Ala Arg Ala Glu Val Asp
            115                 120                 125

```
Leu Ala Glu Ser Ala Arg Lys Ala Thr Arg Leu Ser Ala Glu Ala Ala
        130                 135                 140

Lys Ala Ala Ala Glu Val Glu Lys Asp Leu Val Gly Leu Arg Gly Ala
145                 150                 155                 160

Ala Gly Lys Leu Asn Leu Ala Ala Arg Ala Gly Ser Lys Ala Gln Glu
            165                 170                 175

Arg Ala Asn Glu Asp Ser Ile Glu Ala Asn Glu Leu Ala Gln Ala Thr
        180                 185                 190

Ala Ala Ala Gly Ala Glu Ala Glu Ala Lys Ala Asn Ala Ala Gln Glu
            195                 200                 205

Ala Gly Ala Ser Ala Leu Ala Ile Ala Gln Ala Leu Asn Ile Glu
        210                 215                 220

Gln Glu Thr Val Lys Leu Thr Arg Gln Ala Gln Asn Thr Arg Leu Arg
225                 230                 235                 240

Ser Glu Asn Ile Leu Ala Ala Ser Asn Ala Arg Ala Ile Ala Ser
            245                 250                 255

Ala Glu Ala Glu Ala Ser Ser Asp Leu Asn Asn Arg Ala Asn Ala Ala
        260                 265                 270

Arg Ser Asn Ala Arg Ala Ala Glu Thr Arg Ala Val Ala Thr Glu
275                 280                 285

Ala Ala Ser Thr Ala Glu Ile Ala Ala Tyr Ser Ser Glu Lys Gly
        290                 295                 300

Glu Ile Thr Asn Pro Gly Pro Leu Pro Lys Ile Val Ser Val Thr Ala
305                 310                 315                 320

Gly Leu Thr Gln Asn Glu Ile Ala Gly Ser Gly Ala Ala Ala Ser Ala
            325                 330                 335

Ser Ala Ser Ala Leu Ala Ser Ala Ser Ala Gly Ala Gly Ala Gly Ala
        340                 345                 350

Gly Ala Gly Ala Gly Ala Ser Ala Gly Ala Gly Ala Val Ala Gly Ala
            355                 360                 365

Gly Ala Gly Ala Gly Ala Gly Ser Ala Gly Ala Ser Ala Gly Ala
        370                 375                 380

Asn Ala Gly Ala Gly Ala Ser Ser Leu Leu Leu Pro Gln Ser Lys Leu
385                 390                 395                 400

His Pro Ile Ser Arg Ser Ser Ala Ser Ala Ser Ala Ser Ala Glu Ala
            405                 410                 415

Glu Ala Asn Ser Ser Ala Tyr Ala
            420

<210> SEQ ID NO 25
<211> LENGTH: 459
<212> TYPE: PRT
<213> ORGANISM: Polistes dominula

<400> SEQUENCE: 25

Gln Ser Ser Ser Val Thr Ala Ala Ala Ser Ala Ser Ala Ser Ser
1               5                   10                  15

Glu Ser Arg Ser Ser Arg Gln Arg Ser Ser Thr Arg Ser Leu Leu Asp
            20                  25                  30

Leu Val Ser Ser Ala Arg Asn Asn Ala Ala Ser Thr Ala Ser Val Ala
        35                  40                  45

Ala Gly Ala Arg Ala Ala Leu Gln Ala Ser Arg Ser Ala Asn Ala Ala
    50                  55                  60

Gln Ala Glu Ala Leu Ala Gln Ala Arg Asn Ser Ala Ala Gln Asn Ala
65                  70                  75                  80
```

```
Lys Ala Arg Ala Ala Ala Ala Ala Ser Ala Ile Asn Ala Ala
                85              90              95

Ala Ser Ser Gln Gly Arg Ala Thr Val Gln Ala Thr Ala Val
            100             105             110

Ala Ala Gln Ala Leu Ser Lys Ser Ala Leu Gln Ala Gln Ser Ala Ala
            115             120             125

Ser Ser Ser Lys Ser Glu Ala Ala Gln Ala Ser Asn Ser Ala Asn Ala
130             135             140

Gly Ala Ala Ala Leu Ala Thr Ala Ser Ala Gln Ala Arg Ala Thr Lys
145             150             155             160

Lys Ala Ala Leu Ala Phe Ala Ala Ala Ala Glu Ala Ser Ala Lys
                165             170             175

Ala Ala Ala Ala Arg Ala Ala Ala Ala Glu Ala Ala Arg
                180             185             190

Arg Ala Val Gln Ala Gln Arg Asp Ser Asn Asn Ala Gly Ser Leu Ala
                195             200             205

Ala Lys Ala Gln Ala Glu Ala Arg Ala Ala Ala Ala Ala Ser Ala
    210             215             220

Ala Arg Ile Ala Ala Ser Thr Ala Asp Asp Ala Ser Ala Gln Ala Asn
225             230             235             240

Ala Arg Leu Lys Ala Val Thr Ser Ile Ala Ala Ser Ser Asp Arg Ala
                245             250             255

Lys Ala Ser Asp Ala Arg Ala Ser Ala Glu Ala Ala Gly Ser Ala Arg
                260             265             270

Ser Ser Ser Arg Gly Ala Gln Pro Ser Trp Leu Thr Arg Gln Ala Ser
                275             280             285

Ser Ser Ser Arg Ala Ser Ser Ser Ser Ala Ser Ala Glu Ser
                290             295             300

Asp Ala Asp Ser Val Ser Ile Ala Ser Ala Ser Arg Ala Arg Ala
305             310             315             320

Ser Ala Asp Ser Glu Ala Arg Ser Ser Arg Ser Asp Ala Asp Ser
                325             330             335

Ser Ser Arg Ser Asp Ala Asp Ser Ser Ser Arg Ser Asp Ala Asp Ser
                340             345             350

Ser Ser Arg Ser Asp Ala Asp Ser Ser Ser Arg Ser Val Ala Gly Ser
                355             360             365

Ser Ser Arg Ser Ala Thr Gly Ser Ser Ser Arg Ser Ser Ala Asn
                370             375             380

Val Ala Ala Asn Ser Ala Ser Ser Ser Gln Ala Gly Ser Ala Ala Gly
385             390             395             400

Ser Ser Gly Arg Ser Ala Ala Gly Ala Ser Ala Asp Ala Ser Ala Asp
                405             410             415

Ala Ser Ala Asp Val Ser Ala Gly Ser Ser Ala Asp Ser Ser Val Asp
                420             425             430

Val Ser Ala Glu Ser Ser Ser Ser Ser Trp Ser Ser Ser Asp Gln Asn
                435             440             445

Val Trp Ser Leu Ser Glu Thr Leu Pro Ser Tyr
450             455

<210> SEQ ID NO 26
<211> LENGTH: 340
<212> TYPE: PRT
<213> ORGANISM: Polistes dominula
```

```
<400> SEQUENCE: 26

Asp Pro Gln Arg Ser Gly Ser Ser Glu Ser Ser Ala Ser Ser Trp
1               5                   10                  15

Ser Ser Ser Ser Ala Ser Ser Leu Ser Ser Glu Ala Ser Ser Ala
            20                  25                  30

Ser Ser Ala Asn Ser Ala Ser Ser Gly Ser Asp Glu Ser Arg Val Arg
            35                  40                  45

Ala Trp Asn Arg Gly Arg Gly Gly Ser Asp Ser Leu Val Leu Ser Val
    50                  55                  60

Asp Ser Ser Ala Asp Ser Arg Ala Arg Glu Leu Ile Glu Thr Asp Ala
65                  70                  75                  80

Gly Leu Asn Val Ala Ala Ala Ser Ala Gln Ala Asn Ala Glu Asp Gln
                85                  90                  95

Ala Arg Ala Ala Ala Ser Ala Asp Val Thr Ala Asn Arg Ala Thr Ala
            100                 105                 110

Lys Ala Leu Ala Leu Ala Glu Ala Ala Val Arg Ala Glu Asn Ala Ala
            115                 120                 125

Ile Val Arg Val Arg Gln Ala Leu Thr Ala Ala Gln Asp Leu Val Ala
    130                 135                 140

Ala Ser Ser Arg Ala Arg Ala Ala Ser Arg Ala Ala Trp Glu Ala Ala
145                 150                 155                 160

Lys Glu Ser Ala Ala Ala Ala Trp Ala Ser Asn Asn Gln Val Arg
                165                 170                 175

Ala Asn Ala Asp Ser Leu Ile Ala Asn Arg Ala Ala Ala Leu Leu
            180                 185                 190

Ala Ala Ala Glu Glu Ala Leu Gln Arg Ala Thr Ala Ser Gln Asn Ser
            195                 200                 205

Ala Ala Glu Ala Ala Ala Lys Ala Arg Ala Ala Arg Ala Asn Ala
            210                 215                 220

Ala Thr Thr Arg Ala Ala Ala Ser Ala Val Leu Ala Ser Ala Arg Ala
225                 230                 235                 240

Arg Ala Ala Ile Thr Arg Ala Ser Gly Ala Gln Ile Thr Ala Ser Ala
                245                 250                 255

Lys Ala Thr Ser Ala Ser Gln Val Gln Asp Arg Ala Asn Ile Ala Gln
                260                 265                 270

Gly Ala Ala Ser Ala Leu Ala Glu Ser Arg Ala Glu Ala Ala Ala Ser
            275                 280                 285

Ala Ala Ala Ala Gln Ala Ala Val Ala Glu Ala Asn Ala Gln Val
            290                 295                 300

Ala Arg Leu Ser Lys Ser Ser Gly Asp Ala Ser Ser Glu Ser Ser Ala
305                 310                 315                 320

Ser Ala Ser Ser Ser Ala Ser Ala Ser Ser Ser Ser Ser Ser Ser Ser
                325                 330                 335

Ser Ser Ser Asp
            340

<210> SEQ ID NO 27
<211> LENGTH: 358
<212> TYPE: PRT
<213> ORGANISM: Polistes dominula

<400> SEQUENCE: 27

Asn Pro Ala Ser Leu Asp Ser Ser Glu Leu Ser Leu Ser Ser Glu
1               5                   10                  15
```

```
Ala Ser Ser Ser Ser Tyr Ser Ser Ser Ser Ser Ser Ser Ser
             20                  25                  30

Ser Ser Ala Arg Ser Ser Asp Gly Arg Thr Pro Asn Val Ile Leu
         35                  40                  45

Asn Lys Pro Pro Gln Leu Gly Ala Ser Ala Ala Glu Ile Ala Ser Ala
 50                  55                  60

Leu Ser Asn Asn Ala Ala Asn Ala Ala Ser Asn Ala Lys Ser Ala Gln
 65                  70                  75                  80

Ala Thr Arg Ala Thr Ala Ile Ala Arg Thr Lys Ala Ala Val Ala
                 85                  90                  95

Ala Ala Arg Ala Ala Ala Arg Thr Arg Glu Ala Ala Ala Ala Arg
            100                 105                 110

Ala Ala Ala Asn Ala Gln Ala Gln Ala Ala Arg Ala Ser Ala Ala
            115                 120                 125

Ile Ser Ala Val Ala Ala Ala Glu Ala Ala Ala Gln Lys Ala Ala Ser
130                 135                 140

Ala Gly Ser Gly Ala Leu Ala Ala Ser Val Arg Ser Asn Lys Ala Ser
145                 150                 155                 160

Glu Glu Ser Leu Ala Val Gln Asn Arg Ala Asn Gly Asp Ala Glu Gln
                165                 170                 175

Ala Ser Arg Ala Ala Ala Ala Leu Ala Ala Ala Ile Arg Thr Arg
            180                 185                 190

Asp Asp Ala Ala Ala Thr Arg Lys Gln Ala Ala Arg Leu Arg Ala Asp
                195                 200                 205

Ala Ala Ala Ala Asn Ala Asn Asn Arg Ala Thr Ser Leu Ala Glu
            210                 215                 220

Ala Ser Ala Asn Gln Ala Ala Arg Ala Asn Ser Ala Ser Asp Asp Ala
225                 230                 235                 240

Ser Ser Ala Gln Ala Ala Ala Leu Ala Gln Ala Asn Ala Glu Ala Ser
                245                 250                 255

Leu Thr Ala Ser Ile Thr Ser Ile Gln Ser Val Arg Ser Ala Arg Thr
                260                 265                 270

Asp Ser Glu Thr Ala Gln Asp Gln Ala Ala Ala Ala Lys Ala Ser
            275                 280                 285

Pro Gln Ile Ser Thr Lys Asp Gly Val Val Val Gly Phe Gly Thr Asp
290                 295                 300

Ala Gly Ser Ser Ser Gln Leu Lys Ala Gln Val Ser Ala Leu Asn Arg
305                 310                 315                 320

Ala Ser Ser Arg Val Ser Ser Gly Thr Ala Arg Ser Ser Pro Arg Ser
                325                 330                 335

Leu Ser Asp Ala Ser Ser Glu Ala Ser Ala Ser Ala Asn Ala Ser Ser
                340                 345                 350

Asp Ser Ser Ser Ser Ala
            355

<210> SEQ ID NO 28
<211> LENGTH: 360
<212> TYPE: PRT
<213> ORGANISM: Polistes dominula

<400> SEQUENCE: 28

Ile Glu Asp Val Gly Ala Asp Ala Glu Ser Ala Gln Ser Ala Ala
1               5                   10                  15

Glu Ser Ser Ser Gly Ala Asn Glu Ser Gly Gly Glu Ser Ser Ser
             20                  25                  30
```

Ser Ser Ala Ser Val Ser Val Ser Ala Ser Ala Ser Ser Ser Glu
         35                  40                  45

Ser Lys Arg Ser Gly Val Ala Ile Glu Gly Ala Leu Val Gly Thr Gly
 50                  55                  60

Ala Ala Ser Ser Ala Ala Ala Ser Ala Glu Leu Leu Ser Asp Thr Leu
 65                  70                  75                  80

Gly Leu Gly Gln Thr Ser Ala Gln Ala Gln Ala Ala Val Glu Glu
                 85                  90                  95

Ala Asn Val Ser Ser Asn Ala Asn Asn Lys Ala Ser Gln Trp Ala Ala
                100                 105                 110

Gln Ala Ala Ala Ala Ala Thr Ala Ala Ala Ala Ser Gln Glu Asn Ala
                115                 120                 125

Ala Ala Leu Ala Arg Ala Ser Ala Glu Ala Ser Gln Ser Ala Ala Arg
                130                 135                 140

Ala Thr Ser Arg Ala Glu Ala Asn Ala Ser Ala Ala Lys Ala Ser Ala
145                 150                 155                 160

Glu Lys Val Trp Ile Leu Ala Gln Asp Ser Ala Gln Ala Gln Ala Arg
                165                 170                 175

Ala Thr Glu Arg Ser Glu Ser Ser Asn Arg Asp Ala Ala Ala Ser Ala
                180                 185                 190

Ala Ala Ala Ile Glu Ala Glu Ser Lys Ala Ala Lys Ala Leu Lys Ala
                195                 200                 205

Ile Ala Asp Ala Lys Ala Lys Ala Ala Ala Val Ala Ala Gln Ala
                210                 215                 220

Glu Ala Ala Ala Ala Ala Ala Ala Lys Ala Arg Ala Glu Ala
225                 230                 235                 240

Glu Ser Gly Ala Ala Val Ala Ala Ala Arg Ala Val Ala Gln Ala
                245                 250                 255

Glu Ala Ala Ala Ser Ser Arg Asn Asn Arg Gln Ala Gly Ile Ala Gln
                260                 265                 270

Ala Gly Ala Val Ala Ala Ala Gln Thr Arg Ala Leu Ala Ser Ser Val
                275                 280                 285

Ala Ala Thr Ala Lys Ala Ala Tyr Ala Asn Ala Asp Val Gln Ala
                290                 295                 300

Leu Arg Ala Ser Glu Trp Asp Ser Ala Ser Ser Ser Ser Ser Ser
305                 310                 315                 320

Ser Ser Ser Ser Ala Ser Ala Ser Ala Ser Asn Ser Asn Ser
                325                 330                 335

Ser Ser Gly Arg Ile Ser Ser Ser Asp Ala Ser Ser Ser Ala Glu Ala
                340                 345                 350

Glu Ser Asp Ala Ser Ser Arg Val
                355                 360

<210> SEQ ID NO 29
<211> LENGTH: 314
<212> TYPE: PRT
<213> ORGANISM: Apis dorsata

<400> SEQUENCE: 29

Gly Leu Glu Gly Ser Gly Asn Ser Leu Pro Glu Leu Val Lys Gly Ser
1               5                   10                  15

Ala Ser Ala Thr Ala Ser Thr Ala Val Thr Ala Arg Ser Gly Leu Arg
                20                  25                  30

Ala Gly Gln Val Ala Leu Ala Ser Gln Lys Asp Ala Val Leu Gln Ala

```
                35                  40                  45
Glu Ala Ala Ser Ala Ala Ser Glu Ala Arg Ala Ala Asp Leu
 50                  55                  60
Thr Ala Lys Leu Ser Gln Ser Ala Ser Val Gln Ser Gln Ala Ala
65                  70                  75                  80
Ala Lys Gly Lys Glu Thr Glu Ala Ala Val Gly Gln Ala Arg Ala
                85                  90                  95
Gly Leu Glu Ser Val Ser Ile Ala Ala Ser Ala Thr Ser Ala Ala Lys
                100                 105                 110
Glu Ala Ser Thr Ala Ala Lys Thr Ala Ala Ser Ala Leu Ser Thr Ala
                115                 120                 125
Thr Val Gln Ala Lys Ile Ala Glu Arg Ala Ala Lys Ala Glu Ala Val
                130                 135                 140
Ala Ser Glu Glu Ala Lys Val Lys Ala Ile Ala Ala Asn Leu Ala
145                 150                 155                 160
Ala Ala Ala Ser Ala Ala Ala Glu Ala Ala Leu Lys Ala Glu Lys Val
                165                 170                 175
Ala Glu Glu Ala Ile Ala Arg Ala Ala Ser Lys Ala Ala Ala Arg
                180                 185                 190
Ala Ala Ala Ala Ala Leu Ala Ser Ser Lys Glu Ala Thr Ala Ser
                195                 200                 205
Ala Arg Asn Ala Ala Glu Ser Glu Ala Arg Asn Glu Val Ala Val Leu
                210                 215                 220
Ile Ala Glu Ile Asp Lys Lys Ser Arg Glu Ile Asp Ala Ala Thr Ser
225                 230                 235                 240
Leu Asn Ala Arg Ala Ala Ala Lys Ala Ser Ser Arg Asn Val Glu Thr
                245                 250                 255
Ala Thr Ile Gly Ala Asn Ile Asp Ser Ser Lys Gln Val Val Ser Ile
                260                 265                 270
Pro Val Glu Ile Lys Lys Phe Pro Glu Pro Glu Leu Ser Thr Ser Trp
                275                 280                 285
Arg Glu Asp Glu Glu Val Thr Lys Gly Lys Lys Glu Asp Ile Asn Val
                290                 295                 300
Asn Gly Phe Glu Leu Lys Ser Asn Val Phe
305                 310

<210> SEQ ID NO 30
<211> LENGTH: 287
<212> TYPE: PRT
<213> ORGANISM: Apis dorsata

<400> SEQUENCE: 30

Arg Val Ile Asn Gln Ser Leu Lys Ser Asn Val Asp Ile Gln Gly Ala
1               5                   10                  15
Ala Gly Gln Val Gly Asp Gly Ser Tyr Val Phe Gly Ser Ser Ile Glu
                20                  25                  30
Asn Ala Leu Lys Val Ala Arg Ala Ser Glu Asn Val Gly Leu Asn Leu
                35                  40                  45
Glu Leu Asn Ala Gly Ala Arg Ala Ala Ser Val Ala Ala Ala Ala Gln
                50                  55                  60
Ala Lys Asn Thr Glu Ala Ala Glu Ala Gly Ala Asn Ala Ala Leu Ala
65                  70                  75                  80
Ala Ala Ile Ala Lys Arg Glu Glu Ala Ile Lys Ala Ser Glu Ile Ala
                85                  90                  95
```

```
Ser Gln Leu Leu Thr Asn Ala Ala Lys Ala Ala Glu Ala Thr Val Ser
                100                 105                 110

Ala Thr Lys Arg Ala Ala Gln Leu Thr Ala Ala Lys Glu Ala Thr
            115                 120                 125

Arg Ala Ser Ala Ala Ala Ala Glu Ala Ala Thr Glu Ala Gln Val Lys
        130                 135                 140

Ala Asn Ala Asp Ser Ile Ile Thr Lys Arg Ala Ala Ile Ala Glu Ala
145                 150                 155                 160

Gln Ala Ala Ala Glu Ala Gln Val Lys Ala Ile Ala Arg Lys Ser
                165                 170                 175

Ala Ala Asn Phe Leu Ala Lys Ala Gln Val Ala Ala Thr Glu Ser
            180                 185                 190

Glu Ala Thr Lys Leu Ala Ala Glu Ala Ala Val Ala Leu Thr Asn Ala
            195                 200                 205

Glu Val Ala Val Asn Gln Ala Arg Asn Ala Gln Ala Thr Ala Ser Thr
        210                 215                 220

Gln Ala Ser Ala Ala Val Arg Val Asp Ser Gln Ala Ala Asn Ala Glu
225                 230                 235                 240

Ala Ala Ala Val Ala Gln Ala Glu Thr Leu Leu Val Thr Ala Glu Ala
                245                 250                 255

Val Ala Ala Glu Ala Glu Ala Ala Ser Lys Ala Ala Ser Leu Ala
            260                 265                 270

Lys Lys Ile Val Asp Glu Lys Lys Ile Arg Val Glu Lys Leu Glu
            275                 280                 285

<210> SEQ ID NO 31
<211> LENGTH: 314
<212> TYPE: PRT
<213> ORGANISM: Apis dorsata

<400> SEQUENCE: 31

Gly Val Glu Glu Phe Lys Ala Thr Glu Val Ile Gly Lys Lys Leu
1               5                   10                  15

Glu Val Asp Leu Leu Lys Asn Val Asp Thr Ser Ala Lys Arg Lys Glu
            20                  25                  30

Asn Gly Ala Pro Val Leu Gly Lys Asn Ile Phe Lys Ser Leu Glu Lys
        35                  40                  45

Ile Lys Ala Ser Ala Gly Ala Asp Ala Lys Thr Ser Ala Val Val Lys
    50                  55                  60

Ala Ser Ala Leu Ala Leu Ala Glu Ala Tyr Leu Arg Ala Ser Ala Leu
65                  70                  75                  80

Ser Ala Ala Ala Ser Ala Lys Ala Ala Ala Leu Lys Asn Ala Gln
                85                  90                  95

Gln Ala Gln Leu Val Ala Gln Glu Lys Ala Leu Ala Ala Leu Lys Ala
                100                 105                 110

Gln Ser Glu Glu Glu Ala Ala Ser Ala Arg Ala Asn Ala Ala Ala
            115                 120                 125

Ala Thr Gln Ser Ala Val Glu Arg Ala Gln Ala Ser Ser Arg Ile Ala
        130                 135                 140

Met Ala Ala Gln Asp Val Ala Ser Asp Leu Gln Lys Arg Thr Ser Thr
145                 150                 155                 160

Lys Ala Ala Ala Glu Ala Ala Ala Thr Leu Arg Gln Ser Gln Asp Ala
                165                 170                 175

Glu Gln Thr Lys Trp Asn Ala Lys Ser Ala Leu Glu Ala Ser Ala Ala
            180                 185                 190
```

Ala Ala Ala Ala Glu Thr Lys Thr Thr Ala Ser Ser Glu Ala Ala Ser
            195                 200                 205

Ala Ala Ala Lys Lys Ala Ala Ala Ile Ala Ser Asp Ala Asp Gly Ala
    210                 215                 220

Glu Arg Ser Ala Ser Thr Glu Ala Gln Ser Ala Ala Lys Ile Glu Ser
225                 230                 235                 240

Val Ala Ala Ala Glu Gly Ser Ala Asn Ser Ala Ser Glu Asp Ser Gln
                245                 250                 255

Ala Ala Gln Leu Glu Ala Ser Ala Ala Ala Arg Ala Asn Val Ala Ala
            260                 265                 270

Ala Ile Gly Asp Gly Ala Ile Ser Gly Leu Gly Gln Asp Ala Gly Ala
        275                 280                 285

Ala Ala Gln Leu Leu Ala Gln Ala Lys Ala Leu Ala Glu Val Ser Ser
    290                 295                 300

Lys Ser Glu Asn Ile Glu Asp Lys Lys Phe
305                 310

<210> SEQ ID NO 32
<211> LENGTH: 323
<212> TYPE: PRT
<213> ORGANISM: Apis dorsata

<400> SEQUENCE: 32

Ala Ser Glu Glu Val Glu Val Arg Asp Lys Thr Lys Thr Ser Thr Ala
1               5                   10                  15

Val Lys Ser Glu Lys Val Glu Val Val Pro Ala Lys Asp Glu Leu
            20                  25                  30

Lys Leu Thr Ser Glu Pro Ile Leu Gly Arg Arg Val Gly Thr Gly Ala
        35                  40                  45

Ser Glu Val Ala Ser Ser Ser Gly Glu Ala Ile Ala Ile Ser Leu Gly
    50                  55                  60

Ala Gly Gln Ala Ala Ala Glu Ser Gln Ala Val Ala Ala Ser Gln Ser
65                  70                  75                  80

Lys Thr Ala Ala Asn Ala Ala Ile Asn Ala Ser Glu Leu Ala Asn Lys
                85                  90                  95

Val Ala Ala Leu Val Ala Gly Ala Thr Ala Gln Ala Arg Ala Ala
            100                 105                 110

Ala Ala Ser Ser Asp Ala Leu Lys Ala Ser Leu Ala Thr Glu Glu Ser
        115                 120                 125

Ala Glu Glu Ala Glu Ala Val Ala Ala Lys Ala Ala Ala Glu
    130                 135                 140

Lys Ala Glu Ser Leu Ala Arg Asn Leu Ala Ser Ala Ser Ala Arg Ala
145                 150                 155                 160

Ala Leu Ser Ser Glu Lys Ala Asn Glu Leu Ala Gln Ala Glu Ser Ala
                165                 170                 175

Ala Ala Ala Glu Ala Gln Ala Lys Thr Ala Ala Ala Lys Ala Ala
            180                 185                 190

Glu Ile Ala Leu Lys Val Ala Asp Ile Ala Val Lys Ala Glu Ala Asp
        195                 200                 205

Ala Ala Ala Ala Val Ala Ala Lys Ala Arg Ala Val Ala Asp
    210                 215                 220

Ala Ala Ala Ala Arg Ala Ala Val Asn Ala Ile Ala Lys Ala Glu
225                 230                 235                 240

Glu Glu Ala Ser Ala Gln Ala Glu Asn Thr Ala Gly Val Leu Gln Ala

```
                245                 250                 255
Ala Ala Ser Ala Ala Glu Ser Arg Ala Ala Ala Thr Ala Ala
            260                 265                 270

Ala Thr Ser Glu Ala Ala Glu Ala Gly Pro Leu Ala Gly Glu Leu
            275                 280                 285

Lys Pro Pro Gln Trp Lys Arg Val Pro Val Lys Glu Glu Trp Gln
            290                 295                 300

Thr Ser Thr Lys Glu Glu Trp Lys Ala Thr Asn Glu Glu Trp Glu Pro
305                 310                 315                 320

Val Ala Lys

<210> SEQ ID NO 33
<211> LENGTH: 312
<212> TYPE: PRT
<213> ORGANISM: Apis florea

<400> SEQUENCE: 33

Gly Leu Glu Arg Pro Gly Asn Ser Leu Pro Glu Leu Val Lys Gly Ser
1               5                   10                  15

Ala Ser Ala Thr Ala Ser Thr Ala Val Thr Ala Arg Ser Gly Leu Arg
            20                  25                  30

Ala Gly Gln Val Ala Leu Ala Ser Gln Lys Asp Ala Val Leu Gln Ala
        35                  40                  45

Glu Ala Ala Ser Ala Ala Ser Glu Ala Arg Ala Ala Asp Leu
    50                  55                  60

Thr Ala Lys Leu Ser Gln Glu Ser Ala Ser Leu Gln Ser Gln Ala Ala
65                  70                  75                  80

Ala Lys Gly Lys Glu Thr Glu Glu Ala Val Gly Gln Ala Arg Ala
            85                  90                  95

Gly Leu Glu Ser Val Ser Ile Ala Ala Ser Ala Thr Ser Ala Ala Lys
            100                 105                 110

Glu Ala Ser Thr Ala Ala Arg Ser Ala Ala Ser Ala Leu Ser Thr Ala
            115                 120                 125

Thr Val Gln Ala Lys Ile Ala Glu Arg Ala Ala Lys Ala Glu Ala Ile
        130                 135                 140

Ala Ser Glu Glu Ala Lys Ala Lys Ala Ile Ala Ala Ala Asn Leu Ala
145                 150                 155                 160

Ala Ala Ala Asn Ala Ala Ala Glu Ala Ala Leu Lys Ala Glu Lys Val
            165                 170                 175

Ala Glu Glu Ala Ile Ala Arg Val Ala Ser Ala Lys Ala Ala Arg
        180                 185                 190

Ala Ala Ala Ala Ala Leu Ala Ser Ser Lys Glu Ala Ala Val Ala Ser
            195                 200                 205

Ala Arg Asn Ala Ala Glu Ser Glu Ala Arg Ser Glu Val Ala Val Leu
        210                 215                 220

Ile Ala Glu Ile Asp Lys Lys Ser Arg Glu Ile Asp Ala Ala Thr Ser
225                 230                 235                 240

Leu Asn Ala Arg Ala Ala Ala Lys Ala Ser Ser Arg Asn Val Glu Thr
            245                 250                 255

Ala Thr Ile Gly Ala Asn Ile Asp Ser Ser Lys Gln Val Val Ser Ile
            260                 265                 270

Pro Val Glu Lys Lys Leu Pro Glu Pro Glu Leu Ser Thr Ser Trp Gly
            275                 280                 285

Glu Asp Glu Glu Ile Thr Lys Lys Lys Glu Asp Val Asn Leu Asn Gly
```

```
            290                 295                 300
Phe Asp Val Phe Val Asn Ala Ser
305                 310
```

<210> SEQ ID NO 34
<211> LENGTH: 288
<212> TYPE: PRT
<213> ORGANISM: Apis florea

<400> SEQUENCE: 34

```
Arg Val Ile Asn Arg Glu Ser Leu Lys Thr Asn Val Glu Ile Gln Gly
1               5                   10                  15

Ala Ala Gly Glu Val Gly Asp Gly Ser Asp Ala Asn Gly Ser Ser Ile
            20                  25                  30

Glu Asn Ala Leu Gln Val Ala Arg Ala Ser Glu Asn Val Gly Leu Asn
        35                  40                  45

Leu Glu Leu Asn Ala Gly Ala Arg Ala Ala Ser Val Ala Ala Ala Ala
    50                  55                  60

Gln Ala Lys Asn Thr Glu Ala Ala Glu Ala Gly Ala Asn Ala Ala Leu
65                  70                  75                  80

Ala Ala Ala Ile Ala Lys Arg Glu Glu Ala Ile Lys Ala Ser Glu Ile
                85                  90                  95

Ala Ser Gln Leu Leu Thr Asn Ala Ala Lys Ala Ala Glu Ala Thr Val
            100                 105                 110

Ser Ala Thr Lys Arg Ala Ala Gln Leu Thr Ala Ala Lys Glu Ala
        115                 120                 125

Thr Arg Ala Ser Ala Ala Ala Glu Ala Ala Thr Glu Ala Gln Val
    130                 135                 140

Lys Ala Asn Ala Asp Ser Ile Val Thr Lys Arg Ala Ala Ile Ala Glu
145                 150                 155                 160

Ala Gln Ala Ala Ala Glu Ala Gln Ala Lys Ala Ala Ile Ala Arg Lys
                165                 170                 175

Ser Ala Ala Asn Phe Leu Ala Lys Ala Gln Val Ala Ala Ala Ala Glu
            180                 185                 190

Ser Glu Ala Thr Lys Leu Ala Ala Glu Ala Thr Val Ala Leu Thr Asn
        195                 200                 205

Ala Glu Val Ala Val Asn Gln Ala Arg Asn Ala Gln Ala Thr Ala Ser
    210                 215                 220

Thr Gln Ala Ser Ser Ala Val Arg Val Asp Ser Gln Ala Ala Asn Ala
225                 230                 235                 240

Glu Ala Ala Ala Val Ala Ala Glu Thr Leu Leu Val Thr Ala Glu
                245                 250                 255

Ala Val Ala Ala Glu Ala Glu Ala Ala Asn Lys Ala Ala Ser Leu
            260                 265                 270

Ala Lys Lys Ile Val Asp Glu Lys Lys Ile Arg Val Glu Lys Leu Glu
        275                 280                 285
```

<210> SEQ ID NO 35
<211> LENGTH: 316
<212> TYPE: PRT
<213> ORGANISM: Apis florea

<400> SEQUENCE: 35

```
Gly Val Glu Glu Phe Lys Ser Ser Ala Thr Glu Glu Val Ile Gly Lys
1               5                   10                  15

Asn Leu Glu Val Asp Leu Leu Lys Asn Val Asp Thr Ser Ala Lys Arg
```

```
            20                  25                  30
Arg Glu Asn Gly Ala Pro Val Leu Gly Lys Asn Val Phe Lys Ser Leu
            35                  40                  45

Glu Lys Ile Lys Ser Leu Ala Gly Ala Asp Ala Lys Ala Ser Ala Val
        50                  55                  60

Val Lys Ala Ser Ala Leu Ala Leu Ala Glu Ala Tyr Leu Arg Ala Ser
65                  70                  75                  80

Ala Leu Ser Ala Ala Ser Ala Lys Ala Val Ala Ala Leu Lys Asn
                85                  90                  95

Ala Gln Gln Ala Gln Leu Val Ala Gln Glu Lys Ala Leu Ala Ala Leu
                100                 105                 110

Lys Ala Gln Ser Glu Glu Ala Ala Ser Ala Arg Ala Asn Ala Ala
            115                 120                 125

Ala Ala Ala Thr Gln Ser Ala Val Glu Arg Ala Gln Val Ser Ser Arg
        130                 135                 140

Ile Ala Thr Ala Ala Gln Asn Val Ala Ser Asp Leu Gln Lys Arg Val
145                 150                 155                 160

Ser Thr Lys Ala Ala Ala Glu Ala Ala Thr Leu Arg Glu Leu Gln
                165                 170                 175

Asn Ala Glu Gln Thr Lys Trp Ser Ala Asn Val Ala Leu Glu Val Ser
                180                 185                 190

Ala Ala Ala Thr Ala Ala Glu Thr Lys Thr Thr Ala Ser Ser Glu Ala
            195                 200                 205

Ala Thr Ala Ala Ala Lys Lys Ala Ala Ile Ala Ser Asp Ala Asp
        210                 215                 220

Gly Ala Glu Arg Ser Ala Ser Thr Glu Ala Gln Ser Ala Ala Lys Ile
225                 230                 235                 240

Glu Gly Val Ala Ala Ala Glu Gly Ser Ala Asn Thr Ala Ser Glu Asp
                245                 250                 255

Ser Gln Ala Ala Gln Leu Glu Ala Ser Ala Ala Arg Ala Asn Val
            260                 265                 270

Ala Ala Ala Val Gly Asp Gly Ala Ile Leu Gly Leu Gly Gln Asp Ala
        275                 280                 285

Gly Ala Ala Ala Gln Leu Leu Ala Gln Ala Lys Ala Leu Ala Glu Val
            290                 295                 300

Ser Ser Lys Ser Glu Asn Ile Glu Asp Lys Lys Phe
305                 310                 315

<210> SEQ ID NO 36
<211> LENGTH: 323
<212> TYPE: PRT
<213> ORGANISM: Apis florea

<400> SEQUENCE: 36

Ala Ser Glu Glu Val Glu Ala Arg Glu Lys Thr Lys Ala Ser Thr Ala
1               5                   10                  15

Val Lys Ser Glu Lys Val Glu Val Val Pro Ala Lys Asp Glu Leu
                20                  25                  30

Lys Leu Thr Ser Glu Pro Ile Ile Gly Arg Arg Val Gly Thr Gly Ala
            35                  40                  45

Ser Glu Val Ala Ser Ser Thr Gly Glu Ala Ile Ala Ile Ser Leu Gly
        50                  55                  60

Val Gly Gln Ala Ala Ala Glu Ser Gln Ala Val Ala Ala Leu Gln Ser
65                  70                  75                  80
```

```
Lys Thr Ala Ala Asn Ala Ala Ile Ser Ala Ser Glu Leu Ala Asn Lys
            85                  90                  95

Val Ala Ala Leu Val Val Gly Ala Thr Ala Ala Gln Ala Arg Ala Ala
            100                 105                 110

Thr Ala Ser Ser Gly Ala Leu Lys Ala Ser Leu Ala Thr Glu Glu Ser
            115                 120                 125

Ala Glu Glu Ala Glu Ala Ala Val Ala Ala Lys Ala Ala Ala Glu
            130                 135             140

Lys Ala Glu Ser Leu Ala Arg Asn Leu Ala Ser Ala Arg Ala
145                 150                 155                 160

Ala Leu Ser Ser Glu Lys Ala Asn Glu Leu Ala Gln Ala Glu Ser Ala
            165                 170                 175

Ala Ala Ala Glu Ala Gln Ala Lys Thr Ala Ala Ala Lys Ala Ala
            180                 185                 190

Glu Ile Ala Leu Lys Val Ser Glu Ile Ala Val Lys Ala Glu Ala Asp
            195                 200                 205

Ala Ala Ala Ala Val Ala Ala Ala Lys Ala Arg Ala Val Ala Asp
            210                 215                 220

Ala Ala Ala Ala Arg Ala Ala Val Asn Ala Ile Ala Lys Ala Glu
225                 230                 235                 240

Glu Glu Ala Ser Ala Gln Ala Glu Asn Thr Ala Gly Val Ser Gln Ala
            245                 250                 255

Ala Ala Ser Ala Ala Ala Glu Ser Arg Ala Ala Ala Ala Ala Ala
            260                 265                 270

Ala Thr Ser Glu Ala Ala Ala Glu Ala Gly Ser Leu Ala Gly Glu Leu
            275                 280                 285

Lys Pro Pro Gln Trp Lys Arg Val Pro Val Lys Lys Glu Glu Trp Gln
            290                 295                 300

Thr Ser Thr Lys Glu Glu Trp Lys Ala Ser Asn Glu Glu Trp Glu Pro
305                 310                 315                 320

Val Ala Lys

<210> SEQ ID NO 37
<211> LENGTH: 314
<212> TYPE: PRT
<213> ORGANISM: Apis mellifera

<400> SEQUENCE: 37

Gly Leu Glu Gly Pro Gly Asn Ser Leu Pro Glu Leu Val Lys Gly Ser
1               5                   10                  15

Ala Ser Ala Thr Ala Ser Thr Ala Val Thr Ala Arg Ser Gly Leu Arg
            20                  25                  30

Ala Gly Gln Val Ala Leu Ala Ser Gln Lys Asp Ala Val Leu Gln Ala
            35                  40                  45

Gln Ala Ala Ala Ser Ala Ala Ser Glu Ala Arg Ala Ala Ala Asp Leu
            50                  55                  60

Thr Ala Lys Leu Ser Gln Glu Ser Ala Ser Val Gln Ser Gln Ala Ala
65                  70                  75                  80

Ala Lys Gly Lys Glu Thr Glu Glu Ala Ala Val Gly Gln Ala Arg Ala
            85                  90                  95

Gly Leu Glu Ser Val Ser Met Ala Ala Ser Ala Thr Ser Ala Ala Lys
            100                 105                 110

Glu Ala Ser Thr Ala Ala Lys Ala Ala Ala Ser Ala Leu Ser Thr Ala
            115                 120                 125
```

```
Val Val Gln Ala Lys Ile Ala Glu Arg Ala Ala Lys Ala Glu Ala Val
    130                 135                 140
Ala Ser Asp Glu Ala Lys Ala Lys Ala Ile Ala Ala Asn Leu Ala
145                 150                 155                 160
Ala Glu Ala Ser Val Ala Ala Glu Ala Ala Leu Lys Ala Glu Lys Val
                165                 170                 175
Ala Glu Glu Ala Ile Ala Arg Ala Ala Ser Lys Ala Ala Ala Arg
                180                 185                 190
Ala Ala Ala Ala Ala Leu Ala Ser Ser Lys Glu Ala Ala Thr Ala Ser
            195                 200                 205
Ala Arg Asn Ala Ala Glu Ser Glu Ala Arg Asn Glu Val Ala Val Leu
    210                 215                 220
Ile Ala Glu Ile Asp Lys Lys Ser Arg Glu Ile Asp Ala Ala Ser Ser
225                 230                 235                 240
Leu Asn Ala Arg Ala Ala Lys Ala Ser Ser Arg Asn Val Glu Thr
                245                 250                 255
Ala Thr Ile Gly Ala Asn Ile Asn Ser Ser Lys Gln Val Ser Ile
                260                 265                 270
Pro Val Glu Ile Lys Lys Phe Ser Glu Pro Glu Val Ser Thr Ser Trp
                275                 280                 285
Arg Glu Asp Glu Glu Val Thr Lys Glu Lys Lys Glu His Ile Asn Leu
    290                 295                 300
Asn Asp Phe Asp Leu Lys Ser Asn Val Phe
305                 310

<210> SEQ ID NO 38
<211> LENGTH: 290
<212> TYPE: PRT
<213> ORGANISM: Apis mellifera

<400> SEQUENCE: 38

Arg Val Ile Asn His Glu Ser Leu Lys Thr Ser Glu Asp Ile Gln Gly
1               5                   10                  15
Gly Tyr Ser Ala Gly Ile Val Gly Asp Gly Ser Asp Ala Leu Gly Ser
                20                  25                  30
Ser Ile Glu Asn Ala Gln Lys Val Ala Arg Ala Ala Glu Asn Val Gly
            35                  40                  45
Leu Asn Leu Glu Leu Gly Ala Gly Ala Arg Ala Ser Val Ala Ala
    50                  55                  60
Ala Ala Gln Ala Lys Asn Thr Glu Ala Ala Glu Ala Gly Ala Asn Ala
65                  70                  75                  80
Ala Leu Ala Ala Ala Ile Ala Lys Arg Glu Glu Ala Ile Lys Ala Ser
                85                  90                  95
Glu Ile Ala Asn Gln Leu Leu Thr Asn Ala Ala Lys Ala Glu Ala
                100                 105                 110
Thr Val Ser Ala Thr Lys Arg Ala Ala Gln Leu Thr Ala Ala Ala Lys
            115                 120                 125
Glu Ala Thr Arg Ala Ser Ala Ala Ala Glu Ala Ala Thr Glu Ala
    130                 135                 140
Gln Val Lys Ala Asn Ala Asp Ser Ile Ile Thr Lys Arg Ala Ala Ile
145                 150                 155                 160
Ala Glu Ala Gln Ala Ala Glu Ala Gln Val Lys Ala Ala Ile Ala
                165                 170                 175
Arg Lys Ser Ala Ala Asn Phe Leu Ala Lys Ala Gln Ile Ala Ala Ala
                180                 185                 190
```

```
Ala Glu Ser Glu Ala Thr Lys Leu Ala Ala Glu Ala Val Ala Leu
            195                 200                 205

Thr Asn Ala Glu Val Ala Val Asn Gln Ala Arg Asn Ala Gln Ala Asn
210                 215                 220

Ala Ser Thr Gln Ala Ser Met Ala Val Arg Val Asp Ser Gln Ala Ala
225                 230                 235                 240

Asn Ala Glu Ala Ala Val Ala Gln Ala Glu Thr Leu Leu Val Thr
            245                 250                 255

Ala Glu Ala Val Ala Ala Ala Glu Glu Val Ala Asn Lys Ala Ala
            260                 265                 270

Thr Phe Ala Lys Gln Ile Val Asn Glu Lys Lys Ile His Val Ala Lys
            275                 280                 285

Leu Glu
    290

<210> SEQ ID NO 39
<211> LENGTH: 316
<212> TYPE: PRT
<213> ORGANISM: Apis mellifera

<400> SEQUENCE: 39

Gly Val Glu Glu Phe Lys Ser Ser Ala Thr Glu Glu Val Ile Ser Lys
1               5                   10                  15

Asn Leu Glu Val Asp Leu Leu Lys Asn Val Asp Thr Ser Ala Lys Arg
            20                  25                  30

Arg Glu Asn Gly Ala Pro Val Leu Gly Lys Asn Thr Leu Gln Ser Leu
        35                  40                  45

Glu Lys Ile Lys Thr Ser Ala Ser Val Asn Ala Lys Ala Ala Ala Val
    50                  55                  60

Val Lys Ala Ser Ala Leu Ala Leu Ala Glu Ala Tyr Leu Arg Ala Ser
65                  70                  75                  80

Ala Leu Ser Ala Ala Ala Ser Ala Lys Ala Ala Ala Leu Lys Asn
            85                  90                  95

Ala Gln Gln Ala Gln Leu Asn Ala Gln Glu Lys Ser Leu Ala Ala Leu
            100                 105                 110

Lys Ala Gln Ser Glu Glu Glu Ala Ala Ser Ala Arg Ala Asn Ala Ala
            115                 120                 125

Thr Ala Ala Thr Gln Ser Ala Leu Glu Arg Ala Gln Ala Ser Ser Arg
            130                 135                 140

Leu Ala Thr Val Ala Gln Asn Val Ala Ser Asp Leu Gln Lys Arg Thr
145                 150                 155                 160

Ser Thr Lys Ala Ala Glu Ala Ala Ala Thr Leu Arg Gln Leu Gln
            165                 170                 175

Asp Ala Glu Arg Thr Lys Trp Ser Ala Asn Ala Ala Leu Glu Val Ser
            180                 185                 190

Ala Ala Ala Ala Ala Glu Thr Lys Thr Thr Ala Ser Ser Glu Ala
            195                 200                 205

Ala Asn Ala Ala Ala Lys Lys Ala Ala Ala Ile Ala Ser Asp Ala Asp
            210                 215                 220

Gly Ala Glu Arg Ser Ala Ser Thr Glu Ala Gln Ser Ala Ala Lys Ile
225                 230                 235                 240

Glu Ser Val Ala Ala Ala Glu Gly Ser Ala Asn Ser Ala Ser Glu Asp
            245                 250                 255

Ser Arg Ala Ala Gln Leu Glu Ala Ser Thr Ala Ala Arg Ala Asn Val
```

```
                    260                 265                 270
Ala Ala Ala Val Gly Asp Gly Ala Ile Ile Gly Leu Gly Glu Glu Ala
            275                 280                 285

Gly Ala Ala Ala Gln Leu Leu Ala Gln Ala Lys Ala Leu Ala Glu Val
            290                 295                 300

Ser Ser Lys Ser Glu Asn Ile Glu Asp Lys Lys Phe
305                 310                 315

<210> SEQ ID NO 40
<211> LENGTH: 323
<212> TYPE: PRT
<213> ORGANISM: Apis mellifera

<400> SEQUENCE: 40

Ala Arg Glu Glu Val Glu Thr Arg Asp Lys Thr Lys Thr Ser Thr Val
1               5                   10                  15

Val Lys Ser Glu Lys Val Glu Val Ala Pro Ala Lys Asp Glu Leu
            20                  25                  30

Lys Leu Thr Ser Glu Pro Ile Phe Gly Arg Arg Val Gly Thr Gly Ala
            35                  40                  45

Ser Glu Val Ala Ser Ser Gly Glu Ala Ile Ala Ile Ser Leu Gly
        50                  55                  60

Ala Gly Gln Ser Ala Ala Glu Ser Gln Ala Leu Ala Ala Ser Gln Ser
65                  70                  75                  80

Lys Thr Ala Ala Asn Ala Ala Ile Gly Ala Ser Glu Leu Thr Asn Lys
                85                  90                  95

Val Ala Ala Leu Val Ala Gly Ala Thr Gly Ala Gln Ala Arg Ala Thr
            100                 105                 110

Ala Ala Ser Ser Ser Ala Leu Lys Ala Ser Leu Ala Thr Glu Glu Ala
            115                 120                 125

Ala Glu Glu Ala Glu Ala Ala Val Ala Asp Ala Lys Ala Ala Ala Glu
            130                 135                 140

Lys Ala Glu Ser Leu Ala Lys Asn Leu Ala Ser Ala Ser Ala Arg Ala
145                 150                 155                 160

Ala Leu Ser Ser Glu Arg Ala Asn Glu Leu Ala Gln Ala Glu Ser Ala
                165                 170                 175

Ala Ala Ala Glu Ala Gln Ala Lys Thr Ala Ala Ala Lys Ala Ala
            180                 185                 190

Glu Ile Ala Leu Lys Val Ala Glu Ile Ala Val Lys Ala Glu Ala Asp
                195                 200                 205

Ala Ala Ala Ala Val Ala Ala Lys Ala Arg Ala Val Ala Asp
            210                 215                 220

Ala Ala Ala Ala Arg Ala Ala Val Asn Ala Ile Ala Lys Ala Glu
225                 230                 235                 240

Glu Glu Ala Ser Ala Gln Ala Glu Asn Ala Ala Gly Val Leu Gln Ala
                245                 250                 255

Ala Ala Ser Ala Ala Ala Glu Ser Arg Ala Ala Ala Ala Ala Ala
            260                 265                 270

Ala Thr Ser Glu Ala Ala Ala Glu Ala Gly Pro Leu Ala Gly Glu Met
            275                 280                 285

Lys Pro Pro His Trp Lys Trp Glu Arg Ile Pro Val Lys Lys Glu Glu
            290                 295                 300

Trp Lys Thr Ser Thr Lys Glu Glu Trp Lys Thr Thr Asn Glu Glu Trp
305                 310                 315                 320
```

Glu Val Lys

<210> SEQ ID NO 41
<211> LENGTH: 288
<212> TYPE: PRT
<213> ORGANISM: Bombus impatiens

<400> SEQUENCE: 41

Glu Gly His Val Val Lys Arg Asp Lys Glu Leu Lys Ala Pro Ala Pro
1               5                   10                  15

Leu Pro Glu Leu Leu Gly Asp Gly Ser Asp Ala Leu Gly Ala Ser Met
            20                  25                  30

Glu Asn Gly Ile Lys Val Ala Arg Ala Ser Gln Asn Val Gly Leu Ser
        35                  40                  45

Thr Glu Leu Asn Ala Ala Ala Arg Ala Ala Ala Ala Ala Ala Thr Lys
    50                  55                  60

Gln Ala Lys Asp Thr Glu Ala Glu Ala Gly Ala Gly Ala Ala Ile
65                  70                  75                  80

Ala Val Ala Ile Ala Lys Arg Glu Glu Ala Ile Lys Ala Ser Glu Leu
                85                  90                  95

Ala Ser Lys Leu Leu Thr Ala Ala Val Gly Ser Ser Glu Ala Ala Ala
            100                 105                 110

Ser Ala Ser Ala Arg Ala Ala Gln Leu Thr Ala Ala Ala Ser Ala Ala
        115                 120                 125

Ala Lys Ala Ser Ala Ser Ala Ser Asp Ala Ser Ala Glu Ala Gln Val
    130                 135                 140

Arg Ala Asn Ala Glu Ala Asn Ile Ala Lys Arg Ala Ser Ala Ala Glu
145                 150                 155                 160

Ala Lys Ala Ala Ala Glu Ala Ser Leu Lys Ala Glu Leu Ala Lys Lys
                165                 170                 175

Ala Ala Ala Gly Leu Leu Ala Lys Ala Arg Leu Ala Ala Ser Ala Glu
            180                 185                 190

Ser Glu Ala Thr Lys Leu Ala Ala Glu Ala Glu Val Ala Leu Ala Lys
        195                 200                 205

Ala Arg Val Ala Val Glu Gln Ser Gln Ser Ala Gln Ala Thr Ala Thr
    210                 215                 220

Ala Gln Ala Ala Thr Ala Val Gln Leu Gln Ser Gln Ala Ala Asn Ala
225                 230                 235                 240

Glu Ala Ser Ala Val Ala Gln Ala Glu Thr Leu Leu Val Thr Ala Glu
                245                 250                 255

Ala Val Ser Ala Ala Glu Ala Glu Ala Ala Thr Lys Ala Thr Gly Trp
            260                 265                 270

Ala Lys Asn Val Ile Asn Lys Lys Leu Leu Leu Ala Lys Ile Asp
        275                 280                 285

<210> SEQ ID NO 42
<211> LENGTH: 308
<212> TYPE: PRT
<213> ORGANISM: Bombus terrestris

<400> SEQUENCE: 42

Gly Gln Ser Ser Pro Leu Leu Glu Ile Val Gln Gly Ser Ala Ser Ala
1               5                   10                  15

Thr Ala Ser Thr Ala Val Thr Ala Arg Ser Gly Leu Arg Ala Gly Gln
            20                  25                  30

Val Ala Val Ala Ser Gln Lys Asp Ala Thr Leu Gln Ala Asp Ala Ser

```
                35                  40                  45
Ala Ala Ala Ala Ala Ala Arg Ala Ser Ala Asp Gln Ser Ala Ser
 50                  55                  60

Leu Ala Gln Gln Ser Ala Ser Leu Gln Ser Lys Ala Ala Arg Ala
 65                  70                  75                  80

Lys Ser Ala Glu Glu Ser Ala Ala Thr Ala Lys Ala Glu Leu Gln
                 85                  90                  95

Ala Glu Ser Ile Ala Ala Ser Ala Ser Ser Asn Ala Arg Glu Ala
                100                 105                 110

Ala Ser Ala Lys Ala Ser Ala Ser Ala Met Ser Ser Ala Ala Val Gln
            115                 120                 125

Ala Lys Leu Ala Glu Lys Thr Ala Lys Asn Gln Ala Leu Ala Ser Glu
    130                 135                 140

Glu Ala Lys Leu Lys Ala Ala Ala Ala Ser Ala Ala Ala Ala Ala
145                 150                 155                 160

Ser Ala Ala Ala Glu Ala Ala Leu Lys Ala Glu Arg Ile Ala Glu Glu
                165                 170                 175

Ala Ile Ala Lys Ala Ala Ala Lys Ala Ala Ala Arg Ala Ala Ala
                180                 185                 190

Ala Ala Leu Asn Ser Ala Lys Glu Ala Ala Thr Ser Ser Ala Arg Ser
        195                 200                 205

Ala Ala Glu Ala Glu Ala Lys Ser Glu Val Ala Ile Leu Ile Ser Glu
    210                 215                 220

Leu Asp Lys Lys Ser Arg Glu Val Ala Ala Ser Ala Ser Ala Lys Ala
225                 230                 235                 240

Arg Ala Ala Ala Ala Ser Ser Arg Asn Ala Glu Thr Ala Val Ile
                245                 250                 255

Gly Ala Asn Ile Asn Val Ala Lys Glu Val Leu Ala Ile Pro Ile Glu
                260                 265                 270

Pro Lys Lys Leu Pro Glu Pro Glu Leu Ala Leu Lys Glu Glu Asn Val
        275                 280                 285

Ala Val Ala Ser Ser Glu Ser Glu Val Lys Val Glu Thr Ser Ser Glu
    290                 295                 300

Ala Trp Ser Ile
305

<210> SEQ ID NO 43
<211> LENGTH: 295
<212> TYPE: PRT
<213> ORGANISM: Bombus terrestris

<400> SEQUENCE: 43

Glu Gly His Val Val Lys Arg Asp Lys Glu Leu Lys Ala Pro Ala Leu
 1               5                  10                  15

Pro Glu Leu Leu Gly Asp Gly Ser Asp Thr Leu Gly Ala Ser Met Glu
                20                  25                  30

Asn Gly Ile Lys Val Ala Arg Ala Ser Gln Asn Val Gly Leu Arg Thr
                35                  40                  45

Glu Leu Asn Ala Ala Ala Arg Ala Ala Ala Ala Ala Thr Lys Gln
 50                  55                  60

Ala Lys Asp Thr Glu Ala Ala Glu Ala Gly Ala Ala Ala Ile Ala
 65                  70                  75                  80

Ile Ala Ile Ala Lys Arg Glu Glu Ala Ile Lys Ala Ser Glu Leu Ala
                 85                  90                  95
```

```
Ser Lys Leu Leu Thr Ala Ala Gly Ser Ser Glu Ala Ala Val Ser
            100                 105                 110

Ala Thr Val Arg Ala Ala Gln Leu Thr Ala Ala Ser Ala Ala Ala
            115                 120                 125

Lys Ala Ser Ala Ser Ala Ser Glu Ala Ser Ala Glu Ala Gln Val Arg
130                 135                 140

Ala Asn Ala Glu Ala Asn Ile Ala Lys Lys Ala Ser Ala Ala Glu Ala
145                 150                 155                 160

Lys Ala Ala Ala Glu Ala Gln Val Lys Ala Leu Ala Lys Lys Ala
                165                 170                 175

Ala Ala Gly Phe Leu Ala Lys Ala Arg Leu Ala Ser Ala Glu Ser
            180                 185                 190

Glu Ala Thr Lys Leu Ala Ala Glu Ala Glu Val Ala Leu Ala Lys Ala
            195                 200                 205

Arg Val Ala Val Asp Gln Ser Gln Ser Ala Gln Ala Thr Ala Thr Ala
            210                 215                 220

Gln Ala Ala Thr Ala Val Gln Leu Gln Ser Gln Ala Ala Asn Ala Glu
225                 230                 235                 240

Ala Ser Ala Val Ala Gln Ala Glu Thr Leu Leu Val Thr Ala Glu Ala
                245                 250                 255

Val Ser Ala Ala Glu Ala Glu Ala Ala Thr Lys Ala Thr Ser Trp Gly
            260                 265                 270

Glu Glu Cys His Gln Arg Glu Lys Val Thr Phe Ser Glu Asp Arg Leu
            275                 280                 285

Asn Glu Arg Gln Asp Asn Trp
            290                 295

<210> SEQ ID NO 44
<211> LENGTH: 313
<212> TYPE: PRT
<213> ORGANISM: Bombus terrestris

<400> SEQUENCE: 44

Gly Ser Val Glu Leu Gly Ala Pro Lys Gln Glu Ser Val Leu Val Glu
1               5                   10                  15

Gln Leu Leu Leu Lys Asn Val Glu Thr Ser Ala Lys Arg Lys Glu Asn
            20                  25                  30

Gly Ala Pro Lys Leu Gly Glu Ser Thr Ala Ala Leu Ala Ser Thr
            35                  40                  45

Lys Ala Thr Ala Ala Ala Glu Ala Lys Ala Ser Ala Lys Val Lys Ala
50                  55                  60

Ser Ala Leu Ala Leu Ala Glu Ala Phe Leu Arg Ala Ser Ala Ala Phe
65                  70                  75                  80

Ala Ala Ala Ser Ala Lys Ala Ala Ala Ala Val Lys Glu Ala Thr Gln
                85                  90                  95

Ala Gln Leu Leu Ala Gln Glu Lys Ala Leu Ile Ala Leu Lys Thr Gln
            100                 105                 110

Ser Glu Gln Gln Ala Ala Ser Ala Arg Ala Asp Ala Ala Ala Ala
            115                 120                 125

Ala Val Ser Ala Leu Glu Arg Ala Gln Ala Ser Ser Arg Ala Ala Thr
            130                 135                 140

Thr Ala Gln Asp Ile Ser Ser Asp Leu Glu Lys Arg Val Ala Thr Ser
145                 150                 155                 160

Ala Ala Ala Glu Ala Gly Ala Thr Leu Arg Ala Glu Gln Ser Ala Ala
                165                 170                 175
```

-continued

```
Gln Ser Lys Trp Ser Ala Ala Leu Ala Ala Gln Thr Ala Ala Ala
            180                 185                 190

Ala Ala Ile Glu Ala Lys Ala Thr Ala Ser Ser Glu Ser Thr Ala Ala
        195                 200                 205

Ala Thr Ser Lys Ala Ala Val Leu Thr Ala Asp Thr Ser Ser Ala Glu
    210                 215                 220

Ala Ala Ala Ala Glu Ala Gln Ser Ala Ser Arg Ile Ala Gly Thr
225                 230                 235                 240

Ala Ala Thr Glu Gly Ser Ala Asn Trp Ala Ser Glu Asn Ser Arg Thr
                245                 250                 255

Ala Gln Leu Glu Ala Ser Ala Ser Lys Ala Thr Ala Ala Ala
            260                 265                 270

Val Gly Asp Gly Ala Ile Ile Gly Leu Ala Arg Asp Ala Ser Ala Ala
        275                 280                 285

Ala Gln Ala Ala Ala Glu Val Lys Ala Leu Ala Glu Ala Ser Ala Ser
    290                 295                 300

Leu Gly Ala Ser Glu Lys Asp Lys Lys
305                 310

<210> SEQ ID NO 45
<211> LENGTH: 338
<212> TYPE: PRT
<213> ORGANISM: Bombus terrestris

<400> SEQUENCE: 45

Gly Lys Pro Leu Ile Ala Asn Ala Gln Ile Gly Lys Val Lys Thr Glu
1               5                   10                  15

Thr Ser Ser Ser Glu Ile Glu Thr Leu Val Ser Gly Ser Gln Thr
            20                  25                  30

Leu Val Ala Gly Ser Glu Thr Leu Ala Ser Glu Ser Glu Ala Leu Ala
        35                  40                  45

Ser Lys Ser Glu Ala Leu Thr Ser Glu Ala Glu Ile Ala Ser Val Thr
    50                  55                  60

Thr Lys Asp Glu Leu Ile Leu Lys Gly Glu Ala Ile Thr Gly Lys Lys
65                  70                  75                  80

Leu Gly Thr Gly Ala Ser Glu Val Ala Ala Ser Gly Glu Ala Ile
                85                  90                  95

Ala Thr Thr Leu Gly Ala Gly Gln Ala Ala Glu Ala Gln Ala Ala
        100                 105                 110

Ala Ala Ala Gln Ala Lys Ser Ala Ala Ala Ala Asn Ala Gly
    115                 120                 125

Glu Ser Ser Asn Ser Ala Ala Leu Val Ala Ala Ala Ala
    130                 135                 140

Gln Gly Lys Ala Ala Ala Ala Ala Ala Thr Lys Ala Ser Leu
145                 150                 155                 160

Glu Ala Ala Asp Ala Ala Glu Glu Ala Glu Ser Ala Val Ala Leu Ala
                165                 170                 175

Arg Ala Ala Ser Ala Lys Ala Glu Ala Leu Ala Ser Thr Ala Ala Ala
            180                 185                 190

Ala Asn Thr Arg Ala Ala Leu Gln Ala Glu Lys Ser Asn Glu Leu Ala
        195                 200                 205

Gln Ala Glu Ala Ala Ala Ala Glu Ala Gln Ala Lys Ala Ala
    210                 215                 220

Ala Ala Lys Ala Thr Gln Leu Ala Leu Lys Val Ala Glu Thr Ala Val
```

```
225                 230                 235                 240

Lys Thr Glu Ala Asp Ala Ala Ala Ala Val Ala Ala Lys Ala
                245                 250                 255

Arg Ala Val Ala Asp Ala Ala Ala Ser Arg Ala Thr Ala Val Asn Ala
                260                 265                 270

Ile Ala Glu Ala Glu Glu Arg Asp Ser Ala Gln Ala Glu Asn Thr Ala
                275                 280                 285

Gly Val Ala Gln Ala Ala Leu Ala Ala Ala Glu Ala Gln Asp Ser Cys
                290                 295                 300

Ile Gly Ala Ala Ala Thr Pro Arg His Ser Ser Tyr Ala Trp Trp
305                 310                 315                 320

Lys Leu Arg Ile Thr Ser Leu Ile Val Ile Leu Ser Pro Arg Asn Arg
                325                 330                 335

Arg Thr

<210> SEQ ID NO 46
<211> LENGTH: 392
<212> TYPE: PRT
<213> ORGANISM: Camponotus floridanus

<400> SEQUENCE: 46

Gly Val Val Asp Ser Ala Ala Ser Ser Ala Gln Ala Ser Ala Ser
1               5                   10                  15

Ala Ser Ser Ser Ser Ser Ile Gly Gln Tyr Gly Lys Gln Ser His
                20                  25                  30

Gly Ile Trp Gly Lys Glu Glu Lys Phe Glu Gly Leu Asp Lys Lys
                35                  40                  45

Ser Leu Asn Thr Phe Pro Leu Lys Tyr Gly Val Lys Asn Gly Gly Leu
50                  55                  60

Asp Val Ala Lys Gly Ala Ala Val Ile Glu Ser Ala Ile Ser Asp Val
65                  70                  75                  80

Ser Thr Leu Thr Glu Gln Arg Ser Leu Gln Asp Leu Gly Leu Gly Val
                85                  90                  95

Ile Ala Asn Ser Ala Glu Ile Leu Ala Ser Ser Gln Ala Ala Ala Ser
                100                 105                 110

Ala Ser Ala Gly Ala Gln Ala Asn Ser Leu Glu Glu Gln Ser Leu Ala
                115                 120                 125

Ala Ile Glu Leu Ala Ser Lys Ala Glu Phe Pro Gly Ala Ile Ile Thr
                130                 135                 140

Ala Lys Ala Ala Lys Ala Ala Glu Ala Thr Ala Val Ala Val Ala Arg
145                 150                 155                 160

Ala Glu Ala Ala Ala Ala Ser Lys Ile Ser Ser Glu Asp Ser Ala
                165                 170                 175

Ala Glu Ala Arg Ser Ala Ala Leu Ala Glu Ala Lys Ala Asn Ala Ala
                180                 185                 190

Ser Ile Ile Ala Asn Lys Ala Asn Ile Asn Leu Ala Gln Ala Ala Ala
                195                 200                 205

Val Leu Ala Ala Thr Ala Thr Ala Ala Lys Asp Ser Ala Phe Lys Ser
                210                 215                 220

Leu Gln Ala Ala Arg Glu Val Lys Ala Gln Ala Glu Ile Thr Lys
225                 230                 235                 240

Ala Ser Ala Val Ala Leu Val Ala Ile Ser Lys Ala Lys Ala Ala Val
                245                 250                 255

Gly Ser Ala Ala Thr Asp Gln Ala Val Cys Thr Ser Gln Ala Gln Ala
```

```
                260                 265                 270
Ala Ser Gln Ile Gln Ser Arg Ala Ser Ala Ser Glu Ser Ala Ser
                275                 280                 285

Ala Gln Ser Glu Thr Asn Thr Ala Ala Asn Ala Val Ala Ile Ala
        290                 295                 300

Asp Ala Glu Ala Ala Ser Gln Ala Gln Ala Trp Val Glu Ser Phe Lys
305                 310                 315                 320

Arg Asp Pro Trp Val Pro Leu Asn Leu Lys Gly Lys Ala Asn Ala Glu
                325                 330                 335

Ala Ile Ala Ile Gly Lys Gly Tyr Gly Lys Gly Tyr Gly Ser Arg Ser
                340                 345                 350

Ser Ala Asp Ala Ser Ala Ser Ala Glu Ala Ser Ser Ser Val Ser Leu
        355                 360                 365

Gly Asn Gly Tyr His Gly Gln Lys Glu Ser Val Ser Glu Ala Ser Ala
        370                 375                 380

Ala Ser Ser Ser Ser Ala Ala Ala
385                 390

<210> SEQ ID NO 47
<211> LENGTH: 375
<212> TYPE: PRT
<213> ORGANISM: Camponotus floridanus

<400> SEQUENCE: 47

Ser Pro His Lys Glu Ser Lys Ala Ser Ala Ser Ala Ser Ala Ser Ala
1               5                   10                  15

Thr Ala Val Ala Ser Ser Lys Lys Asn Leu His Pro Tyr Pro Ile Pro
                20                  25                  30

Ile Pro Leu Lys Ser Asp His Gly Ile Val Ile Asp Lys Ser Lys Phe
        35                  40                  45

Asn Ile Arg Lys Val Ile Leu Ser Ala Ile Asp Glu Ile Asn Gly Ala
50                  55                  60

Pro Lys Leu Gly Leu Gly Trp Lys Lys Val Ser Trp Ala Leu Glu Asn
65                  70                  75                  80

Ala Lys Ser Asn Ala Gln Ala Ser Ala Glu Ala Val Ala Leu Ile Lys
                85                  90                  95

Lys Ile Thr Lys Ala Leu Ile Val Ala Tyr Ile Lys Ala Ala Lys Ile
                100                 105                 110

Ser Ala His Ala Ser Ala Glu Ala Leu Ala Ala Ala Lys Ala Ala Ala
                115                 120                 125

Gln Ala Gln Gln Ile Ala Glu Ala Lys Gly Arg Ala Ala Ser Gln Ala
        130                 135                 140

Leu Ser Ile Thr Ile Glu Ala Ser Ala Lys Ala Glu Ala Ala Ala Ala
145                 150                 155                 160

Ala Thr Thr Asp Ala Ile Glu Arg Thr Tyr Gln Asp Ala Arg Ala Ala
                165                 170                 175

Thr Ser Ala Gln Thr Lys Ala Ser Gly Glu Ala Glu Asn Ala Asn Arg
        180                 185                 190

Gly Ala Ala Ala Ile Leu Ala Ala Leu Val Arg Ile Ala Glu Ala Ser
        195                 200                 205

Ala Asp Ala Asn Gln Ala Ala Thr Lys Ala Ser Ala Ser Ala Ala Ala
        210                 215                 220

Ala Ser Ala Leu His Ala Lys Ala Asn Ala Ala Ser Gln Ala Ala Ala
225                 230                 235                 240
```

```
Thr Ala Thr Ala Leu Ala Arg Thr Thr Ser Glu Glu Ala Glu Ala Ala
                245                 250                 255

Gln Ala Ser Ala Leu Ala Asn Ala Gln Leu Val Pro Arg Leu Ala Ala
                260                 265                 270

Lys Ala Ser Ala Asp Gln Gln Ala Ala Ser Ala Asn Ala Asp Tyr Leu
                275                 280                 285

Thr Ala Lys Thr Glu Ala Glu Ala Ala Gln Ala Ser Ala Val Asn
                290                 295                 300

Ala Leu Arg Asp Gly Ile Val Val Gly Leu Asn Asp Ala Gly Ala
305                 310                 315                 320

Ser Ala Gln Ala Ser Gln Ala Ser Ala Leu Ala Tyr Ala Asn Gly
                325                 330                 335

Tyr Lys Gly Lys Ile Ala Lys Gly Leu Glu Trp Ser Pro Ser Gln Ser
                340                 345                 350

Tyr Gly Ala Ser Ser Lys Ala Ser Ala Ser Ala Ser Gln Ala
                355                 360                 365

Ser Ser Tyr Gly Lys Gly Trp
370                 375

<210> SEQ ID NO 48
<211> LENGTH: 433
<212> TYPE: PRT
<213> ORGANISM: Camponotus floridanus

<400> SEQUENCE: 48

Trp Val Ala Gly Ser Glu Ala Ser Ala Ser Ala Ser Ala Thr Ser Ser
1               5                   10                  15

Ala Ser Ser Gly Lys Leu Thr Ala Ser Lys Ser Ser Ala Ser Ala Ser
                20                  25                  30

Ala Ser Ala Ser Ser Ser Ala Ser Ser Ser Lys Gly Gly Trp Phe
                35                  40                  45

Asp Gly His Tyr Gly Asp Ile Lys Tyr Lys Gly Lys Lys Ser Ala Ala
                50                  55                  60

Gly Ile Ala Ile Glu Gly Ala Lys Val Gly Thr Gly Ile Ser Asn Thr
65                  70                  75                  80

Ala Ser Ala Ser Ala Glu Ala Leu Ser Arg Gly Leu Gly Ile Gly Gln
                85                  90                  95

Ala Ala Ala Glu Ala Gln Ala Ala Ala Gly Gln Ala Thr Ile Ala
                100                 105                 110

Ala Lys Ser Cys Gln Leu Ala Ala Lys Ser Thr Ala Gln Ala Val Ala
                115                 120                 125

Leu Val Glu Ala Ala Ala Gln Ala Gln Val Glu Thr Ser Asn Lys Ala
                130                 135                 140

Ser Ile Ala Val Lys Lys Ala Ala Phe Ala Lys Ala Lys Leu
145                 150                 155                 160

Val Glu Glu Lys Val Ala Ala Leu Arg Ala Ala Gly Lys Leu Asp
                165                 170                 175

Leu Ala Gly Arg Thr Ala Ala Ala Glu Glu Arg Ala Asn Glu Glu
                180                 185                 190

Ser Val Gly Ala Asn Glu Arg Ala Gln Ala Ser Ala Ser Ala Ala Ala
                195                 200                 205

Glu Ala Glu Ala Lys Ala Asn Ala Ala Gln Val Ala Ala Ala Ser Ala
                210                 215                 220

Lys Ala Ile Ala Glu Ala Ala Val Leu Ile Glu Gln Glu Ala Ala Ala
225                 230                 235                 240
```

```
Leu Val Arg Lys Ala Gln Asn Ser Tyr Leu Asn Ala Glu Ala Ala Thr
                245                 250                 255

Thr Ala Ala Ser Asn Ala Arg Val Ile Ala Ser Ala Gln Ala Glu Ala
            260                 265                 270

Ser Ala Asp Leu Ser Asn Arg Ala Gly Ile Ala Arg Ser Gly Ala Ala
        275                 280                 285

Gly Ala Ala Glu Ala Lys Ala Ile Ala Thr Ser Ala Gly Ser Thr Ala
    290                 295                 300

Glu Ile Ala Ala Tyr Ser Trp Ala Lys Lys Gly Glu Ile Ile Asp Pro
305                 310                 315                 320

Gly Pro Leu Pro Lys Ile Val Ser Val Thr Ala Ala Leu Thr Lys Ser
                325                 330                 335

Lys Val Glu Ala Ile Lys Ile Lys Lys Gly His Glu Ile Glu Lys Gly
            340                 345                 350

Phe Tyr Gly Tyr Lys Gly Gly Ile Ala Ser Ser Ser Ala Ala Ser Ser
        355                 360                 365

Ala Ser Ala Ser Ser Ser Ala Gly Ala Gly Ser Ile Ser Ser Gly Lys
    370                 375                 380

Leu Gly Ser Gln His Ser Ala Ser Ser Ala Ser Ala Ser Ala Lys Ala
385                 390                 395                 400

Asp Ala Gly Ser Ile Ser Ser Gly Lys Leu Gly Ser Gln Tyr Ser Glu
                405                 410                 415

Ser Ser Ala Ser Ala Ser Ala Glu Ala Asp Ser Ser Ala Leu Lys Ala
            420                 425                 430

Trp

<210> SEQ ID NO 49
<211> LENGTH: 397
<212> TYPE: PRT
<213> ORGANISM: Harpegnathos saltator

<400> SEQUENCE: 49

Ser Gly Pro Tyr Ile Ile Gly Lys Pro Val Ala Ala Thr Gly Ser
1               5                   10                  15

Ser Ser Ala Glu Ala Leu Thr Ser Ser Trp Arg Lys Thr Gly Gly Ala
            20                  25                  30

Tyr Ala Gly Ala Ser Ala Ala Ser Ser Lys Thr Gly Asn Asn Ile
        35                  40                  45

Leu Ser Arg Met Gly Thr Thr Lys Leu Ala Thr Thr Met Ala Thr Ser
    50                  55                  60

Ala Ala Val Glu Ala Lys Ala Gly Leu Arg Ala Ser Glu Ile Ala Ala
65                  70                  75                  80

Lys Glu Gln Arg Glu Ala Leu Gln Met Leu Ile Glu Ser Ala Asp Arg
                85                  90                  95

Asn Ala Lys Ala Arg Ile Leu Ala Asp Asp Ala Ala Ile Leu Val Lys
            100                 105                 110

Gly Ser Ala Glu Ala Gln Ser Val Ala Glu Lys Thr Val Ala Val
        115                 120                 125

Glu Glu Thr Ser Ala Ser Leu Ala Ala Ala Ile Glu Ala Glu Ala
    130                 135                 140

Ile Ala Gly Glu Phe Lys Thr Ala Ala Gln Ala Ala Leu Gln Ala Ala
145                 150                 155                 160

Gln Thr Ser Ala Met Ser Leu Lys Thr Ala Ala Ser Thr Gly Leu Met
                165                 170                 175
```

```
Ala Leu Lys Leu Ile Asn Asn Gln Gly Val Ala Ser Glu Asn Ala Ala
                180                 185                 190

Ile Asn Met Lys Lys Ala Val Ala Ile Ile Glu Glu Ala Lys Val Ala
            195                 200                 205

Ala Glu Lys Ala Met Ala Glu Lys Ala Ala Glu Ala Thr Ala
210                 215                 220

Ile Ala Ala Ala Lys Gln Ser Glu Ala Arg Asp Ile Ala Ala Glu Leu
225                 230                 235                 240

Lys Ala Ala His Ala Ala Leu Ile Thr Ala Gln Arg Asn Leu Val Gln
                245                 250                 255

Ala Lys Ala Lys Val Val Met Ser Asn Glu Glu Val Gln Leu Asp Ser
            260                 265                 270

Lys Ser Arg Ala Ala Asp Ala Lys Ile Asn Ala Ile Ala Arg Ala Ala
                275                 280                 285

Ala Lys Ser Ser Ile Arg Arg Glu Glu Leu Ile Glu Ile Gly Ala Glu
            290                 295                 300

Phe Gly Lys Ala Ser Gly Glu Val Ile Ala Thr Gly Thr Arg Ser Thr
305                 310                 315                 320

Gly Gly Lys Ser Ala Val Ala Thr Ala Glu Ala Thr Ser Ser Ala Ser
                325                 330                 335

Ala Ile Gly Ile Lys Lys Gly His Lys Trp Asp Phe His Lys Asn Leu
            340                 345                 350

Gly His Ser Tyr Ala Ala Ala Asp Ala Asp Ala Ser Ser Ser Asn Ile
                355                 360                 365

Ile Ile Gly Gly His Gly Leu Lys Arg Gly Glu Ala Ser Ala Thr Ala
            370                 375                 380

Glu Ala Glu Ala Glu Ser Asp Val Lys Thr Phe Leu Leu
385                 390                 395

<210> SEQ ID NO 50
<211> LENGTH: 395
<212> TYPE: PRT
<213> ORGANISM: Harpegnathos saltator

<400> SEQUENCE: 50

Arg Val Ile Glu Ser Asn Ser Ala Ala Ser Ala Glu Ala Ser Ala Ser
1               5                   10                  15

Ala Ser Ala Gly Asn Ile Val Trp Leu His Asp Lys His Tyr Pro Leu
                20                  25                  30

Lys Glu Arg Lys Glu Lys Asn Leu Trp Lys Glu Gly Lys Asp Gly Leu
            35                  40                  45

Val Glu Thr Ser Leu Asn Val Pro Ala Leu Lys Val Gly Ile Lys Asn
50                  55                  60

Gly Gly Leu Asp Val Ala Lys Gly Ala Ala Val Ile Gln Ser Ala Met
65                  70                  75                  80

Ser Asp Glu Ser Thr Leu Thr Glu Gln Arg Ser Leu Leu Asp Leu Gly
                85                  90                  95

Leu Gly Val Ile Ala Asn Ser Ala Glu Val Trp Ser Glu Thr Gln Ala
            100                 105                 110

Ala Thr Ser Ala Asn Ala Asn Ala Asn Ala Asp Ala Thr Ala Thr Gln
                115                 120                 125

Ala Ile Ala Ala Met Glu Ile Ala Asp Lys Thr Gly Tyr Ile Ala Ala
            130                 135                 140

Ile His Leu Thr Gln Ala Ala Lys Ala Val Glu Ala Ala Met Ala Ser
```

```
            145                 150                 155                 160
Ala Ala Arg Ala Ala Ala Ala Asp Ala Ala Lys Ile Ser Ser Gln
                165                 170                 175
Glu Ala Leu Leu Ala Thr Ser Asn Ala Ala Thr Thr Glu Ala Lys Ala
                180                 185                 190
Asn Ala Ala Ser Ile Ile Ala Asn Lys Ala Asn Ala Glu Met Ala Glu
                195                 200                 205
Ala Ala Ala Met Leu Glu Ala Ala Thr Thr Gln Ala Lys Glu Ser Ala
                210                 215                 220
Ile Lys Ala Gln Lys Ala Ala Gln Glu Ala Ala Lys Ala Gln Ala Glu
225                 230                 235                 240
Val Thr Gln Ala Ser Ala Lys Ser Leu Val Ile Leu Ser Glu Ala Lys
                245                 250                 255
Ala Ala Val Ala Arg Ala Thr Ala Asp Gln Val Val Cys Thr Ser Gln
                260                 265                 270
Ala Gln Ala Ala Ser Gln Ile Gln Ser Arg Ala Ser Ala Ser Glu Ser
                275                 280                 285
Ala Ser Ala Gln Ala Glu Thr Asn Thr Val Ala Ala Glu Ala Val
                290                 295                 300
Ala Ile Ala Asp Ala Gln Thr Ala Ala Gln Ala Lys Asp Trp Glu Gln
305                 310                 315                 320
Lys Leu Arg His Asp Met Trp Met His Phe Asn Met Lys Gly Glu Ala
                325                 330                 335
Lys Ala Glu Ala Lys Ala Val Thr Ile Asn Lys Gly Tyr His Gly Ile
                340                 345                 350
Lys Arg Ala Gly Ala Ile Ser Glu Ala Ser Ala Glu Ala Ser Ser Asn
                355                 360                 365
Val Ser Met Gly Arg His Gly Arg Lys Asp Ser Val Ser Ala Ala Ser
                370                 375                 380
Ala Val Ala Ser Ala Gly Gly Ser Val Asp Leu
385                 390                 395

<210> SEQ ID NO 51
<211> LENGTH: 398
<212> TYPE: PRT
<213> ORGANISM: Harpegnathos saltator

<400> SEQUENCE: 51

Asp His Phe Gly Ser Lys Ser Gly Ala Ser Ala Ser Ala Ser
1               5                   10                  15
Ala Ser Ala Lys Ala Asp Ser Lys Asp Met Arg Ile Leu Val Pro Leu
                20                  25                  30
Leu Lys Lys Gly Glu His His Lys Asp Met Lys Ile Asp Lys Ser Val
                35                  40                  45
Phe Asn Ile Asn Lys Val Val Leu Gly Ala Val Gly Lys Ile Asn Gly
                50                  55                  60
Ala Pro Lys Leu Gly Leu Gly Trp Lys Glu Val Ser Ile Gly Leu Glu
65                  70                  75                  80
Asn Ala Lys Ala Ser Ala Asn Ala Ala Glu Thr Leu Ala Ser Ile
                85                  90                  95
Lys Lys Thr Thr Ser Tyr Tyr Asp Gln Ala Tyr Met Asn Ile Ala Lys
                100                 105                 110
Val Ala Ala Glu Ala Ser Ala Lys Ala Leu Ala Ile Thr Lys Met Ala
                115                 120                 125
```

Leu Glu Thr Gln Lys Ile Ala Glu Ala Lys Gly Glu Ala Ala Ser Gln
130                 135                 140

Ala Leu Ala Lys Ala Thr Val Ser Ser Arg Arg Ala Glu Ala Ala Ala
145                 150                 155                 160

Ala Ala Thr Lys Asp Ala Val Asp Arg Thr Ile Glu Asn Val Lys Ala
            165                 170                 175

Ala Asn Ser Ala Gln Thr Tyr Ala Asn Gly Gln Ala Glu Asn Ala Asn
            180                 185                 190

Arg Asn Ala Ala Ala Met Leu Ala Thr Leu Ile His Met Glu Glu Ser
        195                 200                 205

Ala Ala Met Asn Asn Lys Ala Ala Thr Ala Ser Thr Ala Ser Ala Ala
210                 215                 220

Ala Ala Ser Ala Leu His Ala Lys Ala Asn Ala Val Leu Gln Thr Asp
225                 230                 235                 240

Val Asn Ala Ala Ser Met Ala Ala Met Ser Ala Glu Glu Ala Gly Ala
            245                 250                 255

Ala Gln Ala Ser Ala Leu Arg Ser Gln Gln Leu Ala Ala Ala Ile Leu
            260                 265                 270

Glu Lys Ala Ser Ala Asp Gln Gln Ala Ala Ser Ala Lys Ala Asp Tyr
        275                 280                 285

Asp Ala Ser Thr Thr Glu Ala Arg Ala Ala Gln Ala Ser Ala Ile
290                 295                 300

Asn Ala Leu Arg Asp Gly Ile Val Val Gly Leu Gly Asn Asp Asn Gly
305                 310                 315                 320

Ala Ser Ala Gln Glu Ile Ala Gln Ala Ile Ala Leu Ala Arg Ala Gly
            325                 330                 335

His Asn Glu Tyr Lys Gly His Lys Gly His Asn Glu Tyr Lys Gly His
        340                 345                 350

Lys Gly His Lys Gly Tyr Glu Gly His Lys Met Phe Val Lys Lys Gly
        355                 360                 365

Met Tyr Leu His Gly Ile Glu Glu Ala Ser Ala Glu Ala Ser Ala Ser
370                 375                 380

Ala Ser Ala Glu Ala Ser Ser Arg Ile Met Lys Lys Lys Trp
385                 390                 395

<210> SEQ ID NO 52
<211> LENGTH: 406
<212> TYPE: PRT
<213> ORGANISM: Harpegnathos saltator

<400> SEQUENCE: 52

Gly Glu Val Glu Ser Glu Ala Asn Ala Ala Ser Ala Gln Thr Ser
1               5                   10                  15

Ala Gly Ala Ser Thr Ile Gly His Gly Lys Leu Thr Thr Gln Ala Ser
            20                  25                  30

Ser His Ala Ser Ser Ser Ala Ser Ala Ile Ser Lys Gly Gly Trp Gly
        35                  40                  45

Tyr His Tyr His Gln Gly Asn Thr Lys Ser Lys Met Val Asn Gly Ala
    50                  55                  60

Gly Ile Ala Ile Glu Gly Ala Ile Ile Gly Thr Gly Ile Gly Asn Thr
65                  70                  75                  80

Ala Ser Ala Ser Ala Glu Ala Leu Ser Arg Gly Leu Gly Ile Gly Gln
            85                  90                  95

Ala Ala Ala Glu Ala Gln Ala Ala Ala Gly Gln Ala Ala Ile Ala
            100                 105                 110

-continued

```
Ser Gln Ser Cys Lys Leu Ala Ser Lys Ser Thr Ala Lys Ala Ile Ala
        115                 120                 125

Tyr Val Glu Ala Ala Val Lys Ala Gln Ile Asp Val Ala Asn Lys Ala
        130                 135                 140

Phe Glu Ala Val Glu Lys Ser Ala Ile Ala Ala Lys Ala Ala Lys Ile
145                 150                 155                 160

Thr Glu Glu Asp Val Ala Asn Val Arg Ala Ala Thr Gly Arg Leu Glu
                165                 170                 175

Leu Ala Ser Arg Ala Ala Ser Ala Ala Glu Arg Ala Ser Glu Ser Glu
                180                 185                 190

Ser Glu Ala Ala Asn Glu Arg Thr Gln Ala Ala Ala Ala Ala Ala Ala
        195                 200                 205

Glu Ala Glu Ala Lys Ala Asn Ala Ala Lys Val Ala Ala Val Ala Ala
210                 215                 220

Ser Arg Ile Ala Asp Ala Ala Val Ala Ile Asp Ser Glu Ala Val Met
225                 230                 235                 240

Ser Val Arg Lys Ala Lys Glu Thr Arg Val Asn Ala Arg Ala Ala Gly
                245                 250                 255

Ala Arg Ala Ile Asn Ala Gln Val Ile Ala Ser Ala Glu Ser Glu Ala
                260                 265                 270

Ser Ser Asp Leu Glu Asn Arg Ala Gly Val Ala Arg Ala Ser Ala Ser
        275                 280                 285

Gly Ala Ala Glu Thr Lys Ala Ile Ala Thr Gly Ala Gly Ala Thr Ala
        290                 295                 300

Glu Ile Ala Ala Tyr Ser Gly Ala Asn Lys Gly Glu Leu Ile Asp Ala
305                 310                 315                 320

Gly Pro Leu Pro Lys Ile Ile Ser Val Ile Ala Asp Leu Thr Lys Asp
                325                 330                 335

Glu Val Glu Ala Ile Lys Ile Lys His Gly Arg Asp His Gly Ile His
                340                 345                 350

Lys Glu Ile Ile Tyr Asn Glu Asn Ile Val Glu Ser Ala Ala Ser Ser
        355                 360                 365

Ser Ala Ser Ala Asn Ala Gly Ser Ile Gly Gly Lys Leu Gly Gly
        370                 375                 380

Arg Gly Ile Ala Val Ala Ser Ala Ser Ala Ser Ala Glu Ala Asp Ser
385                 390                 395                 400

Asn Ala Ile Lys Lys Trp
                405
```

<210> SEQ ID NO 53
<211> LENGTH: 403
<212> TYPE: PRT
<213> ORGANISM: Myrmecia forficate

<400> SEQUENCE: 53

```
Ser Gly Pro Arg Leu Leu Gly Gly Arg Ser Ala Ala Ser Ala Ser Ala
1               5                   10                  15

Ser Ala Ser Ala Glu Ala Ser Ala Gly Gly Trp Arg Lys Ser Gly Ala
        20                  25                  30

Ser Ala Ser Ala Ser Ala Lys Gly Ser Ser Asn Ile Leu Ser Arg
                35                  40                  45

Val Gly Ala Ser Arg Ala Ala Thr Leu Val Ala Ser Ala Ala Val
        50                  55                  60

Glu Ala Lys Ala Gly Leu Arg Ala Gly Lys Ala Thr Ala Glu Glu Gln
```

```
            65                  70                  75                  80
Arg Glu Ala Leu Glu Met Leu Thr Leu Ser Ala Asp Lys Asn Ala Glu
                85                  90                  95

Ala Arg Ile Leu Ala Asp Asp Thr Ala Val Leu Val Gln Gly Ser Ala
            100                 105                 110

Glu Ala Gln Ser Val Ala Ala Lys Thr Val Ala Glu Glu Glu
            115                 120                 125

Ser Ala Ser Leu Asp Ala Ala Val Glu Ala Glu Val Ala Ala Ala
        130                 135                 140

Thr Ser Lys Ser Ser Ala Gly Gln Ala Leu Gln Ser Ala Gln Thr Ala
145                 150                 155                 160

Ala Ser Ala Leu Arg Thr Ser Ala Arg Ser Ala Leu Thr Ala Leu Lys
                165                 170                 175

Leu Ala Arg Leu Gln Gly Ala Ala Ser Ser Asn Ala Ala Arg Met Met
            180                 185                 190

Glu Lys Ala Leu Ala Ala Thr Gln Asp Ala Asn Ala Ala Ala Gln Gln
        195                 200                 205

Ala Met Ala Ala Glu Ser Ala Ala Ala Glu Ala Ala Ala Ile Ala Ala
    210                 215                 220

Ala Lys Gln Ser Glu Ala Arg Asp Ala Gly Ala Glu Ala Lys Ala Ala
225                 230                 235                 240

Met Ala Ala Leu Ile Thr Ala Gln Arg Asn Leu Val Gln Ala Asn Ala
                245                 250                 255

Arg Ala Glu Met Ala Ser Glu Glu Ala Glu Leu Asp Ser Lys Ser Arg
            260                 265                 270

Ala Ser Asp Ala Lys Val Asn Ala Val Ala Arg Ala Ala Ser Lys Ser
        275                 280                 285

Ser Ile Arg Arg Asp Glu Leu Ile Glu Ile Gly Ala Glu Phe Gly Lys
    290                 295                 300

Ala Ser Gly Glu Val Ile Ser Thr Gly Thr Arg Ser Asn Gly Gly Gln
305                 310                 315                 320

Asp Ala Ile Ala Thr Ala Glu Ala Ser Ser Ser Ala Ser Ala Val Gly
                325                 330                 335

Ile Lys Lys Thr Ser Gly His Trp Gly Ser Gly Lys Trp Ser Arg Val
            340                 345                 350

Ser Lys Gly Lys Gly Trp Ala Ser Ser Asn Ala Asp Ala Asp Ala Ser
        355                 360                 365

Ser Ser Ser Ile Ile Ile Gly Gly Leu Lys Arg Gly Gly Leu Gly Ser
    370                 375                 380

Glu Ala Ser Ala Ala Ser Ala Glu Ala Glu Ala Ser Ala Gly Thr
385                 390                 395                 400

Leu Leu Leu

<210> SEQ ID NO 54
<211> LENGTH: 392
<212> TYPE: PRT
<213> ORGANISM: Myrmecia forficate

<400> SEQUENCE: 54

Arg Val Ile Glu Ser Ser Ser Ser Ala Ser Ala Gln Ala Ser Ala Ser
1               5                   10                  15

Ala Gly Ser Arg Gly Leu Leu Gly Lys Arg Pro Ile Gly Lys Leu Glu
            20                  25                  30

Trp Gly Lys Glu Glu Lys Lys Leu Glu Glu Leu Asp Glu Glu Ser Leu
```

```
                35                  40                  45
Asn Glu Ala Ala Leu Lys Val Gly Ile Lys Asn Gly Gly Leu Asp Val
 50                  55                  60

Ala Lys Gly Ala Ala Val Leu Glu Ala Ala Met Ser Asp Val Ala Thr
 65                  70                  75                  80

Leu Thr Asp Gln Arg Ser Leu Val Asp Leu Gly Leu Gly Pro Val Ala
                 85                  90                  95

Asn Glu Ala Glu Ile Leu Ala Glu Ala Gln Ala Thr Ser Ala Gln
                100                 105                 110

Ala Gly Ala Val Ala Asn Ser Ala Ala Glu Arg Ala Ile Ala Ala Met
            115                 120                 125

Glu Met Ala Asp Arg Thr Glu Tyr Ile Ala Ala Leu Val Thr Thr Lys
            130                 135                 140

Ala Ala Lys Ala Ala Glu Ala Thr Met Ala Ala Thr Ala Arg Ala Thr
145                 150                 155                 160

Ala Ala Ala Ser Ala Ser Lys Ile Ser Ser Gln Glu Ser Ala Ala Ser
                165                 170                 175

Ala Ala Asn Ala Ala Asn Ala Glu Ala Lys Ala Asn Ala Ala Ser Ile
                180                 185                 190

Ile Ala Asn Lys Ala Asn Ala Val Leu Ala Glu Ala Ala Ala Val Leu
            195                 200                 205

Ala Ala Thr Ala Ala Lys Ala Lys Glu Ser Ala Met Lys Ser Leu Ser
210                 215                 220

Ala Ala Gln Ala Ala Ala Lys Ala Gln Ala Arg Asn Ala Glu Ala Ser
225                 230                 235                 240

Ala Glu Ala Gln Ile Lys Leu Ser Gln Ala Arg Ala Ala Val Ala Arg
                245                 250                 255

Ala Ala Ala Asp Gln Ala Val Cys Ser Ser Gln Ala Gln Ala Ala Ser
                260                 265                 270

Gln Ile Gln Ser Arg Ala Ser Ala Ser Glu Ser Ala Ala Ser Ala Gln
            275                 280                 285

Ser Glu Thr Asn Thr Ala Ala Ala Glu Ala Val Ala Thr Ala Asp Ala
290                 295                 300

Glu Ala Ala Ala Gln Ala Glu Ala Trp Val Met Ser Leu Lys Asn Asp
305                 310                 315                 320

Leu Trp Leu His Leu Asn Met Lys Gly Glu Ala Lys Ala Glu Gly Glu
                325                 330                 335

Ala Val Ser Ile Ser Lys Gly His Arg Gly Gly Ile Arg Ser Gly Ser
                340                 345                 350

Ile Ser Glu Ala Ser Ala Glu Ala Ser Ser Asn Val Ser Met Gly Gly
            355                 360                 365

Arg His Gly Arg Lys Asp Leu Val Ser Glu Ala Leu Ala Gly Ala Ser
            370                 375                 380

Ala Gly Ser Ser Ala Asp Ser Leu
385                 390

<210> SEQ ID NO 55
<211> LENGTH: 375
<212> TYPE: PRT
<213> ORGANISM: Myrmecia forficate

<400> SEQUENCE: 55

Asn Leu Leu Lys Glu Ser Lys Ala Ser Ala Ser Ala Ser Ala
 1               5                   10                  15
```

```
Ser Ala Arg Ala Ser Gly Lys Lys Asn Leu His Val Leu Pro Leu Pro
             20                  25                  30

Lys Lys Ser Glu His Gly Ile Val Ile Asp Lys Ser Val Phe Asp Ile
         35                  40                  45

Lys Asp Val Val Leu Ser Ala Val Asp Glu Ile Asn Gly Ala Pro Lys
     50                  55                  60

Leu Gly Leu Gly Trp Lys Lys Val Ser Met Gly Val Glu Arg Ala Glu
65                  70                  75                  80

Ala Asn Ala Ala Ala Ala Glu Ala Leu Ala Met Ile Lys Lys Ile
                 85                  90                  95

Ala Met Ala Arg Ser Ser Ala Tyr Val Gln Ala Trp Ala Ser Ala
             100                 105                 110

Gln Ala Ser Ala Asp Ala Leu Ala Ser Ala Arg Val Ala Gln Ala Ser
         115                 120                 125

Gln Glu Ala Ala Glu Ala Lys Gly Arg Ala Ala Ser Glu Ala Leu Ser
         130                 135                 140

Arg Ala Ile Glu Ala Ser Ser Arg Ala Asp Ala Ala Ala Ala Ala Thr
145                 150                 155                 160

Leu Asp Ala Met Asp Arg Thr Met Glu Asn Ala Arg Ala Ala Asn Ala
                 165                 170                 175

Ala Gln Thr Gln Ala Ser Gly Gln Ala Glu Asn Ala Asn Arg Ser Ala
             180                 185                 190

Ala Ala Ile Leu Ala Ala Leu Leu Arg Ile Ala Glu Ala Ser Ala Leu
         195                 200                 205

Asn Asn Glu Ala Ala Val Asn Ala Ala Ala Ala Ala Ala Ala Ser
         210                 215                 220

Ala Leu Gln Ala Lys Ala Asn Ala Ala Ser Gln Ala Thr Ala Arg Ala
225                 230                 235                 240

Ala Gly Gln Ala Ser Thr Ala Ala Glu Glu Ala Gln Ser Ala Gln Glu
             245                 250                 255

Ala Ala Asp Lys Asn Ala Glu Leu Thr Thr Val Met Leu Glu Lys Ala
         260                 265                 270

Ser Ala Asp Gln Gln Ala Ala Ser Ala Arg Ala Asp Tyr Tyr Thr Ala
     275                 280                 285

Ser Thr Glu Ala Glu Ala Ala Ala Gln Ala Ser Ala Ile Asn Ala Leu
     290                 295                 300

Arg Asp Gly Ile Val Val Gly Met Gly Asn Asp Ala Gly Ala Ser Ala
305                 310                 315                 320

Gln Ala Met Ala Gln Val Glu Ala Leu Ala Arg Ala Ser Glu His Lys
             325                 330                 335

Ala Leu Gly Glu Lys Lys Lys Gly Leu Val Trp Gly Tyr Gly Ser Lys
             340                 345                 350

Gly Ser Ser Ser Ala Ser Ala Ser Ala Ser Ala Glu Ala Ser
         355                 360                 365

Ser Arg Leu Gly Lys Asp Trp
         370                 375

<210> SEQ ID NO 56
<211> LENGTH: 422
<212> TYPE: PRT
<213> ORGANISM: Myrmecia forficate

<400> SEQUENCE: 56

Ser Glu Leu Glu Ser Glu Ala Ser Ala Ala Ser Ala Gln Ala Glu
1               5                   10                  15
```

```
Ala Ser Ser Ser Gly Arg Ser Gly Lys Leu Ser Ala Ser Gln Ala Ser
            20                  25                  30

Ala Ser Ala Ser Ala Ser Ala Gly Ser Arg Gly Gly Ser Lys
        35                  40                  45

Gly Gly Trp Gly Gln Leu Arg Arg Gly Asp Val Lys Ser Glu Ala Lys
        50                  55                  60

Ser Ala Ala Ala Ile Ala Val Glu Gly Ala Lys Ile Gly Thr Gly Ile
65                  70                  75                  80

Gly Asn Thr Ala Ser Ala Ser Ala Glu Ala Leu Ser Arg Gly Leu Gly
                85                  90                  95

Ile Gly Gln Ala Ala Ala Glu Ala Gln Ala Ala Ala Gly Gln Ala
                100                 105                 110

Glu Val Ala Ala Lys Ser Cys Glu Leu Ala Asp Lys Thr Thr Ala Lys
                115                 120                 125

Ala Val Ala Met Val Glu Ala Ala Glu Ala Glu Ile Glu Val Ala
        130                 135                 140

Asn Gln Glu Val Ala Ala Val Lys Leu Ser Thr Trp Ala Ala Lys Ala
145                 150                 155                 160

Ala Arg Ile Val Glu Glu Asp Ser Ala Ala Val Arg Ala Ala Gly
                165                 170                 175

Lys Leu Leu Leu Ala Ala Arg Ala Ala Ala Ala Glu Arg Arg Ala
                180                 185                 190

Asn Glu Glu Ser Glu Ala Ala Asn Glu Leu Gln Ala Ser Ser Ala
                195                 200                 205

Ala Ala Glu Ala Glu Ala Lys Ala Asn Ala Gly Arg Glu Ala Ala
        210                 215                 220

Ala Ala Ala Leu Ala Ile Ala Glu Ala Val Ala Ile Glu Gln Glu
225                 230                 235                 240

Ala Val Ile Leu Ala Arg Lys Ala Gln Asp Ala Arg Leu Asn Ala Glu
                245                 250                 255

Ala Ala Ala Ala Ala Ala Met Asn Ala Arg Val Ile Ala Ser Ala Glu
                260                 265                 270

Ser Glu Ala Ser Glu Asp Leu Glu Asn Arg Ala Ser Val Ala Arg Ala
                275                 280                 285

Ser Ala Ala Gly Ala Ala Glu Ala Lys Ala Ile Ala Thr Asp Ala Gly
                290                 295                 300

Ala Thr Ala Glu Ile Ala Ala Tyr Ser Trp Ala Lys Lys Gly Glu Leu
305                 310                 315                 320

Ile Asn Pro Gly Pro Leu Pro Lys Ile Ile Ser Val Asn Ala Asp Leu
                325                 330                 335

Ser Lys Ser Glu Val Glu Ala Met Lys Ile Thr Arg Gly Gln Val Gln
                340                 345                 350

Glu Val Lys Lys Ile Ser Thr His Lys Gly Gly Trp Gly Trp Gly Lys
                355                 360                 365

Glu Gly Arg Ser Lys Val Ser Ser Asn Ala Ser Ala Arg Ala Ser Ala
                370                 375                 380

Ser Ala Asn Ala Ala Gly Ser Leu Gly Ser Lys Trp Gly Arg Gln
385                 390                 395                 400

Leu Ser Ala Ser Ser Ala Ser Ala Asp Ala Asn Ala Glu Ala Asp Ser
                405                 410                 415

Gln Leu Leu Lys Val Trp
                420
```

<210> SEQ ID NO 57
<211> LENGTH: 293
<212> TYPE: PRT
<213> ORGANISM: Megachile rotundata

<400> SEQUENCE: 57

```
Arg Ile Ile Val Gly Lys Gly Gly Glu Gly Leu Glu Lys Ser Val His
1               5                   10                  15

Val Gly Ser Ala Arg Leu Val Gly Asp Gly Ser Asp Ser Ser Gly Val
            20                  25                  30

Ser Val Gln Asn Ala Leu Asn Val Val Arg Ala Gly Glu Thr Val Gly
        35                  40                  45

Leu Asn Val Asp Leu Ser Ala Ala Arg Thr Ala Ala Ser Ala Ala
    50                  55                  60

Ala Ser Gln Ala Ala Asp Thr Glu Asn Ala Gly Ala Lys Ala
65                  70                  75                  80

Ala Thr Leu Met Ala Ile Ala Lys Arg Glu Gln Ala Ile Lys Leu Ser
                85                  90                  95

Glu Ile Ala Arg Gly Lys Leu Thr Asp Ala Ala Lys Ala Ala Glu Ala
            100                 105                 110

Leu Val Ser Ala Ala Arg Arg Ala Ala Glu Leu Thr Ala Ala Ala Lys
        115                 120                 125

Ala Ala Ala Gln Ala Ser Ala Ser Ala Ala Asp Ala Ala Ala Gln Ala
    130                 135                 140

Gln Val Lys Ala Asn Ala Asp Ser Ile Ile Ala Lys Lys Ala Gln Ala
145                 150                 155                 160

Ala Glu Ala Gln Ala Ala Ala Glu Ala Ala Ala Lys Ala Glu Met Ala
                165                 170                 175

Lys Lys Ala Ala Ala Ile Leu Leu Ala Lys Ala Gln Asn Ala Ala Lys
            180                 185                 190

Glu Glu Ala Glu Ala Thr Lys Leu Ala Ala Ile Ala Glu Val Ala Ile
        195                 200                 205

Ser Arg Ala Arg Asn Ala Val Glu Lys Ala Gln Gly Ala Gln Ala Ala
    210                 215                 220

Ala Thr Ser Gln Ala Ser Ala Ala Val Arg Leu Glu Ala Arg Ala Ala
225                 230                 235                 240

Asn Ala Glu Ala Asp Ala Val Gly Arg Leu Glu Ala Leu Leu Ala Thr
                245                 250                 255

Ser Glu Ala Val Ala Ala Gly Glu Ser Gln Ala Ser Lys Ala Ser
            260                 265                 270

Ser Glu Ala Lys Ile Ile Thr Asp Gln Lys Ser Glu Val Glu Asp Lys
        275                 280                 285

Gly Trp Lys Ser Asp
    290
```

<210> SEQ ID NO 58
<211> LENGTH: 306
<212> TYPE: PRT
<213> ORGANISM: Megachile rotundata

<400> SEQUENCE: 58

```
Ser Leu Glu Glu Arg Ser Trp Gln Thr Pro Lys Asp Gly Pro Trp Leu
1               5                   10                  15

Glu Lys Asn Leu Leu Ser Lys Leu Glu Thr Ser Ala Met Arg Lys Glu
            20                  25                  30
```

```
Asn Gly Ala Pro Met Leu Gly Leu Gly Lys Lys Val Gln Ile Ser Leu
             35                  40                  45

Gly Arg Ala Lys Ala Ser Ala Ala Glu Ala Lys Ala Gly Ala Ala
 50                  55                  60

Val Lys Ala Ser Ala Leu Ser Leu Ala Glu Ala Val Lys Ala Ala
 65                  70                  75                  80

Ala Lys Ser Ala Ala Ser Ala Lys Ala Ala Ala Val Lys Ala
                 85                  90                  95

Ala Leu Glu Ala Gln Leu Val Ala Gln Ala Lys Ala Leu Ala Leu
                100                 105                 110

Lys Leu Gln Thr Glu Glu Gln Thr Leu Ser Ile Thr Met Ala Ala Leu
            115                 120                 125

Gln Arg Ala Gln Gly Ser Ala Gln Val Gly Ala Ala Ala Gln Asn Leu
    130                 135                 140

Ala Ser Asn Tyr Gln Glu Arg Ala Asn Ala Ala Ala Ala Glu Ala
145                 150                 155                 160

Ala Ala Thr Gln Arg Ala Ala Glu Asn Ala Glu Leu Ser Arg Ala Leu
                    165                 170                 175

Gly Gln Glu Ala Ala Ala Leu Ser Ala Ala Ala Ala Ala Gln Ala
                180                 185                 190

Gln Thr Thr Gly Ser Ser Glu Ala Thr Ser Ala Ala Ala Asn Lys Ala
            195                 200                 205

Ala Val Leu Ala Ala Asp Ala Asp Ser Ala Gln Ala Ala Ala Ser
    210                 215                 220

Glu Ala Gln Ile Glu Gly Arg Ala Asn Arg Glu Gly Ala Ala Asn Leu
225                 230                 235                 240

Ala Ser Gln Asp Thr Ala Thr Ala Gln Leu Glu Ala Ser Ala Ser Ala
                245                 250                 255

Lys Ala Thr Ala Ala Ala Val Gly Asp Gly Val Leu Gly Leu
                260                 265                 270

Gly Leu Asp Gly Ala Ala Ala Gln Ala Gln Ala Gln Ala Lys Ala
    275                 280                 285

Leu Ala Arg Ala Ser Ala Ser Val Gly Ala His Gly Pro Ser Lys Gly
    290                 295                 300

Gly Trp
305

<210> SEQ ID NO 59
<211> LENGTH: 357
<212> TYPE: PRT
<213> ORGANISM: Megachile rotundata

<400> SEQUENCE: 59

Asp Ile Ser Ala Glu Arg Glu Ser Gln Gln Arg Glu Val Ser Lys Lys
 1               5                  10                  15

Lys Val Gln Val Glu Val Arg Glu Lys Lys Glu Trp Asn Arg Glu Ser
            20                  25                  30

Trp Asp Thr Lys Ser Ser Glu Trp Asp Leu Lys Pro Ser Pro Ser Trp
            35                  40                  45

Glu Pro Lys Pro Ser Pro Asn Trp Glu Pro Lys Pro Ser Pro Lys Trp
 50                  55                  60

Glu Pro Lys Ser Ser Gly Trp Asp Asn Ile Asp Ile Lys Gly Gln Gly
 65                  70                  75                  80

Trp Ala Leu Glu Gly Val Asn Val Gly Thr Gly Ser Ala Glu Thr Ala
                 85                  90                  95
```

```
Ala Ala Ser Gly Glu Ala Leu Ala Leu Asn Leu Gly Ile Gly Glu Ala
            100                 105                 110

Ala Ala Ser Ala Gln Ala Ala Ala Gly Gln Ser Asn Ala Ala Ala
            115                 120                 125

Gln Ala Ala Ala Ser Ala Ser Met Met Ser Ser Arg Ala Glu Ser Leu
130                 135                 140

Val Gly Ala Ala Ala Ala Ala Glu Ala Asn Ala Ala Ala Ala Ser Glu
145                 150                 155                 160

Lys Ala Ser Gln Ser Ser Lys Ala Thr Ser Ala Ala Ala Ile Gln Ala
                165                 170                 175

Glu Glu Ala Val Gly Lys Ala Lys Ala Ala Gly Arg Ala Glu Val
            180                 185                 190

Leu Ala Arg Asn Ala Ala Ala Asn Ala Arg Ala Ala Ile Gln Ser
            195                 200                 205

Glu Arg Ala Asn Glu Leu Ala Gln Ala Glu Asp Ala Ala Ala Ala Glu
210                 215                 220

Ala Gln Ala Lys Thr Ala Ala Ala Arg Ala Thr Lys Val Ala Leu
225                 230                 235                 240

Glu Leu Ala Asn Ile Ala Val Arg Ala Glu Ala Ala Ala Ala
            245                 250                 255

Ala Glu Ala Ala Ala Lys Ala Thr Ala Ala Asp Ala Ala Ala Ala
            260                 265                 270

Arg Ala Ala Val Asn Ala Ile Ala Asp Ala Glu Val Glu Ala Ser
            275                 280                 285

Ala Gln Ala Glu Asn Thr Ala Gly Val Ala Gln Ala Ser Ala Ser Ala
            290                 295                 300

Ala Ala Glu Thr Gln Ala Val Ala Ser Ser Ala Ser Ala Thr Ala Glu
305                 310                 315                 320

Ala Ser Ala Glu Ser Gly Ala Ala Lys Gly Glu Leu Ser Leu Pro Lys
                325                 330                 335

Asp Asp His Glu Pro Lys Glu Ile Ile Met Pro Ile Lys Gly Gly
            340                 345                 350

Lys Ser Asn Trp Asp
            355

<210> SEQ ID NO 60
<211> LENGTH: 301
<212> TYPE: PRT
<213> ORGANISM: Osmia cornuta

<400> SEQUENCE: 60

Arg Gly Val Ser Leu Glu Asn Ser His Gly Leu Glu Lys Ser Ser Val
1               5                   10                  15

Ser Ser Ser Ser Ile Lys Val Gly Thr Ala Arg Val Arg Gly Asp Ala
                20                  25                  30

Ser Asp Ala Gly Ala Ile Ser Val Gln Asp Ala Leu Asn Val Val Arg
            35                  40                  45

Ala Gly Glu Gly Val Gly Leu Asn Thr Glu Ser Gly Ala Ala Ala Arg
        50                  55                  60

Thr Ala Ala Lys Ala Ala Ser Gln Ala Ala Asp Thr Glu Asn Ala
65                  70                  75                  80

Glu Ala Gly Ala Lys Ala Ala Ile Leu Met Ala Ile Ser Lys Arg Glu
                85                  90                  95

Glu Ala Ile Lys Leu Ser Glu Ile Ala Arg Gln Arg Leu Thr Thr Ala
```

```
                    100                 105                 110
Ala Lys Ala Ala Glu Ala Leu Val Ser Ala Arg Arg Ala Ala Glu
            115                 120                 125

Leu Thr Ala Ala Lys Ala Ala Thr Gln Ala Ser Ala Thr Ala Ala
            130                 135                 140

Glu Ala Ala Ala Gln Ala Gln Val Lys Ala Asn Ala Asp Ser Ile Ile
145                 150                 155                 160

Ala Lys Lys Ala Gln Ala Val Glu Ala Lys Ala Ala Glu Ala Glu
            165                 170                 175

Val Lys Ala Lys Met Ala Ala Lys Ala Ala Leu Leu Leu Ala Lys
            180                 185                 190

Ala Arg Leu Ala Ala Lys Glu Glu Ala Leu Thr Lys Leu Ala Ala
            195                 200                 205

Ile Ala Gln Val Ala Ile Ala Arg Ala Arg Asn Ala Val Glu Lys Ala
            210                 215                 220

Leu Ser Ala Gln Ser Gly Ala Thr Thr Gln Ser Ser Asn Ala Val Lys
225                 230                 235                 240

Ile Glu Gly Gln Ala Ala Asn Ala Glu Gly Thr Ala Val Gly Arg Leu
            245                 250                 255

Gln Thr Leu Leu Ala Ile Ile Gln Thr Val Ala Ala Glu Ala Asp
            260                 265                 270

Ala Ala Ser Lys Ala Ser Ser Trp Ala Lys Gln Ile Ser Ser Ser Lys
            275                 280                 285

Ser Glu Val Gln Val Lys Gly Trp Lys Ser Gly Ser Val
            290                 295                 300

<210> SEQ ID NO 61
<211> LENGTH: 337
<212> TYPE: PRT
<213> ORGANISM: Osmia cornuta

<400> SEQUENCE: 61

Asp Gly Ser Ile Gly Gln Glu Ser Asn His Gly Thr Val Lys Lys Lys
1               5                   10                  15

Gln Val Gln Val Gln Val Arg Glu Lys Lys Glu Trp Asn Ser Gly Trp
            20                  25                  30

Asp Ser Lys Ser Ser Asn Ala Trp Asp Ser Lys Ser Ser Thr Gly Trp
            35                  40                  45

Glu Ser Gln Ser Lys Gly Lys Ala Val Ala Ile Glu Gly Ala Ala Val
        50                  55                  60

Gly Thr Gly Met Ala Glu Thr Ala Ala Ala Ser Gly Glu Ala Ile Ala
65                  70                  75                  80

Asn Asn Leu Gly Thr Gly Glu Ala Ala Ala Asn Ser Gln Ala Ser Ala
                85                  90                  95

Ala Thr Gln Ser Ala Ile Ala Ala Gln Ser Ala Gly Thr Ala Ser Ala
            100                 105                 110

Leu Ser Thr Asp Ala Ala Lys Leu Ala Ala Asp Ala Ala Gly Ala Gln
            115                 120                 125

Ala Arg Ala Ala Gly Gln Ser Glu Lys Ala Thr Lys Ala Ser Leu Ala
            130                 135                 140

Thr Lys Ser Ala Ala Met Gln Ala Glu Asp Ala Val Ala His Ala Lys
145                 150                 155                 160

Ala Ala Ala Gly Arg Ala Glu Val Leu Ala Arg Asn Ala Ala Ala Ala
            165                 170                 175
```

Asn Ala Arg Ala Ala Leu Gln Ser Glu Lys Ala Asn Glu Leu Ala Gln
            180                 185                 190

Ala Glu Asp Ala Ala Ala Ala Glu Ala Gln Ala Lys Thr Ala Ala Ala
        195                 200                 205

Ala Val Ala Thr Lys Val Ala Leu Gln Leu Ala Gln Ile Ala Val Lys
    210                 215                 220

Ala Glu Ala Ala Ala Ala Ala Ala Ala Ala Ala Lys Ala Thr
225                 230                 235                 240

Lys Ile Ala Asp Ala Ala Ala Arg Ala Ser Val Asn Ala Ile
                245                 250                 255

Ala Gln Ala Glu Val Glu Ala Ser Ala Gln Ala Glu Asn Thr Ala Gly
            260                 265                 270

Val Ser Gln Ala Ala Ala Ser Ala Ser Ala Glu Thr Met Ala Val Ala
        275                 280                 285

Ala Ser Ala Ser Ala Thr Ala Glu Ala Ala Asp Ser Gly Ala Gly
    290                 295                 300

Lys Gly Glu Leu Ser Leu Pro Lys Ser Ser Lys Val Glu Ile Gln Ser
305                 310                 315                 320

Lys Lys Ile Ile Thr Thr Glu Lys Val Asp Lys Ala Ser Ser Gly Trp
                325                 330                 335

Asp

<210> SEQ ID NO 62
<211> LENGTH: 354
<212> TYPE: PRT
<213> ORGANISM: Vespa simillima xanthoptera

<400> SEQUENCE: 62

Gly Pro Ser Arg Leu Ser Glu Thr Ser Asp Ser Ser Ala Ala Ser Trp
1               5                   10                  15

Ser Ser Ser Ser Ser Ser Ser Ser Leu Ser Ser Ser Leu Ala Ser
            20                  25                  30

Asp Ser Ala Ser Ser Ser Ala Ser Gly Ser Ala Ser Ala Ser Ala Ser
        35                  40                  45

Ala Ser Ala Ser Ala Ser Ala Ser Ser Arg Asn Asp Asn Ser Arg Val
    50                  55                  60

Lys Ala Trp Lys Lys Gly Arg Gly Gly Ser Asp Ser Leu Val Leu Ser
65                  70                  75                  80

Ser Asp Ser Ser Glu Asp Ser Lys Ala Arg Glu Leu Leu Glu Thr Asp
                85                  90                  95

Ala Gly Leu Gly Ala Ala Ala Ala Leu Ala Arg Ala Thr Ala Asp Ala
            100                 105                 110

Gln Ala Arg Thr Ala Ala Ser Ala Asp Ala Thr Ala Asn Lys Ala Thr
        115                 120                 125

Ala Lys Ala Leu Val Leu Ala Glu Ala Ala Val Arg Ala Glu Asn Ala
    130                 135                 140

Ala Ile Val Arg Ile Arg Ala Leu Ser Ala Ala Gln Ala Leu Val
145                 150                 155                 160

Ser Ala Ser Asn Arg Ala Lys Ala Ala Ala Arg Ala Ala Arg Glu Ala
                165                 170                 175

Ala Ala Asn Ser Ala Ala Ala Ala Lys Ala Ser Thr Asn Gln Val
            180                 185                 190

Lys Ala Asn Ala Asp Ser Leu Val Ala Asn Arg Ala Ala Ala Ala Leu
        195                 200                 205

```
Leu Ala Ala Ala Glu Glu Ala Leu Gln Lys Ala Ser Ala Ser Gln Asn
210                 215                 220

Ala Ala Ala Glu Ala Ala Ala Lys Ala Arg Ala Ala Asn Ala Asn
225                 230                 235                 240

Ala Ala Thr Thr Arg Ala Ala Ala Ser Ala Ile Leu Ala Glu Ala Arg
                245                 250                 255

Ala Arg Thr Ala Ile Thr Lys Ala Leu Ala Ala Gln Ser Thr Ala Ser
                260                 265                 270

Ala Gln Ala Ser Ser Ala Ser Val Gln Asn Arg Ala Asn Asn Leu
                275                 280                 285

Gln Ala Glu Thr Ala Ser Leu Ala Gln Ser Arg Ala Glu Ala Ala Ile
290                 295                 300

Ala Ala Ala Ala Ala Gln Ala Ala Leu Ala Glu Ala Asn Ala Gln
305                 310                 315                 320

Leu Ala Arg Leu Ser Lys Ala Ser Ala Gly Ala Ser Ser Glu Gly Ser
                325                 330                 335

Ala Ser Ala Ser Ala Ser Ala Ser Ala Ser Ala Ser Ser Ser Ser Ser
                340                 345                 350

Ser Ala

<210> SEQ ID NO 63
<211> LENGTH: 355
<212> TYPE: PRT
<213> ORGANISM: Vespa simillima xanthoptera

<400> SEQUENCE: 63

Ser Ser Ser Ser Ser Ala Glu Ser Ala Ser Ala Thr Ala Ser Ser
1               5                   10                  15

Asp Ala Ser Trp Ser Ala Ser Ser Arg Ser Ser Ala Thr Gly Arg Ala
                20                  25                  30

Pro Asn Val Ile Leu Asn Arg Ala Pro Gln Leu Gly Ala Ser Ala Ala
                35                  40                  45

Ala Ile Ala Ser Ala Arg Ala Ser Thr Ser Asn Ala Ala Ser Asp
50                  55                  60

Glu Lys Ser Ala Arg Glu Thr Arg Ala Thr Ala Leu Ala Arg Ser Arg
65                  70                  75                  80

Ala Ala Val Thr Ala Ala Arg Ala Ala Arg Thr Gln Glu Ala
                85                  90                  95

Val Ala Ala Ala Lys Ala Ala Ser Arg Ala Gln Ala Leu Ala Ala Ala
                100                 105                 110

Lys Ser Ser Ala Ala Ile Ser Ala Leu Ala Ala Gly Glu Ala Ala Ala
                115                 120                 125

Gln Lys Ala Asp Ala Ala Ala Leu Ala Ala Leu Ala Ala Asn Gln Arg
                130                 135                 140

Ser Val Lys Ala Ala Glu Asn Gly Leu Ala Val Gln Asn Arg Ala Asn
145                 150                 155                 160

Gly Glu Ala Glu Gln Ala Ser Arg Ala Ala Ala Asn Leu Ala Ala
                165                 170                 175

Ala Ile Arg Thr Arg Asp Asn Ala Leu Glu Thr Arg Arg Glu Ala Ala
                180                 185                 190

Arg Leu Lys Ala Leu Ala Thr Ala Ala Ala Asn Ala Asn Asn Lys Ala
                195                 200                 205

Thr Ser Leu Ala Glu Ala Ser Ala Asn Gln Ala Ala Glu Ala Ser Ser
                210                 215                 220
```

```
Ala Ala Glu Asp Thr Ser Ser Ala Gln Ser Ala Val Ala Gln Ala
225                 230                 235                 240

Glu Ala Ala Glu Thr Leu Asn Val Asn Leu Ala Ile Leu Glu Ser Thr
                245                 250                 255

Gln Ser Ser Arg Gln Asp Ser Asn Val Ala Lys Ala Glu Ala Ser Ala
                260                 265                 270

Ala Ala Lys Ala Ser Pro Gly Thr Ala Thr Arg Asp Gly Val Asn Leu
            275                 280                 285

Gly Leu Ala Ser Asp Ala Gly Ala Ala Gln Leu Lys Ala Gln Ala
290                 295                 300

Ala Ala Leu Ala Arg Ala Ser Ser Arg Ile Ser Ser Gly Pro Ala Leu
305                 310                 315                 320

Ser Ala Trp Lys Trp Arg Asn Glu Asp Ser Ser Glu Ser Ser Thr Ser
                325                 330                 335

Ala Ile Ala Ser Ser Ser Ala Ser Ser Ser Ser Ser Arg Ser Ala
            340                 345                 350

Ser Gly Asn
        355

<210> SEQ ID NO 64
<211> LENGTH: 457
<212> TYPE: PRT
<213> ORGANISM: Vespa simillima xanthoptera

<400> SEQUENCE: 64

Ala Glu Ser Ser Ser Ser Ser Ala Ala Ser Ser Ala Ser Ser Ser
1               5                   10                  15

Ser Ser Glu Ser Arg Gly Gln Leu Leu Leu Pro Leu Glu Arg Ser Ser
                20                  25                  30

Thr Arg Ser Leu Leu Asp Leu Val Ser Ser Ala Arg Ser Asn Thr Ala
            35                  40                  45

Ile Thr Ala Ser Ser Ala Ala Ala Ala Lys Ala Thr Leu Arg Ala Ile
        50                  55                  60

Lys Ala Ala Asn Ser Ala Gln Gly Glu Ala Leu Ala Gln Ala Thr Ala
65                  70                  75                  80

Ser Ala Ala Ser Asn Ala Lys Ala Arg Ala Thr Ala Ala Ala Ala Ala
                85                  90                  95

Gln Ala Thr Asn Ala Ala Val Asn Ala Gln Gly Lys Ala Ser Ala Gln
            100                 105                 110

Ala Ile Ala Thr Ala Glu Ala Ala Glu Ala Leu Thr Lys Ser Ala Leu
        115                 120                 125

Gln Ala Gln Ser Ala Ala Ser Ser Lys Ser Glu Ala Ala Gln Ala
130                 135                 140

Ser Thr Ser Ala Asn Ala Gly Ala Gly Ala Leu Ala Thr Ala Ser Ala
145                 150                 155                 160

Gln Ala Leu Ser Ala Lys Lys Ala Ala Leu Ala Tyr Ala Ser Ala Ala
                165                 170                 175

Ala Asp Ala Ser Thr Ala Ala Lys Ala Arg Ala Ala Val Ala Ala
            180                 185                 190

Ala Glu Ala Ala Thr Arg Thr Ala Val Gln Ala Glu Arg Asp Ser Thr
        195                 200                 205

Asn Ala Ala Ser Leu Ala Ala Lys Ala Gln Ala Glu Ala Arg Ala Ala
    210                 215                 220

Ala Ala Ala Ala Ala Ala Ala Arg Leu Ala Ala Ser Ala Ala Ala Asp
225                 230                 235                 240
```

```
Ala Ser Ala Gln Ala Asp Ala Arg Val Arg Thr Ala Ser Ile Glu Ala
                245                 250                 255

Ala Ala Ser Ala Arg Thr Lys Ala Ser Asn Ala Gln Ala Thr Ala Glu
            260                 265                 270

Ala Ala Ala Ile Ala Arg Ser Ser Arg Asp Ala Gln Ala Asn Trp
        275                 280                 285

Val Asp Asn Arg Ser Ser Ala Ser Ser Ser Ala Ser Ala Ser Ala
    290                 295                 300

Ser Val Ser Ala Ser Ala Ser Gly Glu Ala Asp Ser Glu Ala Asp Ser
305                 310                 315                 320

Asp Ala Ser Ala Ser Ala Arg Ser Ala Ala Asp Ser Asn Ala Gly Ser
                325                 330                 335

Ser Ser Gly Leu Ala Ala Asp Ser Ala Ala Asp Thr Ala Ala Gly Ser
            340                 345                 350

Thr Ala Gly Ser Ala Ala Arg Leu Ser Ala Gly Ser Ala Ala Gly Ser
        355                 360                 365

Ile Ala Arg Ser Ala Ala Gly Ser Thr Ala Gly Ser Ser Thr Gly Ser
    370                 375                 380

Gly Ala Gly Ala Ser Ala Glu Gly Ser Ser Asn Ala Ser Ser Gly Thr
385                 390                 395                 400

Ser Ala Gly Ala Ser Ser Gly Ala Ser Thr Gly Ala Ser Ala Gly Ala
                405                 410                 415

Ser Ala Thr Ala Ser Ala Asp Asn Ser Ala Asp Asn Ser Ala Glu Ala
            420                 425                 430

Leu Ser Ser Ser Ala Glu Ser Ser Ser Ser Trp Ser Ser
        435                 440                 445

Ser Gln Asn Ile Trp Ser Gln Asp Trp
    450                 455

<210> SEQ ID NO 65
<211> LENGTH: 486
<212> TYPE: PRT
<213> ORGANISM: Vespa simillima xanthoptera

<400> SEQUENCE: 65

Asp Arg Ser Trp Ala Ala Ser Asp Ala Asn Ala Glu Ala Ser Ala Ala
1               5                   10                  15

Val Glu Ser Pro Ser Leu Trp Glu Asp Ser Ser Ala Ser Ala Gly
                20                  25                  30

Ala Ser Asn Ala Ala Glu Ser Ser Leu Trp Glu Asp Ser Ser
            35                  40                  45

Glu Asn Thr Gly Ala Ser Thr Ala Ala Glu Ser Ser Ser Leu Trp Glu
    50                  55                  60

Asp Ser Ser Ser Ala Ser Ala Arg Ala Ser Thr Ala Ala Gly Ser Ser
65                  70                  75                  80

Ser Ala Trp Glu Asp Ser Ser Ile Thr Asn Ala Arg Glu Ser Gly Ala
                85                  90                  95

Ser Gly Ser Leu Ser Ser Trp Glu Asp Ser Ser Ala Ser Ala Ser
            100                 105                 110

Ser Ser Thr Ser Ala Ser Ala Ser Ser Ser Ser Ser Ser Ser Ser
        115                 120                 125

Ile Ser Ser Ser Ala Ser Ser Ser Ala Ser Ala Ser Ala Ser
    130                 135                 140

Thr Glu Ala Ser Asn Glu Ser Arg Arg Gly Ile Ala Ile Glu Gly Ala
```

```
            145                 150                 155                 160
Leu Val Gly Thr Gly Ala Ala Ser Thr Ala Ala Ser Ala Glu Met
                165                 170                 175
Leu Ser Asp Thr Leu Gly Leu Gly Gln Ser Ala Leu Gln Ala Gln Thr
                180                 185                 190
Ala Ser Val Thr Gln Ala Asn Ile Ala Ser Asp Ala Ser Asn Gln Ala
                195                 200                 205
Asn Arg Leu Ala Ala Ala Ala Ala Ala Met Ser Ala Ala Ala Ser
    210                 215                 220
Ala Gln Glu Asn Ala Ala Ser Leu Ala Arg Ala Ser Ala Ser Ala Ser
225                 230                 235                 240
Glu Ser Ala Ala Ser Ala Ser Lys Ala Glu Ser Ala Glu Ala
                245                 250                 255
Ala Lys Ser Ser Ala Glu Lys Cys Leu Leu Ala Gln Asn Ser Ala
                260                 265                 270
Gln Ala Gln Ala Arg Ala Thr Glu Gln Ser Glu Ser Asn Arg Asp
                275                 280                 285
Ser Ala Ala Asn Ala Ala Ala Ala Glu Ala Glu Arg Lys Ala Thr
    290                 295                 300
Leu Ala Leu Lys Ala Ile Ala Asp Ala Lys Ala Lys Ala Gly Val Ala
305                 310                 315                 320
Val Ala Ala Gln Ser Glu Ala Ala Ala Ala Ala Ala Lys
                325                 330                 335
Ala Arg Ala Asp Ala Glu Ala Gly Ala Asn Leu Ala Ala Ala Arg
                340                 345                 350
Ala Val Ala Ala Ala Glu Ala Ala Ser Arg Arg Asn Asp Arg Gln
                355                 360                 365
Ala Gly Ile Ala Gln Ala Gly Ala Ser Ala Ala Glu Thr Arg Ala
                370                 375                 380
Leu Ala Ser Ser Ala Ala Ala Thr Ala Lys Ala Ala Tyr Ala Asn
385                 390                 395                 400
Ala Asp Ile Arg Ala Leu Ser Ala Ala Ala Leu Glu Ser Ser Ile Ser
                405                 410                 415
Ser Ser Ser Ser Thr Ser Ala Ser Ala Ser Ser Ala Ser Ser
                420                 425                 430
Gly Ala Ser Ser Asp Ser Ser Ser Gly Ala Ser Ser Gly Ala Ser Ser
                435                 440                 445
Asp Ser Ser Ser Asn Ser Ser Ser Asp Ser Ser Leu Leu Gly Asp
    450                 455                 460
Asp Ala Ser Thr Ser Ala Ser Ser Thr Ala Glu Ala Glu Ser Arg Thr
465                 470                 475                 480
Ser Ser Leu Ile Leu Asn
                485

<210> SEQ ID NO 66
<211> LENGTH: 350
<212> TYPE: PRT
<213> ORGANISM: Vespa analis

<400> SEQUENCE: 66

Gly Pro Ser Arg Leu Ser Glu Thr Ser Asp Ser Ser Ala Ala Ser Trp
1               5                   10                  15

Ser Ser Ser Ser Ser Ser Ser Ser Leu Ser Ser Ser Leu Ala Ser
                20                  25                  30
```

Asp Ser Ala Ser Ser Ala Ser Thr Ser Ala Ser Ala Ser
        35                  40                  45

Ala Ser Ala Ser Ser Arg Asn Asp Asn Ser Arg Ile Lys Ala Trp Lys
 50                  55                  60

Lys Gly Arg Gly Gly Ser Asp Ser Leu Val Leu Ser Ser Asp Ser Ser
65                  70                  75                  80

Glu Asp Ser Lys Ala Arg Glu Leu Leu Glu Thr Asp Ala Gly Leu Gly
                85                  90                  95

Ala Ala Ala Ala Leu Ala Arg Ala Thr Ala Asp Ala Gln Ala Arg Thr
            100                 105                 110

Ala Ala Ser Ala Asp Ala Thr Ala Asn Arg Ala Thr Thr Lys Ala Leu
        115                 120                 125

Ala Leu Ala Glu Ala Ala Val Arg Ala Glu Asn Ala Ala Ile Leu Arg
    130                 135                 140

Ile Arg Arg Ala Leu Ser Ala Ala Gln Thr Leu Val Ser Ala Ser Asn
145                 150                 155                 160

Arg Ala Lys Ala Ala Ala Arg Ala Ala Arg Glu Ala Ala Ala Asn Ser
                165                 170                 175

Ala Ala Ala Ala Ala Lys Ala Ser Thr Asn Gln Val Lys Ala Asn Ala
            180                 185                 190

Asp Ser Leu Val Ala Asn Arg Ala Ala Ala Leu Leu Ala Ala Ala
        195                 200                 205

Glu Glu Ala Leu Gln Arg Ala Ser Ala Ser Gln Asn Ala Ala Ala Glu
    210                 215                 220

Ala Ala Ala Lys Ala Arg Ala Ala Asn Ala Asn Ala Ala Thr Thr
225                 230                 235                 240

Arg Ala Ala Ala Ser Ala Ile Leu Ala Glu Ala Arg Ala Arg Thr Ala
                245                 250                 255

Ile Thr Lys Ala Val Ala Ala Gln Ser Thr Ala Ser Ala Gln Ala Ser
            260                 265                 270

Ser Ala Ser Gln Val Gln Asn Arg Ala Asn Asn Leu Gln Ala Glu Thr
        275                 280                 285

Ala Ser Ser Ala Gln Ser Arg Ala Glu Ala Ala Ile Ala Ala Ala Ala
    290                 295                 300

Ala Gln Ala Ala Ala Val Ala Glu Ala Asn Ala Gln Leu Ala Arg Leu
305                 310                 315                 320

Ser Lys Ala Ser Ala Gly Ala Ser Ser Glu Gly Ser Ala Ser Thr Ser
                325                 330                 335

Val Ser Ala Ser Ala Ser Ala Ser Ser Ser Ser Ser Ala
            340                 345                 350

<210> SEQ ID NO 67
<211> LENGTH: 355
<212> TYPE: PRT
<213> ORGANISM: Vespa analis

<400> SEQUENCE: 67

Ser Ser Ser Ser Ser Ala Glu Ser Ser Ala Ser Ala Thr Ala Ser Ser
1               5                   10                  15

Asp Ala Ser Trp Ser Ala Ser Arg Ser Ser Ala Ile Gly Arg Ala
            20                  25                  30

Pro Asn Val Ile Leu Asn Arg Ala Pro Gln Leu Gly Ala Ser Ala Ala
        35                  40                  45

Ala Ile Ala Ser Ala Arg Ala Ser Ala Ser Thr Asn Ala Ala Ser Asp
    50                  55                  60

Glu Lys Ser Ala Arg Asp Thr Arg Ala Thr Ala Leu Ala Arg Ser Arg
65                  70                  75                  80

Ala Ala Val Thr Ala Ala Arg Ala Ala Arg Thr Gln Glu Ala
            85                  90                  95

Val Ala Ala Ala Lys Ala Ser Arg Ala Gln Ala Leu Ala Ala
                100                 105                 110

Lys Ser Ser Ala Ala Ile Ser Ala Leu Ala Ala Gly Glu Ala Ala
            115                 120                 125

Gln Lys Ala Asp Ala Ala Leu Ala Ala Leu Ala Ala Asn Gln Arg
130                 135                 140

Ser Val Lys Ala Ala Glu Asn Gly Leu Ala Val Gln Asn Arg Ala Asn
145                 150                 155                 160

Gly Glu Ala Glu Gln Ala Ser Arg Ala Ala Ala Asn Leu Ala Ala
                165                 170                 175

Ala Ile Arg Thr Arg Asp Asn Ala Leu Glu Thr Arg Arg Glu Ala Ala
                180                 185                 190

Arg Leu Lys Ala Leu Ala Thr Ala Ala Ala Asn Ala Asn Asn Lys Ala
            195                 200                 205

Thr Ser Leu Ala Glu Ala Ser Ala Asn Gln Ala Thr Glu Ala Ser Ser
210                 215                 220

Ala Ala Glu Asp Thr Ser Ser Ala Gln Ser Ala Ala Val Ala Gln Ala
225                 230                 235                 240

Glu Ala Ala Lys Thr Leu Asn Val Asn Leu Ala Ile Leu Glu Ser Ala
            245                 250                 255

Gln Ser Ser Arg Gln Asp Ser Asn Val Ala Lys Ala Glu Ala Ser Ala
                260                 265                 270

Ala Ala Lys Ala Ser Pro Gly Thr Ala Thr Arg Asp Gly Val Asp Leu
            275                 280                 285

Gly Leu Ala Ser Asp Ala Gly Ala Ala Ala Gln Leu Lys Ala Gln Ala
290                 295                 300

Ala Ala Leu Ala Arg Ala Ser Ser Arg Ile Ser Ser Gly Pro Ala Leu
305                 310                 315                 320

Ser Ala Trp Lys Arg Arg Asn Glu Glu Ser Ser Glu Ser Ser Ala Ser
            325                 330                 335

Ala Ile Ala Ser Ser Ser Thr Ser Ser Ser Ser Ser Arg Ser Ala
                340                 345                 350

Ser Gly Asn
355

<210> SEQ ID NO 68
<211> LENGTH: 457
<212> TYPE: PRT
<213> ORGANISM: Vespa analis

<400> SEQUENCE: 68

Ala Glu Ser Ser Ser Ser Ser Ala Ala Ser Ser Ala Ser Ser Ser
1               5                   10                  15

Ser Ser Glu Ser Arg Gly Gln Leu Leu Leu Pro Leu Glu Arg Ser Ser
            20                  25                  30

Thr Arg Ser Leu Leu Asp Leu Val Ser Ser Ala Arg Ser Asn Thr Ala
            35                  40                  45

Ile Thr Ala Ser Ser Ala Ala Ala Ala Lys Ala Thr Leu Arg Ala Ile
        50                  55                  60

Lys Ala Ala Asn Ser Ala Gln Gly Glu Ala Leu Ala Gln Ala Thr Ala

```
            65                  70                  75                  80
        Ser Ala Ala Ser Asn Ala Lys Ala Arg Ala Thr Ala Ala Ala Ala Ala
                        85                  90                  95

Gln Ala Thr Asn Ala Ala Val Asn Ala Gln Gly Lys Ala Ser Ala Gln
                    100                 105                 110

Ala Ile Ala Thr Ala Glu Ala Ala Glu Ala Leu Thr Lys Ser Ala Leu
                    115                 120                 125

Gln Ala Gln Ser Ala Ala Ser Ser Ser Lys Ser Glu Ala Ala Gln Ala
                    130                 135                 140

Ser Thr Ser Ala Asn Ala Gly Ala Gly Ala Leu Ala Thr Ala Ser Ala
        145                 150                 155                 160

Gln Ala Leu Ser Ala Lys Lys Ala Ala Leu Ala Tyr Ala Ser Ala Ala
                        165                 170                 175

Ala Asp Ala Ser Thr Ala Ala Lys Ala Arg Ala Ala Val Ala Ala
                    180                 185                 190

Ala Glu Ala Ala Thr Arg Thr Ala Val Gln Ala Glu Arg Asp Ser Thr
                    195                 200                 205

Asn Ala Ala Ser Leu Ala Ala Lys Ala Gln Ala Glu Ala Arg Ala Ala
                    210                 215                 220

Ala Ala Ala Ala Ala Ala Arg Leu Ala Ala Ser Ala Ala Ala Asp
        225                 230                 235                 240

Ala Ser Ala Gln Ala Asp Ala Arg Val Arg Thr Ala Ser Ile Glu Ala
                        245                 250                 255

Ala Ala Ser Ala Arg Thr Lys Ala Ser Asn Gln Ala Thr Ala Glu
                    260                 265                 270

Ala Ala Ala Ile Ala Arg Ser Ser Arg Asp Ala Gln Ala Asn Trp
                    275                 280                 285

Val Asp Asn Arg Ser Ser Ala Ser Ser Ser Ser Ala Ser Ala Ser Ala
                    290                 295                 300

Ser Val Ser Ala Ser Ala Ser Gly Glu Ala Asp Ser Glu Ala Asp Ser
        305                 310                 315                 320

Asp Ala Ser Ala Ser Ala Arg Ser Ala Ala Asp Ser Asn Ala Gly Ser
                    325                 330                 335

Ser Ser Gly Leu Ala Ala Asp Ser Ala Ala Asp Thr Ala Ala Gly Ser
                    340                 345                 350

Thr Ala Gly Ser Ala Ala Arg Leu Ser Ala Gly Ser Ala Ala Gly Ser
                    355                 360                 365

Ile Ala Arg Ser Ala Ala Gly Ser Thr Ala Gly Ser Ser Thr Gly Ser
                    370                 375                 380

Gly Ala Gly Ala Ser Ala Glu Gly Ser Ser Asn Ala Ser Ser Gly Thr
        385                 390                 395                 400

Ser Ala Gly Ala Ser Gly Ala Ser Thr Gly Ala Ser Ala Gly Ala
                    405                 410                 415

Ser Ala Thr Ala Ser Ala Asp Asn Ser Ala Asp Asn Ser Ala Glu Ala
                    420                 425                 430

Leu Ser Ser Ser Ser Ala Glu Ser Ser Ser Ser Ser Trp Ser Ser Ser
                    435                 440                 445

Ser Gln Asn Ile Trp Ser Gln Asp Trp
                    450                 455

<210> SEQ ID NO 69
<211> LENGTH: 522
<212> TYPE: PRT
<213> ORGANISM: Vespa analis
```

<400> SEQUENCE: 69

| | | | | | | | | | | | | | | |
|---|---|---|---|---|---|---|---|---|---|---|---|---|---|---|
|Asp|Arg|Ser|Trp|Ala|Ala|Ser|Asp|Ala|Asn|Ala|Glu|Ala|Ser|Ala|Ala|
|1| | | |5| | | | |10| | | | |15| |

| | | | | | | | | | | | | | |
|---|---|---|---|---|---|---|---|---|---|---|---|---|---|
|Ala|Glu|Ser|Ser|Ser|Leu|Trp|Glu|Asp|Ser|Ser|Ala|Ser|Ala|Gly|
| | | |20| | | | |25| | | | |30| |

| | | | | | | | | | | | | | |
|---|---|---|---|---|---|---|---|---|---|---|---|---|---|
|Ala|Ser|Ala|Pro|Ala|Glu|Ser|Ser|Ser|Leu|Trp|Glu|Asp|Ser|Ser|Ser|
| | |35| | | | |40| | | | |45| | |

| | | | | | | | | | | | | | |
|---|---|---|---|---|---|---|---|---|---|---|---|---|---|
|Arg|Asn|Ala|Gly|Ala|Ser|Ser|Ala|Ala|Glu|Ser|Ser|Ser|Leu|Trp|Glu|
| |50| | | | |55| | | | |60| | | |

| | | | | | | | | | | | | | |
|---|---|---|---|---|---|---|---|---|---|---|---|---|---|
|Asp|Ser|Ser|Ser|Ala|Ser|Ala|Arg|Ala|Ser|Ala|Ala|Ala|Glu|Ser|Ser|
|65| | | | |70| | | | |75| | | | |80|

| | | | | | | | | | | | | | |
|---|---|---|---|---|---|---|---|---|---|---|---|---|---|
|Ser|Ala|Trp|Glu|Asp|Ser|Ser|Ile|Ala|Asn|Ala|Arg|Glu|Ser|Gly|Gln|
| | | | |85| | | | |90| | | | |95| |

| | | | | | | | | | | | | | |
|---|---|---|---|---|---|---|---|---|---|---|---|---|---|
|Ser|Arg|Ser|Ser|Ser|Ser|Trp|Glu|Asp|Ser|Ser|Ile|Asp|Asn|Ala|Arg|
| | | |100| | | | |105| | | | |110| | |

| | | | | | | | | | | | | | |
|---|---|---|---|---|---|---|---|---|---|---|---|---|---|
|Glu|Ser|Gly|Ala|Ser|Gly|Ser|Ser|Ser|Trp|Glu|Asp|Ser|Ser|Asn|
| | | |115| | | | |120| | | | |125| |

| | | | | | | | | | | | | | |
|---|---|---|---|---|---|---|---|---|---|---|---|---|---|
|Ala|Ser|Asp|Ser|Ser|Ser|Thr|Ser|Ala|Ser|Ala|Ser|Ser|Ser|Ser|
| |130| | | | |135| | | | |140| | | |

| | | | | | | | | | | | | | |
|---|---|---|---|---|---|---|---|---|---|---|---|---|---|
|Ser|Ser|Ser|Ser|Ile|Ser|Ser|Thr|Ser|Ser|Ser|Ser|Ala|Ser|
|145| | | | |150| | | | |155| | | | |160|

| | | | | | | | | | | | | | |
|---|---|---|---|---|---|---|---|---|---|---|---|---|---|
|Ala|Ser|Ser|Ser|Thr|Glu|Ala|Ser|Asn|Glu|Ser|Arg|Arg|Gly|Ile|Ala|
| | | |165| | | | |170| | | | |175| | |

| | | | | | | | | | | | | | |
|---|---|---|---|---|---|---|---|---|---|---|---|---|---|
|Ile|Glu|Gly|Ala|Leu|Val|Gly|Thr|Gly|Ala|Ala|Ser|Thr|Ala|Ala|Ala|
| | | |180| | | | |185| | | | |190| | |

| | | | | | | | | | | | | | |
|---|---|---|---|---|---|---|---|---|---|---|---|---|---|
|Ser|Ala|Glu|Met|Leu|Ser|Asp|Thr|Leu|Gly|Leu|Gly|Gln|Ser|Ala|Leu|
| | | |195| | | | |200| | | | |205| | |

| | | | | | | | | | | | | | |
|---|---|---|---|---|---|---|---|---|---|---|---|---|---|
|Gln|Ala|Gln|Thr|Ala|Ser|Val|Thr|Gln|Ala|Asn|Ile|Ala|Ser|Asp|Ala|
| |210| | | | |215| | | | |220| | | | |

| | | | | | | | | | | | | | |
|---|---|---|---|---|---|---|---|---|---|---|---|---|---|
|Ser|Asn|Gln|Ala|Asn|Arg|Leu|Ala|Ala|Ala|Ala|Ala|Ala|Met|Ser|
|225| | | | |230| | | | |235| | | | |240|

| | | | | | | | | | | | | | |
|---|---|---|---|---|---|---|---|---|---|---|---|---|---|
|Ala|Ala|Ala|Ser|Ala|Gln|Glu|Asn|Ala|Ala|Ser|Leu|Ala|Arg|Ala|Ser|
| | | |245| | | | |250| | | | |255| | |

| | | | | | | | | | | | | | |
|---|---|---|---|---|---|---|---|---|---|---|---|---|---|
|Ala|Ser|Ala|Ser|Glu|Ser|Ala|Ala|Ser|Ala|Ala|Ser|Lys|Ala|Glu|Ala|
| | | |260| | | | |265| | | | |270| | |

| | | | | | | | | | | | | | |
|---|---|---|---|---|---|---|---|---|---|---|---|---|---|
|Ser|Ala|Glu|Ala|Ala|Lys|Ser|Ser|Ala|Glu|Lys|Cys|Leu|Leu|Ala|
| | |275| | | | |280| | | | |285| | | |

| | | | | | | | | | | | | | |
|---|---|---|---|---|---|---|---|---|---|---|---|---|---|
|Gln|Asn|Ser|Ala|Gln|Ala|Gln|Ala|Arg|Ala|Thr|Glu|Gln|Ser|Glu|Ser|
| |290| | | | |295| | | | |300| | | | |

| | | | | | | | | | | | | | |
|---|---|---|---|---|---|---|---|---|---|---|---|---|---|
|Ser|Asn|Arg|Asp|Ser|Ala|Ala|Asn|Ala|Ala|Ala|Ala|Glu|Ala|Glu|
|305| | | | |310| | | | |315| | | | |320|

| | | | | | | | | | | | | | |
|---|---|---|---|---|---|---|---|---|---|---|---|---|---|
|Arg|Lys|Ala|Ile|Met|Ala|Leu|Lys|Ala|Ile|Ala|Asp|Ala|Lys|Ala|Lys|
| | | |325| | | | |330| | | | |335| | |

| | | | | | | | | | | | | | |
|---|---|---|---|---|---|---|---|---|---|---|---|---|---|
|Ala|Gly|Ala|Ala|Val|Ala|Ala|Gln|Ser|Glu|Ala|Ala|Ala|Ala|Ala|
| | | |340| | | | |345| | | | |350| | |

| | | | | | | | | | | | | | |
|---|---|---|---|---|---|---|---|---|---|---|---|---|---|
|Ala|Ala|Ala|Lys|Ala|Arg|Ala|Asp|Ala|Glu|Ala|Gly|Ala|Ser|Leu|Ala|
| | | |355| | | | |360| | | | |365| | |

| | | | | | | | | | | | | | |
|---|---|---|---|---|---|---|---|---|---|---|---|---|---|
|Ala|Ala|Ala|Arg|Ala|Val|Ala|Ala|Glu|Ala|Ala|Ala|Ser|Arg|Arg|
| | | |370| | | | |375| | | | |380| | |

| | | | | | | | | | | | | | |
|---|---|---|---|---|---|---|---|---|---|---|---|---|---|
|Asn|Asp|Arg|Gln|Ala|Gly|Ile|Ala|Gln|Ala|Gly|Ala|Ser|Ala|Ala|Ala|
|385| | | | |390| | | | |395| | | | |400|

| | | | | | | | | | | | | | |
|---|---|---|---|---|---|---|---|---|---|---|---|---|---|
|Glu|Thr|Arg|Ala|Leu|Ala|Ser|Ser|Ala|Ala|Ala|Thr|Ala|Lys|Ala|Ala|

```
                    405                 410                 415
Ala Tyr Ala Asn Ala Asp Ile Arg Ala Leu Ser Ala Ala Leu Glu
                420                 425                 430

Ser Ser Ile Ser Ser Ser Ser Ala Ser Ala Ser Ser Ala Ser Ser
                435                 440                 445

Ser Ala Ser Ser Gly Ala Ile Ser Gly Ser Ser Gly Ser Ser Ser
                450                 455                 460

Gly Ser Ser Ile Gly Ser Ser Gly Ala Ser Ser Gly Ala Ser Ser
465                 470                 475                 480

Ser Ala Ser Ser Asp Ser Ser Asp Ser Ser Asp Ser Ile Ser
                485                 490                 495

Leu Leu Gly Asp Asp Ala Ser Ser Ala Ser Ser Ala Ala Asp Ala
                500                 505                 510

Glu Ser Arg Thr Ser Ser Leu Ile Leu Asn
                515                 520

<210> SEQ ID NO 70
<211> LENGTH: 350
<212> TYPE: PRT
<213> ORGANISM: Vespa mandarinia

<400> SEQUENCE: 70

Gly Pro Ser Arg Leu Ser Glu Thr Ser Asp Ser Ser Ala Ala Ser Trp
1               5                   10                  15

Ser Ser Ser Ser Ser Ser Ser Ser Leu Ser Ser Ser Leu Ala Ser
                20                  25                  30

Asp Ser Ala Ser Ser Ala Ser Ala Ser Ala Ser Ala Ser
                35                  40                  45

Ala Ser Ala Ser Ser Arg Asn Asp Asn Ser Arg Val Lys Ala Trp Lys
50                  55                  60

Lys Gly Arg Gly Gly Ser Asp Ser Leu Val Leu Ser Ser Asp Ser Ser
65                  70                  75                  80

Glu Asp Ser Lys Ala Arg Glu Leu Leu Glu Thr Asp Ala Gly Leu Gly
                85                  90                  95

Ala Ala Ala Ala Leu Ala Arg Ala Thr Ala Asp Ala Gln Ala Arg Thr
                100                 105                 110

Ala Ala Ser Ala Asp Ala Thr Ala Asn Lys Ala Thr Ala Lys Ala Leu
                115                 120                 125

Ala Leu Ala Glu Ala Ala Val Arg Ala Glu Asn Ala Ala Ile Leu Arg
                130                 135                 140

Ile Arg Arg Ala Leu Ser Ala Ala Gln Ala Leu Val Ser Ala Ser Asn
145                 150                 155                 160

Arg Ala Lys Ala Ala Arg Ala Ala Arg Glu Ala Ala Ala Asn Ser
                165                 170                 175

Ala Ala Ala Ala Ala Lys Ala Ser Thr Asn Gln Val Lys Ala Asn Ala
                180                 185                 190

Asp Ser Leu Val Ala Asn Arg Ala Ala Ala Leu Leu Ala Ala Ala
                195                 200                 205

Glu Glu Ala Leu Gln Lys Ala Ser Ala Ser Gln Asn Ala Ala Ala Glu
                210                 215                 220

Ala Ala Ala Lys Ala Arg Ala Ala Asn Ala Asn Ala Ala Thr Thr
225                 230                 235                 240

Arg Ala Ala Ala Ser Ala Ile Leu Ala Glu Ala Arg Ala Arg Val Ala
                245                 250                 255
```

-continued

```
Ile Thr Lys Ala Val Ala Ala Gln Ser Thr Ala Ser Ala Gln Ala Ser
            260                 265                 270

Ser Ala Ser Gln Ile Gln Asn Arg Ala Asn Asn Leu Gln Ala Gln Ile
        275                 280                 285

Ala Ser Leu Ala Gln Ser Arg Ala Glu Ala Ala Ile Ala Ala Ala Ala
    290                 295                 300

Ala Gln Ala Ala Ala Val Ala Glu Ala Asn Ser Gln Leu Ala Arg Leu
305                 310                 315                 320

Ser Lys Ser Ser Ala Gly Ala Ser Ser Glu Gly Ser Ala Ser Ala Ser
                325                 330                 335

Ala Ser Ala Ser Ala Ser Ala Ser Ser Ser Ser Ser Ala
            340                 345                 350

<210> SEQ ID NO 71
<211> LENGTH: 355
<212> TYPE: PRT
<213> ORGANISM: Vespa mandarinia

<400> SEQUENCE: 71

Asn Ser Ser Ser Ala Glu Ser Ser Ala Ser Ala Thr Ala Ser Ser
1               5                   10                  15

Asp Ala Ser Trp Ser Thr Ser Arg Ser Ser Ala Ile Gly Arg Ala
            20                  25                  30

Pro Asn Val Ile Leu Asn Arg Ala Pro Gln Leu Gly Ala Ser Ala Ala
        35                  40                  45

Ala Ile Ala Ser Ala Arg Ala Ser Ala Ser Ala Asn Ala Ala Ser Asp
    50                  55                  60

Glu Lys Ser Ala Arg Glu Thr Arg Ala Thr Ala Leu Ala Arg Ser Arg
65                  70                  75                  80

Ala Ala Val Thr Ala Ala Arg Ala Ala Ala Arg Thr Gln Glu Ala
                85                  90                  95

Val Ala Ala Ala Lys Ala Ser Arg Ala Gln Ala Leu Ala Ala Ala
            100                 105                 110

Lys Ser Ser Ala Ala Ile Ser Ala Leu Ala Ala Gly Glu Ala Ala Ala
    115                 120                 125

Gln Lys Ala Asp Ala Ala Ala Leu Ala Ala Leu Ile Ala Asn Gln Arg
    130                 135                 140

Ser Ala Lys Ala Ala Glu Asn Gly Leu Ala Val Gln Asn Arg Ala Asn
145                 150                 155                 160

Gly Glu Ala Glu Gln Ala Ser Arg Ala Ala Ala Asn Leu Ala Ala
                165                 170                 175

Ala Ile Arg Thr Arg Asp Asn Ala Leu Glu Thr Arg Lys Glu Ala Ala
        180                 185                 190

Arg Leu Lys Ala Leu Ala Thr Ala Ala Ala Asn Ala Asn Asn Lys Ala
        195                 200                 205

Thr Ser Leu Ala Glu Ala Ser Ala Asn Gln Ala Ala Glu Ala Ser Ser
    210                 215                 220

Ala Ala Glu Asp Thr Ser Ser Ala Gln Cys Ala Ala Val Ala Gln Ala
225                 230                 235                 240

Glu Ala Ala Glu Thr Leu Asn Val Asn Leu Ala Ile Leu Glu Ser Thr
                245                 250                 255

Gln Ser Ser Arg Gln Asp Ser Asn Val Ala Lys Ala Glu Ala Ser Ala
            260                 265                 270

Ala Ala Lys Ala Ser Ala Gly Thr Ala Thr Arg Asp Gly Val Asp Leu
        275                 280                 285
```

```
Gly Leu Ala Ser Asp Ala Gly Ala Ala Gln Leu Lys Ser Gln Ala
        290             295                 300

Ala Ala Leu Gly Arg Ala Ser Ser Arg Ile Ser Ser Gly Pro Ala Leu
305                 310                 315                 320

Ser Ala Trp Lys Trp Arg Asn Glu Glu Ser Glu Ser Ser Ala Ser
                325                 330                 335

Ala Ile Ala Ser Ser Ser Ala Ser Ser Ser Ser Ser Arg Ser Ala
            340                 345                 350

Ser Gly Asn
        355

<210> SEQ ID NO 72
<211> LENGTH: 449
<212> TYPE: PRT
<213> ORGANISM: Vespa mandarinia

<400> SEQUENCE: 72

Ala Glu Ser Ser Ser Ser Ser Ala Ala Ser Ser Ala Ser Ser Ser
1               5                   10                  15

Ser Ser Glu Ser Arg Gly Gln Leu Leu Leu Pro Leu Glu Arg Ser Ser
                20                  25                  30

Thr Arg Ser Leu Leu Asp Leu Val Ser Ser Ala Arg Ser Asn Ala Ala
            35                  40                  45

Ile Thr Ala Ser Ser Ala Ala Ala Lys Ala Thr Leu Arg Ala Ser
        50                  55                  60

Lys Ala Ala Asn Ser Ala Gln Gly Glu Ala Leu Ala Gln Ala Thr Ala
65                  70                  75                  80

Ser Ala Ala Ser Asn Ala Lys Ala Arg Ala Thr Ala Ala Ala Ala
                85                  90                  95

Gln Ala Thr Asn Ala Ala Val Asn Ala Gln Gly Lys Ala Ser Ala Gln
                100                 105                 110

Ala Ile Ala Thr Ala Glu Ala Ala Glu Ala Leu Thr Lys Ser Ala Leu
            115                 120                 125

Gln Ala Gln Ser Ala Ala Ser Ser Ser Lys Ser Glu Ala Ala Gln Ala
130                 135                 140

Ser Thr Ser Ala Asn Ala Gly Ala Ser Ala Leu Ala Thr Ala Ser Ala
145                 150                 155                 160

Gln Ala Leu Ser Ala Lys Lys Ala Ala Leu Ala Tyr Ala Ser Ala Ala
                165                 170                 175

Ala Asp Ala Asn Thr Ala Ala Ala Lys Ala Arg Ala Ala Val Ala Ala
            180                 185                 190

Ala Glu Ala Ala Thr Arg Thr Ala Val Gln Ala Glu Arg Asp Ser Thr
        195                 200                 205

Asn Ala Ala Ser Leu Ala Ala Lys Ala Gln Glu Ala Arg Ala Ala
210                 215                 220

Ala Ala Ala Ala Ala Ala Arg Leu Ala Ala Ser Ala Ala Ala Asp
225                 230                 235                 240

Ala Ser Ala Gln Ala Asp Ala Arg Val Arg Thr Ala Ser Ile Glu Ala
                245                 250                 255

Ala Ala Ser Thr Arg Thr Lys Ala Ser Asn Ala Gln Ala Thr Ala Glu
            260                 265                 270

Ala Ala Ala Ile Ala Arg Ser Ser Arg Asp Ala Gln Ala Asn Trp
        275                 280                 285

Val Asp Asn Arg Ser Ser Ala Ser Ser Ser Ser Ala Ser Ala Ser Ala
```

```
    290                 295                 300

Ser Ala Ser Ala Ser Ala Ser Gly Glu Ala Asp Ser Glu Ala Asp Ser
305                 310                 315                 320

Asp Ala Ile Ala Ser Ala Arg Ser Ala Ala Asp Ser Asn Ile Gly Ser
                325                 330                 335

Ser Ser Gly Ser Ala Ala Asp Ser Ala Ala Gly Ser Ser Ala Gly Ser
            340                 345                 350

Ala Ala Arg Leu Ser Ala Gly Ser Ala Ala Gly Ser Ile Ala Arg Ser
        355                 360                 365

Ala Ala Gly Ser Ala Ala Gly Ser Ser Ala Gly Ser Gly Ala Gly Ala
    370                 375                 380

Ser Ala Glu Gly Ser Ser Ser Ala Ser Ser Gly Ala Ser Ser Gly Ala
385                 390                 395                 400

Ser Ala Gly Ala Ser Ala Gly Ala Ser Ala Ala Ala Ser Ala Asp Asn
                405                 410                 415

Ser Ala Asp Asn Ser Ala Glu Ala Leu Ser Ser Ser Ser Ala Glu Ser
            420                 425                 430

Ser Ser Ser Ser Trp Ser Ser Ser Ser Gln Asn Ile Trp Ser Gln Asp
        435                 440                 445

Trp

<210> SEQ ID NO 73
<211> LENGTH: 518
<212> TYPE: PRT
<213> ORGANISM: Vespa mandarinia
<220> FEATURE:
<221> NAME/KEY: misc_feature
<222> LOCATION: (77)..(77)
<223> OTHER INFORMATION: Xaa can be any naturally occurring amino acid

<400> SEQUENCE: 73

Asp Arg Ser Trp Ala Ala Ser Asp Ala Asn Ala Glu Ala Ser Ala Ala
1               5                   10                  15

Ala Glu Ser Ser Ser Leu Trp Glu Asp Ser Ser Ser Ala Ser Ala Gly
            20                  25                  30

Ala Ser Ala Ala Gly Glu Ser Ser Ser Leu Trp Glu Asp Ser Ser Ser
        35                  40                  45

Ala Ser Ala Gly Thr Ser Ala Ala Gly Glu Ser Ser Ser Leu Trp Glu
    50                  55                  60

Asp Ser Ser Ser Ala Ser Ala Gly Thr Ser Ala Ala Xaa Glu Ser Ser
65                  70                  75                  80

Ser Leu Trp Glu Asp Ser Ser Ser Ala Ser Ala Arg Ala Ser Ala Ala
                85                  90                  95

Ala Glu Ser Ser Ser Ala Trp Glu Asp Ser Ser Ile Ala Asn Ala Arg
            100                 105                 110

Glu Ser Gly Ala Ser Gly Ser Leu Ser Ser Trp Glu Asp Ser Ser Ser
        115                 120                 125

Gly Ser Ala Ser Ser Ser Thr Ser Ala Ser Ala Ser Ser Ser Ser Ser
    130                 135                 140

Ser Ser Ser Ser Ile Ser Ser Ser Ala Ser Ser Ser Ser Ser Ala Ser
145                 150                 155                 160

Ala Ser Ala Ser Thr Glu Thr Ser Asn Glu Ser Arg Arg Gly Ile Ala
                165                 170                 175

Ile Glu Gly Ala Leu Val Gly Thr Gly Ala Ala Ser Thr Ala Ala Ala
            180                 185                 190
```

```
Ser Ala Glu Met Leu Ser Asn Thr Leu Gly Leu Gly Gln Ser Gly Leu
            195                 200                 205

Gln Ala Gln Thr Ala Ser Val Met Gln Ala Asn Ile Ala Ser Asp Ala
        210                 215                 220

Ser Asn Gln Ala Asn Arg Leu Ala Thr Ala Ala Ala Ala Ala Met Ser
225                 230                 235                 240

Ala Ala Ala Ser Ala Gln Glu Asn Ala Ala Ser Leu Ala Arg Ala Ser
                245                 250                 255

Ala Ser Ala Ser Glu Ser Ala Ala Ser Ala Ser Ser Arg Ala Glu Ala
            260                 265                 270

Ser Ala Glu Ala Ala Lys Ser Ser Ala Glu Lys Cys Leu Leu Leu Ala
        275                 280                 285

Gln Asn Ser Ala Gln Ala Gln Ala Arg Ala Thr Glu Gln Ser Glu Ser
    290                 295                 300

Ser Asn Arg Asp Ser Ala Ala Asn Ala Ala Ala Ala Glu Ala Glu
305                 310                 315                 320

Arg Lys Ala Ile Leu Ala Leu Lys Ala Ile Ala Asp Ala Lys Ala Lys
                325                 330                 335

Ala Gly Ala Ala Val Ala Ala Gln Ser Glu Ala Ala Ala Ala Ala
            340                 345                 350

Ala Ala Ala Lys Ala Arg Ala Asp Ala Glu Gly Ala Ser Leu Ala
        355                 360                 365

Ala Ala Arg Ala Val Ala Ala Glu Ala Ala Ser Arg Arg
    370                 375                 380

Asn Asp Arg Gln Ala Gly Ile Ala Gln Ala Gly Ala Ser Ala Ala Ala
385                 390                 395                 400

Glu Thr Arg Ala Leu Ala Ser Ala Ala Thr Ala Lys Ala Ala
                405                 410                 415

Ala Tyr Ala Asn Ala Asp Ile Arg Ala Leu Ser Ala Ala Leu Glu
            420                 425                 430

Ser Ser Ile Ser Ser Ser Ser Ala Ser Ala Ser Ala Ser Leu
        435                 440                 445

Ser Thr Ser Ser Gly Ser Ser Gly Ser Ser Ser Gly Ser Ser Ser
    450                 455                 460

Gly Ala Ser Ser Ala Ser Ser Ser Ala Ser Ser Ser Ala Ser Ser
465                 470                 475                 480

Asp Ser Ser Ser Asp Ser Arg Ser Asp Ser Ile Ser Leu Leu Gly Asp
                485                 490                 495

Asp Ala Ser Ser Ser Ala Ser Ser Ala Ala Glu Ala Glu Ser Arg Thr
            500                 505                 510

Ser Ser Leu Ile Leu Asn
        515

<210> SEQ ID NO 74
<211> LENGTH: 365
<212> TYPE: PRT
<213> ORGANISM: Tenodera australasiae

<400> SEQUENCE: 74

Ser Pro Leu Glu Asp Lys Tyr Asp Gln Lys Tyr Glu Val Glu Asp Tyr
1               5                   10                  15

Arg Gly Gly Ser Glu Asp Thr Lys Ala Ala Ile Asn Asp Asn Ala Ala
            20                  25                  30

Arg Val Ala Ser His Ser Ala Lys Ser His Val Asn Lys Ala Leu Val
        35                  40                  45
```

Val Glu Ala Ala Arg Leu Asn Ala Gln Ile Ala Lys Asp Arg Asn
    50                  55                  60

Tyr Tyr Ala Arg Glu Tyr Thr Lys Leu Ala Glu Ser Lys Lys Arg
 65                  70                  75                  80

Ala Arg Gln Tyr Gly Gln Leu Ala Asp Met Glu Ala Gly Arg Ile Gly
                 85                  90                  95

Gln His Glu His Met Gln Gln Glu Trp Asn Ser Lys Ala Arg Glu Ser
            100                 105                 110

Glu Ala Gln Cys Lys Ala Thr Glu Ala Lys Ala Gln Glu Glu Tyr Thr
            115                 120                 125

Lys Ala Arg Asp Glu Arg Gln Lys Ser Leu Val Ser Asn Ala Glu Ala
            130                 135                 140

Ala Met His Asp Ala Gln Ala Thr Val Asp Thr Met Lys Ser Glu Arg
145                 150                 155                 160

Ala Tyr Glu Ile Gly Lys Glu Leu Met Arg Lys Ala Glu Asn Ala Arg
                165                 170                 175

Asn Asp Ala Ser Asn His Tyr Gln Arg Ala Lys Glu Asn Arg Glu Arg
                180                 185                 190

Ala Asn Ser Glu Thr Val Lys Ser His Gln Gln Ala Gln Asp Ala Gln
                195                 200                 205

Arg His Asn Ala Ala Ser Lys Ala Tyr Gln Gln Asp Gly Leu Arg Thr
            210                 215                 220

Arg Met Ala Ser Arg Ile Asn Ile Met Lys Tyr Ile Gln Ser Ser Leu
225                 230                 235                 240

Leu Ala Glu Arg Ala Ala Asn Gln Ala Arg Ile Glu Gln Leu Lys Ser
                245                 250                 255

Glu Trp Tyr Glu Lys Ala Ala Asn Glu Tyr Ser Arg Met Ser Glu Glu
                260                 265                 270

Asn Ala Ala Ile Ser Lys Leu Ala Gly Ser Glu Glu His Tyr Phe Ala
                275                 280                 285

Gln Arg Ala Lys Arg Asn Glu Gly Lys Ala Tyr Glu Leu Ser Gln Ser
            290                 295                 300

Lys Arg Met Met Gly Ser Glu Ala Ala Ala Gly Glu Leu Leu Ala
305                 310                 315                 320

Met Ser Gln Ala Lys Asp Asp Glu Thr Glu Asp Glu Lys His Phe Asp
                325                 330                 335

Phe Pro Ile Tyr Glu Ser Asp Pro Thr Lys Leu Ser Pro Ser Pro
                340                 345                 350

Asp Glu Lys Asp Leu Thr Tyr Gly Ser Gly Glu Gly Leu
            355                 360                 365

<210> SEQ ID NO 75
<211> LENGTH: 342
<212> TYPE: PRT
<213> ORGANISM: Tenodera australasiae

<400> SEQUENCE: 75

Gly Lys Lys His Glu Val Met Thr Tyr Gly Ser Gly Tyr Lys His Met
1               5                   10                  15

Gly Gly Glu Thr Tyr Glu Asp Val Gly Thr Gly Asn Arg Leu Gly Ser
                20                  25                  30

Thr Ala Phe Asp Ile Met Glu Ala Ala Asp Glu Asn Thr Glu Arg Ala
            35                  40                  45

Ser His Thr Phe Gly Ser Lys Ser Ala Ala Tyr Ser Ser Asp Ala Asp

```
                    50                  55                  60
Leu Phe Ile Glu Leu Leu Arg Glu Lys Arg Glu Thr Arg Ala Asn His
 65                  70                  75                  80

Gly Lys Arg Ala Glu Ser Gln Ala Val Leu Ala Asn Glu Ser Tyr Gln
                    85                  90                  95

Lys Ser Gln Leu His Lys Arg Gln Ala Lys Asp Lys Gln Ala Ile Ser
                100                 105                 110

Lys Glu Tyr Glu Glu Arg Ala Gln Lys His Asp Arg Leu Ser Lys Glu
                115                 120                 125

Gln Asp Met Lys Glu His Asp Asp Tyr Arg Lys Ser Asn Ala Glu Asp
            130                 135                 140

Thr Glu Leu Arg Asn Ser Val Glu Arg Ser Asn Tyr Asp His Val Met
145                 150                 155                 160

Ala Leu Gly Tyr His Glu Leu Ser Gln Leu Glu Met Gly Glu Thr Asn
                    165                 170                 175

Gln Cys Glu Gln Leu Ser Arg Glu Leu Gln Ser Arg Ala Glu Glu Tyr
                180                 185                 190

Phe Asn Leu Ala Lys Glu Leu Lys Glu Lys Ala Lys Lys Glu Lys Glu
                195                 200                 205

Asn Ala Arg Ile Lys Lys Ala Lys Ala Lys Glu Glu Glu Ala Arg Ala
210                 215                 220

Glu Glu Tyr Glu Asn Ala Phe Thr Glu Asn Ser Lys Lys Val Leu Thr
225                 230                 235                 240

Tyr Lys Phe Tyr Glu Leu Glu Phe Gly Met Lys Ala Leu Asn Glu His
                    245                 250                 255

His Gln Ala Glu Ser Ala Arg Val Arg His Phe Leu Gln Ile Leu
                260                 265                 270

Glu Gln His Asn Ser Gln His Ala Asp Met Leu Trp Gly Tyr Ala Gln
                275                 280                 285

Gln Glu Asp Lys Asp Gly Arg Ser Phe Thr Gly Tyr Ala Thr Glu Leu
            290                 295                 300

Ser Lys Gln Thr Lys Met Leu Thr Ala Thr Ala His Leu Met Lys
305                 310                 315                 320

Gln His Arg Tyr Thr Gly Met Glu Met Tyr Ser Lys Gln Pro Phe Pro
                    325                 330                 335

His Ser Asn Tyr His Gly
                340

<210> SEQ ID NO 76
<211> LENGTH: 361
<212> TYPE: PRT
<213> ORGANISM: Archimantis monstrosa

<400> SEQUENCE: 76

Ser Pro Leu Glu Glu Lys Tyr Asp Glu Lys Ser Glu Ala Asp Asp Tyr
 1               5                  10                  15

Gln Ser Glu Asp Ser Ser Ala Ala Ile His Asp Gln Thr Thr Lys Ile
                20                  25                  30

Ala Thr Asn Ala Val Lys Thr Tyr Ala Asn Lys Ala Lys Ala Thr Glu
            35                  40                  45

Ser Lys Ala Lys Leu Tyr His Gln Tyr Ser Lys Asp Arg Ala Tyr Tyr
        50                  55                  60

Ser Arg Glu Tyr Glu Lys Met Gly Glu Glu Tyr Met Lys Lys Ser Lys
 65                  70                  75                  80
```

Glu Tyr Glu Gln Leu Tyr Ile Ala Glu Ala Arg Ile Ser Leu His
            85                  90                  95

Glu Asn Lys Gln Lys Glu Trp Asp Thr Lys Gly Arg Glu Ala Asn Val
        100                 105                 110

Gly Ile Arg Glu Tyr Glu Thr Lys Ser Gln Gln Ala Ser Ser Lys Lys
        115                 120                 125

Asn Glu Leu Leu Glu Glu Ser Ile Ile Ala Ala Val Gln Ala Ala Ile
    130                 135                 140

His Glu Thr Gln Ala Thr Gly Tyr Leu Leu Lys Ser Glu Ala Ala Asn
145                 150                 155                 160

Gly Ile Ala Arg Asn Met Leu Gln Ile Ala Glu Ser Ile Arg Asp Glu
                165                 170                 175

Ala Ser Asn His Tyr Gln Ile Gly Lys Glu Glu Leu Asn Arg Ala Thr
            180                 185                 190

Ala Gln Lys Val Lys Ala Gln Gln Ala Glu Asp Ser Gln Arg His
        195                 200                 205

His Ala Ala Ala Arg Ala Tyr Gln Gln Asp Ser Leu Arg Ser Arg Met
    210                 215                 220

Ala Ser Arg Ala Asn Asn Met Gln Tyr Met Gln Asn Ser Leu Leu Ala
225                 230                 235                 240

Glu Arg Ala His Ser Leu Ser Thr Glu Asn Thr Leu Glu Ser Glu Leu
                245                 250                 255

Tyr Gly Lys Glu Ala Asp Glu Leu Ala Lys Met Ser Glu Glu Ser Ala
            260                 265                 270

Ala Ile Ser Lys Ile Cys Ser Gly Glu Glu Arg Ser Tyr Arg Asn Met
        275                 280                 285

Ala Lys Gln Ser Glu Val Lys Ala Tyr Glu Tyr Ser Val Ser Lys Asn
    290                 295                 300

Met Met Gly Ala Asp Met Thr Asp Thr Ala Ala Met Ala Asn Gly Asp
305                 310                 315                 320

Glu Ala Lys Gln Gly Asp Asp Glu Gly Gln Met Tyr Arg Ser Pro
                325                 330                 335

Asn Ile Pro Ala Glu Asp Ser Thr Lys Asn Leu Ser Tyr Asn Leu Lys
            340                 345                 350

Asp Ser Thr Glu Gly Glu Gly Met Ser
        355                 360

<210> SEQ ID NO 77
<211> LENGTH: 351
<212> TYPE: PRT
<213> ORGANISM: Archimantis monstrosa

<400> SEQUENCE: 77

Gly Lys Lys His Glu Ala Leu Thr Phe Gly Ser Gly Tyr Lys Ser Thr
1               5                   10                  15

Tyr Gly Glu Gly Glu Thr Phe Asp Asp Glu Asp Gln Ala Leu Arg
            20                  25                  30

Asn Glu Arg Val Pro Val Gly Ala Leu Ser Ala Ala Ile Ile Asn Pro
        35                  40                  45

Tyr Ala Leu His Ser Glu Glu Gly Arg Ile Ala Tyr Asp Thr Ser Ser
    50                  55                  60

Gln Tyr Tyr Ala Asn Lys Ala Glu Gly Ser Ala Asp Leu Ser Arg Glu
65                  70                  75                  80

Lys Lys Gln Met His Gly Glu Tyr His Gly Lys Ala Ala Thr Tyr Ala
                85                  90                  95

Ser Arg Ala Asn Glu Ala Tyr Lys Lys Ser Gln Leu His Lys Arg Gln
            100                 105                 110

Ala Lys Asp Lys Gln Ala Ile Ala Lys Glu Tyr Glu Glu Arg Ala Gln
            115                 120                 125

Lys His Glu Ser Arg Ser Lys Ala Leu Asp Val Arg Asp Gln Asp Asp
        130                 135                 140

Glu Arg Lys Ser Val Thr Glu Met Glu Glu Tyr Ala Arg Ala Leu Lys
145                 150                 155                 160

Ile Ala Asn Leu Ala Leu Val Phe Ala Gly Ile Tyr Gln Glu Thr Gly
                165                 170                 175

Arg Leu Gln Leu Glu Ala Thr Asn Val Phe Glu Gln Phe His Lys Met
                180                 185                 190

Leu Ser Thr Lys Gly Glu Glu Tyr Lys Gln Ala Glu Glu Tyr Lys
            195                 200                 205

Glu Lys Ala Asn Lys Glu Lys Glu Ala Ala Ile Gln Gln Ala Lys
        210                 215                 220

Ser Lys Glu Leu Asn Ala Lys Ala Gln Glu Tyr Glu Asn Ile Phe Ile
225                 230                 235                 240

Glu Ser Ser Lys Lys Leu Ala Ala Asn Arg Tyr Tyr Glu Leu Glu Phe
                245                 250                 255

Lys Met Lys Ala Glu Asn Glu Arg His His Ala Glu Leu Ala Arg Ile
            260                 265                 270

Arg Ser Arg Phe Leu Ser Arg Leu Ala Asn Tyr Asn Arg Glu Gln Ala
        275                 280                 285

Glu Ala Val Leu Arg Phe Ala Arg Ser Glu Arg Lys Asp Gly Glu Ile
        290                 295                 300

Phe Arg Arg Asn Ala Ile Glu Leu Tyr Lys Glu Thr Arg Ala Leu Ala
305                 310                 315                 320

Ala Thr Ala Ala Arg Val Met Lys Gln His Arg Tyr Thr Gly Gln Glu
                325                 330                 335

Ile Tyr Thr Lys Gln Pro Phe Pro His Ser Asn Tyr His Gly Ala
            340                 345                 350

<210> SEQ ID NO 78
<211> LENGTH: 363
<212> TYPE: PRT
<213> ORGANISM: Pseudomantis albofimbriata

<400> SEQUENCE: 78

Ser Pro Leu Glu Glu Lys Tyr Gly Glu Lys Tyr Gly Asp Met Glu Glu
1               5                   10                  15

Tyr Gln Arg Gly Thr Glu Asp Ser Arg Ala Val Ile Asn Asp His Thr
                20                  25                  30

Ala Lys Val Ala Ser Gln Ser Ala Arg Gly Met Val Asn Lys Ala Lys
            35                  40                  45

Thr Thr Glu Ala Ala Ala Arg Ser Asn Glu Gln Leu Ser Lys Asp Arg
        50                  55                  60

Gln Tyr Tyr Tyr Arg Glu Tyr Leu Lys Lys Ala Asp Tyr His Lys Lys
65                  70                  75                  80

Lys Ala Leu Glu Tyr Glu Gln Leu Ser Ala Ala Glu Asn Ala Lys Ile
                85                  90                  95

Ala Tyr His Glu Ser Lys Gln Lys Asp Trp Glu Thr Lys Ala Arg Glu
            100                 105                 110

Ser Asp Val Gln Cys Arg Asp Ala Glu Ala Lys Tyr Glu Gln Ser Tyr

```
                115                 120                 125
Thr Arg Ser Arg Glu Leu Lys Arg Glu Ser Ile Ile Ala Tyr Val Gln
130                 135                 140

Ala Ala Met His His Ala Glu Ala Ser Gly Asp His Met Lys Ala Asp
145                 150                 155                 160

Arg Ala Lys Asp Ile Ala Arg Asp Met Met Arg Lys Ala Glu Ser Leu
                165                 170                 175

Arg Gly Asp Ala Ser Asn His Tyr Gln Arg Ser Glu Glu Asp Lys Asn
            180                 185                 190

Lys Ala Arg Ser Glu Lys Val Lys Ala His Gln Asn Ala Asp Asn Ser
        195                 200                 205

Gln Arg His His Thr Ala Cys Arg Ala Tyr Asp Gln Glu Gly Leu Lys
210                 215                 220

Thr Arg Leu Ser Ser Lys Ala Asn Met Met Arg Gln Ile His Ser Ser
225                 230                 235                 240

Leu Leu Ala Glu Arg Ser His Ser Leu Ala Arg Glu Asp Gly Leu Ala
                245                 250                 255

Ala Asp Leu Ser His Lys Leu Ala Glu Glu Leu Ala Arg Met Ser Glu
            260                 265                 270

Glu Ser Gly Ala Ile Ser Lys Ile Asn Ser Gly Glu Arg Gly Tyr
        275                 280                 285

Ser Asn Lys Val Arg Gln Asp Glu Val Lys Ala His Glu Leu Ala Val
290                 295                 300

Ser Lys Arg Met Met Gly Ala Glu Val Ala Asp Asn Ser Glu Met Ile
305                 310                 315                 320

Ser Leu Ala Gln Ala Lys Asp Gly Ser Leu Asp Gly Glu Asn Tyr
                325                 330                 335

Lys Leu Ser Thr Phe Tyr Ala Asp Asp Ser Thr Lys Asn Met Leu Pro
            340                 345                 350

Asp Ser Arg Gly Gln Met Ser Tyr Gly Asp Glu
        355                 360

<210> SEQ ID NO 79
<211> LENGTH: 348
<212> TYPE: PRT
<213> ORGANISM: Pseudomantis albofimbriata

<400> SEQUENCE: 79

Gly Lys Asn His Glu Val Met Thr Tyr Gly Ser Gly Tyr Lys Thr Met
1               5                   10                  15

Gly Asp Glu Gly Gly Ser Gly Val Gly Asn Glu Gly Glu Asp Tyr Gln
            20                  25                  30

Asp Asn Glu Gly Ala Thr Ala Thr Ile Leu Asp Glu Ser Thr His
        35                  40                  45

His Thr Glu Glu Ala Arg Asp Ile Phe Gly Thr Arg Ser Glu Ala His
    50                  55                  60

Ala Tyr Ser Ala Glu Met Phe Ala Asp Leu Val Arg Glu Lys Arg Gln
65                  70                  75                  80

Ala Ser Ile Glu Ser His Lys Lys Ala Glu Asp Tyr Ala Val Arg Ala
                85                  90                  95

Asn Glu Glu Tyr Lys Lys Ser Gln Leu Leu Lys Arg Gln Ala Arg Asp
            100                 105                 110

Lys Gln Ala Ile Ala Lys Gln Tyr Glu Glu Lys Ala Gln Lys Tyr Asp
        115                 120                 125
```

```
Arg Ile Ser Lys Gln Gln Asp Ile Lys Glu Gln Asp Asp Tyr Arg Lys
        130                 135                 140

Ser Asp Ala Glu Ser Glu Glu Tyr Lys Arg Ser Ile Ala Val Ala Asn
145                 150                 155                 160

Ala Ala Leu Ala Leu Ala Ser Ala Tyr Glu Glu Ala Ser Arg Met Glu
                165                 170                 175

Leu Asp Ala Thr Gly Glu Met Glu Gln Gln Ser Lys Glu Leu Tyr Thr
                180                 185                 190

Lys Ser Glu Glu Tyr Asn Lys Val Ala Glu Glu Cys Ile Thr Arg Ala
            195                 200                 205

Lys Lys Glu Lys Glu Leu Ala Arg Ile Glu Glu Ala Lys Gly Lys Glu
        210                 215                 220

Ala Glu Ala Lys Ser Gln Glu Tyr Glu Asn Phe Ala Thr Asp Asn Asn
225                 230                 235                 240

Lys Lys Tyr Asn Ala Met Lys Phe Tyr Gly Trp Glu Phe Lys Met Lys
                245                 250                 255

Ala Glu Asn Glu Arg His Asn Ala Asp Tyr Cys Arg Ile Lys Ser Arg
                260                 265                 270

Tyr Leu Ala Gln Leu Ser Asn Tyr Asn Arg Glu Gln Ala Glu Ala Leu
            275                 280                 285

Tyr His Phe Ala Ala Ala Gln Arg Lys Asp Ala Glu Leu Phe His Arg
        290                 295                 300

Tyr Ala Met Glu Leu Tyr Lys Gln Thr Arg Val Leu Thr Ala Ser Ala
305                 310                 315                 320

Ala Gln Ile Met Lys Gln His Arg Tyr Thr Gly Gln Glu Ile Tyr Ser
                325                 330                 335

Lys Gln Pro Phe Pro His Ser Asn Tyr His Gly Ala
            340                 345

<210> SEQ ID NO 80
<211> LENGTH: 30
<212> TYPE: DNA
<213> ORGANISM: Artificial Sequence
<220> FEATURE:
<223> OTHER INFORMATION: Synthetic Primer

<400> SEQUENCE: 80
ctcttgcaga ggccgcgttg cgagcgtccg                                      30

<210> SEQ ID NO 81
<211> LENGTH: 30
<212> TYPE: DNA
<213> ORGANISM: Artificial Sequence
<220> FEATURE:
<223> OTHER INFORMATION: Synthetic Primer

<400> SEQUENCE: 81
ctcttgcaga ggcccatttg cgagcgtccg                                      30

<210> SEQ ID NO 82
<211> LENGTH: 45
<212> TYPE: DNA
<213> ORGANISM: Artificial Sequence
<220> FEATURE:
<223> OTHER INFORMATION: Synthetic Primer

<400> SEQUENCE: 82
cctgaaaaat catcaacaag cgcaattaaa cgcccaggaa aagtc                     45
```

UNITED STATES PATENT AND TRADEMARK OFFICE
CERTIFICATE OF CORRECTION

PATENT NO. : 10,870,875 B2
APPLICATION NO. : 15/527266
DATED : December 22, 2020
INVENTOR(S) : Tara D. Sutherland et al.

Page 1 of 1

It is certified that error appears in the above-identified patent and that said Letters Patent is hereby corrected as shown below:

On the Title Page

Item (73), update, "Commonwealth Scientific and Industrial Research Organisation, Campbell (AU)" with --Commonwealth Scientific and Industrial Research Organisation, Acton (AU)--

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*